(12) United States Patent
Aay et al.

(10) Patent No.: US 8,637,499 B2
(45) Date of Patent: Jan. 28, 2014

(54) BENZOXAZEPINES AS INHIBITORS OF PI3K/MTOR AND METHODS OF THEIR USE AND MANUFACTURE

(75) Inventors: Naing Aay, San Mateo, CA (US); Arlyn Arcalas, South San Francisco, CA (US); Joerg Bussenius, Foster City, CA (US); Steven Charles DeFina, Oakland, CA (US); Larisa Dubenko, San Francisco, CA (US); Jason R. Harris, San Bruno, CA (US); Eileen E. Jackson-Ugueto, Basel (CH); Angie Inyoung Kim, San Mateo, CA (US); Jean-Claire Limun Manalo, Daly City, CA (US); Michael Pack, Fukuoka (JP); Csaba J. Peto, Alameda, CA (US); Kenneth D. Rice, San Rafael, CA (US); Tsze H. Tsang, El Cerrito, CA (US); Owen Joseph Bowles, Pacifica, CA (US); Jeffry Kimo Curtis, San Anselmo, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 13/322,160

(22) PCT Filed: May 25, 2010

(86) PCT No.: PCT/US2010/036032
§ 371 (c)(1),
(2), (4) Date: Jun. 29, 2012

(87) PCT Pub. No.: WO2010/138487
PCT Pub. Date: Dec. 2, 2010

(65) Prior Publication Data
US 2012/0258953 A1 Oct. 11, 2012

Related U.S. Application Data

(60) Provisional application No. 61/217,146, filed on May 26, 2009.

(51) Int. Cl.
*A61P 35/00* (2006.01)
*A61K 31/553* (2006.01)
*C07D 267/14* (2006.01)

(52) U.S. Cl.
USPC .................. 514/211.09; 540/552

(58) Field of Classification Search
USPC .................. 514/211.09; 540/552
See application file for complete search history.

(56) References Cited

U.S. PATENT DOCUMENTS

| | | | |
|---|---|---|---|
| 5,221,681 | A | 6/1993 | Kabbe et al. |
| 7,521,457 | B2 | 4/2009 | Stadtmueller et al. |
| 8,247,403 | B2 | 8/2012 | Shirai et al. |
| 2006/0148800 | A1 | 7/2006 | Stadtmueller et al. |
| 2010/0298290 | A1 | 11/2010 | Anand et al. |
| 2010/0305093 | A1* | 12/2010 | Anand et al. ............ 514/210.21 |

FOREIGN PATENT DOCUMENTS

| | | |
|---|---|---|
| CN | 101497612 | 8/2009 |
| EP | 0496238 | 7/1992 |
| EP | 0540334 | 1/1996 |
| WO | 0116263 | 3/2001 |
| WO | 0116274 | 3/2001 |
| WO | 0116275 | 3/2001 |
| WO | 0116276 | 3/2001 |
| WO | 02096873 | 12/2002 |
| WO | 03075858 | 9/2003 |
| WO | 2006021544 | 3/2006 |
| WO | 2008/108445 | 9/2008 |
| WO | 2008/144483 | 11/2008 |
| WO | 2009026444 | 2/2009 |
| WO | 2009096631 | 6/2009 |

OTHER PUBLICATIONS ptcl.chem.ox.ac.uk/MSDS (2003); 1 pg.*
International Search Report mailed Sep. 21, 2010, for PCT/US2010/036032.
Dancey, J. E., "Inhibitors of the mammalian target of rapamycin" Expert Opinion on Investigational Drugs, Ashley Publications LTD., London, GB, vol. 14, No. 3, Mar. 1, 2005.

* cited by examiner

*Primary Examiner* — Shirley V Gembeh
(74) *Attorney, Agent, or Firm* — Honigman Miller Schwartz and Cohn LLP; Heidi M. Berven; Jonathan P. O'Brien

(57) ABSTRACT

The invention is directed to Compounds of Formula (I): the invention provides compounds that inhibit, regulate, and/or modulate PI3K and/or mTOR that are useful in the treatment of hyperproliferative diseases, such as cancer, in mammals. This invention also provides methods of making the compound methods of using such compounds in the treatment of hyperproliferative diseases in mammals, especially humans, and to pharmaceutical compositions containing such compounds. For example, cancer in which activity against PI3fC-alph mTOR, or both contributes to its pathology and/or symptomatology include breast cancer mantle cell lymphoma, renal cell carcinoma, acute myelogenous leukemia, chronic myelogenous leukemia, NPM/ALK-transformed anaplastic large cell lymphoma, diffu large B cell lymphoma, rhabdomyosarcoma, ovarian cancer, endometrial cancer, cervic cancer, non small cell lung carcinoma, small cell lung carcinoma, adenocarcinoma, col cancer, rectal cancer, gastric carcinoma, hepatocellular carcinoma, melanoma, pancreat cancer, prostate carcinoma, thyroid carcinoma, anaplastic large cell lymphoma, hemangiom glioblastoma, or head and neck cancer.

(I)

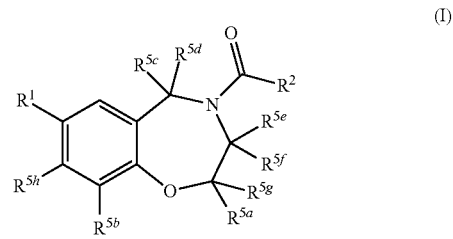

23 Claims, No Drawings

BENZOXAZEPINES AS INHIBITORS OF PI3K/MTOR AND METHODS OF THEIR USE AND MANUFACTURE

CROSS-REFERENCE TO RELATED APPLICATIONS

This application is a United States National Phase filing of PCT/US2010/036032, filed May 25, 2010, which claims priority to U.S. Provisional Application No. 61/217,146, filed May 26, 2009, the entire contents of which are incorporated herein by reference.

BACKGROUND OF THE INVENTION

1. Field of the Invention

This invention relates to the field of protein kinases and inhibitors thereof. In particular, the invention relates to inhibitors of mammalian target of rapamycin (mTOR) signaling pathways, and methods of their use.

2. Background of the Invention

Phosphatidylinositol 3-kinase (PI3Kα), a dual specificity protein kinase, is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., *Cancer Res* 2004, 64, 7678-7681; Levine et al., *Clin Cancer Res* 2005, 11, 2875-2878; Wang et al., *Hum Mutat* 2005, 25, 322; Lee et al., *Gynecol Oncol* 2005, 97, 26-34), cervical cancer, breast cancer (Bachman, et al. *Cancer Biol Ther* 2004, 3, 772-775; Levine, et al., supra; Li et al., *Breast Cancer Res Treat* 2006, 96, 91-95; Saal et al., *Cancer Res* 2005, 65, 2554-2559; Samuels and Velculescu, *Cell Cycle* 2004, 3, 1221-1224), colorectal cancer (Samuels, et al. *Science* 2004, 304, 554; Velho et al. *Eur J Cancer* 2005, 41, 1649-1654), endometrial cancer (Oda et al. *Cancer Res.* 2005, 65, 10669-10673), gastric carcinomas (Byun et al., *Int J Cancer* 2003, 104, 318-327; Li et al., supra; Velho et al., supra; Lee et al., *Oncogene* 2005, 24, 1477-1480), hepatocellular carcinoma (Lee et al., id.), small and non-small cell lung cancer (Tang et al., *Lung Cancer* 2006, 51, 181-191; Massion et al., *Am J Respir Crit. Care Med* 2004, 170, 1088-1094), thyroid carcinoma (Wu et al., *J Clin Endocrinol Metab* 2005, 90, 4688-4693), acute myelogenous leukemia (AML) (Sujobert et al., *Blood* 1997, 106, 1063-1066), chronic myelogenous leukemia (CML) (Hickey and Cotter *J Biol Chem* 2006, 281, 2441-2450), and glioblastomas (Hartmann et al. *Acta Neuropathol* (Berl) 2005, 109, 639-642; Samuels et al., supra).

The mammalian target, mTOR, is a protein kinase that integrates both extracellular and intracellular signals of cellular growth, proliferation, and survival. Extracellular mitogenic growth factor signaling from cell surface receptors and intracellular pathways that convey hypoxic stress, energy and nutrient status all converge at mTOR. mTOR exists in two distinct complexes: mTOR complex 1 (mTORC1) and mTOR complex 2 (mTORC2). mTORC1 is a key mediator of transcription and cell growth (via its substrates p70S6 kinase and 4E-BP1) and promotes cell survival via the serum and glucocorticoid-activated kinase SGK, whereas mTORC2 promotes activation of the pro-survival kinase AKT. Given its central role in cellular growth, proliferation and survival, it is perhaps not surprising that mTOR signaling is frequently dysregulated in cancer and other diseases (Bjornsti and Houghton *Rev Cancer* 2004, 4(5), 335-48; Houghton and Huang *Microbiol Immunol* 2004, 279, 339-59; Inoki, Corradetti et al. *Nat Genet.* 2005, 37(1), 19-24).

mTOR is a member of the PIKK (PI3K-related Kinase) family of atypical kinases which includes ATM, ATR, and DNAPK, and its catalytic domain is homologous to that of PI3K. Dyregulation of PI3K signaling is a common function of tumor cells. In general, mTOR inhibition may be considered as a strategy in many of the tumor types in which PI3K signaling is implicated such as those discussed below.

Inhibitors of mTOR may be useful in treating a number of cancers, including the following: breast cancer (Nagata, Lan et al., *Cancer Cell* 2004, 6(2), 117-27; Pandolfi N Engl *J Med* 2004, 351(22), 2337-8; Nahta, Yu et al. *Nat Clin Pract Oncol* 2006, 3(5), 269-280); antle cell lymphoma (MCL) (Dal Col, Zancai et al. *Blood* 2008, 111(10), 5142-51); renal cell carcinoma (Thomas, Tran et al. *Nat Med* 2006, 12(1), 122-7; Atkins, Hidalgo et al. *J Clin Oncol* 2004, 22(5), 909-18; Motzer, Hudes et al. *J Clin Oncol* 2007, 25(25), 3958-64); acute myelogenous leukemia (AML) (Sujobert, Bardet et al. *Blood* 2005, 106(3), 1063-6; Billottet, Grandage et al. *Oncogene* 2006, 25(50), 6648-6659; Tamburini, Elie et al. *Blood* 2007, 110(3), 1025-8); chronic myelogenous leukemia (CML) (Skorski, Bellacosa et al. *Embo J* 1997, 16(20), 6151-61; Bai, Ouyang et al. *Blood* 2000, 96(13), 4319-27; Hickey and Cotter *Biol Chem* 2006, 281(5), 2441-50); diffuse large B cell lymphoma (DLBCL) (Uddin, Hussain et al. *Blood* 2006, 108(13), 4178-86); several subtypes of sarcoma (Hernando, Charytonowicz et al. *Nat Med* 2007, 13(6), 748-53; Wan and Helman *Oncologist* 2007, 12(8), 1007-18); rhabdomyosarcoma (Cao, Yu et al. *Cancer Res* 2008, 68(19), 8039-8048; Wan, Shen et al. *Neoplasia* 2006, 8(5), 394-401); ovarian cancer (Shayesteh, Lu et al. *Nat Genet,* 1999, 21(1), 99-102; (Lee, Choi et al. *Gynecol Oncol* 2005, 97(1) 26-34); endometrial tumors (Obata, Morland et al. *Cancer Res* 1998, 58(10), 2095-7; Lu, Wu et al. *Clin Cancer Res* 2008, 14(9), 2543-50); non small cell lung carcinoma (NSCLC) (Tang, He et al. *Lung Cancer* 2006, 51(2), 181-91; Marsit, Zheng et al. *Hum Pathol* 2005, 36(7), 768-76); small cell, squamous, large cell and adenocarcinoma (Massion, Taflan et al. *Am J Respir Crit. Care Med* 2004, 170(10), 1088-94); lung tumors in general (Kokubo, Gemma et al. *Br J Cancer* 2005, 92(9), 1711-9; Pao, Wang et al. *Pub Library of Science Med* 2005, 2(1), e17); colorectal tumors (Velho, Oliveira et al. *Eur J Cancer* 2005, 41(11), 1649-54; Foukas, Claret et al. *Nature,* 2006, 441 (7091), 366-370), particularly those that display microsatellite instability (Goel, Arnold et al. *Cancer Res* 2004, 64(9), 3014-21; Nassif, Lobo et al. *Oncogene* 2004, 23(2), 617-28), KRAS-mutated colorectal tumors (Bos *Cancer Res* 1989. 49(17), 4682-9; Fearon *Ann N Y Acad Sci* 1995, 768, 101-10); gastric carcinomas (Byun, Cho et al. *Int J Cancer* 2003, 104(3), 318-27); hepatocellular tumors (Lee, Soung et al. *Oncogene* 2005, 24(8), 1477-80); liver tumors (Hu, Huang et al. *Cancer* 2003, 97(8), 1929-40; Wan, Jiang et al. *Cancer Res Clin Oncol* 2003, 129(2), 100-6); primary melanomas and associated increased tumor thickness (Guldberg, thor Staten et al. *Cancer Res* 1997, 57(17), 3660-3; Tsao, Zhang et al. *Cancer Res* 2000, 60(7), 1800-4; Whiteman, Zhou et al. *Int J Cancer* 2002, 99(1), 63-7; Goel, Lazar et al. *J Invest Dermatol* 126(1), 2006, 154-60); pancreatic tumors (Asano, Yao et al. *Oncogene* 2004, 23(53), 8571-80); prostate carcinoma (Cairns, Okami et al. *Cancer Res* 1997, 57(22), 4997-5000; Gray, Stewart et al. *Br J Cancer* 1998, 78(10), 1296-300; Wang, Parsons et al. *Clin Cancer Res* 1998, 4(3), 811-5; Whang, Wu et al. *Proc Natl Acad Sci USA* 1998, 95(9), 5246-50; Majumder and Sellers *Oncogene* 2005, 24(50) 7465-74; Wang, Garcia et al. *Proc Natl Acad Sci USA* 2006, 103(5), 1480-5; (Lu, Ren et al. *Int J Oncol* 2006, 28(1), 245-51; Mulholland, Dedhar et al. *Oncogene* 25(3), 2006, 329-37; Xin, Teitell et al. *Proc Natl Acad Sci USA* 12006, 03(20), 7789-94; Mikhailova, Wang et al. *Adv Exp Med Biol* 2008, 617, 397-405; Wang, Mikhailova et al. *Oncogene* 2008, 27(56), 7106-7117); thyroid carcinoma, particularly in the anaplastic subtype (Garcia-Rostan, Costa et al. *Cancer Res* 2005, 65(22), 10199-207); follicular thyroid carcinoma (Wu, Mambo et al. *J Clin Endocrinol Metab* 2005, 90(8), 4688-93); anaplastic large cell lymphoma (ALCL); hamaratomas, angiomyelolipomas, TSC-associated and sporadic lymphangioleiomyomatosis: Cowden's disease (multiple hamaratoma syndrome) (Bissler, McCormack et al. *N Engl J Med* 2008, 358(2), 140-151); sclerosing hemangioma (Randa M. S. Amin *Pathology International* 2008, 58(1), 38-44); Peutz-Jeghers syndrome (PJS); head and neck cancer (Gupta, McKenna et al. *Clin Cancer Res* 2002, 8(3), 885-892); neurofibromatosis (Ferner *Eur J Hum Genet.* 2006, 15(2), 131-138; Sabatini *Nat Rev Cancer* 2006, 6(9), 729-734; Johannessen, Johnson et al. *Current Biology* 2008, 18(1), 56-62); macular degeneration; macular edema; myeloid leukemia; systemic lupus; and autoimmune lymphoproliferative syndrome (ALPS).

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

We recognized the important role of PI3K and mTOR in biological processes and disease states and, therefore, realized that inhibitors of these protein kinases would be desirable. Accordingly, the invention provides compounds that inhibit, regulate, and/or modulate PI3K and/or mTOR that are useful in the treatment of hyperproliferative diseases, such as cancer, in mammals. This invention also provides methods of making the compound, methods of using such compounds in the treatment of hyperproliferative diseases in mammals, especially humans, and to pharmaceutical compositions containing such compounds.

A first aspect of the invention provides a compound of Formula I:

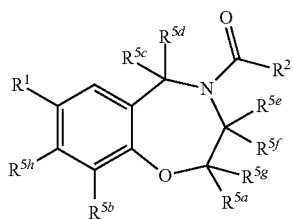

I or a single stereoisomer or mixture of isomers thereof and additionally optionally as a pharmaceutically acceptable salt thereof, where $R^1$ is phenyl optionally substituted with one, two, or three $R^6$ groups; or $R^1$ is heteroaryl optionally substituted with one, two, or three $R^7$;

$R^2$ is —$NR^3R^4$;

$R^3$ is hydrogen, alkyl, or alkoxycarbonylalkyl; and $R^4$ is optionally substituted cycloalkyl, optionally substituted phenyl, optionally substituted phenylalkyl, optionally substituted heteroaryl, or optionally substituted heteroarylalkyl; or $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$;

HET is (a) a saturated or partially unsaturated, but non-aromatic, monocyclic 5- to 8-membered ring optionally containing an additional one or two ring heteroatoms which are independently oxygen, sulfur, or nitrogen where the remaining ring atoms are carbon; or (b) a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; or (c) a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; or (d) a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring;

$R^{5a}$ and $R^{5c}$ are independently hydrogen or alkyl;

$R^{5h}$ is hydrogen or halo;

$R^{5b}$ is hydrogen, amino, or halo;

$R^{5d}$, $R^{5e}$, $R^{5f}$, and $R^{5g}$ are hydrogen;

each $R^6$, when $R^6$ is present, is independently nitro; cyano; halo; alkyl; alkenyl; alkynyl; halo; haloalkyl; —$OR^{8a}$; —$NR^8R^{8a}$; —$C(O)NR^8R^{8a}$; —$NR^8C(O)OR^9$; —$NR^8C(O)R^9$; —$NR^8S(O)_2R^{8a}$; —$NR^8C(O)NR^{8a}R^9$; carboxy, —$C(O)OR^9$; alkylcarbonyl; alkyl substituted with one or two —$C(O)NR^8R^{8a}$; heteroaryl optionally substituted with 1, 2, or 3 $R^{14}$; or optionally substituted heterocycloalkyl;

each $R^7$, when $R^7$ is present, is independently oxo; nitro; cyano; alkyl; alkenyl; alkynyl; halo; haloalkyl; hydroxyalkyl; alkoxyalkyl; —$OR^{8a}$; —$SR^{13}$; —$S(O)R^{13}$; —$S(O)_2R^{13}$; —$NR^8R^{8a}$; $C(O)NR^8R^{8a}$; —$NR^8C(O)OR^9$; —$NR^8C(O)R^9$; —$NR^8S(O)_2R^{8a}$; —$NR^8C(O)NR^{8a}R^9$; carboxy; —$C(O)OR^9$; alkylcarbonyl; —$S(O)_2NR^8R^9$; alkyl substituted with one or two —$NR^8R^{8a}$; alkyl substituted with one or two —$NR^8C(O)R^{8a}$; optionally substituted cycloalkyl; optionally substituted cycloalkylalkyl; optionally substituted heterocycloalkyl; optionally substituted heterocycloalkylalkyl; optionally substituted heteroaryl; or optionally substituted heteroarylalkyl;

$R^8$ is hydrogen, alkyl, alkenyl, alkynyl, hydroxyalkyl, or haloalkyl;

$R^{8a}$ is hydrogen, alkyl, alkenyl, alkynyl, haloalkyl, hydroxyalkyl, cyanoalkyl, aminoalkyl, alkylaminoalkyl, dialkylaminoalkyl, alkoxyalkyl, optionally substituted cycloalkyl, optionally substituted cycloalkylalkyl, optionally substituted heterocycloalkyl, optionally substituted heterocycloalkylalkyl, optionally substituted phenyl, optionally substituted phenylalkyl, optionally substituted heteroaryl, or optionally substituted heteroarylalkyl;

$R^9$ is alkyl, alkenyl, alkynyl, hydroxyalkyl, alkoxyalkyl, haloalkyl, or optionally substituted heterocycloalkylalkyl;

$R^{10}$, $R^{10a}$, $R^{10b}$, $R^{10c}$, $R^{10d}$, $R^{10e}$, and $R^{10f}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or two of $R^{10}$, $R^{10a}$, $R^{10b}$, $R^{10c}$, $R^{10d}$, $R^{10e}$, and $R^{10f}$ when attached to the same carbon form oxo, imino, or thiono;

$R^{11}$ hydrogen, alkyl, or alkenyl;

$R^{11a}$ hydrogen, alkyl, or alkenyl;

$R^{12}$ is alkyl, or optionally substituted heteroaryl;

$R^{13}$ is alkyl or haloalkyl; and each $R^{14}$, when $R^{14}$ is present, is independently amino, alkylamino, dialkylamino, acylamino, halo, hydroxy, alkyl, haloalkyl, hydroxyalkyl, aminoalkyl, alkylaminoalkyl, dialkylaminoalkyl, alkoxycarbonyl, aminocarbonyl, alkylaminocarbonyl, dialkylaminocarbonyl, or optionally substituted phenyl.

In a second aspect, the invention is directed to a pharmaceutical composition which comprises 1) a compound of Formula I or a single stereoisomer or mixture of isomers thereof, optionally as a pharmaceutically acceptable salt thereof and 2) a pharmaceutically acceptable carrier, excipient, or diluent.

In a third aspect of the invention is a method of inhibiting the in vivo activity of PI3K and additionally optionally mTOR, the method comprising administering to a patient an effective PI3K-inhibiting and additionally optionally mTOR-inhibiting amount of a Compound of Formula Ia Compound of Formula I or a single stereoisomer or mixture of stereoisomers thereof, optionally as a pharmaceutically acceptable salt or solvate thereof or pharmaceutical composition thereof.

In a fourth aspect, the Invention provides a method for treating a disease, disorder, or syndrome which method comprises administering to a patient a therapeutically effective amount of a compound of Formula I or a single stereoisomer or mixture of isomers thereof, optionally as a pharmaceutically acceptable salt or solvate thereof, or a pharmaceutical composition comprising a therapeutically effective amount of a compound of Formula I or a single stereoisomer or mixture of isomers thereof, optionally as a pharmaceutically acceptable salt or solvate thereof, and a pharmaceutically acceptable carrier, excipient, or diluent.

In a fifth aspect, the Invention provides a method for making a Compound of Formula I(a) which method comprises (a) reacting the following intermediate, or a salt thereof:

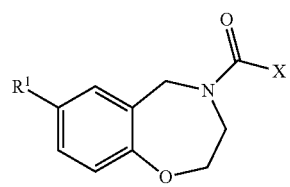

where X is halo and $R^1$ is as defined in the Summary of the Invention for a Compound of Formula I; with an intermediate of formula $R^2H$ where $R^2$ is as defined in the Summary of the Invention for a Compound of Formula I to yield a Compound of the Invention of Formula I(a)

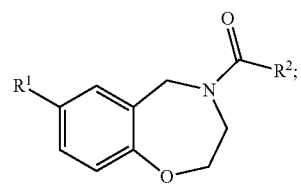

and optionally separating individual isomers; and optionally modifying any of the $R^1$ and $R^2$ groups; and optionally forming a pharmaceutically acceptable salt thereof or (b) reacting the following intermediate, or a salt thereof:

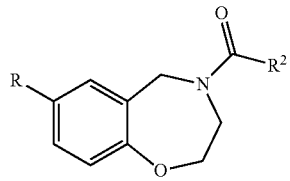

where R is halo or —B(OR')$_2$ (where both R' are hydrogen or the two R' together form a boronic ester), and $R^2$ is as defined in the Summary of the Invention for a Compound of Formula I; with an intermediate of formula $R^1Y$ where Y is halo when R is —B(OR)$_2$ and Y is —B(OR)$_2$ when R is halo, and $R^2$ is as defined in the Summary of the Invention for a Compound of Formula I to yield a Compound of the Invention of Formula I(a); and optionally separating individual isomers; and optionally modifying any of the $R^1$ and $R^2$ groups; and optionally forming a pharmaceutically acceptable salt, hydrate, solvate or combination thereof.

DETAILED DESCRIPTION OF THE INVENTION

Abbreviations and Definitions

The following abbreviations and terms have the indicated meanings throughout:

| Abbreviation | Meaning |
| --- | --- |
| AcOH | acetic acid |
| br | broad |
| ° C. | degrees Celsius |
| conc | concentrated |
| d | doublet |

| Abbreviation | Meaning |
| --- | --- |
| dd | doublet of doublet |
| dt | doublet of triplet |
| DCM | dichloromethane |
| DIEA or DIPEA | N,N-di-isopropyl-N-ethylamine |
| DMA | N,N-dimethylacetamide |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| equiv | equivalents |
| g | gram(s) |
| GC/MS | gas chromatography/mass spectrometry |
| h or hr | hour(s) |
| HATU | 2-(1H-7-azabenzotriazol-1-yl)-1,1,3,3-tetramethyl uronium hexafluorophosphate |
| HPLC | high pressure liquid chromatography |
| L | liter(s) |
| LC/MS | liquid chromatography/mass spectrometry |
| M | molar or molarity |
| m | Multiplet |
| MeOH | methanol |
| mg | milligram(s) |
| MHz | megahertz (frequency) |
| min | minute(s) |
| mL | milliliter(s) |
| μL | microliter(s) |
| μM | micromolar |
| μmol | micromole(s) |
| mM | Millimolar |
| mmol | millimole(s) |
| mol | mole(s) |
| MS | mass spectral analysis |
| Ms | mesyl |
| N | normal or normality |
| nM | Nanomolar |
| NMR | nuclear magnetic resonance spectroscopy |
| q | Quartet |
| quant | quantitative |
| rt | Room temperature |
| s | Singlet |
| t or tr | Triplet |
| THF | tetrahydrofuran |
| Ts | tosyl |

The symbol "—" means a single bond, "=" means a double bond, "≡" means a triple bond, "=====" means a single or double bond. The symbol "⌇" refers to a group on a double-bond as occupying either position on the terminus of a double bond to which the symbol is attached; that is, the geometry, E- or Z—, of the double bond is ambiguous. When a group is depicted removed from its parent Formula, the "⌇" symbol will be used at the end of the bond which was theoretically cleaved in order to separate the group from its parent structural Formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual Formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

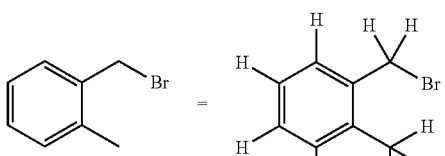

If a group "R" is depicted as "floating" on a ring system, as for example in the Formula:

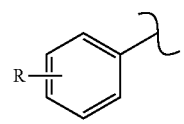

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused or bridged ring system, as for example in the Formula e:

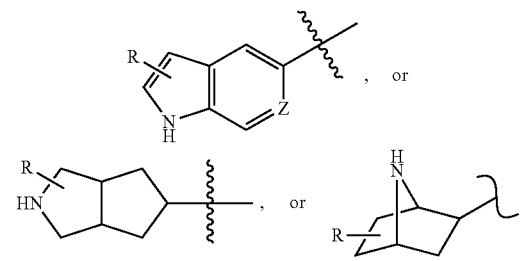

then, unless otherwise defined, a substituent "R" may reside on any atom of the fused or bridged ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "Z" equals =CH—) from one of the ring atoms, so long as a stable structure is formed. In the example depicted, the "R" group may reside on either the 5-membered or the 6-membered ring of the fused or bridged ring system.

When a group "R" is depicted as existing on a ring system containing saturated carbons, as for example in the Formula:

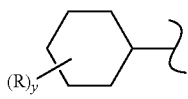

where, in this example, "y" can be more than one, assuming each replaces a currently depicted, implied, or expressly defined hydrogen on the ring; then, unless otherwise defined, where the resulting structure is stable, two "R's" may reside on the same carbon. In another example, two R's on the same carbon, including that carbon, may form a ring, thus creating a spirocyclic ring structure with the depicted ring as for example in the Formula:

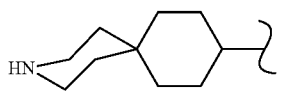

"Acyl" means a —C(O)R radical where R is alkyl, haloalkyl, alkenyl, cycloalkyl, cycloalkylalkyl, aryl, aralkyl, heteroaryl, heteroaralkyl, heterocycloalkyl, or heterocycloalkylalkyl, as defined herein, e.g., acetyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a compound of the invention means introducing the compound of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a means a linear monovalent hydrocarbon radical of two to six carbon atoms or a branched monovalent hydrocarbon radical of three to 6 carbon atoms which radical contains at least one double bond, e.g., ethenyl, propenyl, 1-but-3-enyl, and 1-pent-3-enyl, and the like.

"Alkoxy" means an —OR group where R is alkyl group as defined herein. Examples include methoxy, ethoxy, propoxy, isopropoxy, and the like.

"Alkoxyalkyl" means an alkyl group, as defined herein, substituted with at least one, specifically one, two, or three, alkoxy groups as defined herein. Representative examples include methoxymethyl and the like.

"Alkoxycarbonyl" means a —C(O)R group where R is alkoxy, as defined herein.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a —C(O)R group where R is alkyl, as defined herein.

"Alkylsulfonyl" means an —S(O)$_2$R group where R is alkyl, as defined herein.

"Alkylsulfonylalkyl" means an alkyl group, as defined herein, substituted with at least one, preferably one or two, alkylsulfonyl groups as defined herein.

"Alkynyl" means a linear monovalent hydrocarbon radical of two to six carbon atoms or a branched monovalent hydrocarbon radical of three to 6 carbon atoms which radical contains at least one triple bond, e.g., ethynyl, propynyl, butynyl, pentyn-2-yl and the like.

"Amino" means —NH$_2$.

"Aminoalkyl" means an alkyl group substituted with at least one, specifically one, two or three, amino groups.

"Aminoalkyloxy" means an —OR group where R is aminoalkyl, as defined herein.

"Aminocarbonyl" means a —C(O)NH$_2$ group.

"Alkylaminocarbonyl" means a —C(O)NHR group where R is alkyl as defined herein.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Arylalkyloxy" means an —OR group where R is arylakyl, as defiend herein.

"Cyanoalkyl" means an alkyl group, as defined herein, substituted with one or two cyano groups.

"Cycloalkyl" means a monocyclic or fused or bridged bicyclic or tricyclic, saturated or partially unsaturated (but not aromatic), monovalent hydrocarbon radical of three to ten carbon ring atoms. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, cyclohex-3-enyl, or (1r,3r,5R,7R)-tricyclo[3.3.1.1$^{3,7}$]decan-2-yl, and the like.

"Cycloalkylalkyl" means an alkyl group substituted with at least one, specifically one or two, cycloalkyl group(s) as defined herein.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminoalkyloxy" means an —OR group where R is dialkylaminoalkyl, as defined herein. Representative examples include 2-(N,N-diethylamino)-ethyloxy, and the like.

"Dialkylaminocarbonyl" means a —C(O)NRR' group where R and R' are alkyl as defined herein.

"Halogen" or "halo" refers to fluorine, chlorine, bromine and iodine.

"Haloalkoxy" means an —OR' group where R' is haloalkyl as defined herein, e.g., trifluoromethoxy or 2,2,2-trifluoroethoxy, and the like.

"Haloalkyl" mean an alkyl group substituted with one or more halogens, specifically 1, 2, 3, 4, 5, or 6 halo atoms, e.g., trifluoromethyl, 2-chloroethyl, and 2,2-difluoroethyl, and the like.

"Heteroaryl" means a monocyclic or fused or bridged bicyclic monovalent radical of 5 to 14 ring atoms containing one or more, specifically one, two, three, or four ring heteroatoms where each heteroatom is independently —O—, —S(O)$_n$— (n is 0, 1, or 2), —NH—, —N=, or N-oxide, with the remaining ring atoms being carbon, wherein the ring comprising a monocyclic radical is aromatic and wherein at least one of the fused rings comprising the bicyclic radical is aromatic. One or two ring carbon atoms of any nonaromatic rings comprising a bicyclic radical may be replaced by a —C(O)—, —C(S)—, or —C(=NH)— group. Unless stated otherwise, the valency may be located on any atom of any ring of the heteroaryl group, valency rules permitting. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, 2,3-dihydrobenzofuranyl, benzo[d][1,3]dioxolyl, 2,3-dihydrobenzo[b][1,4]dioxinyl, thiazolyl, isothiazolyl, thiadiazolyl, benzothiazolyl, benzothienyl, and the derivatives thereof, or N-oxide or a protected derivative thereof. The term "5- or 6-membered heteroaryl" describes a subset of the term "heteroaryl."

"Heteroarylalkyl" means an alkyl group, as defined herein, substituted with at least one, specifically one or two heteroaryl group(s), as defined herein.

"Heterocycloalkyl" means a saturated or partially unsaturated (but not aromatic) monovalent monocyclic group of 3 to 8 ring atoms or a saturated or partially unsaturated (but not aromatic) monovalent fused or bridged, bicyclic or tricyclic group of 5 to 12 ring atoms in which one or more, specifically one, two, three, or four ring heteroatoms where each heteroatom is independently O, $S(O)_n$ (n is 0, 1, or 2), —N=, or —NH—, the remaining ring atoms being carbon. One or two ring carbon atoms may be replaced by a —C(O)—, —C(S)—, or —C(=NH)— group. Unless otherwise stated, the valency of the group may be located on any atom of any ring within the radical, valency rules permitting. When the point of valency is located on a nitrogen atom, $R^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydrocyclopenta[c]pyrrolyl, octahydroindolyl, octahydroisoindolyl, decahydroisoquinolyl, tetrahydrofuryl, tetrahydropyranyl, (3aR,6aS)-5-methyloctahydrocyclopenta[c]pyrrolyl, and (3aS,6aR)-5-methyl-1,2,3,3a,4,6a-hexahydrocyclopenta[c]pyrrolyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

"Heterocycloalkyloxy" means an —OR group where R is heterocycloalkyl, as defined herein.

"Hydroxyalkyl" means an alkyl group, as defined herein, substituted with at least one, preferably 1, 2, 3, or 4, hydroxy groups.

"Phenylalkyl" means an alkyl group, as defined herein, substituted with one or two phenyl groups.

"Phenylalkyloxy" means an —OR group where R is phenylalkyl, as defined herein.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise. A list of exemplary optional substitutions is presented below in the definition of "substituted."

"Optionally substituted aryl" means an aryl group, as defined herein, optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy; or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo.

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups independently acyl, acyloxy, acylamino, alkyl, haloalkyl, alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, or cyano. Within the above optional substitutents on "cycloalkyl", the alkyl and alkenyl, either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, or dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo.

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two, or three substituents independently acyl, acylamino, acyloxy, haloalkyl, alkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or phenylalkyl. Within the optional substituents on "heterocycloalkyl", the alkyl and alkenyl, either alone or as part of another group (including, for example, the alkyl in alkoxycarbonyl), are independently optionally substituted with one, two, three, four, or five halo.

"Optionally substituted heterocycloalkylalkyl" means an alkyl group, as defined herein, substituted with at least one, specifically one or two, optionally substituted heterocycloalkyl group(s) as defined herein.

"Optionally substituted phenyl" means a phenyl group optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy, or aryl is pentafluorophenyl. Within the optional substituents on "phenyl", the alkyl and alkenyl, either alone or as part of another group (including, for example, the alkyl in alkoxycarbonyl), are independently optionally substituted with one, two, three, four, or five halo.

"Optionally substituted phenylalkyl" means an alkyl group, as defined herein, substituted with one or two optionally substituted phenyl groups, as defined herein.

"Optionally substituted phenylsulfonyl" means an —S(O)$_2$R group where R is optionally substituted phenyl, as defined herein.

"Oxo" means an oxygen which is attached via a double bond.

"Yield" for each of the reactions described herein is expressed as a percentage of the theoretical yield.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine."Platin(s)," and "platin-containing agent(s)" include, for example, cisplatin, carboplatin, and oxaliplatin.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Preventing" or "prevention" of a disease, disorder, or syndrome includes inhibiting the disease from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

"Treating" or "treatment" of a disease, disorder, or syndrome, as used herein, includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

EMBODIMENTS OF THE INVENTION

The following paragraphs present a number of embodiments of compounds of the invention. In each instance the embodiment includes both the recited compounds, as well as a single stereoisomer or mixture of stereoisomers thereof, as well as a pharmaceutically acceptable salt thereof.

Embodiments (A1)

In another embodiment, the Compound of Formula I is that where $R^{5a}$ is hydrogen or alkyl and $R^{5c}$, $R^{5d}$, $R^{5e}$, $R^{5f}$, and $R^{5g}$ are hydrogen; and all other groups are as defined in the Summary of the Invention for a Compound of Formula I. In another embodiment, the Compound of Formula I is that where $R^{5a}$ is alkyl and $R^{5c}$, $R^{5d}$, $R^{5e}$, $R^{5f}$, and $R^{5g}$ are hydrogen; and all other groups are as defined in the Summary of the Invention for a Compound of Formula I.

Embodiments (A2)

In another embodiment, the Compound of Formula I is that where $R^{5b}$ is hydrogen, amino, or halo and $R^{5a}$, $R^{5c}$, $R^{5d}$, $R^{5e}$, $R^{5f}$, $R^{5g}$, and $R^{5h}$ are hydrogen; and all other groups are as defined in the Summary of the Invention for a Compound of Formula I. In another embodiment, the Compound of Formula I is that where $R^{5b}$ is halo and $R^{5a}$, $R^{5c}$, $R^{5d}$, $R^{5e}$, $R^{5f}$, $R^{5g}$, and $R^{5h}$ are hydrogen; and all other groups are as defined in the Summary of the Invention for a Compound of Formula I. In another embodiment, the Compound of Formula I is that where $R^{5b}$ is fluoro and $R^{5a}$, $R^{5c}$, $R^{5d}$, $R^{5e}$, $R^{5f}$, $R^{5g}$, and $R^{5h}$ are hydrogen; and all other groups are as defined in the Summary of the Invention for a Compound of Formula I. In another embodiment, the Compound of Formula I is that where $R^{5b}$ is amino; $R^{5a}$, $R^{5c}$, $R^{5d}$, $R^{5e}$, $R^{5f}$, $R^{5g}$, and $R^{5h}$ are hydrogen; and all other groups are as defined in the Summary of the Invention for a Compound of Formula I.

Embodiments (A3)

In another embodiment, the Compound of Formula I is that where $R^{5c}$ is hydrogen or alkyl and $R^{5a}$, $R^{5d}$, $R^{5e}$, $R^{5f}$, and $R^{5g}$ are hydrogen; and all other groups are as defined in the Summary of the Invention for a Compound of Formula I. In another embodiment, the Compound of Formula I is that where $R^{5c}$ is alkyl and $R^{5a}$, $R^{5d}$, $R^{5e}$, $R^{5f}$, and $R^{5g}$ are hydrogen; and all other groups are as defined in the Summary of the Invention for a Compound of Formula I.

Embodiments (A4)

In another embodiment, the Compound of Formula I is that where $R^{5h}$ is hydrogen or halo and $R^{5a}$, $R^{5c}$, $R^{5d}$, $R^{5e}$, $R^{5f}$, $R^{5g}$, and $R^{5b}$ are hydrogen; and all other groups are as defined in the Summary of the Invention for a Compound of Formula I. In another embodiment, the Compound of Formula I is that where $R^{5h}$ is halo and $R^{5a}$, $R^{5c}$, $R^{5d}$, $R^{5e}$, $R^{5f}$, $R^{5g}$, and $R^{5b}$ are hydrogen; and all other groups are as defined in the Summary of the Invention for a Compound of Formula I. In another embodiment, the Compound of Formula I is that where $R^{5h}$ is fluoro and $R^{5a}$, $R^{5c}$, $R^{5d}$, $R^{5e}$, $R^{5f}$, $R^{5g}$, and $R^{5b}$ are hydrogen; and all other groups are as defined in the Summary of the Invention for a Compound of Formula I.

Embodiment (B)

Another embodiment of the Invention is directed to a Compound of Formula I(a)

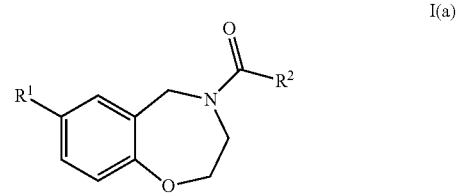

I(a)

where $R^1$, $R^2$, and all other groups are as defined in the Summary of the Invention for a Compound of Formula I.

Embodiment (B1)

In another embodiment, the Compound is according to Formula I(a) where
$R^1$ is phenyl substituted with one or two $R^6$ groups; or
$R^1$ is heteroaryl optionally substituted with one, two, or three $R^7$;
$R^2$ is —$NR^3R^4$;
$R^3$ is hydrogen, alkyl, or alkoxycarbonylalkyl; and $R^4$ is optionally substituted cycloalkyl, optionally substituted phenyl, optionally substituted phenylalkyl, or optionally substituted heteroarylalkyl; or
$R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$;
HET is
  (a) a saturated or partially unsaturated, but non-aromatic, monocyclic 5- to 8-membered ring optionally containing an additional one or two ring heteroatoms which are independently oxygen, sulfur, or nitrogen where the remaining ring atoms are carbon; or
  (b) a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; or
  (c) a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; or
  (d) a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring;
each $R^6$, when $R^6$ is present, is independently nitro, —$NR^8R^{8a}$, —$C(O)NR^8R^{8a}$, —$NR^8C(O)OR^9$, or heteroaryl optionally substituted with 1, 2, or 3 $R^{14}$;

each R$^7$, when present, is independently alkyl, cycloalkyl, halo, —NR$^8$R$^{8a}$, —C(O)NR$^8$R$^{8a}$, —NR$^8$C(O)OR$^9$, —NR$^8$C(O)R$^9$, —NR$^8$S(O)$_2$R$^{8a}$, or —S(O)$_2$NR$^8$R$^9$;
R$^8$ is hydrogen, alkyl, or alkenyl;
R$^{8a}$ is hydrogen, alkyl, haloalkyl, optionally substituted heterocycloalkyl, or optionally substituted phenylalkyl;
R$^9$ is alkyl or haloalkyl; and
R$^{10}$, R$^{10a}$, R$^{10b}$, R$^{10c}$, R$^{10d}$, R$^{10e}$, and R$^{10f}$ are independently hydrogen, halo, alkyl, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; or two of R$^{10}$, R$^{10a}$, R$^{10b}$, R$^{10c}$, R$^{10d}$, R$^{10e}$, and R$^{10f}$ when attached to the same carbon form oxo, imino, or thiono;
R$^{11}$ hydrogen, alkyl, or alkenyl;
R$^{11a}$ hydrogen, alkyl, or alkenyl;
R$^{12}$ is alkyl, or optionally substituted heteroaryl; and
each R$^{14}$, when present, is halo, alkyl, or alkoxycarbonyl.

Embodiment (B1a)

In another embodiment, the Compound is according to Formula I(a) where
R$^1$ is phenyl substituted with one or two R$^6$ groups; or
R$^1$ is heteroaryl optionally substituted with one, two, or three R$^7$;
R$^2$ is —NR$^3$R$^4$;
R$^3$ is hydrogen, alkyl, or alkoxycarbonylalkyl; and R$^4$ is cycloalkyl, phenylalkyl, heteroarylalkyl, phenyl, or phenyl substituted with one or two alkyl; or
R$^3$ and R$^4$ together with the nitrogen to which they are attached form HET optionally substituted on any substitutable atom of the ring with R$^{10}$, R$^{10a}$, R$^{10b}$, R$^{10c}$, R$^{10d}$, R$^{10e}$, and R$^{10f}$;
HET is
(a) a saturated or partially unsaturated, but non-aromatic, monocyclic 5- to 8-membered ring optionally containing an additional one or two ring heteroatoms which are independently oxygen, sulfur, or nitrogen where the remaining ring atoms are carbon; or
(b) a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; or
(c) a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; or
(d) a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring;

each R$^6$, when R$^6$ is present, is independently nitro, —NR$^8$R$^{8a}$, —C(O)NR$^8$R$^{8a}$, —NR$^8$C(O)OR$^9$, or heteroaryl optionally substituted with 1, 2, or 3 R$^{14}$;
each R$^7$, when present, is independently alkyl, cycloalkyl, halo, —NR$^8$R$^{8a}$, —C(O)NR$^8$R$^{8a}$, —NR$^8$C(O)OR$^9$, —NR$^8$C(O)R$^9$, —NR$^8$S(O)$_2$R$^{8a}$, or —S(O)$_2$NR$^8$R$^9$;
R$^8$ is hydrogen, alkyl, or alkenyl;
R$^{8a}$ is hydrogen, alkyl, haloalkyl, heterocycloalkyl, or phenylalkyl;
R$^9$ is alkyl or haloalkyl; and
R$^{10}$, R$^{10a}$, R$^{10b}$, R$^{10c}$, R$^{10d}$, R$^{10e}$, and R$^{10f}$ are independently hydrogen, halo, alkyl, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, cycloalkyl, cycloalkylalkyl, phenyl, phenylalkyl, phenyloxy, phenyloxyalkyl, heterocycloalkyl, heterocycloalkylalkyl, heteroaryl, or heteroarylalkyl where the ring portion of any R$^{10}$, R$^{10a}$, R$^{10b}$, R$^{10c}$, R$^{10d}$, R$^{10e}$, and R$^{10f}$ phenyl, phenylalkyl, phenyloxy, phenyloxyalkyl, heteroaryl, or heteroarylalkyl is optionally substituted with one, two, or three groups which are independently halo, hydroxy, nitro, alkyl, haloalkyl, alkylcarbonyl, alkoxy, amino, alkylamino, dialkylamino, or cycloalkyl; or two of R$^{10}$, R$^{10a}$, R$^{10b}$, R$^{10c}$, R$^{10d}$, R$^{10e}$, and R$^{10f}$ when attached to the same carbon form oxo, imino, or thiono;
R$^{11}$ hydrogen, alkyl, or alkenyl;
R$^{12a}$ hydrogen, alkyl, or alkenyl;
R$^{12}$ is alkyl, or optionally substituted heteroaryl; and
each R$^{14}$, when present, is halo, alkyl, or alkoxycarbonyl.

Embodiment (B2)

In another embodiment, the Compound is according to Formula I(a) where
R$^1$ is as defined in the Summary of the Invention for a Compound of Formula I;
R$^2$ is —NR$^3$R$^4$ where R$^3$ is hydrogen, alkyl, or alkoxycarbonylalkyl; and R$^4$ is optionally substituted cycloalkyl, optionally substituted phenyl, optionally substituted phenylalkyl, or optionally substituted heteroarylalkyl; or
R$^2$ is —NR$^3$R$^4$ where R$^3$ and R$^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with R$^{10}$, R$^{10a}$, and R$^{10b}$; or
R$^2$ is —NR$^3$R$^4$ where R$^3$ and R$^4$ together with the nitrogen to which they are attached form HET according to formula (a):

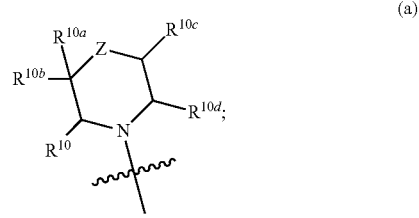

(a)

where Z is a bond, —C(O)—, —O—, —S—, —S(O)—, —S(O)$_2$—, —N(R$^z$)—, —C(R$^{10e}$)(R$^{10f}$)—, or C$_{2-3}$-alkylene; or $R^2$ is —$NR^3R^4$ where $R^3$ and $R^4$ together with the nitrogen to which they are attached form HET according to formula (b):

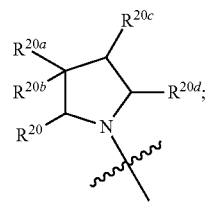

where
(a) $R^{20}$ and $R^{20c}$ or $R^{20}$ and $R^{20d}$ together with the carbons to which they are bonded form a cycloalkyl or hetercyloalkyl such that HET is a bridged bicyclic moiety; or
(b) $R^{20a}$ and $R^{20c}$ together with the carbons to which they are bonded form a cycloalkyl or hetercyloalkyl such that HET is a fused bicyclic moiety; or
(c) $R^{20a}$ and $R^{20b}$ together with the carbon to which they are attached form cycloalkyl or heterocycloalkyl such that HET is a spirocyclic bicyclic moiety;
where the cycloalkyl and heterocycloalkyl are optionally substituted with $R^{10}$ and $R^{10a}$; and the remaining of $R^{20}$, $R^{20a}$, $R^{20b}$, $R^{20c}$, and $R^{20d}$ are hydrogen; or
$R^2$ is —$NR^3R^4$ where $R^3$ and $R^4$ together with the nitrogen to which they are attached form HET according to formula (b):

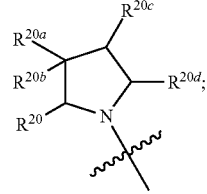

where $R^{20}$ and $R^{20d}$ together with the carbons to which they are bonded form a cycloalkyl or hetercyloalkyl and $R^{20a}$ and $R^{20c}$ together with the carbons to which they are bonded form a cycloalkyl or hetercyloalkyl such that HET is a tricyclic moiety where the cycloalkyl and heterocycloalkyl are optionally substituted with $R^{10}$ and $R^{10a}$; and and $R^{20b}$ is hydrogen; or
$R^2$ is —$NR^3R^4$ where $R^3$ and $R^4$ together with the nitrogen to which they are attached form HET according to formula (c):

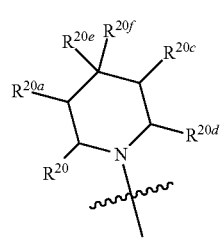

where
(a) $R^{20}$ and $R^{20d}$ or $R^{20}$ and $R^{20e}$ together with the carbons to which they are bonded form a cycloalkyl or hetercyloalkyl such that HET is a bridged bicyclic moiety
(b) $R^{20e}$ and $R^{20f}$ together with the carbons to which they are bonded form cycloalkyl or heterocycloalkyl such that HET is a spirocyclic bicyclic moiety,
(c) $R^{20}$ and $R^{20a}$ or $R^{20a}$ and $R^{20e}$ together with the carbons to which they are bonded form a cycloalkyl or hetercyloalkyl such that HET is a fused bicyclic moiety;
where the cycloalkyl and heterocycloalkyl are optionally substituted with $R^{10}$ and $R^{10a}$; and where the remaining of $R^{20}$, $R^{20a}$, $R^{20b}$, $R^{20c}$, $R^{20d}$, $R^{20e}$, and $R^{20f}$ and $R^{10}$, $R^{10a}$, $R^{10b}$, $R^{10c}$, $R^{10d}$, $R^{10e}$, and $R^{10f}$, respectively; or
$R^2$ is —$NR^3R^4$ where $R^3$ and $R^4$ together with the nitrogen to which they are attached form HET according to formula (d), (e), or (f):

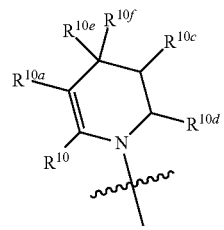

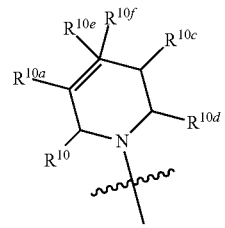

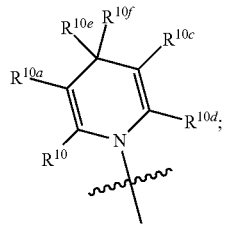

$R^{10}$, $R^{10a}$, $R^{10b}$, $R^{10c}$, $R^{10d}$, $R^{10e}$, and $R^{10f}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)$R^{12}$; —C(O)$NR^{11}R^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or two of $R^{10}$, $R^{10a}$, $R^{10b}$, $R^{10c}$, $R^{10d}$, $R^{10d}$, $R^{10e}$, and $R^{10f}$ when attached to the same carbon form oxo, imino, or thiono;

$R^{11}$ hydrogen, alkyl, or alkenyl;

$R^{11a}$ hydrogen, alkyl, or alkenyl; and $R^{12}$ is alkyl, or optionally substituted heteroaryl.

Embodiment (B2a)

In another embodiment, the Compound is according to Formula I(a) where $R^1$ is phenyl substituted with one or two $R^6$ groups; or $R^1$ is heteroaryl optionally substituted with one, two, or three $R^7$;

$R^2$ is —$NR^3R^4$ where $R^3$ is hydrogen, alkyl, or alkoxycarbonylalkyl; and $R^4$ is optionally substituted cycloalkyl, optionally substituted phenyl, optionally substituted phenylalkyl, or optionally substituted heteroarylalkyl; or $R^2$ is —$NR^3R^4$ where $R^3$ and $R^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with $R^{10}$, $R^{10a}$, and $R^{10b}$; or $R^2$ is —$NR^3R^4$ where $R^3$ and $R^4$ together with the nitrogen to which they are attached form HET according to formula (a):

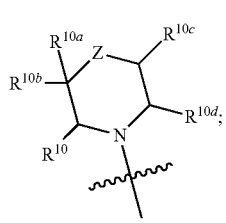

(a)

where Z is a bond, —C(O)—, —O—, —S—, —S(O)—, —S(O)$_2$—, —N(R$^z$)—, —C(R$^{10e}$)(R$^{10f}$)—, or C$_{2-3}$-alkylene; or $R^2$ is —$NR^3R^4$ where $R^3$ and $R^4$ together with the nitrogen to which they are attached form HET according to formula (b):

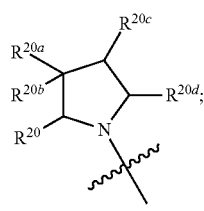

(b)

where (a) $R^{20}$ and $R^{20c}$ or $R^{20}$ and $R^{20d}$ together with the carbons to which they are bonded form a cycloalkyl or hetercyloalkyl such that HET is a bridged bicyclic moiety; or (b) $R^{20a}$ and $R^{20c}$ together with the carbons to which they are bonded form a cycloalkyl or hetercyloalkyl such that HET is a fused bicyclic moiety; or (c) $R^{20a}$ and $R^{20b}$ together with the carbon to which they are attached form cycloalkyl or heterocycloalkyl such that HET is a spirocyclic bicyclic moiety;

where the cycloalkyl and heterocycloalkyl are optionally substituted with $R^{10}$ and $R^{10a}$; and the remaining of $R^{20}$, $R^{20a}$, $R^{20b}$, $R^{20c}$, and $R^{20d}$ are hydrogen; or $R^2$ is —$NR^3R^4$ where $R^3$ and $R^4$ together with the nitrogen to which they are attached form HET according to formula (b):

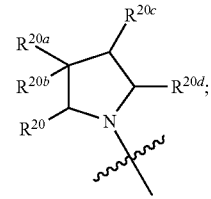

(b)

where $R^{20}$ and $R^{20d}$ together with the carbons to which they are bonded form a cycloalkyl or hetercyloalkyl and $R^{20a}$ and $R^{20c}$ together with the carbons to which they are bonded form a cycloalkyl or hetercyloalkyl such that HET is a tricyclic moiety where the cycloalkyl and heterocycloalkyl are optionally substituted with $R^{10}$ and $R^{10a}$; and and $R^{20b}$ is hydrogen; or $R^2$ is —$NR^3R^4$ where $R^3$ and $R^4$ together with the nitrogen to which they are attached form HET according to formula (c):

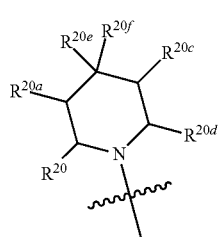

(c)

where (a) $R^{20}$ and $R^{20d}$ or $R^{20}$ and $R^{20c}$ together with the carbons to which they are bonded form a cycloalkyl or hetercyloalkyl such that HET is a bridged bicyclic moiety (b) $R^{20e}$ and $R^{20f}$ together with the carbons to which they are bonded form cycloalkyl or heterocycloalkyl such that HET is a spirocyclic bicyclic moiety, (c) $R^{20}$ and $R^{20a}$ or $R^{20a}$ and $R^{20e}$ together with the carbons to which they are bonded form a cycloalkyl or hetercyloalkyl such that HET is a fused bicyclic moiety;

where the cycloalkyl and heterocycloalkyl are optionally substituted with $R^{10}$ and $R^{10a}$; and the remaining of $R^{20}$, $R^{20a}$, $R^{20c}$, $R^{20d}$, $R^{20e}$, and $R^{20f}$ are $R^{10}$, $R^{10a}$, $R^{10c}$, $R^{10d}$, $R^{10e}$, and $R^{10f}$, respectively; or $R^2$ is —$NR^3R^4$ where $R^3$ and $R^4$ together with the nitrogen to which they are attached form HET according to formula (d), (e), or (f):

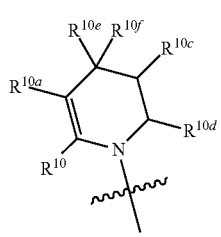

(d)

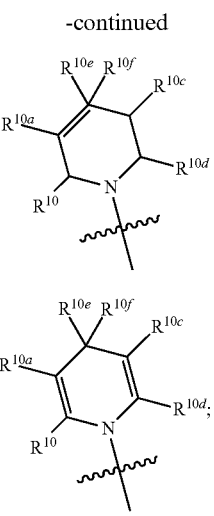

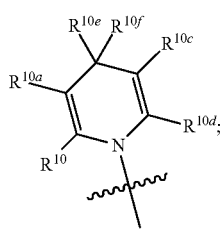

each R⁶, when present, is independently nitro, —NR⁸R⁸ᵃ, —C(O)NR⁸R⁸ᵃ, —NR⁸C(O)OR⁹, or heteroaryl optionally substituted with 1, 2, or 3 R¹⁴;

each R⁷, when present, is independently alkyl, cycloalkyl, —NR⁸R⁸ᵃ, —C(O)NR⁸R⁸ᵃ, —NR⁸C(O)OR⁹, or —NR⁸C(O)R⁹;

R⁸ is hydrogen, alkyl, or alkenyl;

R⁸ᵃ is hydrogen, alkyl, haloalkyl, optionally substituted heterocycloalkyl, or optionally substituted phenylalkyl;

R⁹ is alkyl or haloalkyl; and

R¹⁰, R¹⁰ᵃ, R¹⁰ᵇ, R¹⁰ᶜ, R¹⁰ᵈ, R¹⁰ᵉ, and R¹⁰ᶠ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R¹², —C(O)NR¹¹R¹¹ᵃ, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; or R¹⁰ᵃ and R¹⁰ᵇ together form oxo; or R¹⁰ᵉ and R¹⁰ᶠ together form oxo;

Rᶻ is hydrogen, alkyl, haloalkyl, haloalkenyl, hydroxyalkyl, alkylsulfonyl, hydroxy, alkoxy, alkoxycarbonyl, —C(O)R¹², —C(O)NR¹¹R¹¹ᵃ, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl;

R¹¹ hydrogen, alkyl, or alkenyl;

R¹¹ᵃ hydrogen, alkyl, or alkenyl;

R¹² is alkyl, or optionally substituted heteroaryl; and each R¹⁴, when present, is halo, alkyl, or alkoxycarbonyl.

Embodiment (B3)

In another embodiment, the Compound is according to Formula I(a) where

R¹ is phenyl substituted with one or two R⁶ groups; or

R¹ is heteroaryl optionally substituted with one, two, or three R⁷;

R² is —NR³R⁴ where R³ is hydrogen, alkyl, or alkoxycarbonylalkyl; and R⁴ is optionally substituted cycloalkyl, optionally substituted phenyl, optionally substituted phenylalkyl, or optionally substituted heteroarylalkyl; or R² is —NR³R⁴ and R³ and R⁴ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with R¹⁰, R¹⁰ᵃ, and R¹⁰ᵇ; or R² is —NR³R⁴ where R³ and R⁴ together with the nitrogen to which they are attached form HET according to formula (a):

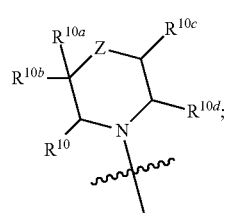

where Z is a bond, —C(O)—, —O—, —S—, —S(O)—, —S(O)₂—, —N(Rᶻ)—, —C(R¹⁰ᵉ)(R¹⁰ᶠ)—, or C₂₋₃-alkylene; Rᶻ is hydrogen, alkyl, haloalkyl, haloalkenyl, hydroxyalkyl, alkylsulfonyl, hydroxy, alkoxy, alkoxycarbonyl, —C(O)R¹², —C(O)NR¹¹R¹¹ᵃ, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl; and R¹⁰, R¹⁰ᵃ, R¹⁰ᵇ, R¹⁰ᶜ and R¹⁰ᵈ are independently hydrogen, alkyl, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R¹², —C(O)NR¹¹R¹¹ᵃ, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; or R¹⁰ᵃ and R¹⁰ᵇ together form oxo; or R¹⁰ᵉ and R¹⁰ᶠ together form oxo; or R² is —NR³R⁴ where R³ and R⁴ together with the nitrogen to which they are attached form HET according to formula (b):

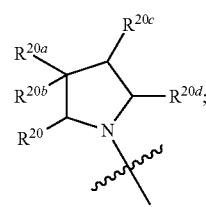

where (a) R²⁰ and R²⁰ᶜ or R²⁰ and R²⁰ᵈ together with the carbons to which they are bonded form a cycloalkyl or hetercycloalkyl such that HET is a bridged bicyclic moiety; or (b) R²⁰ᵃ and R²⁰ᶜ together with the carbons to which they are bonded form a cycloalkyl or heterocyloalkyl such that HET is a fused bicyclic moiety; or (c) $R^{20a}$ and $R^{20b}$ together with the carbon to which they are attached form cycloalkyl or heterocycloalkyl such that HET is a spirocyclic bicyclic moiety;

where the cycloalkyl and heterocycloalkyl are optionally substituted with $R^{10}$ and $R^{10a}$ where $R^{10}$ and $R^{10a}$ are independently hydroxy, alkyl, haloalkyl, or optionally substituted phenyl; and the remaining of $R^{20}$, $R^{20a}$, $R^{20b}$, $R^{20c}$, and $R^{20d}$ are hydrogen; or $R^2$ is —$NR^3R^4$ where $R^3$ and $R^4$ together with the nitrogen to which they are attached form HET according to formula (b):

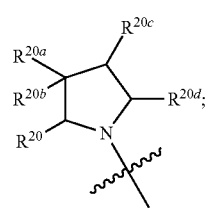
(b)

where $R^{20}$ and $R^{20d}$ together with the carbons to which they are bonded form a cycloalkyl or hetercyloalkyl and $R^{20a}$ and $R^{20c}$ together with the carbons to which they are bonded form a cycloalkyl or hetercyloalkyl such that HET is a tricyclic moiety, and where the cycloalkyl and heterocycloalkyl are optionally substituted with $R^{10}$ and $R^{10a}$; and $R^{20b}$ is hydrogen; or $R^2$ is —$NR^3R^4$ where $R^3$ and $R^4$ together with the nitrogen to which they are attached form HET according to formula (c):

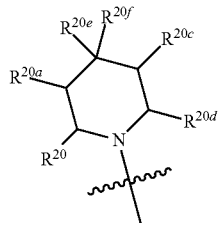
(c)

where (d) $R^{20}$ and $R^{20d}$ or $R^{20}$ and $R^{20c}$ together with the carbons to which they are bonded form a cycloalkyl or hetercyloalkyl such that HET is a bridged bicyclic moiety (e) $R^{20e}$ and $R^{20f}$ together with the carbons to which they are bonded form cycloalkyl or heterocycloalkyl such that HET is a spirocyclic bicyclic moiety, (f) $R^{20}$ and $R^{20a}$ or $R^{20a}$ and $R^{20e}$ together with the carbons to which they are bonded form a cycloalkyl or hetercyloalkyl such that HET is a fused bicyclic moiety;

where the cycloalkyl is optionally substituted with $R^{10}$ and $R^{10a}$ where $R^{10}$ and $R^{10a}$ are independently alkyl or together form oxo; and the remaining of $R^{20}$, $R^{20a}$, $R^{20c}$, $R^{20d}$, $R^{20e}$, and $R^{20f}$ are $R^{10}$, $R^{10a}$, $R^{10c}$, $R^{10d}$, $R^{10e}$, and $R^{10f}$, respectively, and the $R^{10}$, $R^{10a}$, $R^{10c}$, $R^{10d}$, $R^{10e}$, and $R^{10f}$ are independently hydrogen, hydroxy, alkyl, halo, haloalkyl, hydroxyalkyl, optionally substituted phenyl, or amino, or $R^{10e}$ and $R^{10f}$ together form oxo; or $R^2$ is —$NR^3R^4$ where $R^3$ and $R^4$ together with the nitrogen to which they are attached form HET according to formula (d), (e), or (f):

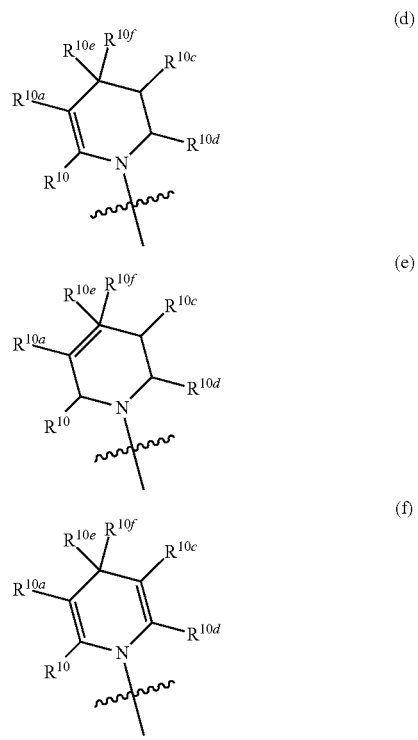

where $R^{10}$, $R^{10a}$, $R^{10b}$, $R^{10c}$, $R^{10d}$, $R^{10e}$, and $R^{10f}$ are independently hydrogen, hydroxy, alkyl, haloalkyl, or optionally substituted phenyl; or, in formula (d) and (f), $R^{10e}$ and $R^{10f}$ together form oxo;

each $R^6$, when present, is independently nitro, —$NR^8R^{8a}$, —$C(O)NR^8R^{8a}$, —$NR^8C(O)OR^9$, or heteroaryl optionally substituted with 1, 2, or 3 $R^{14}$;

each $R^7$, when present, is independently alkyl, cycloalkyl, —$NR^8R^{8a}$, —$C(O)NR^8R^{8a}$, —$NR^8C(O)OR^9$, or —$NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and $R^{11}$ hydrogen, alkyl, or alkenyl;

$R^{11a}$ hydrogen, alkyl, or alkenyl;

$R^{12}$ is alkyl, or optionally substituted heteroaryl; and each $R^{14}$, when present, is halo, alkyl, or alkoxycarbonyl.

Embodiments (C)

In another embodiment, the Compound is according to Formula I(a) where $R^1$ is heteroaryl optionally substituted with one, two, or three $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is heteroaryl optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is heteroaryl substituted with one or two $R^7$; and $R^2$, $R^7$ and all other groups are as defined in the Summary of the Invention for a Compound of Formula I or as defined in any one of embodiments B, B1, B1a, B2, B2a, and B3.

Embodiments (C1)

In another embodiment, the Compound is according to Formula I(a) where $R^1$ is a 9-membered heteroaryl optionally substituted with one, two, or three $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is a 9-membered heteroaryl optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is a 9-membered heteroaryl substituted with one or two $R^7$; and $R^2$, $R^7$ and all other groups are as defined in the Summary of the Invention for a Compound of Formula I or as defined in any one of embodiments B, B1, B1a, B2, B2a, and B3.

Embodiments (C2)

In another embodiment, the Compound is according to Formula I(a) where $R^1$ is benzimidazolyl, 1H-imidazo[4,5-b]pyridinyl, 3H-imidazo[4,5-b]pyridinyl, thiazolo[4,5-b]pyridinyl, or thiazolo[5,4-b]pyridinyl where $R^1$ is optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is benzimidazolyl, 1H-imidazo[4,5-b]pyridinyl, 3H-imidazo[4,5-b]pyridinyl, thiazolo[4,5-b]pyridinyl, or thiazolo[5,4-b]pyridinyl where $R^1$ is optionally substituted with one or two $R^7$; each $R^7$, when present, is alkyl, haloalkyl, cycloalkyl, —$NR^8R^{8a}$, or —$NR^8C(O)OR^9$; and $R^8$, $R^{8a}$, $R^9$, $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is benzimidazolyl, 1H-imidazo[4,5-b]pyridinyl, 3H-imidazo[4,5-b]pyridinyl, thiazolo[4,5-b]pyridinyl, or thiazolo[5,4-b]pyridinyl where $R^1$ is optionally substituted with one or two $R^7$; each $R^7$, when present, is alkyl, haloalkyl, cycloalkyl, —$NR^8R^{8a}$, or —$NR^8C(O)OR^9$; $R^8$ is hydrogen; $R^{8a}$ is hydrogen, alkyl, or haloalkyl; $R^9$ is alkyl; and $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is benzimidazolyl, 1H-imidazo[4,5-b]pyridinyl, 3H-imidazo[4,5-b]pyridinyl, thiazolo[4,5-b]pyridinyl, or thiazolo[5,4-b]pyridinyl where $R^1$ is optionally substituted with one or two $R^7$; each $R^7$, when present, is alkyl, haloalkyl, cycloalkyl, —$NR^8R^{8a}$, or —$NR^8C(O)OR^9$; $R^8$ is hydrogen; $R^{8a}$ is hydrogen, $C_{1-3}$-alkyl, or haloalkyl; $R^9$ is $C_{1-3}$-alkyl; and $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is benzimidazol-6-yl, 2-methyl-benzimidazol-6-yl, 2-cyclopropyl-benzimidazol-6-yl, 2-trifluoromethyl-benzimidazol-6-yl, 2-amino-benzimidazol-6-yl, 2-(2,2,2-trifluoroethylamino)-benzimidazol-6-yl, 2-(2-monofluoroethylamino)-benzimidazol-6-yl, 2-(2,2-difluoroethylamino)-benzimidazol-6-yl, 2-(methoxycarbonylamino)-benzimidazol-6-yl, imidazo[4,5-b]pyridin-6-yl, 2-methyl-imidazo[4,5-b]pyridin-6-yl, 2-amino-imidazo[4,5-b]pyridin-6-yl, 2-cyclopropyl-imidazo[4,5-b]pyridin-6-yl, or 2-trifluoromethyl-imidazo[4,5-b]pyridin-6-yl; and $R^2$ and all other groups are as defined in the Summary of the Invention for a Compound of Formula I or as defined in any one of embodiments B, B1, B1a, B2, B2a, and B3.

Embodiments (C3)

In another embodiment, the Compound is according to Formula I(b)

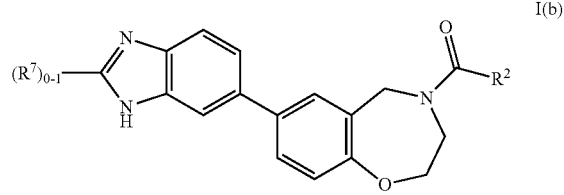

where $R^2$ and $R^7$, when present, are as defined in the Summary of the Invention for a Compound of Formula I or as defined in any one of embodiments B, B1, B1a, B2, B2a, and B3. In another embodiment, the Compound is according to Formula I(b) where $R^7$, when present, is alkyl, haloalkyl, cycloalkyl, —$NR^8R^{8a}$, or —$NR^8C(O)OR^9$; $R^2$, $R^8$, $R^{8a}$, $R^9$, and all other groups are as defined in the Summary of the Invention for a Compound of Formula I or as defined in any one of embodiments B, B1, B1a, B2, B2a, and B3. In another embodiment, the Compound is according to Formula I(b) where $R^7$, when present, is alkyl, haloalkyl, cycloalkyl, —$NR^8R^{8a}$, or —$NR^8C(O)OR^9$; $R^8$ is hydrogen; $R^{8a}$ is hydrogen, alkyl, or haloalkyl; $R^9$ is alkyl; and $R^2$ is as defined in the Summary of the Invention for a Compound of Formula I or as defined in any one of embodiments B, B1, B1a, B2, B2a, and B3. In another embodiment, the Compound is according to Formula I(b) where $R^7$, when present, is $C_{1-3}$-alkyl, haloalkyl, cycloalkyl, —$NR^8R^{8a}$, or —$NR^8C(O)OR^9$; $R^8$ is hydrogen; $R^{8a}$ is hydrogen, $C_{1-3}$-alkyl, or haloalkyl; $R^9$ is $C_{1-3}$-alkyl; and $R^2$ is as defined in the Summary of the Invention for a Compound of Formula I or as defined in any one of embodiments B, B1, B1a, B2, B2a, and B3.

Embodiments (C4)

In another embodiment, the Compound is according to Formula I(c1) or I(c2)

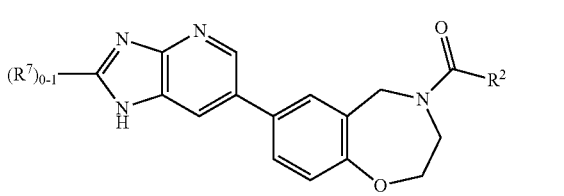

-continued

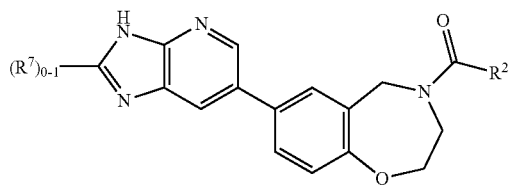

I(c2)

where $R^2$ and $R^7$ are as defined in the Summary of the Invention for a Compound of Formula I or as defined in any one of embodiments B, B1, B1a, B2, B2a, and B3. In another embodiment, the Compound is according to Formula I(c1) or I(c2) where $R^7$, when present, is alkyl, haloalkyl, cycloalkyl, —$NR^8R^{8a}$, or —$NR^8C(O)OR^9$; $R^2$, $R^8$, $R^{8a}$, $R^9$, and all other groups are as defined in the Summary of the Invention for a Compound of Formula I or as defined in any one of embodiments B, B1, B1a, B2, B2a, and B3. In another embodiment, the Compound is according to Formula I(c1) or I(c2) where $R^7$, when present, is alkyl, haloalkyl, cycloalkyl, —$NR^8R^{8a}$, or —$NR^8C(O)OR^9$; $R^8$ is hydrogen; $R^{8a}$ is hydrogen, alkyl, or haloalkyl; $R^9$ is alkyl; and $R^2$ is as defined in the Summary of the Invention for a Compound of Formula I or as defined in any one of embodiments B, B1, B1a, B2, B2a, and B3. In another embodiment, the Compound is according to Formula I(c1) or I(c2) where $R^7$, when present, is $C_{1-3}$-alkyl, haloalkyl, cycloalkyl, —$NR^8R^{8a}$, or —$NR^8C(O)OR^9$; $R^8$ is hydrogen; $R^{8a}$ is hydrogen, $C_{1-3}$-alkyl, or haloalkyl; $R^9$ is $C_{1-3}$-alkyl; and $R^2$ is as defined in the Summary of the Invention for a Compound of Formula I or as defined in any one of embodiments B, B1, B1a, B2, B2a, and B3.

Embodiments (C5)

In another embodiment, the Compound is according to Formula I(d1) or I(d2)

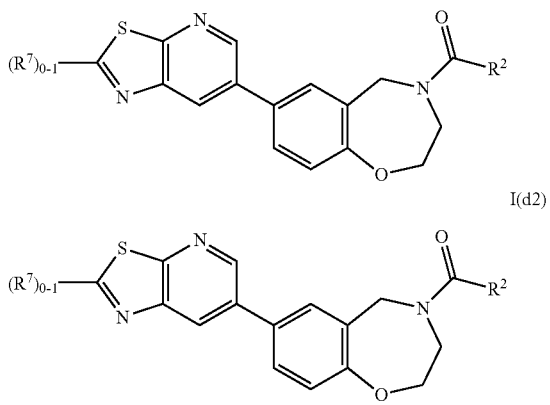

I(d1)

I(d2)

where $R^2$ and $R^7$ are as defined in the Summary of the Invention for a Compound of Formula I or as defined in any one of embodiments B, B1, B1a, B2, B2a, and B3. In another embodiment, the Compound is according to Formula I(d1) or I(d2) where $R^7$, when present, is alkyl, haloalkyl, cycloalkyl, —$NR^8R^{8a}$, or —$NR^8C(O)OR^9$; $R^2$, $R^8$, $R^{8a}$, $R^9$, K and all other groups are as defined in the Summary of the Invention for a Compound of Formula I or as defined in any one of embodiments B, B1, B1a, B2, B2a, and B3. In another embodiment, the Compound is according to Formula I(d1) or I(d2) where $R^7$, when present, is alkyl, haloalkyl, cycloalkyl, —$NR^8R^{8a}$, or —$NR^8C(O)OR^9$; $R^8$ is hydrogen; $R^{8a}$ is hydrogen, alkyl, or haloalkyl; $R^9$ is alkyl; and $R^2$ is as defined in the Summary of the Invention for a Compound of Formula I or as defined in any one of embodiments B, B1, B1a, B2, and B3. In another embodiment, the Compound is according to Formula I(d1) or I(d2) where $R^7$, when present, is $C_{1-3}$-alkyl, haloalkyl, cycloalkyl, —$NR^8R^{8a}$, or —$NR^8C(O)OR^9$; $R^8$ is hydrogen; $R^{8a}$ is hydrogen, $C_{1-3}$-alkyl, or haloalkyl; $R^9$ is $C_{1-3}$-alkyl; and $R^2$ is as defined in the Summary of the Invention for a Compound of Formula I or as defined in any one of embodiments B, B1, B1a, B2, B2a, and B3.

Embodiments (C6)

In another embodiment, the Compound is according to Formula I(a) where $R^1$ is a 6-membered heteroaryl optionally substituted with one, two, or three $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is a 6-membered heteroaryl optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is a 6-membered heteroaryl substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazinyl, pyridazinyl, pyridinyl, or pyrimidinyl where $R^1$ is optionally substituted with one or two $R^7$; and $R^2$, $R^7$, and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazinyl, pyridazinyl, pyridinyl, or pyrimidinyl where $R^1$ is substituted with one or two $R^7$; and $R^2$, $R^7$, and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazinyl, pyridazinyl, pyridinyl, or pyrimidinyl where $R^1$ is optionally substituted with one or two $R^7$; $R^7$ is halo, optionally substituted heteroaryl, —$NR^8S(O)_2R^{8a}$, —$S(O)_2NR^8R^9$, —$C(O)NR^8R^{8a}$, or —$NR^8R^{8a}$; $R^2$, $R^8$, $R^{8a}$, and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazinyl, pyridazinyl, pyridinyl, or pyrimidinyl where $R^1$ is optionally substituted with one or two $R^7$; $R^7$ is halo, optionally substituted heteroaryl, —$NR^8S(O)_2R^{8a}$, —$S(O)_2NR^8R^9$, —$C(O)NR^8R^{8a}$, or —$NR^8R^{8a}$; each $R^8$ is hydrogen; each $R^{8a}$ is independently hydrogen or alkyl; $R^9$ is hydrogen or alkyl; $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazinyl, pyridazinyl, pyridinyl, or pyrimidinyl where $R^1$ is optionally substituted with one or two $R^7$; $R^7$ is optionally substituted heteroaryl, —$C(O)NR^8R^{8a}$ or —$NR^8R^{8a}$; $R^2$, $R^8$, $R^{8a}$, and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazinyl, pyridazinyl, pyridinyl, or pyrimidinyl where $R^1$ is optionally substituted with one or two $R^7$; $R^7$ is optionally substituted heteroaryl, —C(O)$NR^8R^{8a}$ or —$NR^8R^{8a}$; $R^8$ is hydrogen; and $R^{8a}$ is hydrogen or alkyl; and $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazin-2-yl, 5-amino-pyrazin-2-yl, pyridazin-3-yl, pyridazin-4-yl, pyridazin-5-yl, pyridazin-6-yl, 6-amino-pyridazin-3-yl, pyrimidin-2-yl, pyrimidin-4-yl, pyrimidin-5-yl, pyrimidin-6-yl, 2-amino-pyrimidin-5-yl, pyridin-2-yl, pyridin-3-yl, pyridin-4-yl, pyridin-5-yl, pyridin-6-yl, 5-methylaminocarbonyl-pyridin-2-yl, 4-methylaminocarbonyl-pyridin-3-yl, or 4-(imidazol-2-yl)-pyridin-3-yl; and $R^2$ is as defined in the Summary of the Invention for a Compound of Formula I or as defined in any one of embodiments B, B1, B1a, B2, B2a, and B3.

Embodiments (C6a)

In another embodiment, the Compound is according to Formula I(a) where $R^1$ is pyridin-3-yl optionally substituted with one, two, or three $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyridin-3-yl optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyridin-3-yl where $R^1$ is optionally substituted with one or two $R^7$; $R^7$ is halo, alkoxy, —$NR^8S(O)_2R^{8a}$, —$S(O)_2NR^8R^9$, —C(O)$NR^8R^{8a}$, or —$NR^8R^{8a}$; $R^2$, $R^8$, $R^{8a}$, and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyridin-3-yl where $R^1$ is optionally substituted with one or two $R^7$; $R^7$ is halo, alkoxy, —$NR^8S(O)_2R^{8a}$, —$S(O)_2NR^8R^9$, —C(O)$NR^8R^{8a}$, or —$NR^8R^{8a}$; each $R^8$ is hydrogen; each $R^{8a}$ is independently hydrogen or alkyl; $R^9$ is hydrogen or alkyl; $R^2$ and all other groups are as defined in the Summary of the Invention for a Compound of Formula I or as defined in any one of embodiments B, B1, B1a, B2, B2a, and B3.

Embodiments (C7)

In another embodiment, the Compound is according to Formula I(a) where $R^1$ is a 5-membered heteroaryl optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is a 5-membered heteroaryl substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazolyl or thiazolyl, where $R^1$ is optionally substituted with one or two $R^7$; and $R^2$, $R^7$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazolyl or thiazolyl, where $R^1$ is optionally substituted with one or two $R^7$; each $R^7$, when present, is alkyl, —$NR^8$, $R^{8a}$, or —$NR^8C(O)R^9$; and $R^2$, $R^8$, $R^{8a}$, $R^9$, and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazolyl or thiazolyl, where $R^1$ is optionally substituted with one or two $R^7$; each $R^7$, when present, is alkyl, —$NR^8R^{8a}$, or —$NR^8C(O)R^9$; $R^8$ is hydrogen; $R^{8a}$ is hydrogen, alkyl, or benzyl; $R^9$ is alkyl; and $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazolyl or thiazolyl, where $R^1$ is optionally substituted with one or two $R^7$; each $R^7$, when present, is $C_{1-3}$-alkyl, —$NR^8R^{8a}$, or —$NR^8C(O)R^9$; $R^8$ is hydrogen; $R^{8a}$ is hydrogen, $C_{1-3}$-alkyl, or benzyl; $R^9$ is $C_{1-3}$-alkyl; and $R^2$ and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is pyrazol-1-yl, pyrazol-3-yl, pyrazol-4-yl, pyrazol-5-yl, 5-phenylmethylamino-pyrazol-3-yl, 5-amino-pyrazol-3-yl, thiazol-2-yl, thiazol-4-yl, thiazol-5-yl, 2-methylcarbonylamino-thiazol-5-yl, or 2-amino-thiazol-5-yl; and $R^2$ and all other groups are as defined in the Summary of the Invention for a Compound of Formula I or as defined in any one of embodiments B, B1, B1a, B2, B2a, and B3.

Embodiments (C8)

In another embodiment, the Compound is according to Formula I(a) where $R^1$ is phenyl substituted with one, two, or three $R^6$ groups; each $R^6$ is independently nitro; cyano; halo; alkyl; alkenyl; alkynyl; halo; haloalkyl; —$OR^{8a}$; —$NR^8R^{8a}$; —C(O)$NR^8R^{8a}$; —$NR^8C(O)OR^9$; —$NR^8C(O)R^9$; —$NR^8S(O)_2R^{8a}$; —$NR^8C(O)NR^{8a}R^9$; carboxy, —C(O)$OR^9$; alkylcarbonyl; alkyl substituted with one or two —C(O)$NR^8R^{8a}$; heteroaryl optionally substituted with 1, 2, or 3 $R^{14}$; or optionally substituted heterocycloalkyl; and all other groups are as defined in the Summary of the Invention for a Compound of Formula I or as defined in any one of embodiments B, B1, B1a, B2, B2a, and B3. In another embodiment, the Compound is according to Formula I(a) where $R^1$ is phenyl substituted with one or two $R^6$ groups; each $R^6$ is independently nitro; cyano; halo; alkyl; alkenyl; alkynyl; halo; haloalkyl; —$OR^{8a}$; —$NR^8R^{8a}$; —C(O)$NR^8R^{8a}$; —$NR^8C(O)OR^9$; —$NR^8C(O)R^9$; —$NR^8S(O)_2R^{8a}$; —$NR^8C(O)NR^{8a}R^9$; carboxy, —C(O)$OR^9$; alkylcarbonyl; alkyl substituted with one or two —C(O)$NR^8R^{8a}$; heteroaryl optionally substituted with 1, 2, or 3 $R^{14}$; or optionally substituted heterocycloalkyl; and all other groups are as defined in the Summary of the Invention for a Compound of Formula I or as defined in any one of embodiments B, B1, B1a, B2, B2a, and B3.

Embodiments (C8a)

In another embodiment, the Compound is according to Formula I(a) where $R^1$ is phenyl substituted with one or two $R^6$ groups; each $R^6$ is independently —$OR^{8a}$; —$NR^8R^{8a}$;

—C(O)NR$^8$R$^{8a}$; or heteroaryl optionally substituted with 1, 2, or 3 R$^{14}$; and all other groups are as defined in the Summary of the Invention for a Compound of Formula I or as defined in any one of embodiments B, B1, B1a, B2, B2a, and B3. In another embodiment, the Compound is according to Formula I(a) where R$^1$ is phenyl substituted with one or two R$^6$ groups; each R$^6$ is independently —OR$^{8a}$; —NR$^8$R$^{8a}$; —C(O)NR$^8$R$^{8a}$; or heteroaryl optionally substituted with 1, 2, or 3 R$^{14}$; R$^8$ is hydrogen or alkyl; R$^{8a}$ is hydrogen, alkyl, haloalkyl, or optionally substituted heterocycloalkyl; R$^{14}$, when present, is halo; and all other groups are as defined in the Summary of the Invention for a Compound of Formula I or as defined in any one of embodiments B, B1, B1a, B2, B2a, and B3. In another embodiment, the Compound is according to Formula I(a) where R$^1$ is phenyl substituted with one or two R$^6$ groups; each R$^6$ is independently 2,2-difluoroethylaminocarbonyl, N-pyrrolidin-1-ylaminocarbonyl, N-pyrrolidin-2-ylaminocarbonyl, N-pyrrolidin-3-ylaminocarbonyl, imidazol-2-yl, imidazol-4-yl, imidazol-5-yl, pyrazol-1-yl, pyrazol-3-yl, pyrazol-4-yl, pyrazol-5-yl, benzimidazol-2-yl, 5-fluoro-benzimidazol-2-yl, or benzimidazol-6-yl; and all other groups are as defined in the Summary of the Invention for a Compound of Formula I or as defined in any one of embodiments B, B1, B1a, B2, B2a, and B3.

Embodiments (D)

In another embodiment, the Compound is according to Formula I(a) where R$^2$ is —NR$^3$R$^4$ and R$^3$ is hydrogen, alkyl, or alkoxycarbonylalkyl; and R$^4$ is optionally substituted cycloalkyl, optionally substituted phenyl, optionally substituted phenylalkyl, or optionally substituted heteroarylalkyl; and R$^1$ all other groups are as defined in the Summary of the Invention for a Compound of Formula I or as defined in any one of embodiments B, B1, B1a, B2, B2a, B3, (C)—C(8), and (C8a).

Embodiments (D1)

In another embodiment, the Compound is according to Formula I(a) where R$^2$ is —NR$^3$R$^4$ and R$^3$ is alkoxycarbonylalkyl; R$^4$ is optionally substituted phenylalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is alkoxycarbonylalkyl; R$^4$ is phenylalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is ethoxycarbonylmethyl; R$^4$ is benzyl; and R$^1$ and all other groups are as defined in the Summary of the Invention for a Compound of Formula I or as defined in any one of embodiments B, B1, B1a, B2, B2a, B3, (C)-C(8), and (C8a).

Embodiments (D2)

In another embodiment, the Compound is according to Formula I(a) where R$^2$ is —NR$^3$R$^4$ and R$^3$ is hydrogen; and R$^4$ is optionally substituted phenyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is hydrogen; and R$^4$ is phenyl optionally substituted with alkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is hydrogen; and R$^4$ is phenyl or 4-n-pentyl-phenyl; and R$^1$ and all other groups are as defined in the Summary of the Invention for a Compound of Formula I or as defined in any one of embodiments B, B1, B1a, B2, B2a, B3, (C)-C(8), and (C8a).

Embodiments (D3)

In another embodiment, the Compound is according to Formula I(a) where R$^2$ is —NR$^3$R$^4$ and R$^3$ is alkyl; and R$^4$ is optionally substituted phenylalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is alkyl; and R$^4$ is phenylalkyl optionally substituted with alkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is methyl, ethyl, n-propyl, isopropyl, or n-butyl; and R$^4$ is 1-phenylethyl, 2-phenylethyl, phenylmethyl, 3-methyl-phenylmethyl; and R$^1$ and all other groups are as defined in the Summary of the Invention for a Compound of Formula I or as defined in any one of embodiments B, B1, B1a, B2, B2a, B3, (C)-C(8), and (C8a).

Embodiments (D4)

In another embodiment, the Compound is according to Formula I(a) where R$^2$ is —NR$^3$R$^4$ and R$^3$ is alkyl; and R$^4$ is optionally substituted heteroarylalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is alkyl; and R$^4$ is heteroarylalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is methyl; and R$^4$ is pyridinylmethyl; and R$^1$ and all other groups are as defined in the Summary of the Invention for a Compound of Formula I or as defined in any one of embodiments B, B1, B1a, B2, B2a, B3, (C)-C(8), and (C8a).

Embodiments (D5)

In another embodiment, the Compound is according to Formula I(a) where R$^2$ is —NR$^3$R$^4$ and R$^3$ is hydrogen; and R$^4$ is optionally substituted cycloalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ is hydrogen; and R$^4$ is cycloalkyl; and R$^1$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ and $R^3$ is hydrogen; and $R^4$ is (1r,3r,5R,7R)-tricyclo[3.3.1.1$^{3,7}$]decan-2-yl; and $R^1$ and all other groups are as defined in the Summary of the Invention for a Compound of Formula I or as defined in any one of embodiments B, B1, B1a, B2, B2a, B3, (C)-C(8), and (C8a).

Embodiment (D6)

In another embodiment, the Compound is according to Formula I(a) where
$R^1$ is phenyl substituted with one or two $R^6$ groups independently nitro, —$NR^8R^{8a}$, —$C(O)NR^8R^{8a}$, —$NR^8C(O)OR^9$, or heteroaryl optionally substituted with 1, 2, or 3 $R^{14}$; or
$R^1$ is heteroaryl optionally substituted with one, two, or three $R^7$;
$R^2$ is —$NR^3R^4$ where $R^3$ is hydrogen, alkyl, or alkoxycarbonylalkyl; and $R^4$ is optionally substituted cycloalkyl, optionally substituted phenyl, optionally substituted phenylalkyl, or optionally substituted heteroarylalkyl;
each $R^7$, when present, is independently alkyl, —$NR^8R^{8a}$, —$C(O)NR^8R^{8a}$, —$NR^8C(O)OR^9$, or —$NR^8C(O)R^9$;
$R^8$ is hydrogen, alkyl, or alkenyl;
$R^{8a}$ is hydrogen, alkyl, haloalkyl, optionally substituted heterocycloalkyl, or optionally substituted phenylalkyl;
$R^9$ is alkyl or haloalkyl; and
each $R^{14}$, when present, is halo, alkyl, or alkoxycarbonyl.

Embodiments (E)

In another embodiment, the Compound is according to Formula I(a) where $R^2$ is —$NR^3R^4$ and $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$; and HET, $R^{10}$, $R^{10a}$, $R^{10b}$, $R^{10c}$, $R^{10d}$, $R^{10e}$, $R^{10f}$ and all other groups are as defined in the Summary of the Invention for a Compound of Formula I or as defined in any one of embodiments B, B1, B1a, B2, B2a, B3, (C)-C(8), and (C8a).

Embodiments (E1)

In another embodiment, the Compound is according to Formula I(a) where $R^2$ is —$NR^3R^4$ and $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$; HET is a saturated or partially unsaturated, but non-aromatic, monocyclic 5- to 8-membered ring optionally containing an additional one or two ring heteroatoms which are independently oxygen, sulfur, or nitrogen where the remaining ring atoms are carbon; and $R^{10}$, $R^{10a}$, $R^{10b}$, $R^{10c}$, $R^{10d}$, $R^{10e}$, and $R^{10f}$ and all other groups are as defined in the Summary of the Invention for a Compound of Formula I or as defined in any one of embodiments B, B1, B1a, B2, B2a, B3, (C)-C(8), and (C8a).

Embodiments (E2)

In another embodiment, the Compound is according to Formula I(a) where $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$; HET is a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; and $R^{10}$, $R^{10a}$, $R^{10b}$, $R^{10c}$, $R^{10d}$, $R^{10e}$, and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^3$ and $R^4$ together with the nitrogen to which they are attached form HET optionally substituted on any substitutable atom of the ring with $R^{10}$, $R^{10a}$, and $R^{10b}$; $R^{10c}$, $R^{10d}$, $R^{10e}$, and $R^{10f}$ are hydrogen; HET is a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; and $R^{10}$, $R^{10a}$, $R^{10b}$, and all other groups are as defined in the Summary of the Invention for a Compound of Formula I or as defined in any one of embodiments B, B1, B1a, B2, B2a, B3, (C)-C(8), and (C8a).

Embodiments (E3)

In another embodiment, the Compound is according to Formula I(a) where $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$; HET is a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; and $R^{10}$, $R^{10a}$, $R^{10b}$, $R^{10c}$, $R^{10d}$, $R^{10e}$, and $R^{10f}$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^3$ and $R^4$ together with the nitrogen to which they are attached form HET optionally substituted on any substitutable atom of the ring with $R^{10}$, $R^{10a}$, and $R^{10b}$; $R^{10c}$, $R^{10d}$, $R^{10e}$, and $R^{10f}$ are hydrogen; HET is a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; and $R^{10}$, $R^{10a}$, and $R^{10b}$ and all other groups are as defined in the Summary of the Invention for a Compound of Formula I or as defined in any one of embodiments B, B1, B1a, B2, B2a, B3, (C)-C(8), and (C8a).

Embodiments (E4)

In another embodiment, the Compound is according to Formula I(a) where $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$; HET is a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring; and $R^{10}$, $R^{10a}$, $R^{10b}$, $R^{10c}$, $R^{10d}$, $R^{10e}$, and $R^{10f}$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$; HET is a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring; $R^{10}$, $R^{10a}$, $R^{10b}$, $R^{10c}$, $R^{10d}$, $R^{10e}$, and $R^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (F): In another embodiment, the Compound is according to Formula I(a) where $R^2$ is —$NR^3R^4$ and $R^3$ and $R^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with $R^{10}$, $R^{10a}$, and $R^{10b}$; and $R^{10}$, $R^{10a}$, $R^{10b}$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ and $R^3$ and $R^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with $R^{10}$, $R^{10a}$, and $R^{10b}$; $R^{10}$ is hydrogen or phenyl; $R^{10a}$ and $R^{10b}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ and $R^3$ and $R^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with $R^{10}$, $R^{10a}$, and $R^{10b}$; $R^{10}$, $R^{10a}$ and $R^{10b}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (F1)

In another embodiment, the Compound is according to Formula I(a) where
$R^1$ is phenyl substituted with one or two $R^6$ groups independently nitro, —$NR^8R^{8a}$, —$C(O)NR^8R^{8a}$, —$NR^8C(O)OR^9$, or heteroaryl optionally substituted with 1, 2, or 3 $R^{14}$; or
$R^1$ is heteroaryl optionally substituted with one, two, or three $R^7$;
$R^2$ is —$NR^3R^4$ and $R^3$ and $R^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with $R^{10}$, $R^{10a}$, and $R^{10b}$;

each $R^7$, when present, is independently alkyl, —$NR^8R^{8a}$, —$C(O)NR^8R^{8a}$, —$NR^8C(O)OR^9$, or —$NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and $R^{10}$, $R^{10a}$, and $R^{10b}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —$C(O)R^{12}$; —$C(O)NR^{11}R^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or two of $R^{10}$, $R^{10a}$, $R^{10b}$, $R^{10c}$, $R^{10d}$, $R^{10e}$, and $R^{10f}$ when attached to the same carbon form oxo;

$R^{11}$ hydrogen, alkyl, or alkenyl;

$R^{11a}$ hydrogen, alkyl, or alkenyl;

$R^{12}$ is alkyl, or optionally substituted heteroaryl; and each $R^{14}$, when present, is halo, alkyl, or alkoxycarbonyl.

Embodiments (F2)

In another embodiment, the Compound is according to Formula I(a) where
$R^1$ is phenyl substituted with one or two $R^6$ groups independently nitro, —$NR^8R^{8a}$, —$C(O)NR^8R^{8a}$, —$NR^8C(O)OR^9$, or heteroaryl optionally substituted with 1, 2, or 3 $R^{14}$; or
$R^1$ is heteroaryl optionally substituted with one, two, or three $R^7$;
$R^2$ is —$NR^3R^4$ and $R^3$ and $R^4$ together with the nitrogen to which they are attached form HET and HET is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on HET is optionally substituted with $R^{10}$, $R^{10a}$, and $R^{10b}$;

each $R^7$, when present, is independently alkyl, —$NR^8R^{8a}$, —$C(O)NR^8R^{8a}$, —$NR^8C(O)OR^9$, or —$NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and $R^{10}$, $R^{10a}$, and $R^{10b}$ are independently hydrogen, alkyl, or optionally substituted phenyl;

$R^{11}$ hydrogen, alkyl, or alkenyl;

$R^{11a}$ hydrogen, alkyl, or alkenyl;

$R^{12}$ is alkyl, or optionally substituted heteroaryl; and each $R^{14}$, when present, is halo, alkyl, or alkoxycarbonyl.

Embodiments (G)

In another embodiment, the Compound is according to Formula I(a) where $R^2$ is —$NR^3R^4$ and $R^3$ and $R^4$ together with the nitrogen to which they are attached form HET according to formula (a):

(a)

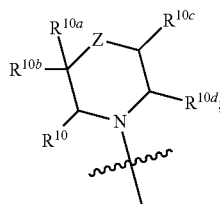

where Z is a bond, —C(O)—, —O—, —S—, —S(O)—, —S(O)$_2$—, —N(R$^z$)—, —C(R$^{10e}$)(R$^{10f}$)—, or C$_{2-3}$-alkylene; R$^z$ is hydrogen, alkyl, haloalkyl, haloalkenyl, hydroxyalkyl, alkylsulfonyl, hydroxy, alkoxy, alkoxycarbonyl, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl; R$^{10}$, R$^{10a}$, R$^{11b}$, R$^{10c}$, R$^{10d}$, R$^{10e}$, and R$^{10f}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or R$^{10a}$ and R$^{10b}$ together form oxo; and all other groups are as defined in the Summary of the Invention for a Compound of Formula I or as defined in any one of embodiments B, B1, B1a, B2, B2a, B3, (C)-C(8), and (C8a).

Embodiments (G1)

In another embodiment, the Compound is according to Formula I(a) where R$^2$ is —NR$^3$R$^4$ and R$^3$ and R$^4$ together with the nitrogen to which they are attached form HET according to formula (a):

(a)

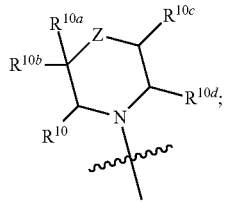

where Z is a bond; R$^{10}$, R$^{10a}$, R$^{10b}$, R$^{10c}$, and R$^{10d}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or R$^{10a}$ and R$^{10b}$ together form oxo; and all other groups are as defined in the Summary of the Invention for a Compound of Formula I or as defined in any one of embodiments B, B1, B1a, B2, B2a, B3, (C)-C(8), and (C8a).

Embodiments (G1a)

In another embodiment, the Compound is according to Formula I(a) where R$^2$ is —NR$^3$R$^4$ and R$^3$ and R$^4$ together with the nitrogen to which they are attached form HET according to formula (a) where Z is bond; one of R$^{10}$, R$^{10a}$, R$^{10b}$, R$^{10c}$, and R$^{10d}$ is alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; the remaining of R$^{10}$, R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G1b)

In another embodiment, the Compound is according to Formula I(a) where R$^2$ is —NR$^3$R$^4$ and R$^3$ and R$^4$ together with the nitrogen to which they are attached form HET according to formula (a) where Z is bond; R$^{10a}$ is hydrogen, hydroxy, optionally substituted phenyl, or optionally substituted phenylalkyl; R$^{10}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ and R$^4$ together with the nitrogen to which they are attached form HET according to formula (a) where Z is bond; R$^{10}$ is alkyl, optionally substituted phenyl, or optionally substituted phenylalkyl; R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G2)

In another embodiment, the Compound is according to Formula I(a) where R$^2$ is —NR$^3$R$^4$ and R$^3$ and R$^4$ together with the nitrogen to which they are attached form HET according to formula (a):

(a)

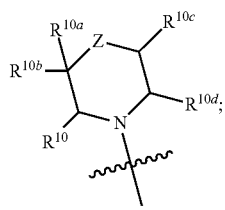

where Z is —O—; R$^{10}$, R$^{10a}$, R$^{10b}$, R$^{10c}$, and R$^{10d}$ are independently hydrogen; halo; alkyl; haloalkyl; haloalkenyl;

hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or R$^{10a}$ and R$^{10b}$ together form oxo; and all other groups are as defined in the Summary of the Invention for a Compound of Formula I. In another embodiment, the Compound is according to Formula I(a) where R$^2$ is —NR$^3$R$^4$ and R$^3$ and R$^4$ together with the nitrogen to which they are attached form HET according to formula (a) where Z is —O—; R$^{10}$, R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G2a)

In another embodiment, the Compound is according to Formula I(a) where R$^2$ is —NR$^3$R$^4$ and R$^3$ and R$^4$ together with the nitrogen to which they are attached form HET according to formula (a) where Z is —O—; one of R$^{10}$, R$^{10a}$, R$^{10b}$, R$^{10c}$, and R$^{10d}$ is alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; the remaining of R$^{10}$, R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G2b)

In another embodiment, the Compound is according to Formula I(a) where R$^2$ is —NR$^3$R$^4$ and R$^3$ and R$^4$ together with the nitrogen to which they are attached form HET according to formula (a) where Z is —O—; R$^{10a}$ is optionally substituted phenyloxyalkyl; R$^{10}$, R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G3)

In another embodiment, the Compound is according to Formula I(a) where R$^2$ is —NR$^3$R$^4$ and R$^3$ and R$^4$ together with the nitrogen to which they are attached form HET according to formula (a):

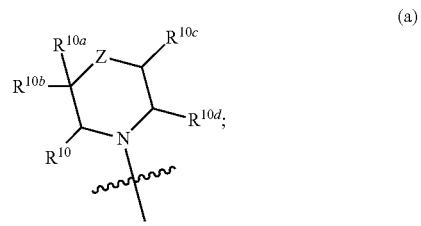

where Z is —S—, —S(O)—, or —S(O)$_2$—; R$^{10}$, R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G4)

In another embodiment, the Compound is according to Formula I(a) where R$^2$ is —NR$^3$R$^4$ and R$^3$ and R$^4$ together with the nitrogen to which they are attached form HET according to formula (a):

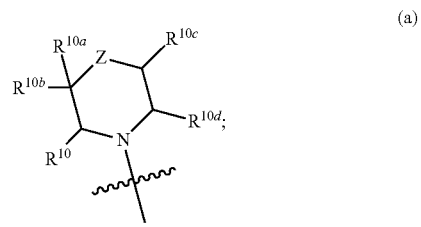

where Z is —N(R$^z$)—; R$^z$ is hydrogen, alkyl, haloalkyl, haloalkenyl, hydroxyalkyl, alkylsulfonyl, hydroxy, alkoxy, alkoxycarbonyl, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl; R$^{10}$, R$^{10a}$, R$^{10b}$, R$^{10c}$, and R$^{10d}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or R$^{10a}$ and R$^{10b}$ together form oxo; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ and R$^4$ together with the nitrogen to which they are attached form HET according to formula (a) where Z is —N(R$^z$)—; R$^{10}$, R$^{10a}$, R$^{10b}$, R$^{10c}$, and R$^{10d}$ are hydrogen; R$^z$ is hydrogen, alkyl, haloalkyl, haloalkenyl, hydroxyalkyl, alkylsulfonyl, hydroxy, alkoxy, alkoxycarbonyl, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl; and all other groups are as defined in the Summary of the Invention for a Compound of Formula I or as defined in any one of embodiments B, B1, B1a, B2, B2a, B3, (C)-C(8), and (C8a).

Embodiments (G4a)

In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; one of $R^z$, $R^{10}$, $R^{10a}$, $R^{10b}$, $R^{10c}$, and $R^{10d}$ is not hydrogen; the remaining of $R^z$, $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G4b)

In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^z$ is alkyl, haloalkyl, haloalkenyl, hydroxyalkyl, alkylsulfonyl, hydroxy, alkoxy, alkoxycarbonyl, $-C(O)R^{12}$, $-C(O)NR^{11}R^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl; $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G4c)

In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^z$ is alkyl, optionally substituted phenyl, optionally substituted phenylalkyl, optionally substituted heteroaryl, or $-C(O)R^{12}$; $R^{10}$, $R^{10a}$, $R^{10b}$, $R^{10c}$, and $R^{10d}$ are hydrogen; and $R^{12}$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^z$ is alkyl; or $R^z$ is phenyl optionally substituted with one, two, or three groups which are independently halo, haloalkyl, hydroxy, alkyl, alkoxy, alkylcarbonyl, and nitro; or $R^z$ is phenylmethyl optionally substituted with one, two, or three groups which are independently halo, haloalkyl, hydroxy, alkyl, alkoxy, alkylcarbonyl, or nitro; or $R^z$ is heteroaryl optionally substituted with one, two, or three groups which are independently halo, haloalkyl, hydroxy, alkyl, alkoxy, alkylcarbonyl, or nitro; and $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G4d)

In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^{10}$ and $R^z$ are independently alkyl, haloalkyl, haloalkenyl, hydroxyalkyl, alkylsulfonyl, hydroxy, alkoxy, alkoxycarbonyl, $-C(O)R^{12}$, $-C(O)NR^{11}R^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl; $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G4e)

In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^{10}$ is optionally substituted phenyl; $R^z$ is alkyl or optionally substituted phenyl; $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^{10}$ is phenyl optionally substituted with one, two, or three groups which are independently halo, haloalkyl, hydroxy, alkyl, alkoxy, alkylcarbonyl, or nitro; $R^z$ is alkyl, or phenyl optionally substituted with one, two, or three groups which are independently halo, haloalkyl, hydroxy, alkyl, alkoxy, alkylcarbonyl, or nitro; $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G4f)

In another embodiment, the Compound is according to Formula I(a) where $R^2$ is $-NR^3R^4$ and $R^3$ and $R^4$ together with the nitrogen to which they are attached form HET according to formula (a) where Z is $-N(R^z)-$; $R^z$ is alkyl; $R^{10a}$ and $R^{10b}$ together form oxo; $R^{10}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G5)

In another embodiment, the Compound is according to Formula I(a) where $R^2$ is $-NR^3R^4$ and $R^3$ and $R^4$ together with the nitrogen to which they are attached form HET according to formula (a):

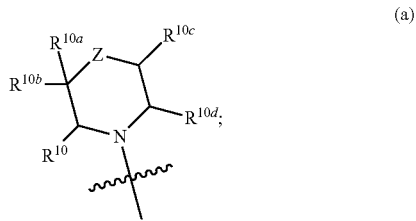

(a)

where Z is —C(R$^{10e}$)(R$^{10f}$)—; R$^{10}$, R$^{10a}$, R$^{10b}$, R$^{10c}$, R$^{10d}$, R$^{10e}$, and R$^{10f}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or R$^{10a}$ and R$^{10b}$ together form oxo; or R$^{10e}$ and R$^{10f}$ together form oxo; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; R$^{10}$, R$^{10a}$, R$^{10b}$, R$^{10c}$, R$^{10d}$, R$^{10e}$, and R$^{10f}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; R$^{10e}$ and R$^{10f}$ together form oxo; R$^{10}$, R$^{10a}$, R$^{10b}$, R$^{10c}$, and R$^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G5a)

In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; one of R$^{10}$, R$^{10a}$, R$^{10b}$, R$^{10c}$, R$^{10d}$, R$^{10e}$, and R$^{10f}$ is alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; the remaining of R$^{10}$, R$^{10a}$, R$^{10b}$, R$^{10c}$, R$^{10d}$, R$^{10e}$, and R$^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G5b)

In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; one of R$^{10}$, R$^{10a}$, R$^{10b}$, R$^{10c}$, R$^{10d}$, R$^{10e}$, and R$^{10f}$ is alkyl, halo, haloalkyl, haloalkenyl, hydroxyalkyl, alkylthio, alkylsulfonyl, hydroxy, alkoxy, cyano, alkoxycarbonyl, —C(O)NR$^{11}$R$^{11a}$, optionally substituted cycloalkyl, optionally substituted phenyl, optionally substituted phenylalkyl, optionally substituted phenyloxy, optionally substituted heterocycloalkyl, or optionally substituted heteroaryl; the remaining of R$^{10}$, R$^{10a}$, R$^{10b}$, R$^{10c}$, R$^{10d}$, R$^{10e}$, and R$^{10f}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; one of R$^{10}$, R$^{10a}$, R$^{10b}$, R$^{10c}$, R$^{10d}$, R$^{10e}$, and R$^{10f}$ is alkyl; halo; haloalkyl; haloalkenyl; hydroxyalkyl; alkylthio; alkylsulfonyl; hydroxy; alkoxy; cyano; alkoxycarbonyl; —C(O)NR$^{11}$R$^{11a}$; phenyl optionally substituted with one, two, or three groups which are independently alkyl, amino, halo, haloalkyl, alkoxy, or haloalkoxy; phenylalkyl optionally substituted with one, two, or three groups which are independently alkyl, amino, halo, haloalkyl, alkoxy, or haloalkoxy; phenyloxy optionally substituted with one, two, or three groups which are alkyl, amino, alkylamino, dialkylamino, halo, haloalkyl, alkoxy, or haloalkoxy; cycloalkyl; heterocycloalkyl; heteroaryl optionally substituted with one or two groups which are independently alkyl or cycloalkyl; the remaining of R$^{10}$, R$^{10a}$, R$^{10b}$, R$^{10c}$, R$^{10d}$, R$^{10e}$, and R$^{10f}$ are hydrogen; R$^{11}$ and R$^{11a}$ are independently hydrogen or alkyl; and all other groups are as defined in the Summary of the Invention for a Compound of Formula I or as defined in any one of embodiments B, B1, B1a, B2, B2a, B3, (C)-C(8), and (C8a).

Embodiments (G5c)

In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; two of R$^{10}$, R$^{10a}$, R$^{10b}$, R$^{10c}$, R$^{10d}$, R$^{10e}$, and R$^{10f}$ are independently alkyl, halo, haloalkyl, hydroxyalkyl, hydroxy, cyano, —C(O)NR$^{11}$R$^{11a}$, or optionally substituted phenyl; the remaining of R$^{10}$, R$^{10a}$, R$^{10b}$, R$^{10c}$, R$^{10d}$, R$^{10e}$, and R$^{10f}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ and R$^3$ and R$^4$ together with the nitrogen to which they are attached form HET according to formula (a) where Z is —C(R$^{10e}$)(R$^{10f}$)—; two of R$^{10}$, R$^{10a}$, R$^{10b}$, R$^{10c}$, R$^{10d}$, R$^{10e}$, and R$^{10f}$ are independently alkyl; halo; haloalkyl; hydroxyalkyl; hydroxy; cyano; —C(O)NR$^{11}$R$^{11a}$; or phenyl optionally substituted with one or two halo, alkyl, haloalkyl, or alkoxy; R$^{11}$ and R$^{11a}$ are independently hydrogen or alkyl; the remaining of R$^{10}$, R$^{10a}$, R$^{10b}$, R$^{10c}$, R$^{10d}$, R$^{10e}$, and R$^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G5d)

In another embodiment, the Compound is according to Formula I(a) where $R^2$ is —$NR^3R^4$ and $R^3$ and $R^4$ together with the nitrogen to which they are attached form HET according to formula (a) where Z is —$C(R^{10e})(R^{10f})$—; one of $R^{10}$, $R^{10a}$, $R^{10b}$, $R^{10c}$, and $R^{10d}$ is optionally substituted phenyl; $R^{10e}$ and $R^{10f}$ together form oxo; the remaining of $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ and $R^3$ and $R^4$ together with the nitrogen to which they are attached form HET according to formula (a) where Z is —$C(R^{10e})(R^{10f})$—; one of $R^{10}$, $R^{10a}$, $R^{10b}$, $R^{10c}$, and $R^{10d}$ is phenyl optionally substituted with one or two halo; $R^{10e}$ and $R^{10f}$ together form oxo; the remaining of $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G5e)

In another embodiment, the Compound is according to Formula I(a) where $R^2$ is —$NR^3R^4$ and $R^3$ and $R^4$ together with the nitrogen to which they are attached form HET according to formula (a) where Z is —$C(R^{10e})(R^{10f})$—; one of $R^{10}$, $R^{10a}$, $R^{10b}$, $R^{10c}$, and $R^{10d}$ is optionally substituted phenyl; $R^{10e}$ and $R^{10f}$ are each halo; the remaining of $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G6)

In another embodiment, the Compound is according to Formula I(a) where $R^2$ is —$NR^3R^4$ and $R^3$ and $R^4$ together with the nitrogen to which they are attached form HET according to formula (a):

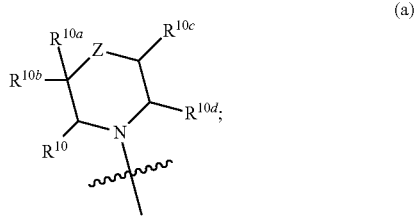

where Z is $C_{2-3}$-alkylene; $R^{10}$, $R^{10a}$, $R^{10b}$, $R^{10c}$, and $R^{10d}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —$C(O)R^{12}$; —$C(O)NR^1R^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or $R^{10a}$ and $R^{10b}$ together form oxo; and all other groups are as defined in the Summary of the Invention for a Compound of Formula I or as defined in any one of embodiments B, B1, B1a, B2, B2a, B3, (C)-C(8), and (C8a).

Embodiments (G6a)

In another embodiment, the Compound is according to Formula I(a) where $R^2$ is —$NR^3R^4$ and $R^3$ and $R^4$ together with the nitrogen to which they are attached form HET according to formula (a) where Z is $C_{2-3}$-alkylene; one of $R^{10}$, $R^{10a}$, $R^{10b}$, $R^{10c}$, and $R^{10d}$ is alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —$C(O)R^{12}$, —$C(O)NR^{11}R^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; or $R^{10a}$ and $R^{10b}$ together form oxo; the remaining of $R^{10}$, $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G6b)

In another embodiment, the Compound is according to Formula I(a) where $R^2$ is —$NR^3R^4$ and $R^3$ and $R^4$ together with the nitrogen to which they are attached form HET according to formula (a) where Z is $C_{2-3}$-alkylene; $R^{10}$ is hydrogen or optionally substituted phenyl; and $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ and $R^3$ and $R^4$ together with the nitrogen to which they are attached form HET according to formula (a) where Z is $C_{2-3}$-alkylene; $R^{10}$ is hydrogen or phenyl; and $R^{10a}$, $R^{10b}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (G7)

In another embodiment, the Compound is according to Formula I(a) where $R^1$ is phenyl substituted with one or two $R^6$ groups which are independently nitro, —$NR^8R^{8a}$, —$C(O)NR^8R^{8a}$, —$NR^8C(O)OR^9$, or heteroaryl optionally substituted with 1, 2, or 3 $R^{14}$; or $R^1$ is heteroaryl optionally substituted with one, two, or three $R^7$;

$R^2$ is —$NR^3R^4$ and $R^3$ and $R^4$ together with the nitrogen to which they are attached form HET according to formula (a):

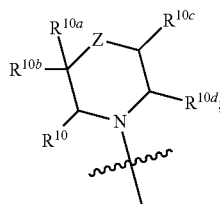

(a)

where Z is a bond, —C(O)—, —O—, —S—, —S(O)—, —S(O)$_2$—, —N(R$^z$)—, —C(R$^{10e}$)(R$^{10f}$)—, or C$_{2-3}$-alkylene;

R$^z$ is hydrogen, alkyl, haloalkyl, haloalkenyl, hydroxyalkyl, alkylsulfonyl, hydroxy, alkoxy, alkoxycarbonyl, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl;

R$^{10}$, R$^{10a}$, R$^{10b}$, R$^{10c}$, R$^{10d}$, R$^{10e}$, and R$^{10f}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —C(O)R$^{12}$; —C(O)NR$^{11}$R$^{11a}$; optionally substituted cycloalkyl; optionally substituted cycloalkylalkyl; optionally substituted phenyl; optionally substituted phenylalkyl; optionally substituted phenyloxy; optionally substituted phenyloxyalkyl; optionally substituted heterocycloalkyl; optionally substituted heterocycloalkylalkyl; optionally substituted heteroaryl; or optionally substituted heteroarylalkyl; or R$^{10a}$ and R$^{10b}$ together form oxo; or R$^{10e}$ and R$^{10f}$ together form oxo;

R$^{11}$ hydrogen, alkyl, or alkenyl;
R$^{11a}$ hydrogen, alkyl, or alkenyl;
R$^{12}$ is alkyl, or optionally substituted heteroaryl; and
each R$^{14}$, when present, is halo, alkyl, or alkoxycarbonyl.

Embodiments (H)

In another embodiment, the Compound is according to Formula I(a) where R$^2$ is —NR$^3$R$^4$ where R$^3$ and R$^4$ together with the nitrogen to which they are attached form HET according to formula (b):

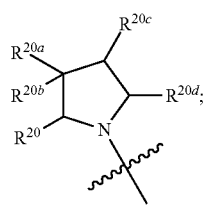

(b)

where
(a) R$^{20}$ and R$^{20c}$ or R$^{20}$ and R$^{20d}$ together with the carbons to which they are bonded form a cycloalkyl or hetercyloalkyl such that HET is a bridged bicyclic moiety; or
(b) R$^{20a}$ and R$^{20c}$ together with the carbons to which they are bonded form a cycloalkyl or hetercyloalkyl such that HET is a fused bicyclic moiety; or
(c) R$^{20a}$ and R$^{20b}$ together with the carbon to which they are attached form cycloalkyl or heterocycloalkyl such that HET is a spirocyclic bicyclic moiety;

where the cycloalkyl and heterocycloalkyl are optionally substituted with R$^{10}$ and R$^{10a}$ and the R$^{10}$ and R$^{10a}$ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; and the remaining of R$^{20}$, R$^{20a}$, R$^{20b}$, R$^{20c}$, and R$^{20d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (H1)

In another embodiment, the Compound is according to Formula I(a) where R$^2$ is —NR$^3$R$^4$ where R$^3$ and R$^4$ together with the nitrogen to which they are attached form HET according to formula (b) where R$^{20a}$ and R$^{20c}$ together with the carbons to which they are bonded form cycloalkyl or heterocycloalkyl such that HET is a fused bicyclic moiety and where the cycloalkyl and heterocycloalkyl are optionally substituted with R$^{10}$ and R$^{10a}$; R$^{20}$, R$^{20b}$, and R$^{20d}$ are hydrogen; R$^{10}$ and R$^{10a}$ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ where R$^3$ and R$^4$ together with the nitrogen to which they are attached form HET according to formula (b) where R$^{20a}$ and R$^{20c}$ together with the carbons to which they are attached form cycloalkyl or heterocycloalkyl such that HET is a fused bicyclic moiety and where the cycloalkyl and heterocycloalkyl are optionally substituted with R$^{10}$ and R$^{10a}$; R$^{20}$, R$^{20b}$, and R$^{20d}$ are hydrogen; R$^{10}$ is hydrogen, alkyl, or phenyl; and R$^{10a}$ is hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where R$^2$ is —NR$^3$R$^4$ where R$^3$ and R$^4$ together with the nitrogen to which they are attached form HET according to formula (b) and is octahydrocyclopenta[c]pyrrolyl, octahydropyrrolo[3,4-c]pyrrolyl, (3aR,6aS)-5-methyloctahydrocyclopenta[c]pyrrolyl, or (3aS,6aR)-5-methyl-1,2,3,3a,4,6a-hexahydrocyclopenta[c]pyrrolyl; and all other groups are as defined in the Summary of the Invention for a Compound of Formula I or as defined in any one of embodiments B, B1, B1a, B2, B2a, B3, (C)-C(8), and (C8a).

Embodiments (H2)

In another embodiment, the Compound is according to Formula I(a) where R$^2$ is —NR$^3$R$^4$ where R$^3$ and R$^4$ together with the nitrogen to which they are attached form HET according to formula (b) where $R^{20}$ and $R^{20d}$ together with the carbons to which they are bonded form a cycloalkyl or hetercyloalkyl such that HET is a bridged bicyclic moiety and where the cycloalkyl and heterocycloalkyl are optionally substituted with $R^{10}$ and $R^{10a}$; $R^{20a}$, $R^{20b}$, and $R^{20c}$ are hydrogen; $R^{10}$ and $R^{10a}$ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)$R^{12}$, C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —NR$^3$R$^4$ where $R^3$ and $R^4$ together with the nitrogen to which they are attached form HET according to formula (b) where $R^{20}$ and $R^{20d}$ together with the carbons to which they are bonded form a cycloalkyl or hetercyloalkyl such that HET is a bridged bicyclic moiety and where the cycloalkyl and heterocycloalkyl are optionally substituted with $R^{10}$ and $R^{10a}$; and the $R^{10}$, $R^{10a}$, $R^{20a}$, $R^{20b}$, and $R^{20c}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (H3)

In another embodiment, the Compound is according to Formula I(a) where $R^2$ is —NR$^3$R$^4$ where $R^3$ and $R^4$ together with the nitrogen to which they are attached form HET according to formula (b) where $R^{20a}$ and $R^{20b}$ together with the carbon to which they are bonded form cycloalkyl or heterocycloalkyl such that HET is a spirocyclic bicyclic moiety, where the cycloalkyl and heterocycloalkyl are optionally substituted with $R^{10}$ and $R^{10a}$; and $R^{20}$, $R^{20c}$, and $R^{20d}$ are hydrogen; $R^{10}$ and $R^{10a}$ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —NR$^3$R$^4$ where $R^3$ and $R^4$ together with the nitrogen to which they are attached form HET according to formula (b) where $R^{20a}$ and $R^{20b}$ together with the carbon to which they are attached form cycloalkyl or heterocycloalkyl such that HET is a spirocyclic bicyclic moiety, where the cycloalkyl and heterocycloalkyl are optionally substituted with $R^{10}$ and $R^{10a}$; and $R^{10}$, $R^{10a}$, $R^{20}$, $R^{20c}$, and $R^{20d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (H4)

In another embodiment, the Compound is according to Formula I(a) where $R^2$ is —NR$^3$R$^4$ where $R^3$ and $R^4$ together with the nitrogen to which they are attached form HET according to formula (b) where $R^{20}$ and $R^{20c}$ together with the carbons to which they are attached form cycloalkyl or heterocycloalkyl such that HET is a bridged bicyclic moiety, where the cycloalkyl and heterocycloalkyl are optionally substituted with $R^{10}$ and $R^{10a}$; and $R^{20a}$, $R^{20b}$, and $R^{20d}$ are hydrogen; $R^{10}$ and $R^{10a}$ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —C(O)R$^{12}$, —C(O)NR$^{11}$R$^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —NR$^3$R$^4$ where $R^3$ and $R^4$ together with the nitrogen to which they are attached form HET according to formula (b) where $R^{20}$ and $R^{20c}$ together with the carbons to which they are attached form cycloalkyl or heterocycloalkyl such that HET is a bridged bicyclic moiety, where the cycloalkyl and heterocycloalkyl are optionally substituted with $R^{10}$ and $R^{10a}$; and $R^{10}$, $R^{10a}$, $R^{20a}$, $R^{20b}$, and $R^{20d}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (H5)

In another embodiment, the Compound is according to Formula I(a) where $R^1$ is phenyl substituted with one or two $R^6$ groups which are independently nitro, —NR$^8$R$^{8a}$, —C(O)NR$^8$R$^{8a}$, —NR$^8$C(O)OR$^9$, or heteroaryl optionally substituted with 1, 2, or 3 $R^{14}$; or $R^1$ is heteroaryl optionally substituted with one, two, or three $R^7$;

$R^2$ is —NR$^3$R$^4$ where $R^3$ and $R^4$ together with the nitrogen to which they are attached form HET according to formula (b):

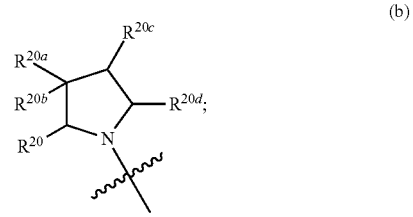

where
(a) $R^{20}$ and $R^{20c}$ or $R^{20}$ and $R^{20d}$ together with the carbons to which they are bonded form a cycloalkyl or hetercyloalkyl such that HET is a bridged bicyclic moiety; or (b) $R^{20a}$ and $R^{20c}$ together with the carbons to which they are bonded form a cycloalkyl or hetercyloalkyl such that HET is a fused bicyclic moiety; or (c) $R^{20a}$ and $R^{20b}$ together with the carbon to which they are attached form cycloalkyl or heterocycloalkyl such that HET is a spirocyclic bicyclic moiety;

where the cycloalkyl and heterocycloalkyl are optionally substituted with $R^{10}$ and $R^{10a}$ where $R^{10}$ and $R^{10a}$ are independently hydroxy, alkyl, haloalkyl, or optionally substituted phenyl; and the remaining of $R^{20}$, $R^{20a}$, $R^{20b}$, $R^{20c}$, and $R^{20d}$ are hydrogen;

each $R^7$, when present, is independently alkyl, —$NR^8R^{8a}$, —$C(O)NR^8R^{8a}$, —$NR^8C(O)OR^9$, or —$NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and each $R^{14}$, when present, is halo, alkyl, or alkoxycarbonyl.

Embodiments (R)

In another embodiment, the Compound is according to Formula I(a) where $R^2$ is —$NR^3R^4$ where $R^3$ and $R^4$ together with the nitrogen to which they are attached form HET according to formula (b):

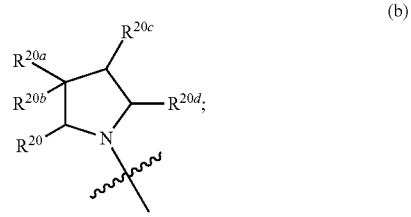

(b)

where $R^{20}$ and $R^{20d}$ together with the carbons to which they are bonded form a cycloalkyl or hetercyloalkyl and $R^{20a}$ and $R^{20c}$ together with the carbons to which they are bonded form a cycloalkyl or heterocycloalkyl such that HET is a tricyclic moiety, where the cycloalkyl and heterocycloalkyl are optionally substituted with $R^{10}$ and $R^{10a}$; and $R^{20b}$ is hydrogen; and all other groups are independently as defined in the Summary of the Invention for a Compound of Formula I or as defined in any one of embodiments B, B1, B1a, B2, B2a, B3, (C)-C(8), and (C8a).

Embodiments (J)

In another embodiment, the Compound is according to Formula I(a) where $R^2$ is —$NR^3R^4$ where $R^3$ and $R^4$ together with the nitrogen to which they are attached form HET according to formula (c):

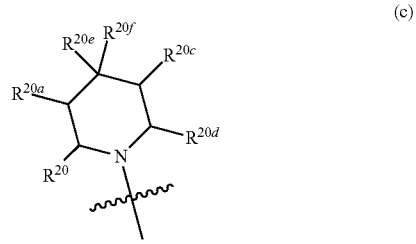

(c)

(a) $R^{20}$ and $R^{20d}$ or $R^{20}$ and $R^{20c}$ together with the carbons to which they are bonded form a cycloalkyl or hetercyloalkyl such that HET is a bridged bicyclic moiety (b) $R^{20e}$ and $R^{20f}$ together with the carbons to which they are bonded form cycloalkyl or heterocycloalkyl such that HET is a spirocyclic bicyclic moiety, (c) $R^{20}$ and $R^{20a}$ or $R^{20a}$ and $R^{20e}$ together with the carbons to which they are bonded form a cycloalkyl or hetercyloalkyl such that HET is a fused bicyclic moiety;

where the cycloalkyl and heterocycloalkyl are optionally substituted with $R^{10}$ and $R^{10a}$; and the remaining of $R^{20}$, $R^{20a}$, $R^{20c}$, $R^{20d}$, $R^{20e}$, and $R^{20f}$ are $R^{10}$, $R^{10a}$, $R^{10c}$, $R^{10d}$, $R^{10e}$, and $R^{10f}$, respectively; each $R^{10}$, each $R^{10a}$, $R^{10c}$, $R^{10d}$, $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a).

Embodiments (J1)

In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety and where the cycloalkyl and heterocycloalkyl are optionally substituted with $R^{10}$ and $R^{10a}$; and $R^{20a}$, $R^{20c}$, $R^{20e}$, and $R^{20f}$ are $R^{10a}$, $R^{10c}$, $R^{10e}$, and $R^{10f}$, respectively; $R^{10}$, each $R^{10a}$, $R^{10c}$, $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively; $R^{10a}$, $R^{10c}$, $R^{10e}$, and $R^{10d}$, and all other groups are independently as defined in the Summary of the Invention for a Compound of Formula I or as defined in any one of embodiments B, B1, B1a, B2, B2a, B3, (C)-C(8), and (C8a).

Embodiments (J1a)

In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10}$, respectively, where $R^{10a}$ and $R^{10c}$ are hydrogen, $R^{10e}$ and $R^{10f}$ together form oxo; and all other groups are as defined in the Summary of the Invention for a Compound of Formula I or as defined in any one of embodiments B, B1, B1a, B2, B2a, B3, (C)-C(8), and (C8a).

Embodiments (J1b)

In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydrogen, hydroxy, or alkyl, and $R^{10f}$ is hydrogen, hydroxy, alkyl, haloalkyl, hydroxyalkyl, amino, halo, or optionally substituted phenyl; and all other groups are as defined in the Summary of the Invention for a Compound of Formula I or as defined in any one of embodiments B, B1, B1a, B2, B2a, B3, (C)-C(8), and (C8a).

Embodiments (J1c)

In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydrogen, and $R^{10f}$ is hydroxy; and all other groups are as defined in the Summary of the Invention for a Compound of Formula I or as defined in any one of embodiments B, Bl, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydrogen, and $R^{10f}$ is alkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydroxy, and $R^{10e}$ is haloalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydroxy, and $R^{10f}$ is alkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is alkyl, and $R^{10f}$ is halo; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydroxy, and $R^{10f}$ is phenyl optionally substituted with one or two halo or haloalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydrogen, and $R^{10f}$ is haloalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydroxy, and $R^{10f}$ is hydroxyalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$ $R^{20e}$, and $R^{20f}$ are $R^{10a}$, $R^{10c}$, $R^{10e}$, and $R^{10f}$, respectively, where $R^{10a}$ and $R^{10c}$ are hydrogen, $R^{10e}$ is hydrogen, and $R^{10f}$ is amino; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20d}$ together with the carbons to which they are attached form cycloalkyl or heterocycloalkyl such that HET forms a bridged bicyclic moiety; and $R^{20a}$, $R^{20c}$, $R^{20e}$, and $R^{20f}$ are $R^{10a}$, $R^{10e}$, $R^{10e}$, and $R^{10f}$, respectively, where $R^{10a}$, $R^{10c}$, and $R^{10e}$ are hydrogen, and $R^{10f}$ is hydroxyalkyl; and all other groups are as defined in the Summary of the Invention for a Compound of Formula I or as defined in any one of embodiments B, B1, B1a, B2, B2a, B3, (C)-C(8), and (C8a).

Embodiments (J2)

In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20c}$ together with the carbons to which they are attached form cycloalkyl or heterocycloalkyl such that HET is a bridged bicyclic moiety, where the cycloalkyl and heterocycloalkyl are optionally substituted with $R^{10}$ and $R^{10a}$; and $R^{20a}$, $R^{20d}$, $R^{20e}$, and $R^{20f}$ are $R^{10a}$, $R^{10d}$, $R^{10e}$, and $R^{10f}$, respectively; $R^{10}$, each $R^{10a}$, $R^{10d}$, $R^{10e}$, and $R^{10f}$, and all other groups are independently as defined in the Summary of the Invention for a Compound of Formula or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20c}$ together with the carbons to which they are attached form cycloalkyl or heterocycloalkyl such that HET is a bridged bicyclic moiety, where the cycloalkyl and heterocycloalkyl are optionally substituted with $R^{10}$ and $R^{10a}$; and $R^{20a}$, $R^{20d}$, $R^{20e}$, and $R^{20f}$ are $R^{10a}$, $R^{10d}$, $R^{10e}$, and $R^{10f}$, respectively where each $R^{10a}$, $R^{10d}$, $R^{10e}$, and $R^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (J3)

In another embodiment, the Compound is according to Formula I(a) where $R^2$ is —$NR^3R^4$ where $R^3$ and $R^4$ together with the nitrogen to which they are attached form HET according to formula (c) where $R^{20e}$ and $R^{20f}$ together with the carbons to which they are attached form cycloalkyl or heterocycloalkyl such that HET is a spirocyclic bicyclic moiety, where the cycloalkyl and heterocycloalkyl are optionally substituted with $R^{10}$ and $R^{10a}$; and $R^{20}$, $R^{20a}$, $R^{20c}$, and $R^{20d}$ are $R^{10}$, $R^{10a}$, $R^{10c}$, and $R^{10d}$, respectively; each $R^{10}$, each $R^{10a}$, $R^{10c}$, and $R^{10d}$, and all other groups are independently as defined in the Summary of the Invention for a Compound of Formula I or as defined in any one of embodiments B, B1, B1a, B2, B2a, B3, (C)-C(8), and (C8a).

Embodiments (J4)

In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20a}$ together with the carbons to which they are attached form cycloalkyl or heterocycloalkyl such that HET is a fused bicyclic moiety, where the cycloalkyl and heterocycloalkyl are optionally substituted with $R^{10}$ and $R^{10a}$; and $R^{20c}$, $R^{20d}$, $R^{20e}$, and $R^{20f}$ are $R^{10c}$, $R^{10d}$, $R^{10e}$, and $R^{10f}$, respectively; $R^{10}$, $R^{10a}$, $R^{10c}$, $R^{10d}$, $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20}$ and $R^{20a}$ together with the carbons to which they are attached form cycloalkyl or heterocycloalkyl such that HET is a fused bicyclic moiety, where the cycloalkyl and heterocycloalkyl are optionally substituted with $R^{10}$ and $R^{10a}$; $R^{20c}$, $R^{20d}$, $R^{20e}$, and $R^{20f}$ are $R^{10c}$, $R^{10d}$, $R^{10e}$, and $R^{10f}$, respectively and $R^{10c}$, $R^{10d}$, $R^{10e}$, and $R^{10f}$ are hydrogen; $R^{10}$, $R^{10a}$, and all other groups are independently as defined in the Summary of the Invention for a Compound of Formula I or as defined in any one of embodiments B, B1, B1a, B2, B2a, B3, (C)-C(8), and (C8a).

Embodiments (J5)

In another embodiment, the Compound is according to Formula I(a) where $R^2$ is —$NR^3R^4$ where $R^3$ and $R^4$ together with the nitrogen to which they are attached form HET according to formula (c) where $R^{20a}$ and $R^{20e}$ together with the carbons to which they are attached form cycloalkyl or heterocycloalkyl such that HET is a fused bicyclic moiety, where the cycloalkyl and heterocycloalkyl are optionally substituted with $R^{10}$ and $R^{10a}$; and $R^{20}$, $R^{20c}$, $R^{20d}$, and $R^{20f}$ are $R^{10}$, $R^{10c}$, $R^{10d}$, and $R^{10f}$, respectively; each $R^{10}$, $R^{10a}$, $R^{10c}$, $R^{10d}$, $R^{10f}$, and all other groups are independently as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) where $R^{20a}$ and $R^{20e}$ together with the carbons to which they are attached form cycloalkyl or heterocycloalkyl such that HET is a fused bicyclic moiety; and $R^{20}$, $R^{20c}$, $R^{20d}$, and $R^{20f}$ are $R^{10}$, $R^{10c}$, $R^{10d}$, and $R^{10f}$, respectively and $R^{10}$, $R^{10c}$, $R^{10d}$, and $R^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiment (J6)

In another embodiment, the Compound is according to Formula I(a) where $R^2$ is —$NR^3R^4$ where $R^3$ and $R^4$ together with the nitrogen to which they are attached form HET according to formula (c) which is according to formula (g)

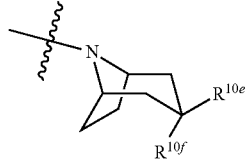

(g)

where $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a).

Embodiment (J6a)

In another embodiment, the Compound is according to Formula I(a) where $R^2$ is —$NR^3R^4$ where $R^3$ and $R^4$ together with the nitrogen to which they are attached form HET according to formula (c) which is according to formula (g) where $R^{10e}$ is hydrogen, alkyl, halo, haloalkyl, hydroxy, or optionally substituted phenyl; $R^{10f}$ is hydrogen, hydroxy, amino, alkyl, hydroxyalkyl, or haloalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is according to formula (g) where $R^{10e}$ is hydrogen, alkyl, halo, haloalkyl, hydroxy, or phenyl optionally substituted with one or two groups which are halo or haloalkyl; $R^{10f}$ is hydrogen, hydroxy, amino, alkyl, hydroxyalkyl, or haloalkyl; and all other groups are as defined in the Summary of the Invention for a Compound of Formula I or as defined in any one of embodiments B, B1, B1a, B2, B2a, B3, (C)-C(8), and (C8a).

Embodiment (J6b)

In another embodiment, the Compound is according to Formula I(a) where $R^2$ is —$NR^3R^4$ where $R^3$ and $R^4$ together with the nitrogen to which they are attached form HET according to formula (c) which is according to formula (g) where $R^{10e}$ and $R^{10f}$ together form oxo; and all other groups are as defined in the Summary of the Invention for a Compound of Formula I or as defined in any one of embodiments B, B1, B1a, B2, B2a, B3, (C)-C(8), and (C8a).

Embodiment (J7)

In another embodiment, the Compound is according to Formula I(a) where $R^2$ is —$NR^3R^4$ where $R^3$ and $R^4$ together with the nitrogen to which they are attached form HET according to formula (c) which is further according to formula (h)

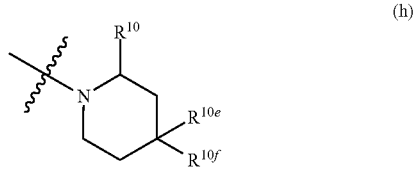

where $R^{10}$, $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a). In another embodiment of embodiment (J7), the Compound is according to Formula I(a) where $R^2$ is —$NR^3R^4$ where $R^3$ and $R^4$ together with the nitrogen to which they are attached form HET according to formula (c) which is further according to formula (h) where one of $R^{10}$, $R^{10e}$, and $R^{10f}$ is not hydrogen and the others are as defined in embodiment (J7); and all other groups are as defined in the Summary of the Invention for a Compound of Formula I or as defined in any one of embodiments B, B1, B1a, B2, B2a, B3, (C)-C(8), and (C8a).

Embodiment (J7a)

In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is hydrogen; $R^{10e}$ is —$C(O)NH_2$, hydroxy, alkoxy, cyano, alkyl, haloalkyl, haloalkenyl, hydroxyalkyl, alkylthio, alkylsulfonyl, optionally substituted cycloalkyl, optionally substituted heterocycloalkyl, optionally substituted phenyl, optionally substituted phenylalkyl, optionally substituted phenyloxy, or optionally substituted heteroaryl; and $R^{10f}$ is hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is hydrogen; $R^{10e}$ is —$C(O)NH_2$, hydroxy, alkoxy, cyano, alkyl, haloalkyl, haloalkenyl, hydroxyalkyl, alkylthio, alkylsulfonyl, cycloalkyl, heterocycloalkyl, phenyl optionally substituted with one or two halo, phenylalkyl optionally substituted with one or two halo, phenyloxy optionally substituted with one or two halo, heteroaryl optionally substituted with one alkyl or cycloalkyl; and $R^{10f}$ is hydrogen; and all other groups are as defined in the Summary of the Invention for a Compound of Formula I or as defined in any one of embodiments B, B1, B1a, B2, B2a, B3, (C)-C(8), and (C8a).

Embodiment (J7b)

In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is alkyl, or optionally substituted phenyl; $R^{10e}$ is hydroxy, alkyl, haloalkyl, or cyano; and $R^{10f}$ is hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is alkyl, or phenyl optionally substituted with one or tow groups which are independently halo, or haloalkyl; $R^{10e}$ is hydroxy, alkyl, haloalkyl, or cyano; and $R^{10f}$ is hydrogen; and all other groups are as defined in the Summary of the Invention for a Compound of Formula I or as defined in any one of embodiments B, B1, B1a, B2, B2a, B3, (C)-C(8), and (C8a).

Embodiment (J7c)

In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10e}$ and $R^{10f}$ together form oxo; and $R^{10}$ and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is hydrogen, or optionally substituted phenyl; $R^{10e}$ and $R^{10f}$ of together form oxo; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is hydrogen, or phenyl optionally substituted with one or two halo; $R^{10e}$ and $R^{10f}$ of together form oxo; and all other groups are as defined in the Summary of the Invention for a Compound of Formula I or as defined in any one of embodiments B, B1, B1a, B2, B2a, B3, (C)-C(8), and (C8a).

Embodiment (J7d)

In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is alkyl, haloalkyl, alkoxycarbonyl, or optionally substituted phenyl; $R^{10e}$ and $R^1$ of are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is alkyl, haloalkyl, alkoxycarbonyl, or phenyl optionally substituted with one, two, or three groups which are independently dialkylamino, alkyl, halo, haloalkyl, or alkoxy; $R^{10e}$ and $R^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiment (J7e)

In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is optionally substituted phenyl; $R^{10e}$ is hydroxy, or halo; and $R^{10f}$ is alkyl, halo, haloalkyl, or hydroxyalkyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is phenyl optionally substituted with one or two halo; $R^{10e}$ is hydroxy, or halo; and $R^{10f}$ is alkyl, halo, haloalkyl, or hydroxyalkyl; and all other groups are as defined in the Summary of the Invention for a Compound of Formula I or as defined in any one of embodiments B, B1, B1a, B2, B2a, B3, (C)-C(8), and (C8a).

Embodiment (J7f)

In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is hydrogen; $R^{10e}$ is hydroxy, halo, alkyl, or cyano; and $R^{10f}$ is alkyl, haloalkyl, halo, —$C(O)NH_2$, or optionally substituted phenyl; and all other groups are as defined in the Summary of the Invention for a Compound of Formula I or as defined in any one of embodiments B, B1, B1a, B2, B2a, B3, (C)-C(8), and (C8a). In another embodiment, the Compound is according to Formula I(a) where $R^2$ is —$NR^3R^4$ where $R^3$ and $R^4$ together with the nitrogen to which they are attached form HET according to formula (c) which is further according to formula (h) where $R^{10}$ is hydrogen; $R^{10e}$ is hydroxy, halo, alkyl, or cyano; and $R^{10f}$ is alkyl, haloalkyl, halo, —$C(O)NH_2$, or phenyl optionally substituted with one or two groups which are independently halo, alkyl, haloalkyl, or alkoxy; and all other groups are as defined in the Summary of the Invention for a Compound of Formula I or as defined in any one of embodiments B, B1, B1a, B2, B2a, B3, (C)-C(8), and (C8a).

Embodiments (J8)

In another embodiment, the Compound is according to Formula I(a) where $R^2$ is —$NR^3R^4$ where $R^3$ and $R^4$ together with the nitrogen to which they are attached form HET according to formula (c):

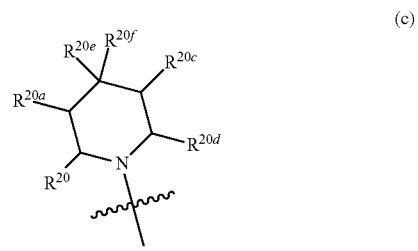

(c)

(a) $R^{20}$ and $R^{20d}$ or $R^{20}$ and $R^{20c}$ together with the carbons to which they are bonded form a cycloalkyl such that HET is a bridged moiety
(b) $R^{20e}$ and $R^{20f}$ together with the carbons to which they are bonded form cycloalkyl such that HET is a spirocyclic moiety,
(c) $R^{20}$ and $R^{20a}$ or $R^{20a}$ and $R^{20e}$ together with the carbons to which they are bonded form a cycloalkyl such that HET is a fused bicyclic moiety;
where the cycloalkyl is optionally substituted with $R^{10}$ and $R^{10a}$ where $R^{10}$ and $R^{10a}$ are independently alkyl or together form oxo; and the remaining of $R^{20}$, $R^{20a}$, $R^{20c}$, $R^{20d}$, $R^{20e}$, and $R^{20f}$ are $R^{10}$, $R^{10a}$, $R^{10e}$, $R^{10d}$, $R^{10e}$, and $R^{10f}$, respectively, where $R^{10}$, $R^{10a}$, $R^{10e}$, $R^{10d}$, $R^{10e}$, and $R^{10f}$ are independently hydrogen, hydroxy, alkyl, halo, haloalkyl, hydroxyalkyl, optionally substituted phenyl, or amino, or $R^{10e}$ and $R^{10f}$ together form oxo;
each $R^7$, when present, is independently alkyl, —$NR^8R^{8a}$, —$C(O)NR^8R^{8a}$, —$NR^8C(O)OR^9$, or —$NR^8C(O)R^9$;
$R^8$ is hydrogen, alkyl, or alkenyl;
$R^{8a}$ is hydrogen, alkyl, haloalkyl, optionally substituted heterocycloalkyl, or optionally substituted phenylalkyl;
$R^9$ is alkyl or haloalkyl; and
each $R^{14}$, when present, is halo, alkyl, or alkoxycarbonyl.

Embodiments (K)

In another embodiment, the Compound of Formula is according to Formula I where $R^2$ is —$NR^3R^4$ where $R^3$ and $R^4$ together with the nitrogen to which they are attached form HET according to formula (d), (e), or (f):

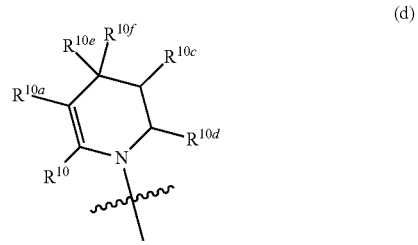

(d)

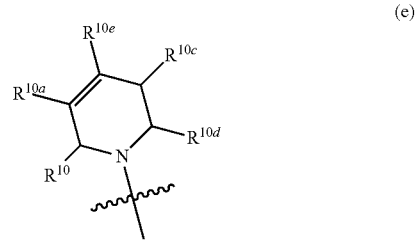

(e)

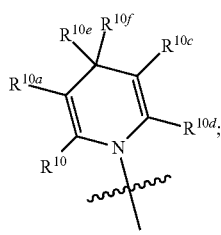

(f)

where all other groups are as defined in the Summary of the Invention for a Compound of Formula I or as defined in any one of embodiments B, B1, B1a, B2, B2a, B3, (C)-C(8), and (C8a). In another embodiment, the Compound of Formula is according to Formula I where $R^2$ is —$NR^3R^4$ where $R^3$ and $R^4$ together with the nitrogen to which they are attached form HET according to formula (d) or (f) where $R^{10}$ is optionally substituted phenyl, $R^{10e}$ and $R^{10f}$ together form oxo, and $R^{10a}$, $R^{10c}$, and $R^{10d}$ are hydrogen; and all other groups are as defined in the Summary of the Invention for a Compound of Formula I or as defined in any one of embodiments B, B1, B1a, B2, B2a, B3, (C)-C(8), and (C8a). In another embodiment, the Compound of Formula is according to Formula I where $R^2$ is —$NR^3R^4$ where $R^3$ and $R^4$ together with the nitrogen to which they are attached form HET according to formula (e) where $R^{10}$ or $R^{10e}$ is optionally substituted phenyl, and the remaining of $R^{10}$, $R^{10a}$, $R^{10c}$, $R^{10d}$, $R^{10e}$, and $R^{10f}$ are hydrogen; and all other groups are as defined in the Summary of the Invention for a Compound of Formula I or as defined in any one of embodiments B, B1, B1a, B2, B2a, B3, (C)-C(8), and (C8a).

Embodiments (K1)

In another embodiment, the Compound of Formula is according to Formula I where $R^1$ is phenyl substituted with one or two $R^6$ groups independently which are independently nitro, —$NR^8R^{8a}$, —$C(O)NR^8R^{8a}$, —$NR^8C(O)OR^9$, or heteroaryl optionally substituted with 1, 2, or 3 $R^{14}$; or $R^1$ is heteroaryl optionally substituted with one, two, or three $R^7$;

$R^2$ is —$NR^3R^4$ where $R^3$ and $R^4$ together with the nitrogen to which they are attached form HET according to formula (d), (e), or (f):

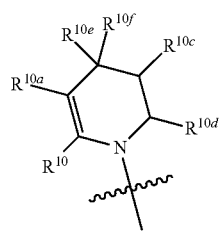

(d)

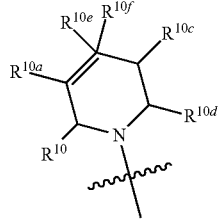

(e)

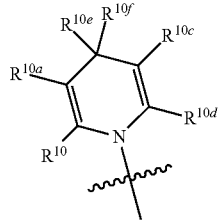

(f)

where $R^{10}$, $R^{10a}$, $R^{10c}$, $R^{10d}$, $R^{10e}$, and $R^{10f}$ are independently hydrogen, hydroxy, alkyl, haloalkyl, or optionally substituted phenyl; or, in formula (d) or (f), $R^{10e}$ and $R^{10f}$ together form oxo;

each $R^7$, when present, is independently alkyl, —$NR^8R^{8a}$, —$C(O)NR^8R^{8a}$, —$NR^8C(O)OR^9$, or —$NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and each $R^{14}$, when present, is halo, alkyl, or alkoxycarbonyl.

In another embodiment (L), the Compound is according to Formula I(e)

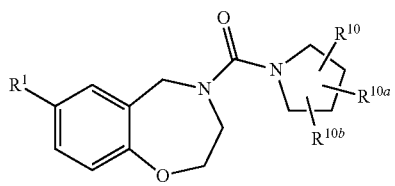

I(e)

where $R^{10}$, $R^{10a}$, $R^{10b}$, and all other groups are independently as defined in the Summary of the Invention for a Compound of Formula I or as defined in any one of embodiments B, B1, B1a, B2, B2a, B3, (C)-C(8), and (C8a).

In another embodiment (M), the Compound of Formula I is according to Formula I(f)

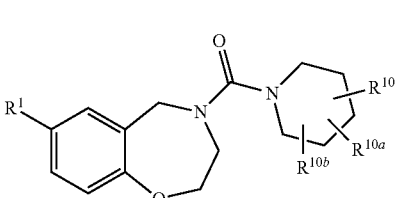

I(f)

where $R^{10}$, $R^{10a}$, $R^{10b}$, and all other groups are independently as defined in the Summary of the Invention for a Compound of Formula I or as defined in any one of embodiments B, B1, B1a, B2, B2a, B3, (C)-C(8), and (C8a).

In another embodiment (N), the Compound of Formula I is according to Formula I(g)

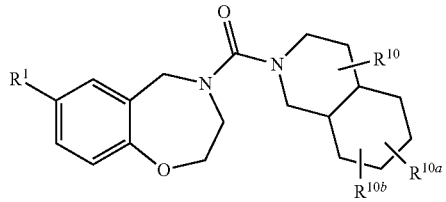

I(g)

where $R^{10}$, $R^{10a}$, and $R^{10b}$, and all other groups are independently as defined in the Summary of the Invention for a Compound of Formula I or as defined in any one of embodiments B, B1, B1a, B2, B2a, B3, (C)-C(8), and (C8a).

In another embodiment (P), the Compound of Formula I is according to Formula I(h)

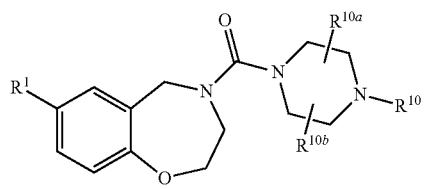

I(h)

where $R^{10}$, $R^{10a}$, $R^{10b}$, and all other groups are independently as defined in the Summary of the Invention for a Compound of Formula I or as defined in any one of embodiments B, B1, B1a, B2, B2a, B3, (C)-C(8), and (C8a).

In another embodiment (O), the Compound of Formula I is according to Formula I(p)

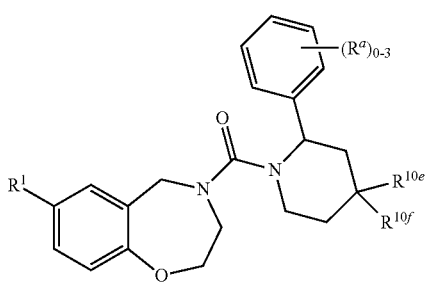

I(p)

where each $R^a$, when $R^a$ is present, is independently alkyl, alkoxy, or halo; and $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a).

In another embodiment (Q1), the Compound of Formula I is according to Formula I(n)

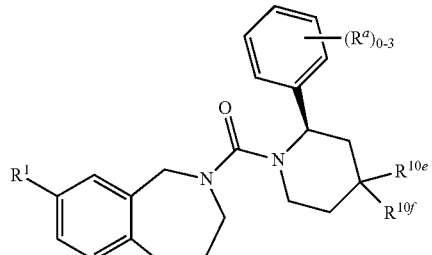

I(n)

where each $R^a$, when $R^a$ is present, is independently alkyl, alkoxy, or halo; and $R^{10e}$, $R^{10f}$, and all other groups are independently as defined in the Summary of the Invention for a Compound of Formula I or as defined in any one of embodiments B, B1, B1a, B2, B2a, B3, (C)-C(8), and (C8a).

In another embodiment, any one of the Compound of Formulae I, I(a), I(b), I(c), I(d), I(e), I(f), I(g), I(h), I(p), and I(n) is that where $R^1$ and/or $R^2$ are independently as defined in any one of the above embodiments.

Embodiment (U)

Another embodiment provides a pharmaceutical composition which comprises 1) a compound, as a single stereoisomer or mixture of isomers thereof, according to any one of Formula I, (I(a), I(b), I(c), I(d), I(e), I(f), I(g), I(h), I(p), and I(n) or according to any one of the above embodiments or a compound in Table 1, optionally as a pharmaceutically acceptable salt thereof, and 2) a pharmaceutically acceptable carrier, excipient, and/or diluent thereof.

Embodiment (V)

Another embodiment is a method of treating disease, disorder, or syndrome where the disease is associated with uncontrolled, abnormal, and/or unwanted cellular activities effected directly or indirectly by PI3K and/or mTOR which method comprises administering to a human in need thereof a therapeutically effective amount of a Compound of any of Formula I, (I(a), I(b), I(c), I(d), I(e), I(f), I(g), I(h), I(p), and I(n), a Compound of any one of the above embodiments, or a Compound from Table 1, optionally as a pharmaceutically acceptable salt or pharmaceutical composition thereof. In another embodiment of embodiment (V), the disease is cancer. In another embodiment of embodiment (V), the disease is cancer and the Compound is of Formula I(a) or a Compound from Table 1.

Embodiment (W)

Another embodiment is directed to a method of treating a disease, disorder, or syndrome which method comprises administering to a patient a therapeutically effective amount of a Compound of any of Formula I, (I(a), I(b), I(c), I(d), I(e), I(f), I(g), I(h), I(p), and I(n), a Compound of any one of the above embodiments, or a Compound from Table 1, optionally as a pharmaceutically acceptable salt thereof, or a pharmaceutical composition comprising a therapeutically effective amount of a Compound of Formula I, (I(a), I(b), I(c), I(d), I(e), I(f), I(g), I(h), I(p), and I(n), a Compound of any one of the above embodiments, or a Compound from Table 1, and a pharmaceutically acceptable carrier, excipient, or diluent. In another embodiment of embodiment (W), the disease is cancer. In another embodiment of embodiment (W), the disease is cancer and the Compound is of Formula I(a) or a Compound from Table 1.

In another embodiment of any of the embodiments of Embodiment (W), the cancer is breast cancer, mantle cell lymphoma, renal cell carcinoma, acute myelogenous leukemia, chronic myelogenous leukemia, NPM/ALK-transformed anaplastic large cell lymphoma, diffuse large B cell lymphoma, rhabdomyosarcoma, ovarian cancer, endometrial cancer, cervical cancer, non small cell lung carcinoma, small cell lung carcinoma, adenocarcinoma, colon cancer, rectal cancer, gastric carcinoma, hepatocellular carcinoma, melanoma, pancreatic cancer, prostate carcinoma, thyroid carcinoma, anaplastic large cell lymphoma, hemangioma, glioblastoma, or head and neck cancer.

Representative Compounds

Representative compounds of Formula I are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Specifically, names in Table 1 were generated using ACD/Labs naming software 8.00 release, product version 8.08 or higher.

TABLE 1

| Entry No. | Structure | Name |
|---|---|---|
| 1 | 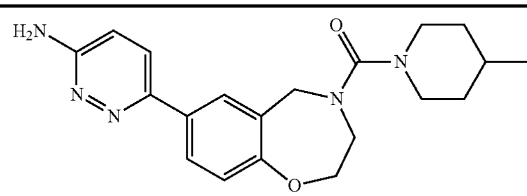 | 6-{4-[(4-methylpiperidin-1-yl)carbonyl]-2,3,4,5-tetrahydro-1,4-benzoxazepin-7-yl}pyridazin-3-amine |
| 2 | 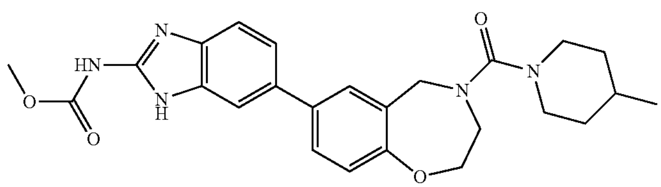 | methyl (6-{4-[(4-methylpiperidin-1-yl)carbonyl]-2,3,4,5-tetrahydro-1,4-benzoxazepin-7-yl}-1H-benzimidazol-2-yl)carbamate |
| 3 | 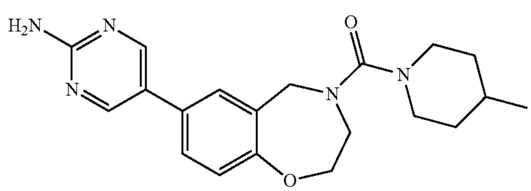 [SMILES: CC1CCN(C(=O)N2CCOc3ccc(-c4cnc(N)nc4)cc3C2)CC1] | 5-{4-[(4-methylpiperidin-1-yl)carbonyl]-2,3,4,5-tetrahydro-1,4-benzoxazepin-7-yl}pyrimidin-2-amine |
| 4 | 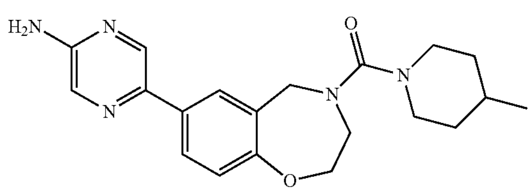 [SMILES: CC1CCN(C(=O)N2CCOc3ccc(-c4cnc(N)cn4)cc3C2)CC1] | 5-{4-[(4-methylpiperidin-1-yl)carbonyl]-2,3,4,5-tetrahydro-1,4-benzoxazepin-7-yl}pyrazin-2-amine |
| 5 | 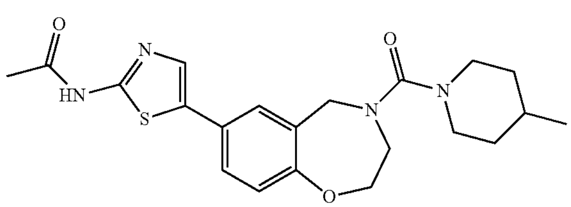 [SMILES: CC(=O)Nc1ncc(-c2ccc3c(c2)CN(C(=O)N2CCC(C)CC2)CCO3)s1] | N-(5-{4-[(4-methylpiperidin-1-yl)carbonyl]-2,3,4,5-tetrahydro-1,4-benzoxazepin-7-yl}-1,3-thiazol-2-yl)acetamide |
| 6 | 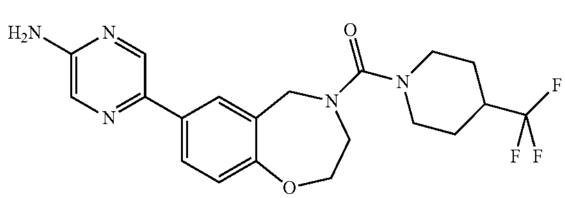 [SMILES: Nc1cnc(-c2ccc3c(c2)CN(C(=O)N2CCC(C(F)(F)F)CC2)CCO3)cn1] | 5-(4-{[4-(trifluoromethyl)piperidin-1-yl]carbonyl}-2,3,4,5-tetrahydro-1,4-benzoxazepin-7-yl)pyrazin-2-amine |

TABLE 1-continued

| Entry No. | Structure | Name |
|---|---|---|
| 7 | 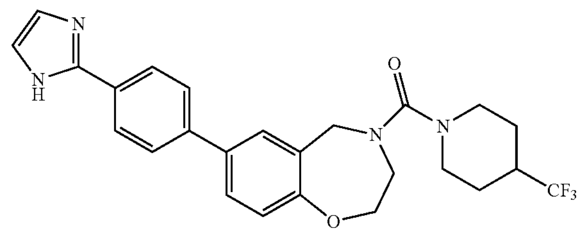 [SMILES: O=C(N1CCC(C(F)(F)F)CC1)N1CCOc2ccc(-c3ccc(-c4ncc[nH]4)cc3)cc2C1] | 7-[4-(1H-imidazol-2-yl)phenyl]-4-{[4-(trifluoromethyl)piperidin-1-yl]carbonyl}-2,3,4,5-tetrahydro-1,4-benzoxazepine |
| 8 | 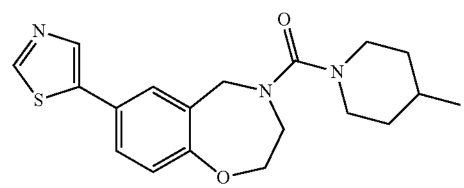 [SMILES: CC1CCN(C(=O)N2CCOc3ccc(-c4cncs4)cc3C2)CC1] | 4-[(4-methylpiperidin-1-yl)carbonyl]-7-(1,3-thiazol-5-yl)-2,3,4,5-tetrahydro-1,4-benzoxazepine |
| 9 | 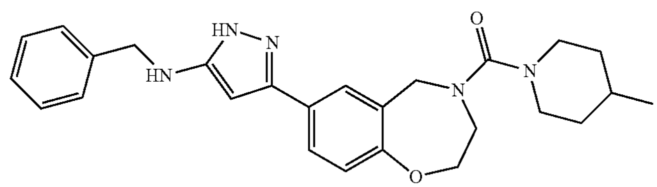 [SMILES: CC1CCN(C(=O)N2CCOc3ccc(-c4cc(NCc5ccccc5)[nH]n4)cc3C2)CC1] | 3-{4-[(4-methylpiperidin-1-yl)carbonyl]-2,3,4,5-tetrahydro-1,4-benzoxazepin-7-yl}-N-(phenylmethyl)-1H-pyrazol-5-amine |
| 10 | 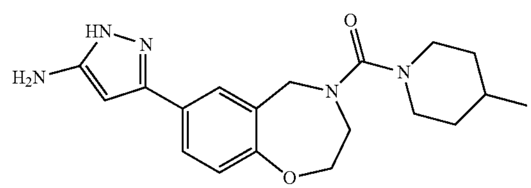 [SMILES: CC1CCN(C(=O)N2CCOc3ccc(-c4cc(N)[nH]n4)cc3C2)CC1] | 3-{4-[(4-methylpiperidin-1-yl)carbonyl]-2,3,4,5-tetrahydro-1,4-benzoxazepin-7-yl}-1H-pyrazol-5-amine |
| 11 | 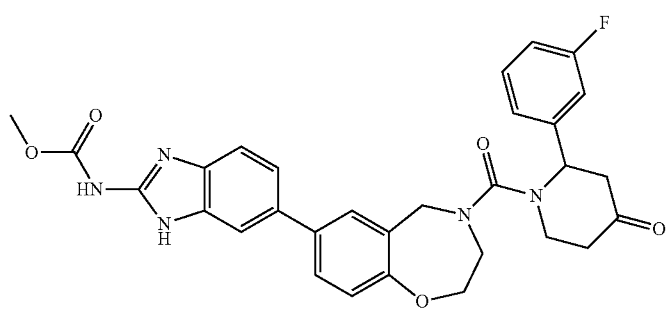 [SMILES: COC(=O)Nc1nc2ccc(-c3ccc4c(c3)CN(C(=O)N3CCC(=O)CC3c3cccc(F)c3)CCO4)cc2[nH]1] | methyl [6-(4-{[2-(3-fluorophenyl)-4-oxopiperidin-1-yl]carbonyl}-2,3,4,5-tetrahydro-1,4-benzoxazepin-7-yl)-1H-benzimidazol-2-yl]carbamate |
| 12 | 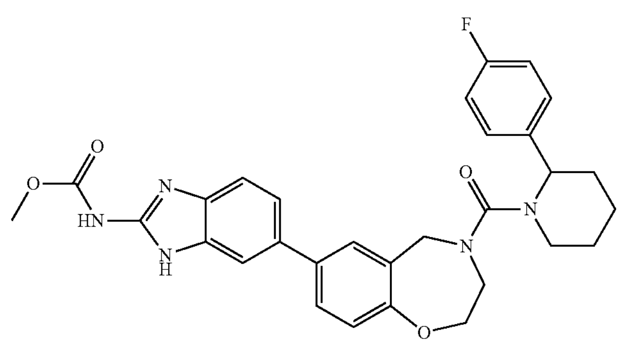 [SMILES: COC(=O)Nc1nc2ccc(-c3ccc4c(c3)CN(C(=O)N3CCCCC3c3ccc(F)cc3)CCO4)cc2[nH]1] | methyl [6-(4-{[2-(4-fluorophenyl)piperidin-1-yl]carbonyl}-2,3,4,5-tetrahydro-1,4-benzoxazepin-7-yl)-1H-benzimidazol-2-yl]carbamate |

TABLE 1-continued

| Entry No. | Structure | Name |
|---|---|---|
| 13 | 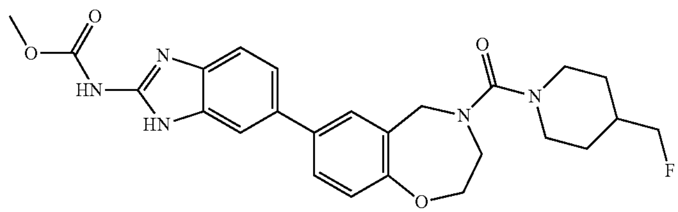 [SMILES: COC(=O)Nc1nc2ccc(-c3ccc4c(c3)CN(C(=O)N3CCC(CF)CC3)CCO4)cc2[nH]1] | methyl [6-(4-{[4-(fluoromethyl)piperidin-1-yl]carbonyl}-2,3,4,5-tetrahydro-1,4-benzoxazepin-7-yl)-1H-benzimidazol-2-yl]carbamate |
| 14 | 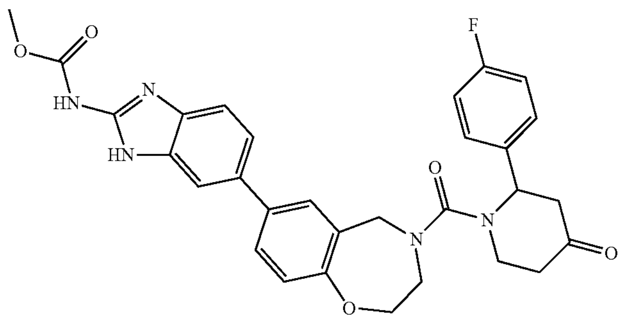 [SMILES: COC(=O)Nc1nc2ccc(-c3ccc4c(c3)CN(C(=O)N3CCC(=O)CC3c3ccc(F)cc3)CCO4)cc2[nH]1] | methyl [6-(4-{[2-(4-fluorophenyl)-4-oxopiperidin-1-yl]carbonyl}-2,3,4,5-tetrahydro-1,4-benzoxazepin-7-yl)-1H-benzimidazol-2-yl]carbamate |
| 15 | 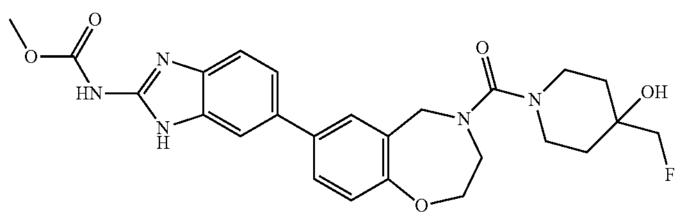 [SMILES: COC(=O)Nc1nc2ccc(-c3ccc4c(c3)CN(C(=O)N3CCC(O)(CF)CC3)CCO4)cc2[nH]1] | methyl [6-(4-{[4-(fluoromethyl)-4-hydroxypiperidin-1-yl]carbonyl}-2,3,4,5-tetrahydro-1,4-benzoxazepin-7-yl)-1H-benzimidazol-2-yl]carbamate |
| 16 | 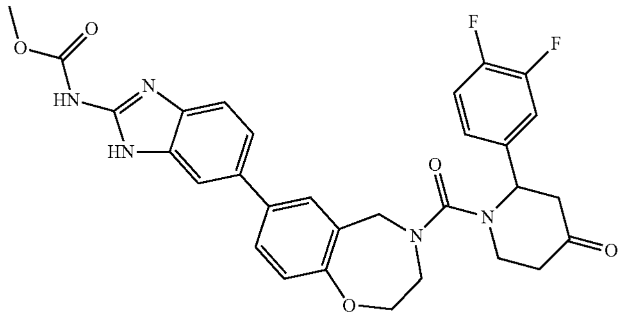 [SMILES: COC(=O)Nc1nc2ccc(-c3ccc4c(c3)CN(C(=O)N3CCC(=O)CC3c3ccc(F)c(F)c3)CCO4)cc2[nH]1] | methyl [6-(4-{[2-(3,4-difluorophenyl)-4-oxopiperidin-1-yl]carbonyl}-2,3,4,5-tetrahydro-1,4-benzoxazepin-7-yl)-1H-benzimidazol-2-yl]carbamate |
| 17 | 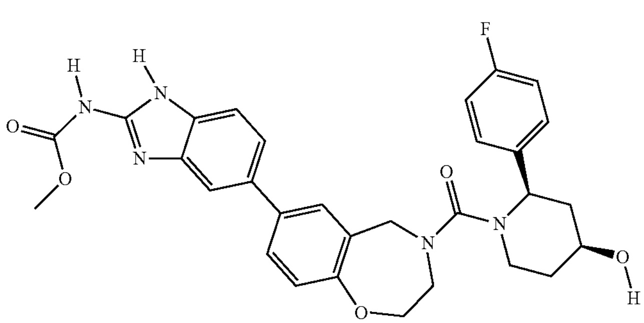 [SMILES: COC(=O)Nc1nc2cc(-c3ccc4c(c3)CN(C(=O)N3CC[C@H](O)C[C@@H]3c3ccc(F)cc3)CCO4)ccc2[nH]1] | (±)-methyl [5-(4-{[(2R,4S)-2-(4-fluorophenyl)-4-hydroxypiperidin-1-yl]carbonyl}-2,3,4,5-tetrahydro-1,4-benzoxazepin-7-yl)-1H-benzimidazol-2-yl]carbamate |

TABLE 1-continued

| Entry No. | Structure | Name |
|---|---|---|
| 18 | 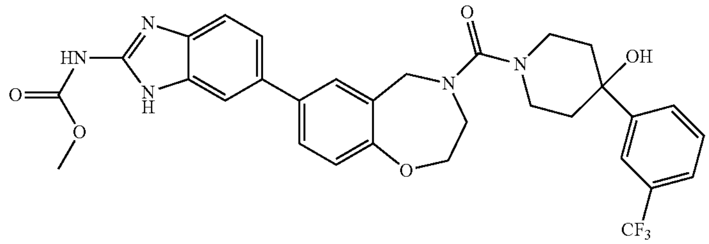 [SMILES: COC(=O)Nc1nc2ccc(-c3ccc4c(c3)CN(C(=O)N3CCC(O)(c5cccc(C(F)(F)F)c5)CC3)CCO4)cc2[nH]1] | methyl {6-[4-({4-hydroxy-4-[3-(trifluoromethyl)phenyl]piperidin-1-yl}carbonyl)-2,3,4,5-tetrahydro-1,4-benzoxazepin-7-yl]-1H-benzimidazol-2-yl}carbamate |
| 19 | 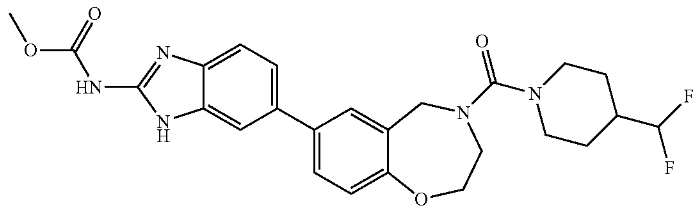 [SMILES: COC(=O)Nc1nc2ccc(-c3ccc4c(c3)CN(C(=O)N3CCC(C(F)F)CC3)CCO4)cc2[nH]1] | methyl [6-(4-{[4-(difluoromethyl)piperidin-1-yl]carbonyl}-2,3,4,5-tetrahydro-1,4-benzoxazepin-7-yl)-1H-benzimidazol-2-yl]carbamate |
| 20 | 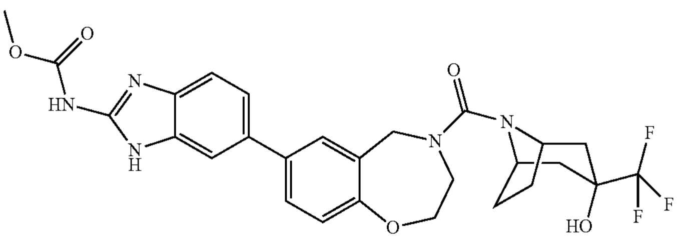 [SMILES: COC(=O)Nc1nc2ccc(-c3ccc4c(c3)CN(C(=O)N3C5CCC3CC(O)(C(F)(F)F)C5)CCO4)cc2[nH]1] | methyl [6-(4-{[3-(endo)-hydroxy-3-(trifluoromethyl)-8-azabicyclo[3.2.1]oct-8-yl]carbonyl}-2,3,4,5-tetrahydro-1,4-benzoxazepin-7-yl)-1H-benzimidazol-2-yl]carbamate |
| 21 | 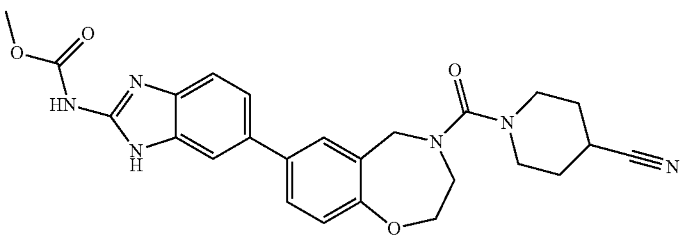 [SMILES: COC(=O)Nc1nc2ccc(-c3ccc4c(c3)CN(C(=O)N3CCC(C#N)CC3)CCO4)cc2[nH]1] | methyl (6-{4-[(4-cyanopiperidin-1-yl)carbonyl]-2,3,4,5-tetrahydro-1,4-benzoxazepin-7-yl}-1H-benzimidazol-2-yl)carbamate |
| 22 | 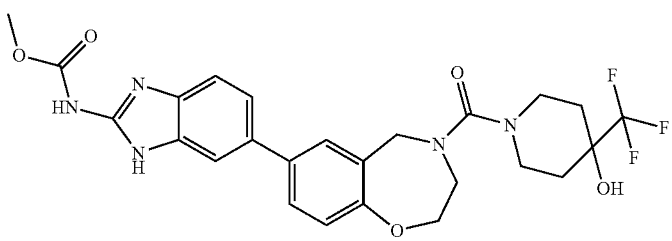 [SMILES: COC(=O)Nc1nc2ccc(-c3ccc4c(c3)CN(C(=O)N3CCC(O)(C(F)(F)F)CC3)CCO4)cc2[nH]1] | methyl [6-(4-{[4-hydroxy-4-(trifluoromethyl)piperidin-1-yl]carbonyl}-2,3,4,5-tetrahydro-1,4-benzoxazepin-7-yl)-1H-benzimidazol-2-yl]carbamate |
| 23 | 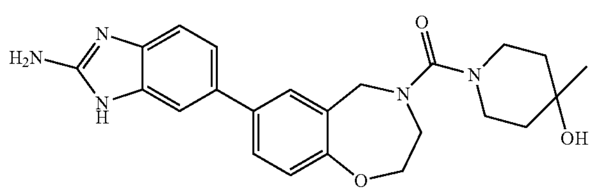 [SMILES: CC1(O)CCN(C(=O)N2CCOc3ccc(-c4ccc5nc(N)[nH]c5c4)cc3C2)CC1] | 1-{[7-(2-amino-1H-benzimidazol-6-yl)-2,3-dihydro-1,4-benzoxazepin-4(5H)-yl]carbonyl}-4-methylpiperidin-4-ol |
| 24 | 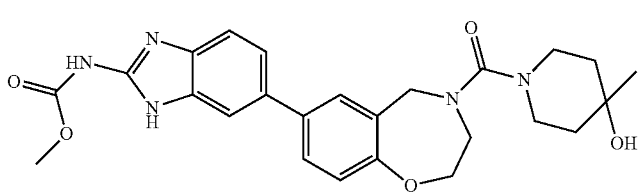 [SMILES: COC(=O)Nc1nc2ccc(-c3ccc4c(c3)CN(C(=O)N3CCC(C)(O)CC3)CCO4)cc2[nH]1] | methyl (6-{4-[(4-hydroxy-4-methylpiperidin-1-yl)carbonyl]-2,3,4,5-tetrahydro-1,4-benzoxazepin-7-yl}-1H-benzimidazol-2-yl)carbamate |

TABLE 1-continued

| Entry No. | Structure | Name |
|---|---|---|
| 25 | 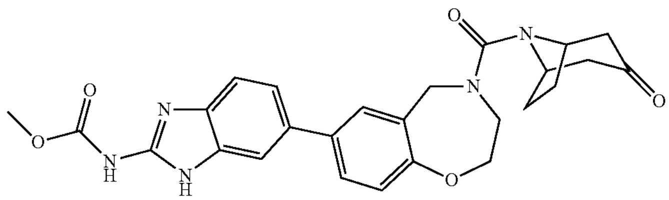 [SMILES: COC(=O)Nc1nc2ccc(-c3ccc4c(c3)CN(C(=O)N3C5CCC3CC(=O)C5)CCO4)cc2[nH]1] | methyl (6-{4-[(3-oxo-8-azabicyclo[3.2.1]oct-8-yl)carbonyl]-2,3,4,5-tetrahydro-1,4-benzoxazepin-7-yl}-1H-benzimidazol-2-yl)carbamate |
| 26 | 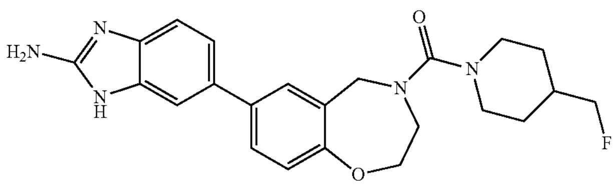 [SMILES: Nc1nc2ccc(-c3ccc4c(c3)CN(C(=O)N3CCC(CF)CC3)CCO4)cc2[nH]1] | 6-(4-{[4-(fluoromethyl)piperidin-1-yl]carbonyl}-2,3,4,5-tetrahydro-1,4-benzoxazepin-7-yl)-1H-benzimidazol-2-amine |
| 27 | 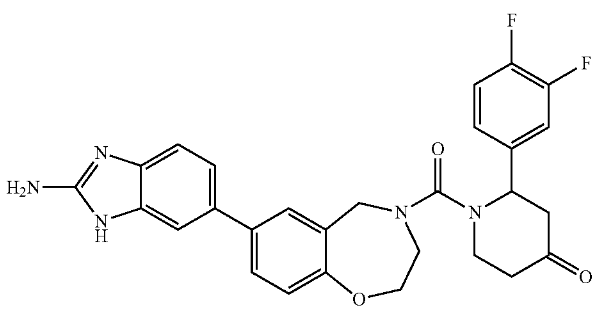 [SMILES: Nc1nc2ccc(-c3ccc4c(c3)CN(C(=O)N3CCC(=O)CC3c3ccc(F)c(F)c3)CCO4)cc2[nH]1] | 1-{[7-(2-amino-1H-benzimidazol-6-yl)-2,3-dihydro-1,4-benzoxazepin-4(5H)-yl]carbonyl}-2-(3,4-difluorophenyl)piperidin-4-one |
| 28 | 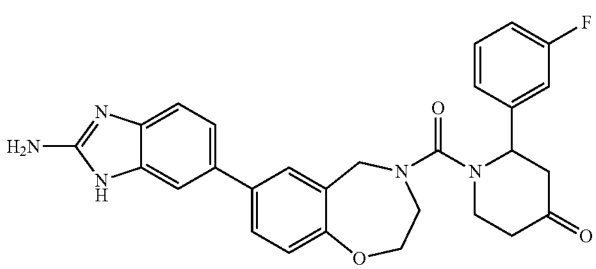 [SMILES: Nc1nc2ccc(-c3ccc4c(c3)CN(C(=O)N3CCC(=O)CC3c3cccc(F)c3)CCO4)cc2[nH]1] | 1-{[7-(2-amino-1H-benzimidazol-6-yl)-2,3-dihydro-1,4-benzoxazepin-4(5H)-yl]carbonyl}-2-(3-fluorophenyl)piperidin-4-one |
| 29 | 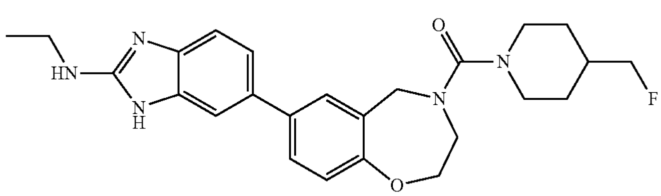 [SMILES: CCNc1nc2ccc(-c3ccc4c(c3)CN(C(=O)N3CCC(CF)CC3)CCO4)cc2[nH]1] | N-ethyl-6-(4-{[4-(fluoromethyl)piperidin-1-yl]carbonyl}-2,3,4,5-tetrahydro-1,4-benzoxazepin-7-yl)-1H-benzimidazol-2-amine |
| 30 | 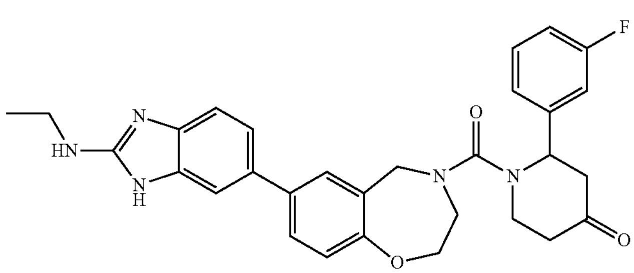 [SMILES: CCNc1nc2ccc(-c3ccc4c(c3)CN(C(=O)N3CCC(=O)CC3c3cccc(F)c3)CCO4)cc2[nH]1] | 1-({7-[2-(ethylamino)-1H-benzimidazol-6-yl]-2,3-dihydro-1,4-benzoxazepin-4(5H)-yl}carbonyl)-2-(3-fluorophenyl)piperidin-4-one |

TABLE 1-continued

| Entry No. | Name |
|---|---|
| 31 | 2-(3-fluorophenyl)-1-{[7-{2-[(2,2,2-trifluoroethyl)amino]-1H-benzimidazol-5-yl}-2,3-dihydro-1,4-benzoxazepin-4(5H)-yl]carbonyl}piperidin-4-one |
| 32 | 1-{[7-{2-[(2-fluoroethyl)amino]-1H-benzimidazol-5-yl}-2,3-dihydro-1,4-benzoxazepin-4(5H)-yl]carbonyl}-2-(3-fluorophenyl)piperidin-4-one |
| 33 | 6-(4-{[4-(1,1-difluoroethyl)piperidin-1-yl]carbonyl}-2,3,4,5-tetrahydro-1,4-benzoxazepin-7-yl)-N-ethyl-1H-benzimidazol-2-amine |
| 34 | methyl [6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-yl]carbamate |
| 35 | methyl [6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-yl]carbamate |
| 36 | methyl [6-(4-{[4-(fluoromethyl)piperidin-1-yl]carbonyl}-2,3,4,5-tetrahydro-1,4-benzoxazepin-7-yl)-1H-imidazo[4,5-b]pyridin-2-yl]carbamate |

TABLE 1-continued

| Entry No. | Structure | Name |
|---|---|---|
| 37 | 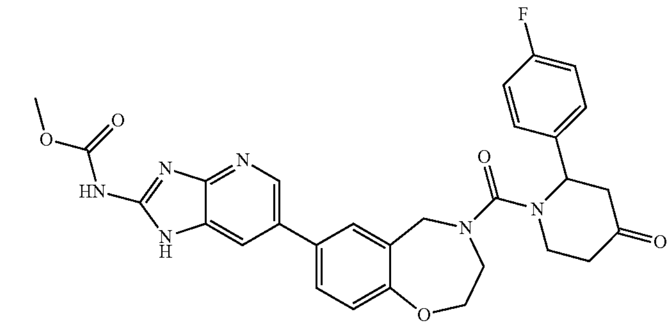 [SMILES: COC(=O)Nc1nc2ncc(-c3ccc4c(c3)CN(C(=O)N3CCC(=O)CC3c3ccc(F)cc3)CCO4)cc2[nH]1] | methyl [6-(4-{[2-(4-fluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate |
| 38 | 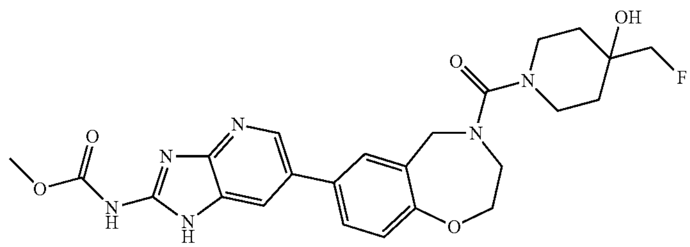 [SMILES: COC(=O)Nc1nc2ncc(-c3ccc4c(c3)CN(C(=O)N3CCC(O)(CF)CC3)CCO4)cc2[nH]1] | methyl [6-(4-{[4-(fluoromethyl)-4-hydroxypiperidin-1-yl]carbonyl}-2,3,4,5-tetrahydro-1,4-benzoxazepin-7-yl)-1H-imidazo[4,5-b]pyridin-2-yl]carbamate |
| 39 | 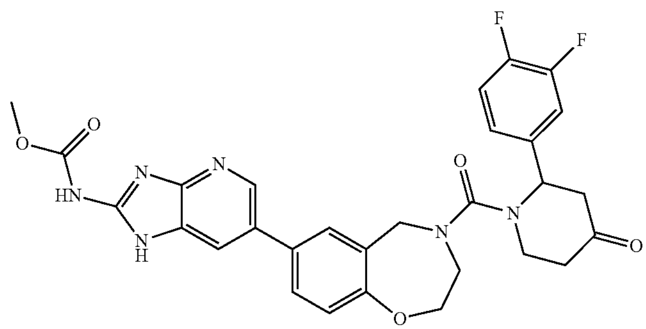 [SMILES: COC(=O)Nc1nc2ncc(-c3ccc4c(c3)CN(C(=O)N3CCC(=O)CC3c3ccc(F)c(F)c3)CCO4)cc2[nH]1] | methyl [6-(4-{[2-(3,4-difluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate |
| 40 | 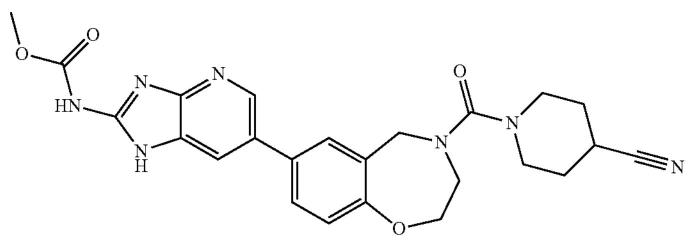 [SMILES: COC(=O)Nc1nc2ncc(-c3ccc4c(c3)CN(C(=O)N3CCC(C#N)CC3)CCO4)cc2[nH]1] | methyl (6-{4-[(4-cyanopiperidin-1-yl)carbonyl]-2,3,4,5-tetrahydro-1,4-benzoxazepin-7-yl}-1H-imidazo[4,5-b]pyridin-2-yl)carbamate |
| 41 | 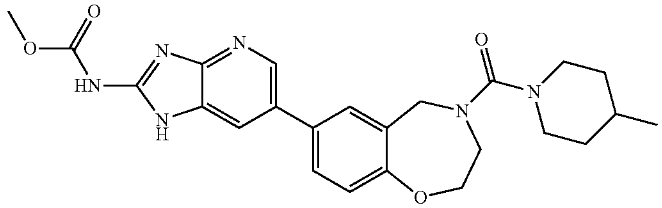 | methyl (6-{4-[(4-methylpiperidin-1-yl)carbonyl]-2,3,4,5-tetrahydro-1,4-benzoxazepin-7-yl}-1H-imidazo[4,5-b]pyridin-2-yl)carbamate |
| 42 | 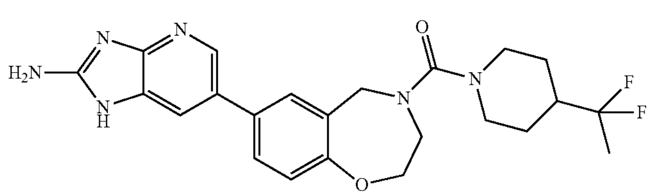 [SMILES: CC(F)(F)C1CCN(C(=O)N2CCOc3ccc(-c4cnc5nc(N)[nH]c5c4)cc3C2)CC1] | 6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-amine |

TABLE 1-continued

| Entry No. | Structure | Name |
|---|---|---|
| 43 | 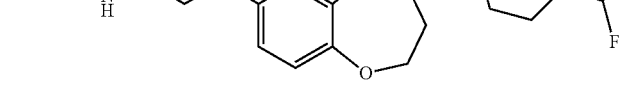 | 6-(4-{[4-(difluoromethyl)piperidin-1-yl]carbonyl}-2,3,4,5-tetrahydro-1,4-benzoxazepin-7-yl)-1H-imidazo[4,5-b]pyridin-2-amine |
| 44 | 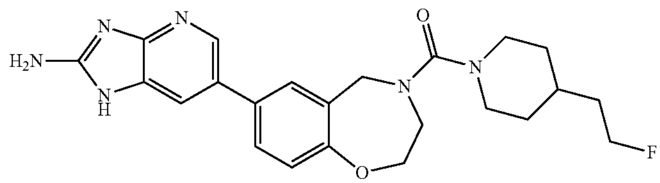 [SMILES: Nc1nc2ncc(-c3ccc4c(c3)CN(C(=O)N3CCC(CCF)CC3)CCO4)cc2[nH]1] | 6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-amine |
| 45 | 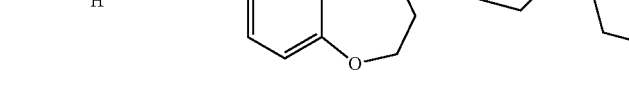 | 6-(4-{[4-(fluoromethyl)piperidin-1-yl]carbonyl}-2,3,4,5-tetrahydro-1,4-benzoxazepin-7-yl)-1H-imidazo[4,5-b]pyridin-2-amine |
| 46 | 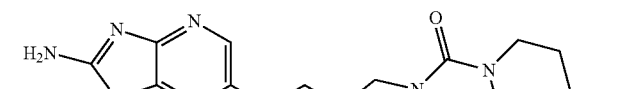 | 1-{[7-(2-amino-1H-imidazo[4,5-b]pyridin-6-yl)-2,3-dihydro-1,4-benzoxazepin-4(5H)-yl]carbonyl}piperidine-4-carbonitrile |
| 47 | 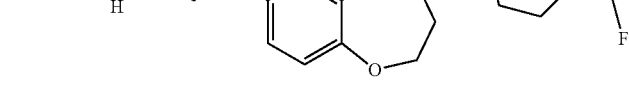 | 1-{[7-(2-amino-1H-imidazo[4,5-b]pyridin-6-yl)-2,3-dihydro-1,4-benzoxazepin-4(5H)-yl]carbonyl}piperidine-4-carboxamide |
| 48 | 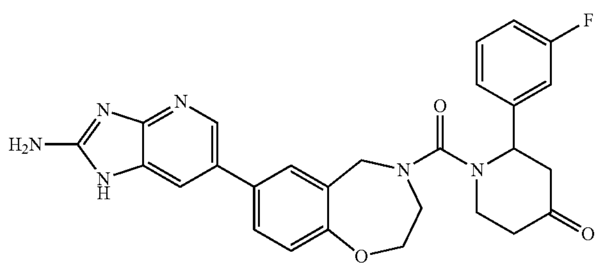 [SMILES: Nc1nc2ncc(-c3ccc4c(c3)CN(C(=O)N3CCC(=O)CC3c3cccc(F)c3)CCO4)cc2[nH]1] | 1-{[7-(2-amino-1H-imidazo[4,5-b]pyridin-6-yl)-2,3-dihydro-1,4-benzoxazepin-4(5H)-yl]carbonyl}-2-(3-fluorophenyl)piperidin-4-one |
| 49 | 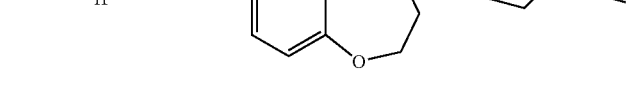 | 8-{[7-(2-amino-1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-(endo)-ol |

TABLE 1-continued

| Entry No. | Structure | Name |
|---|---|---|
| 50 | 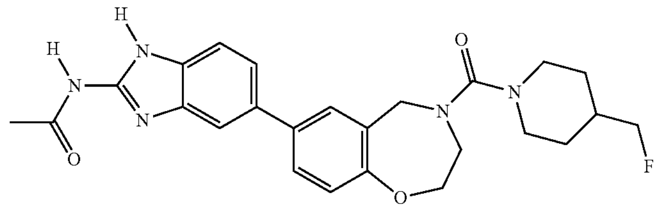 [SMILES: CC(=O)Nc1nc2cc(-c3ccc4c(c3)CN(C(=O)N3CCC(CF)CC3)CCO4)ccc2[nH]1] | N-[5-(4-{[4-(fluoromethyl)piperidin-1-yl]carbonyl}-2,3,4,5-tetrahydro-1,4-benzoxazepin-7-yl)-1H-benzimidazol-2-yl]acetamide |
| 51 | 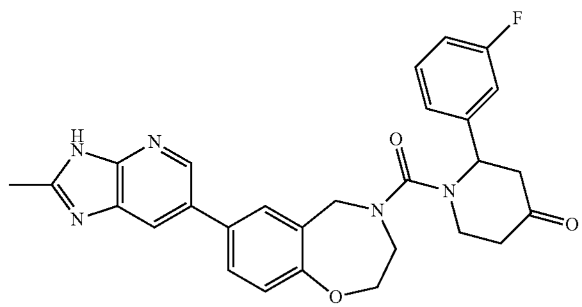 [SMILES: Cc1nc2cc(-c3ccc4c(c3)CN(C(=O)N3CCC(=O)CC3c3cccc(F)c3)CCO4)cnc2[nH]1] | 2-(3-fluorophenyl)-1-{[7-(2-methyl-3H-imidazo[4,5-b]pyridin-6-yl)-2,3-dihydro-1,4-benzoxazepin-4(5H)-yl]carbonyl}piperidin-4-one |
| 52 | 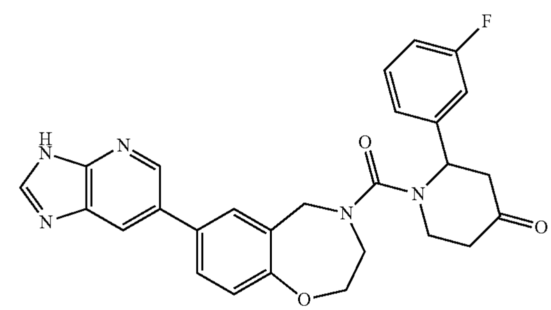 [SMILES: O=C1CCN(C(=O)N2CCOc3ccc(-c4cnc5[nH]cnc5c4)cc3C2)C(c2cccc(F)c2)C1] | 2-(3-fluorophenyl)-1-{[7-(3H-imidazo[4,5-b]pyridin-6-yl)-2,3-dihydro-1,4-benzoxazepin-4(5H)-yl]carbonyl}piperidin-4-one |
| 53 | 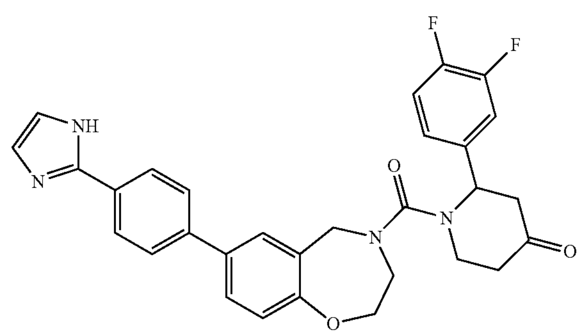 [SMILES: O=C1CCN(C(=O)N2CCOc3ccc(-c4ccc(-c5ncc[nH]5)cc4)cc3C2)C(c2ccc(F)c(F)c2)C1] | 2-(3,4-difluorophenyl)-1-({7-[4-(1H-imidazol-2-yl)phenyl]-2,3-dihydro-1,4-benzoxazepin-4(5H)-yl}carbonyl)piperidin-4-one |
| 54 | 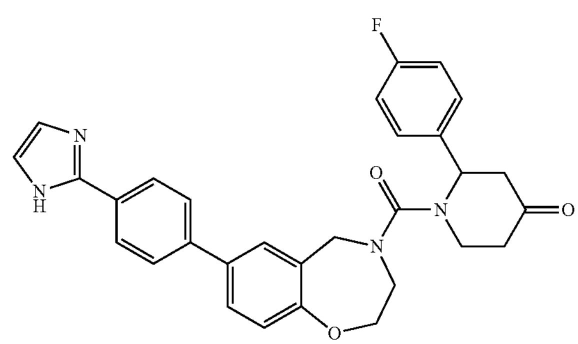 [SMILES: O=C1CCN(C(=O)N2CCOc3ccc(-c4ccc(-c5ncc[nH]5)cc4)cc3C2)C(c2ccc(F)cc2)C1] | 2-(4-fluorophenyl)-1-({7-[4-(1H-imidazol-2-yl)phenyl]-2,3-dihydro-1,4-benzoxazepin-4(5H)-yl}carbonyl)piperidin-4-one |

TABLE 1-continued

| Entry No. | Structure | Name |
|---|---|---|
| 55 | 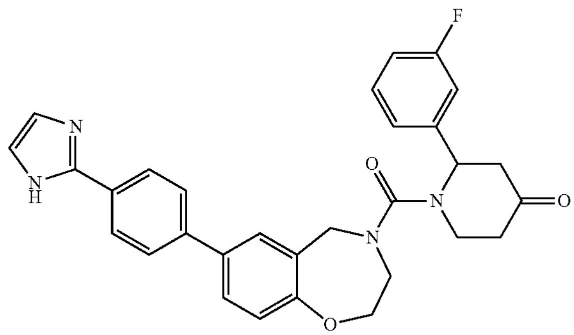 [SMILES: O=C1CCN(C(=O)N2CCOc3ccc(-c4ccc(-c5ncc[nH]5)cc4)cc3C2)C(c2cccc(F)c2)C1] | 2-(3-fluorophenyl)-1-({7-[4-(1H-imidazol-2-yl)phenyl]-2,3-dihydro-1,4-benzoxazepin-4(5H)-yl}carbonyl)piperidin-4-one |
| 56 | 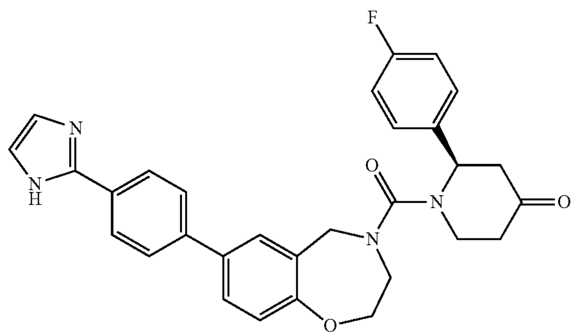 [SMILES: O=C1CCN(C(=O)N2CCOc3ccc(-c4ccc(-c5ncc[nH]5)cc4)cc3C2)[C@@H](c2ccc(F)cc2)C1] | (2R)-2-(4-fluorophenyl)-1-({7-[4-(1H-imidazol-2-yl)phenyl]-2,3-dihydro-1,4-benzoxazepin-4(5H)-yl}carbonyl)piperidin-4-one |
| 57 | 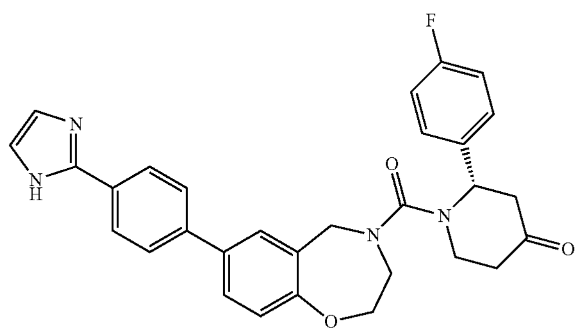 [SMILES: O=C1CCN(C(=O)N2CCOc3ccc(-c4ccc(-c5ncc[nH]5)cc4)cc3C2)[C@H](c2ccc(F)cc2)C1] | (2S)-2-(4-fluorophenyl)-1-({7-[4-(1H-imidazol-2-yl)phenyl]-2,3-dihydro-1,4-benzoxazepin-4(5H)-yl}carbonyl)piperidin-4-one |
| 58 | 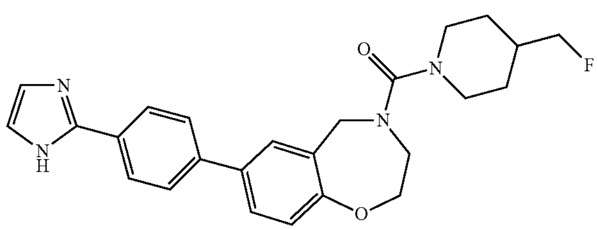 [SMILES: O=C(N1CCC(CF)CC1)N1CCOc2ccc(-c3ccc(-c4ncc[nH]4)cc3)cc2C1] | 4-{[4-(fluoromethyl)piperidin-1-yl]carbonyl}-7-[4-(1H-imidazol-2-yl)phenyl]-2,3,4,5-tetrahydro-1,4-benzoxazepine |
| 59 | 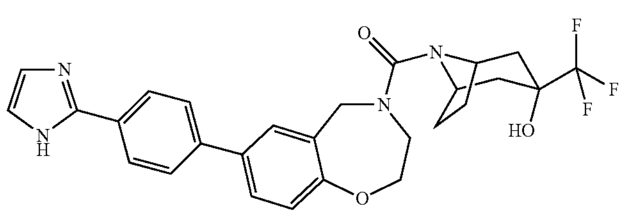 [SMILES: O=C(N1CCOc2ccc(-c3ccc(-c4ncc[nH]4)cc3)cc2C1)N1C2CCC1CC(O)(C(F)(F)F)C2] | 8-({7-[4-(1H-imidazol-2-yl)phenyl]-2,3-dihydro-1,4-benzoxazepin-4(5H)-yl}carbonyl)-3-(trifluoromethyl)-8-azabicyclo[3.2.1]octan-3-(endo)-ol |

TABLE 1-continued

| Entry No. | Structure | Name |
|---|---|---|
| 60 | 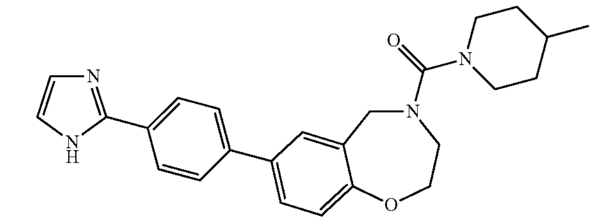 [SMILES: CC1CCN(C(=O)N2CCOc3ccc(-c4ccc(-c5ncc[nH]5)cc4)cc3C2)CC1] | 7-[4-(1H-imidazol-2-yl)phenyl]-4-[(4-methylpiperidin-1-yl)carbonyl]-2,3,4,5-tetrahydro-1,4-benzoxazepine |
| 61 | 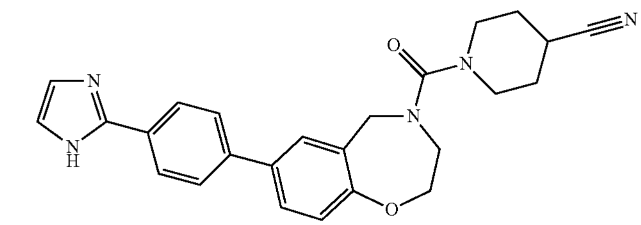 [SMILES: N#CC1CCN(C(=O)N2CCOc3ccc(-c4ccc(-c5ncc[nH]5)cc4)cc3C2)CC1] | 1-({7-[4-(1H-imidazol-2-yl)phenyl]-2,3-dihydro-1,4-benzoxazepin-4(5H)-yl}carbonyl)piperidine-4-carbonitrile |
| 62 | 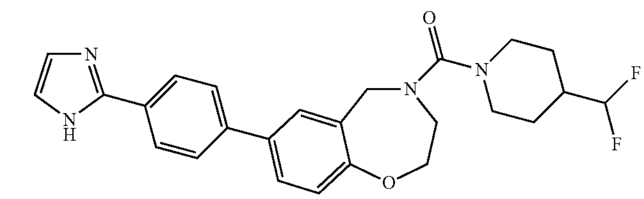 [SMILES: O=C(N1CCC(C(F)F)CC1)N1CCOc2ccc(-c3ccc(-c4ncc[nH]4)cc3)cc2C1] | 4-{[4-(difluoromethyl)piperidin-1-yl]carbonyl}-7-[4-(1H-imidazol-2-yl)phenyl]-2,3,4,5-tetrahydro-1,4-benzoxazepine |
| 63 | 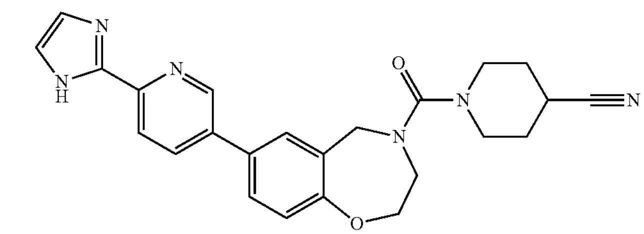 [SMILES: N#CC1CCN(C(=O)N2CCOc3ccc(-c4ccc(-c5ncc[nH]5)nc4)cc3C2)CC1] | 1-({7-[6-(1H-imidazol-2-yl)pyridin-3-yl]-2,3-dihydro-1,4-benzoxazepin-4(5H)-yl}carbonyl)piperidine-4-carbonitrile |
| 64 | 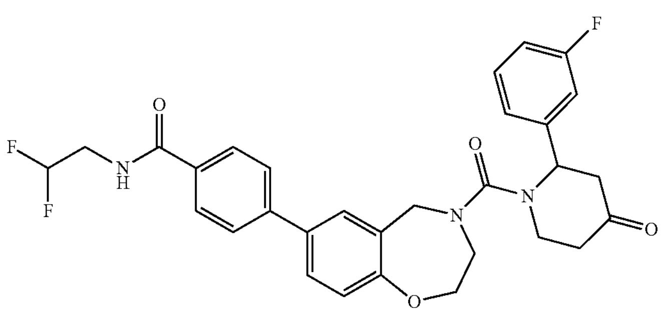 [SMILES: O=C1CCN(C(=O)N2CCOc3ccc(-c4ccc(C(=O)NCC(F)F)cc4)cc3C2)C(c2cccc(F)c2)C1] | N-(2,2-difluoroethyl)-4-(4-{[2-(3-fluorophenyl)-4-oxopiperidin-1-yl]carbonyl}-2,3,4,5-tetrahydro-1,4-benzoxazepin-7-yl)benzamide |
| 65 | 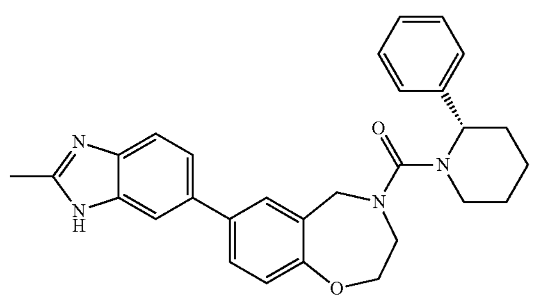 [SMILES: Cc1nc2ccc(-c3ccc4c(c3)CN(C(=O)N3CCCC[C@H]3c3ccccc3)CCO4)cc2[nH]1] | 7-(2-methyl-1H-benzimidazol-6-yl)-4-{[(2S)-2-phenylpiperidin-1-yl]carbonyl}-2,3,4,5-tetrahydro-1,4-benzoxazepine |

TABLE 1-continued

| Entry No. | Structure | Name |
|---|---|---|
| 66 | 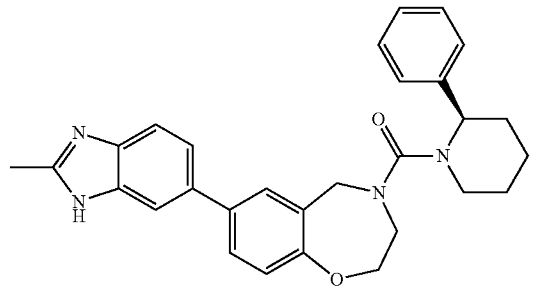 [SMILES: Cc1nc2ccc(-c3ccc4c(c3)CN(C(=O)N3CCCC[C@@H]3c3ccccc3)CCO4)cc2[nH]1] | 7-(2-methyl-1H-benzimidazol-6-yl)-4-{[(2R)-2-phenylpiperidin-1-yl]carbonyl}-2,3,4,5-tetrahydro-1,4-benzoxazepine |
| 67 | 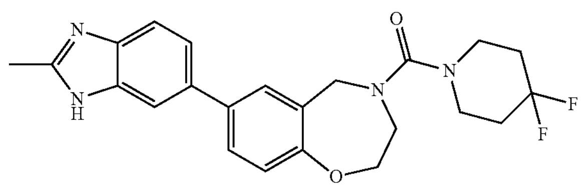 [SMILES: Cc1nc2ccc(-c3ccc4c(c3)CN(C(=O)N3CCC(F)(F)CC3)CCO4)cc2[nH]1] | 4-[(4,4-difluoropiperidin-1-yl)carbonyl]-7-(2-methyl-1H-benzimidazol-6-yl)-2,3,4,5-tetrahydro-1,4-benzoxazepine |
| 68 | 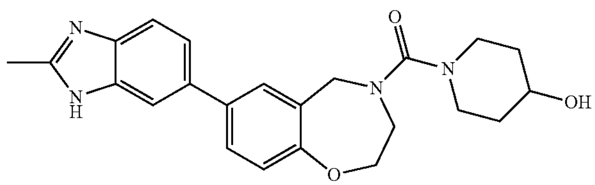 [SMILES: Cc1nc2ccc(-c3ccc4c(c3)CN(C(=O)N3CCC(O)CC3)CCO4)cc2[nH]1] | 1-{[7-(2-methyl-1H-benzimidazol-6-yl)-2,3-dihydro-1,4-benzoxazepin-4(5H)-yl]carbonyl}piperidin-4-ol |
| 69 | 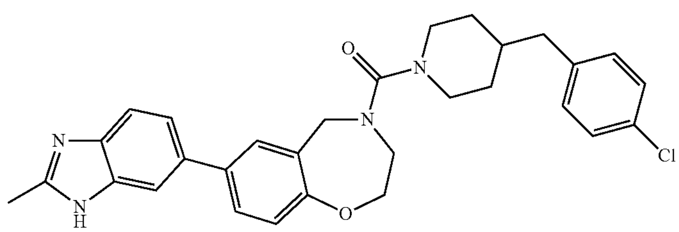 [SMILES: Cc1nc2ccc(-c3ccc4c(c3)CN(C(=O)N3CCC(Cc5ccc(Cl)cc5)CC3)CCO4)cc2[nH]1] | 4-({4-[(4-chlorophenyl)methyl]piperidin-1-yl}carbonyl)-7-(2-methyl-1H-benzimidazol-6-yl)-2,3,4,5-tetrahydro-1,4-benzoxazepine |
| 70 | 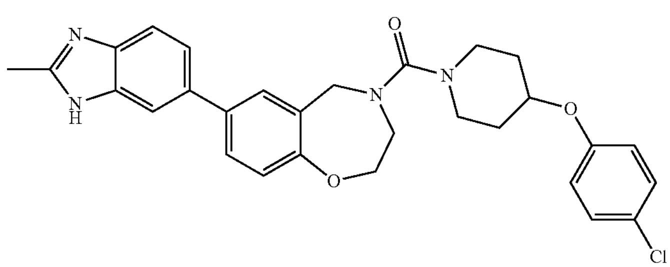 [SMILES: Cc1nc2ccc(-c3ccc4c(c3)CN(C(=O)N3CCC(Oc5ccc(Cl)cc5)CC3)CCO4)cc2[nH]1] | 4-({4-[(4-chlorophenyl)oxy]piperidin-1-yl}carbonyl)-7-(2-methyl-1H-benzimidazol-6-yl)-2,3,4,5-tetrahydro-1,4-benzoxazepine |
| 71 | 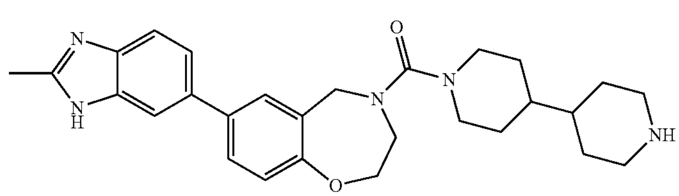 [SMILES: Cc1nc2ccc(-c3ccc4c(c3)CN(C(=O)N3CCC(C5CCNCC5)CC3)CCO4)cc2[nH]1] | 1-{[7-(2-methyl-1H-benzimidazol-6-yl)-2,3-dihydro-1,4-benzoxazepin-4(5H)-yl]carbonyl}-4,4-bipiperidine |
| 72 | 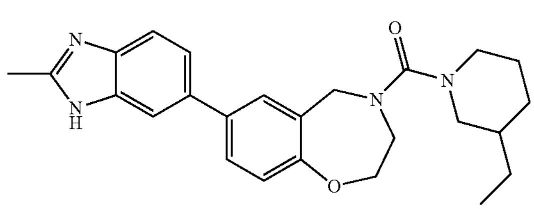 [SMILES: CCC1CCCN(C(=O)N2CCOc3ccc(-c4ccc5nc(C)[nH]c5c4)cc3C2)C1] | 4-[(3-ethylpiperidin-1-yl)carbonyl]-7-(2-methyl-1H-benzimidazol-6-yl)-2,3,4,5-tetrahydro-1,4-benzoxazepine |

TABLE 1-continued

| Entry No. | Structure | Name |
|---|---|---|
| 73 | 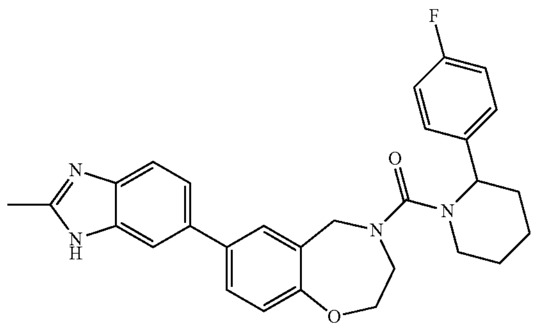 [SMILES: Cc1nc2ccc(-c3ccc4c(c3)CN(C(=O)N3CCCCC3c3ccc(F)cc3)CCO4)cc2[nH]1] | 4-{[2-(4-fluorophenyl)piperidin-1-yl]carbonyl}-7-(2-methyl-1H-benzimidazol-6-yl)-2,3,4,5-tetrahydro-1,4-benzoxazepine |
| 74 | 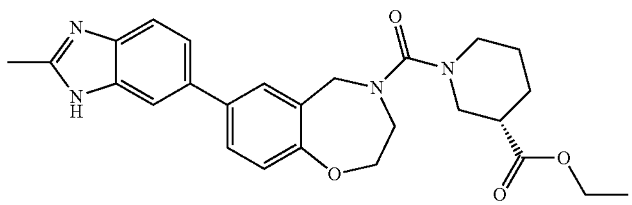 [SMILES: CCOC(=O)[C@H]1CCCN(C(=O)N2CCOc3ccc(-c4ccc5nc(C)[nH]c5c4)cc3C2)C1] | ethyl (3S)-1-{[7-(2-methyl-1H-benzimidazol-6-yl)-2,3-dihydro-1,4-benzoxazepin-4(5H)-yl]carbonyl}piperidine-3-carboxylate |
| 75 | 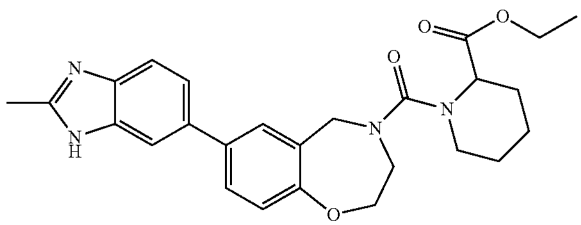 [SMILES: CCOC(=O)C1CCCCN1C(=O)N1CCOc2ccc(-c3ccc4nc(C)[nH]c4c3)cc2C1] | ethyl 1-{[7-(2-methyl-1H-benzimidazol-6-yl)-2,3-dihydro-1,4-benzoxazepin-4(5H)-yl]carbonyl}piperidine-2-carboxylate |
| 76 | 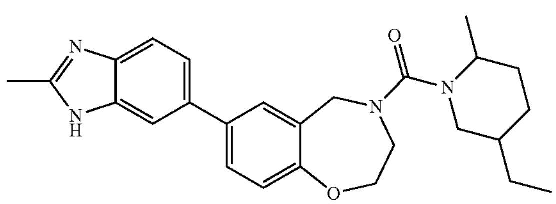 [SMILES: CCC1CCC(C)N(C(=O)N2CCOc3ccc(-c4ccc5nc(C)[nH]c5c4)cc3C2)C1] | 4-[(5-ethyl-2-methylpiperidin-1-yl)carbonyl]-7-(2-methyl-1H-benzimidazol-6-yl)-2,3,4,5-tetrahydro-1,4-benzoxazepine |
| 77 | 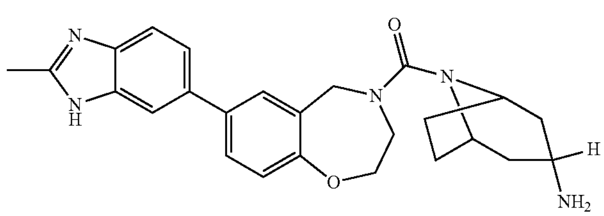 [SMILES: Cc1nc2ccc(-c3ccc4c(c3)CN(C(=O)N3C5CCC3CC(N)C5)CCO4)cc2[nH]1] | 8-{[7-(2-methyl-1H-benzimidazol-6-yl)-2,3-dihydro-1,4-benzoxazepin-4(5H)-yl]carbonyl}-8-azabicyclo[3.2.1]octan-3-(endo)-amine |
| 78 | 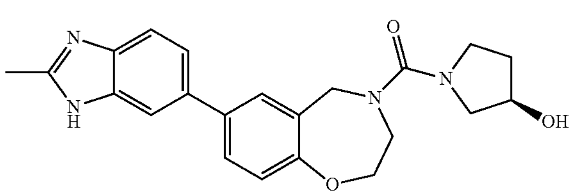 [SMILES: Cc1nc2ccc(-c3ccc4c(c3)CN(C(=O)N3CC[C@@H](O)C3)CCO4)cc2[nH]1] | (3R)-1-{[7-(2-methyl-1H-benzimidazol-6-yl)-2,3-dihydro-1,4-benzoxazepin-4(5H)-yl]carbonyl}pyrrolidin-3-ol |
| 79 | 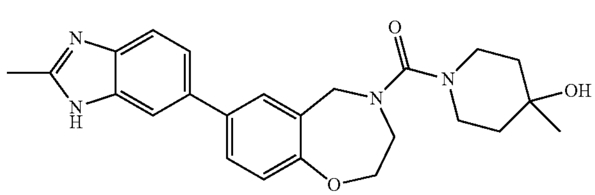 [SMILES: Cc1nc2ccc(-c3ccc4c(c3)CN(C(=O)N3CCC(C)(O)CC3)CCO4)cc2[nH]1] | 4-methyl-1-{[7-(2-methyl-1H-benzimidazol-6-yl)-2,3-dihydro-1,4-benzoxazepin-4(5H)-yl]carbonyl}piperidin-4-ol |

TABLE 1-continued

| Entry No. | Structure | Name |
|---|---|---|
| 80 | 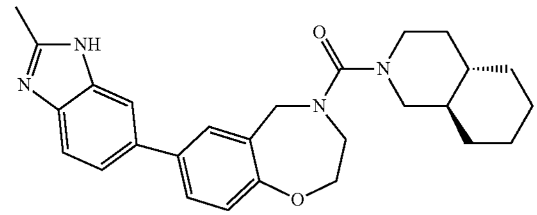 [SMILES: Cc1nc2ccc(-c3ccc4c(c3)CN(C(=O)N3CC[C@@H]5CCCC[C@H]5C3)CCO4)cc2[nH]1] | (±)-7-(2-methyl-1H-benzimidazol-6-yl)-4-[(4aS,8aR)-octahydroisoquinolin-2(1H)-ylcarbonyl]-2,3,4,5-tetrahydro-1,4-benzoxazepine |
| 81 | 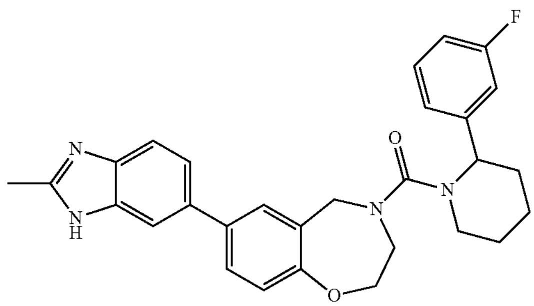 [SMILES: Cc1nc2ccc(-c3ccc4c(c3)CN(C(=O)N3CCCCC3c3cccc(F)c3)CCO4)cc2[nH]1] | 4-{[2-(3-fluorophenyl)piperidin-1-yl]carbonyl}-7-(2-methyl-1H-benzimidazol-6-yl)-2,3,4,5-tetrahydro-1,4-benzoxazepine |
| 82 | 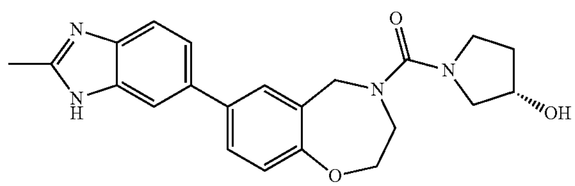 [SMILES: Cc1nc2ccc(-c3ccc4c(c3)CN(C(=O)N3CC[C@H](O)C3)CCO4)cc2[nH]1] | (3S)-1-{[7-(2-methyl-1H-benzimidazol-6-yl)-2,3-dihydro-1,4-benzoxazepin-4(5H)-yl]carbonyl}pyrrolidin-3-ol |
| 83 | 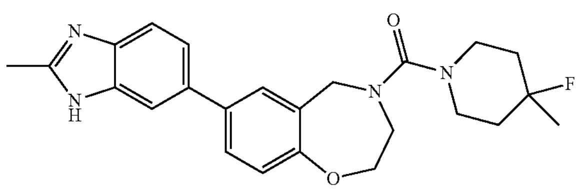 [SMILES: Cc1nc2ccc(-c3ccc4c(c3)CN(C(=O)N3CCC(C)(F)CC3)CCO4)cc2[nH]1] | 4-[(4-fluoro-4-methylpiperidin-1-yl)carbonyl]-7-(2-methyl-1H-benzimidazol-6-yl)-2,3,4,5-tetrahydro-1,4-benzoxazepine |
| 84 | 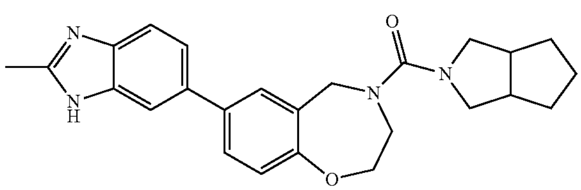 [SMILES: Cc1nc2ccc(-c3ccc4c(c3)CN(C(=O)N3CC5CCCC5C3)CCO4)cc2[nH]1] | 4-(hexahydrocyclopenta[c]pyrrol-2(1H)-ylcarbonyl)-7-(2-methyl-1H-benzimidazol-6-yl)-2,3,4,5-tetrahydro-1,4-benzoxazepine |
| 85 | 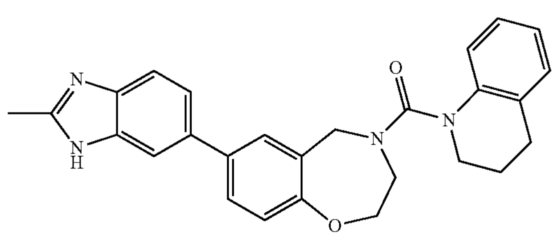 [SMILES: Cc1nc2ccc(-c3ccc4c(c3)CN(C(=O)N3CCCc5ccccc53)CCO4)cc2[nH]1] | 4-(3,4-dihydroquinolin-1(2H)-ylcarbonyl)-7-(2-methyl-1H-benzimidazol-6-yl)-2,3,4,5-tetrahydro-1,4-benzoxazepine |
| 86 | 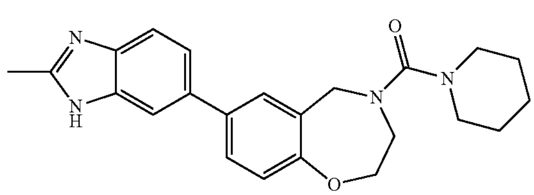 [SMILES: Cc1nc2ccc(-c3ccc4c(c3)CN(C(=O)N3CCCCC3)CCO4)cc2[nH]1] | 7-(2-methyl-1H-benzimidazol-6-yl)-4-(piperidin-1-ylcarbonyl)-2,3,4,5-tetrahydro-1,4-benzoxazepine |

TABLE 1-continued

| Entry No. | Structure | Name |
|---|---|---|
| 87 | 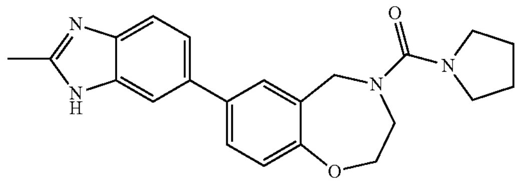 [SMILES: Cc1nc2ccc(-c3ccc4c(c3)CN(C(=O)N3CCCC3)CCO4)cc2[nH]1] | 7-(2-methyl-1H-benzimidazol-6-yl)-4-(pyrrolidin-1-ylcarbonyl)-2,3,4,5-tetrahydro-1,4-benzoxazepine |
| 88 | 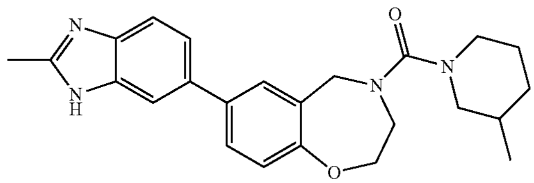 [SMILES: Cc1nc2ccc(-c3ccc4c(c3)CN(C(=O)N3CCCC(C)C3)CCO4)cc2[nH]1] | 7-(2-methyl-1H-benzimidazol-6-yl)-4-[(3-methylpiperidin-1-yl)carbonyl]-2,3,4,5-tetrahydro-1,4-benzoxazepine |
| 89 | 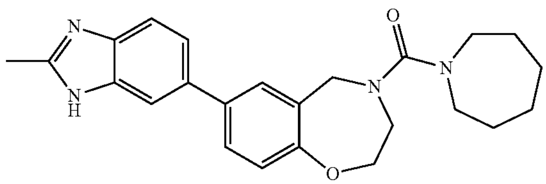 [SMILES: Cc1nc2ccc(-c3ccc4c(c3)CN(C(=O)N3CCCCCC3)CCO4)cc2[nH]1] | 4-(azepan-1-ylcarbonyl)-7-(2-methyl-1H-benzimidazol-6-yl)-2,3,4,5-tetrahydro-1,4-benzoxazepine |
| 90 | 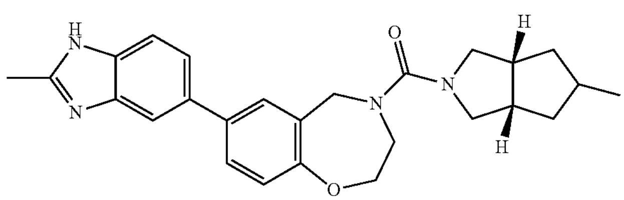 | 7-(2-methyl-1H-benzimidazol-5-yl)-4-{[(3aR,6aS)-5-methylhexahydrocyclopenta[c]pyrrol-2(1H)-yl]carbonyl}-2,3,4,5-tetrahydro-1,4-benzoxazepine |
| 91 | 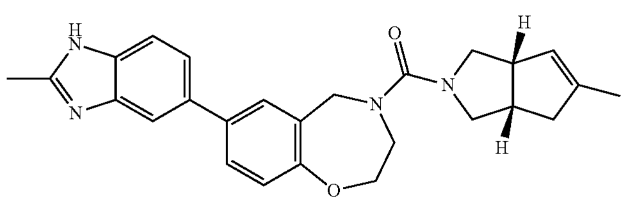 | (±)-7-(2-methyl-1H-benzimidazol-5-yl)-4-{[(3aS,6aR)-5-methyl-3,3a,4,6a-tetrahydrocyclopenta[c]pyrrol-2(1H)-yl]carbonyl}-2,3,4,5-tetrahydro-1,4-benzoxazepine |
| 92 | 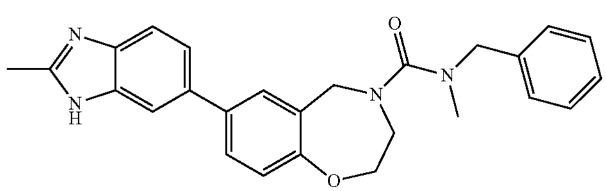 [SMILES: Cc1nc2ccc(-c3ccc4c(c3)CN(C(=O)N(C)Cc3ccccc3)CCO4)cc2[nH]1] | N-methyl-7-(2-methyl-1H-benzimidazol-6-yl)-N-(phenylmethyl)-2,3-dihydro-1,4-benzoxazepine-4(5H)-carboxamide |
| 93 | 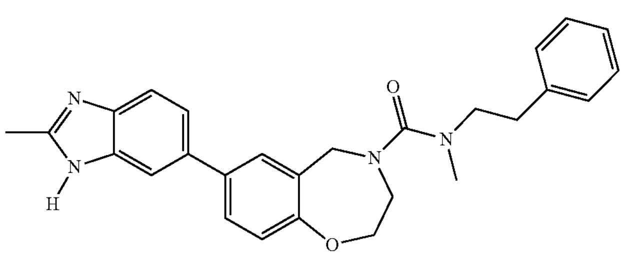 [SMILES: Cc1nc2ccc(-c3ccc4c(c3)CN(C(=O)N(C)CCc3ccccc3)CCO4)cc2[nH]1] | N-methyl-7-(2-methyl-1H-benzimidazol-6-yl)-N-(2-phenylethyl)-2,3-dihydro-1,4-benzoxazepine-4(5H)-carboxamide |

TABLE 1-continued

| Entry No. | Structure | Name |
|---|---|---|
| 94 | 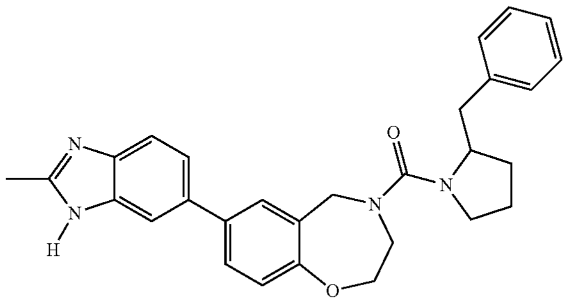 [SMILES: Cc1nc2ccc(-c3ccc4c(c3)CN(C(=O)N3CCCC3Cc3ccccc3)CCO4)cc2[nH]1] | 7-(2-methyl-1H-benzimidazol-6-yl)-4-{[2-(phenylmethyl)pyrrolidin-1-yl]carbonyl}-2,3,4,5-tetrahydro-1,4-benzoxazepine |
| 95 | 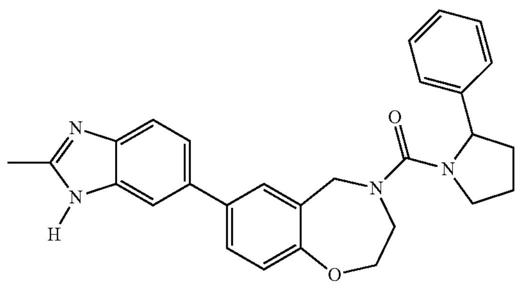 [SMILES: Cc1nc2ccc(-c3ccc4c(c3)CN(C(=O)N3CCCC3c3ccccc3)CCO4)cc2[nH]1] | 7-(2-methyl-1H-benzimidazol-6-yl)-4-[(2-phenylpyrrolidin-1-yl)carbonyl]-2,3,4,5-tetrahydro-1,4-benzoxazepine |
| 96 | 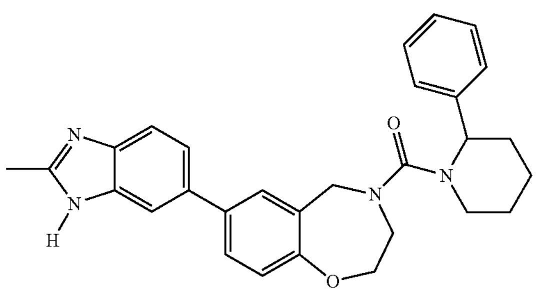 [SMILES: Cc1nc2ccc(-c3ccc4c(c3)CN(C(=O)N3CCCCC3c3ccccc3)CCO4)cc2[nH]1] | 7-(2-methyl-1H-benzimidazol-6-yl)-4-[(2-phenylpiperidin-1-yl)carbonyl]-2,3,4,5-tetrahydro-1,4-benzoxazepine |
| 97 | 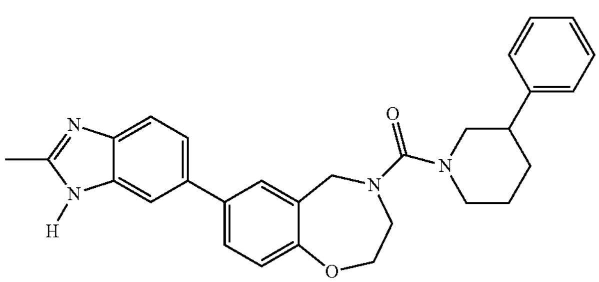 [SMILES: Cc1nc2ccc(-c3ccc4c(c3)CN(C(=O)N3CCCC(c5ccccc5)C3)CCO4)cc2[nH]1] | 7-(2-methyl-1H-benzimidazol-6-yl)-4-[(3-phenylpiperidin-1-yl)carbonyl]-2,3,4,5-tetrahydro-1,4-benzoxazepine |
| 98 | 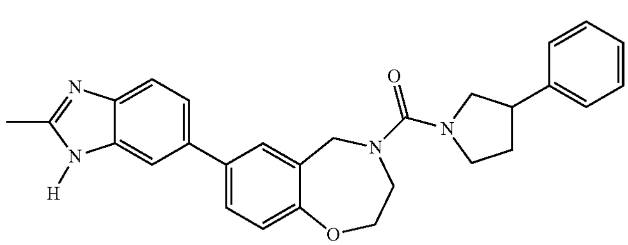 [SMILES: Cc1nc2ccc(-c3ccc4c(c3)CN(C(=O)N3CCC(c5ccccc5)C3)CCO4)cc2[nH]1] | 7-(2-methyl-1H-benzimidazol-6-yl)-4-[(3-phenylpyrrolidin-1-yl)carbonyl]-2,3,4,5-tetrahydro-1,4-benzoxazepine |

TABLE 1-continued

| Entry No. | Structure | Name |
|---|---|---|
| 99 | 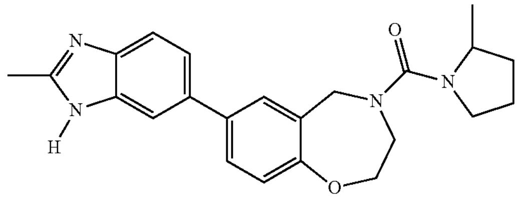 [SMILES: Cc1nc2ccc(-c3ccc4c(c3)CN(C(=O)N3CCCC3C)CCO4)cc2[nH]1] | 7-(2-methyl-1H-benzimidazol-6-yl)-4-[(2-methylpyrrolidin-1-yl)carbonyl]-2,3,4,5-tetrahydro-1,4-benzoxazepine |
| 100 | 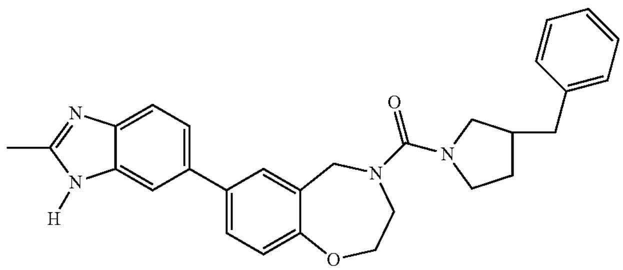 [SMILES: Cc1nc2ccc(-c3ccc4c(c3)CN(C(=O)N3CCC(Cc5ccccc5)C3)CCO4)cc2[nH]1] | 7-(2-methyl-1H-benzimidazol-6-yl)-4-{[3-(phenylmethyl)pyrrolidin-1-yl]carbonyl}-2,3,4,5-tetrahydro-1,4-benzoxazepine |
| 101 | 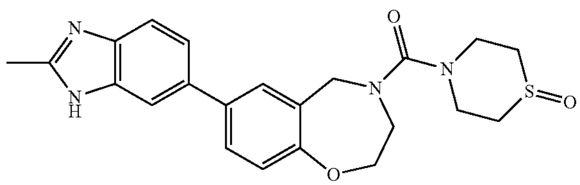 [SMILES: Cc1nc2ccc(-c3ccc4c(c3)CN(C(=O)N3CCS(=O)CC3)CCO4)cc2[nH]1] | 7-(2-methyl-1H-benzimidazol-6-yl)-4-[(1-oxidothiomorpholin-4-yl)carbonyl]-2,3,4,5-tetrahydro-1,4-benzoxazepine |
| 102 | 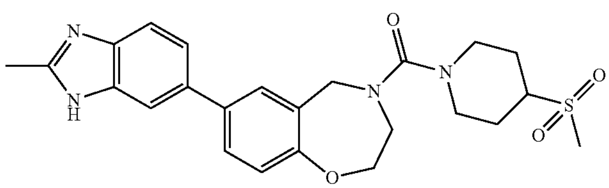 [SMILES: Cc1nc2ccc(-c3ccc4c(c3)CN(C(=O)N3CCC(S(C)(=O)=O)CC3)CCO4)cc2[nH]1] | 7-(2-methyl-1H-benzimidazol-6-yl)-4-{[4-(methylsulfonyl)piperidin-1-yl]carbonyl}-2,3,4,5-tetrahydro-1,4-benzoxazepine |
| 103 | 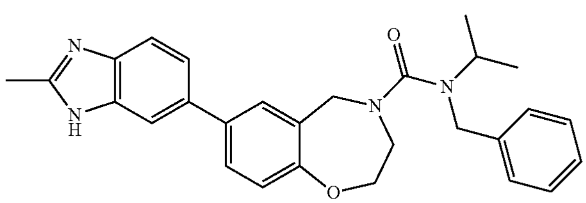 [SMILES: Cc1nc2ccc(-c3ccc4c(c3)CN(C(=O)N(Cc3ccccc3)C(C)C)CCO4)cc2[nH]1] | 7-(2-methyl-1H-benzimidazol-6-yl)-N-(1-methylethyl)-N-(phenylmethyl)-2,3-dihydro-1,4-benzoxazepine-4(5H)-carboxamide |
| 104 | 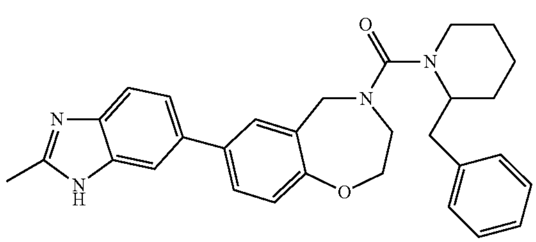 [SMILES: Cc1nc2ccc(-c3ccc4c(c3)CN(C(=O)N3CCCCC3Cc3ccccc3)CCO4)cc2[nH]1] | 7-(2-methyl-1H-benzimidazol-6-yl)-4-{[2-(phenylmethyl)piperidin-1-yl]carbonyl}-2,3,4,5-tetrahydro-1,4-benzoxazepine |
| 105 | 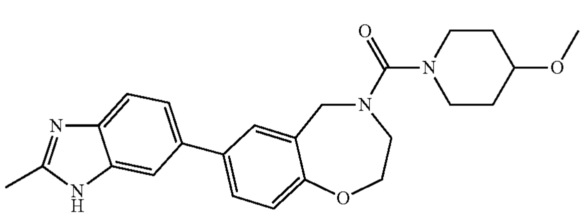 | 7-(2-methyl-1H-benzimidazol-6-yl)-4-{[4-(methyloxy)piperidin-1-yl]carbonyl}-2,3,4,5-tetrahydro-1,4-benzoxazepine |

TABLE 1-continued

| Entry No. | Structure | Name |
|---|---|---|
| 106 | 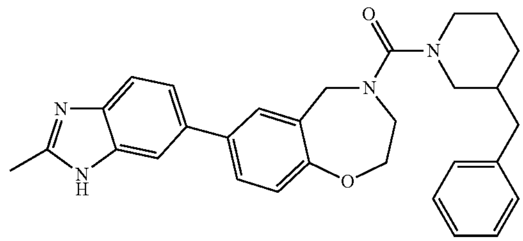 [SMILES: Cc1nc2ccc(-c3ccc4c(c3)CN(C(=O)N3CCCC(Cc5ccccc5)C3)CCO4)cc2[nH]1] | 7-(2-methyl-1H-benzimidazol-6-yl)-4-{[3-(phenylmethyl)piperidin-1-yl]carbonyl}-2,3,4,5-tetrahydro-1,4-benzoxazepine |
| 107 | 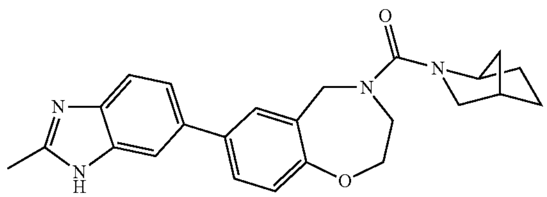 [SMILES: Cc1nc2ccc(-c3ccc4c(c3)CN(C(=O)N3CC5CCC3C5)CCO4)cc2[nH]1] | 4-(2-azabicyclo[2.2.1]hept-2-ylcarbonyl)-7-(2-methyl-1H-benzimidazol-6-yl)-2,3,4,5-tetrahydro-1,4-benzoxazepine |
| 108 | 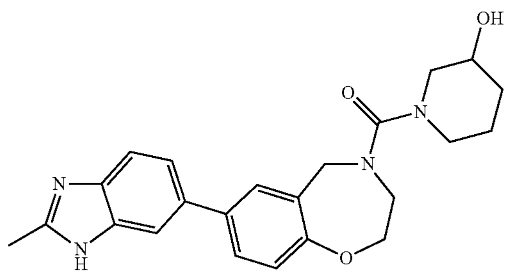 [SMILES: Cc1nc2ccc(-c3ccc4c(c3)CN(C(=O)N3CCCC(O)C3)CCO4)cc2[nH]1] | 1-{[7-(2-methyl-1H-benzimidazol-6-yl)-2,3-dihydro-1,4-benzoxazepin-4(5H)-yl]carbonyl}piperidin-3-ol |
| 109 | 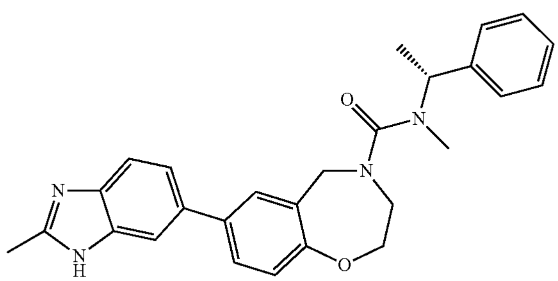 [SMILES: Cc1nc2ccc(-c3ccc4c(c3)CN(C(=O)N(C)[C@H](C)c3ccccc3)CCO4)cc2[nH]1] | N-methyl-7-(2-methyl-1H-benzimidazol-6-yl)-N-[(1R)-1-phenylethyl]-2,3-dihydro-1,4-benzoxazepine-4(5H)-carboxamide |
| 110 | 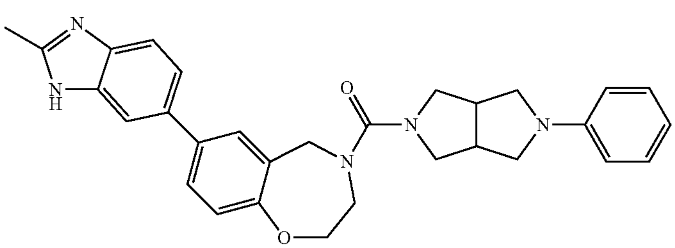 [SMILES: Cc1nc2ccc(-c3ccc4c(c3)CN(C(=O)N3CC5CN(c6ccccc6)CC5C3)CCO4)cc2[nH]1] | 7-(2-methyl-1H-benzimidazol-6-yl)-4-[(5-phenylhexahydropyrrolo[3,4-c]pyrrol-2(1H)-yl)carbonyl]-2,3,4,5-tetrahydro-1,4-benzoxazepine |
| 111 | 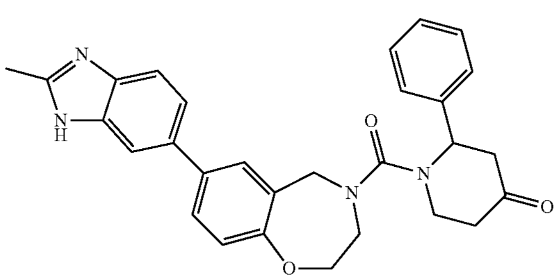 [SMILES: Cc1nc2ccc(-c3ccc4c(c3)CN(C(=O)N3CCC(=O)CC3c3ccccc3)CCO4)cc2[nH]1] | 1-{[7-(2-methyl-1H-benzimidazol-6-yl)-2,3-dihydro-1,4-benzoxazepin-4(5H)-yl]carbonyl}-2-phenylpiperidin-4-one |

TABLE 1-continued

| Entry No. | Structure | Name |
|---|---|---|
| 112 | 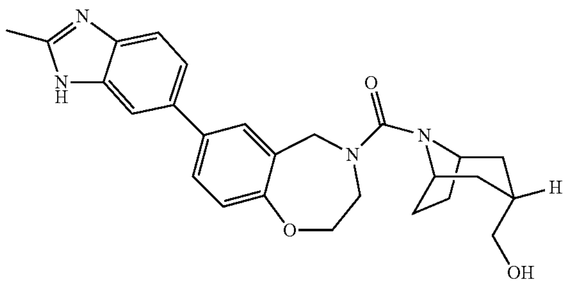 [SMILES: Cc1nc2ccc(-c3ccc4c(c3)CN(C(=O)N3C5CCC3CC(CO)C5)CCO4)cc2[nH]1] | (8-{[7-(2-methyl-1H-benzimidazol-6-yl)-2,3-dihydro-1,4-benzoxazepin-4(5H)-yl]carbonyl}-8-azabicyclo[3.2.1]oct-3-(endo)-yl)methanol |
| 113 | 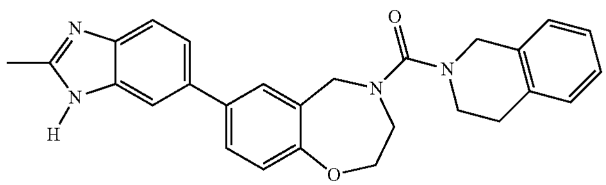 [SMILES: Cc1nc2ccc(-c3ccc4c(c3)CN(C(=O)N3CCc5ccccc5C3)CCO4)cc2[nH]1] | 4-(3,4-dihydroisoquinolin-2(1H)-ylcarbonyl)-7-(2-methyl-1H-benzimidazol-6-yl)-2,3,4,5-tetrahydro-1,4-benzoxazepine |
| 114 | 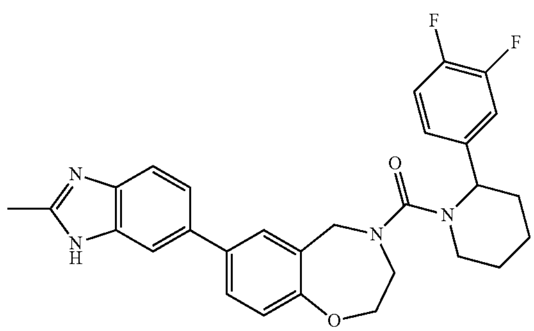 [SMILES: Cc1nc2ccc(-c3ccc4c(c3)CN(C(=O)N3CCCCC3c3ccc(F)c(F)c3)CCO4)cc2[nH]1] | 4-{[2-(3,4-difluorophenyl)piperidin-1-yl]carbonyl}-7-(2-methyl-1H-benzimidazol-6-yl)-2,3,4,5-tetrahydro-1,4-benzoxazepine |
| 115 | 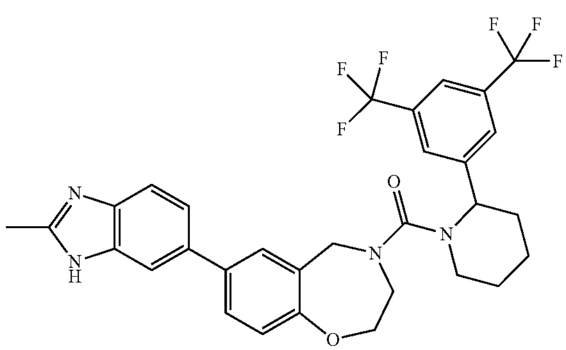 [SMILES: Cc1nc2ccc(-c3ccc4c(c3)CN(C(=O)N3CCCCC3c3cc(C(F)(F)F)cc(C(F)(F)F)c3)CCO4)cc2[nH]1] | 4-({2-[3,5-bis(trifluoromethyl)phenyl]piperidin-1-yl}carbonyl)-7-(2-methyl-1H-benzimidazol-6-yl)-2,3,4,5-tetrahydro-1,4-benzoxazepine |
| 116 | 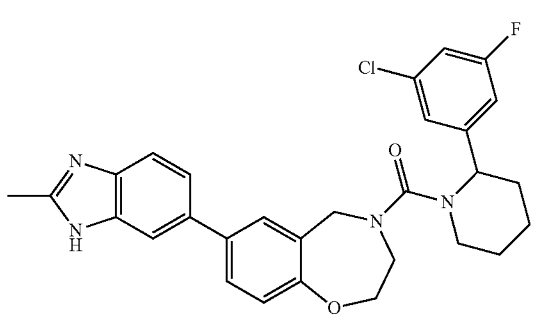 [SMILES: Cc1nc2ccc(-c3ccc4c(c3)CN(C(=O)N3CCCCC3c3cc(F)cc(Cl)c3)CCO4)cc2[nH]1] | 4-{[2-(3-chloro-5-fluorophenyl)piperidin-1-yl]carbonyl}-7-(2-methyl-1H-benzimidazol-6-yl)-2,3,4,5-tetrahydro-1,4-benzoxazepine |

TABLE 1-continued

| Entry No. | Structure | Name |
|---|---|---|
| 117 | 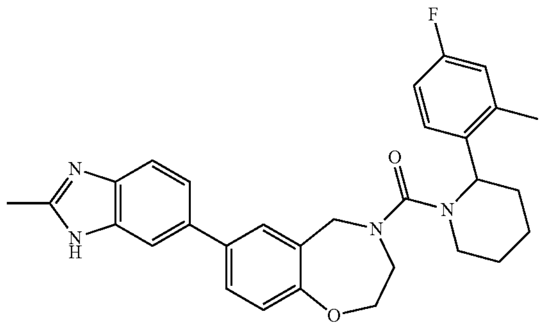 | 4-{[2-(4-fluoro-2-methylphenyl)piperidin-1-yl]carbonyl}-7-(2-methyl-1H-benzimidazol-6-yl)-2,3,4,5-tetrahydro-1,4-benzoxazepine |
| 118 | 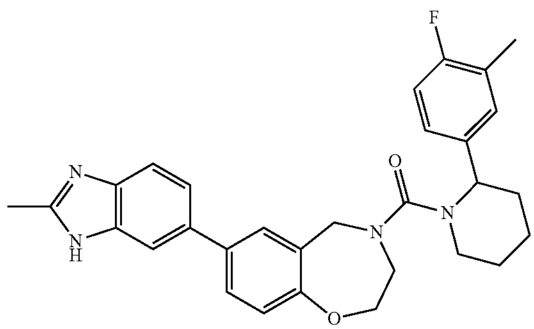 | 4-{[2-(4-fluoro-3-methylphenyl)piperidin-1-yl]carbonyl}-7-(2-methyl-1H-benzimidazol-6-yl)-2,3,4,5-tetrahydro-1,4-benzoxazepine |
| 119 | 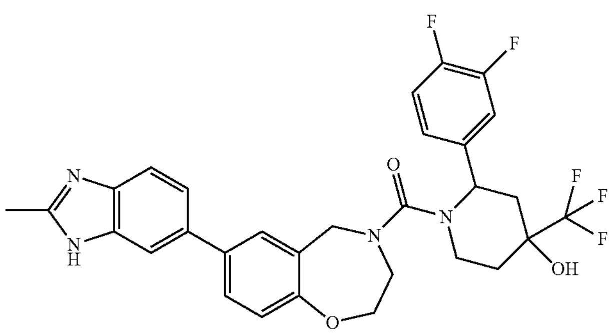 [SMILES: Cc1nc2ccc(-c3ccc4c(c3)CN(C(=O)N3CCC(O)(C(F)(F)F)CC3c3ccc(F)c(F)c3)CCO4)cc2[nH]1] | 2-(3,4-difluorophenyl)-1-{[7-(2-methyl-1H-benzimidazol-6-yl)-2,3-dihydro-1,4-benzoxazepin-4(5H)-yl]carbonyl}-4-(trifluoromethyl)piperidin-4-ol |
| 120 | 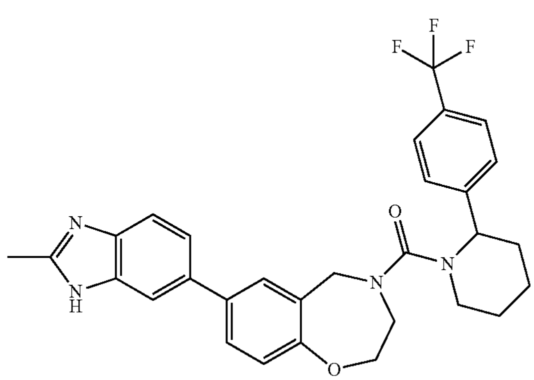 [SMILES: Cc1nc2ccc(-c3ccc4c(c3)CN(C(=O)N3CCCCC3c3ccc(C(F)(F)F)cc3)CCO4)cc2[nH]1] | 7-(2-methyl-1H-benzimidazol-6-yl)-4-({2-[4-(trifluoromethyl)phenyl]piperidin-1-yl}carbonyl)-2,3,4,5-tetrahydro-1,4-benzoxazepine |

TABLE 1-continued

| Entry No. | Structure | Name |
|---|---|---|
| 121 | 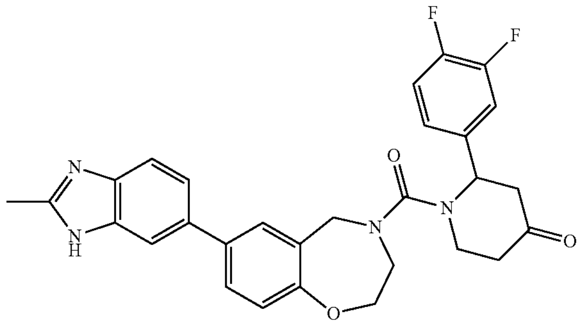 [SMILES: Cc1nc2ccc(-c3ccc4c(c3)CN(C(=O)N3CCC(=O)CC3c3ccc(F)c(F)c3)CCO4)cc2[nH]1] | 2-(3,4-difluorophenyl)-1-{[7-(2-methyl-1H-benzimidazol-6-yl)-2,3-dihydro-1,4-benzoxazepin-4(5H)-yl]carbonyl}piperidin-4-one |
| 122 | 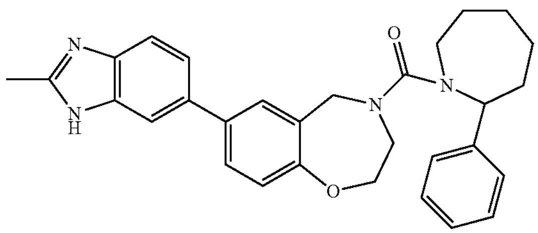 [SMILES: Cc1nc2ccc(-c3ccc4c(c3)CN(C(=O)N3CCCCCC3c3ccccc3)CCO4)cc2[nH]1] | 7-(2-methyl-1H-benzimidazol-5-yl)-4-[(2-phenylazepan-1-yl)carbonyl]-2,3,4,5-tetrahydro-1,4-benzoxazepine |
| 123 | 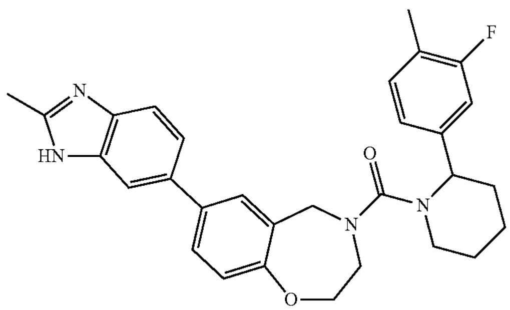 [SMILES: Cc1nc2ccc(-c3ccc4c(c3)CN(C(=O)N3CCCCC3c3ccc(C)c(F)c3)CCO4)cc2[nH]1] | 4-{[2-(3-fluoro-4-methylphenyl)piperidin-1-yl]carbonyl}-7-(2-methyl-1H-benzimidazol-6-yl)-2,3,4,5-tetrahydro-1,4-benzoxazepine |
| 124 | 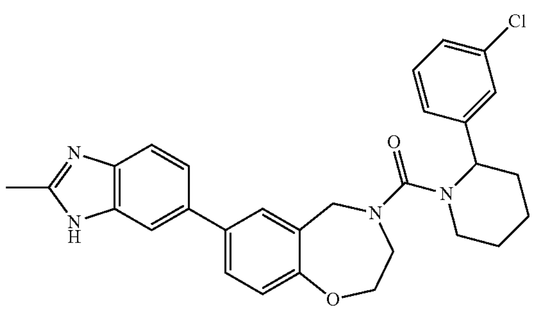 [SMILES: Cc1nc2ccc(-c3ccc4c(c3)CN(C(=O)N3CCCCC3c3cccc(Cl)c3)CCO4)cc2[nH]1] | 4-{[2-(3-chlorophenyl)piperidin-1-yl]carbonyl}-7-(2-methyl-1H-benzimidazol-6-yl)-2,3,4,5-tetrahydro-1,4-benzoxazepine |
| 125 | 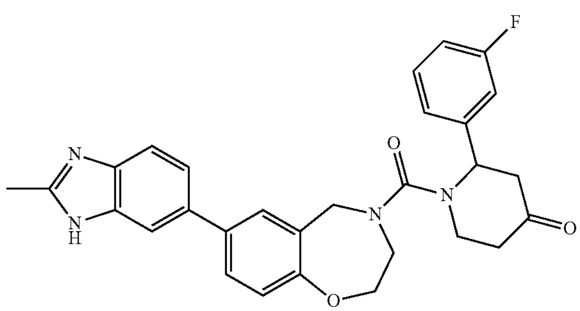 [SMILES: Cc1nc2ccc(-c3ccc4c(c3)CN(C(=O)N3CCC(=O)CC3c3cccc(F)c3)CCO4)cc2[nH]1] | 2-(3-fluorophenyl)-1-{[7-(2-methyl-1H-benzimidazol-6-yl)-2,3-dihydro-1,4-benzoxazepin-4(5H)-yl]carbonyl}piperidin-4-one |

TABLE 1-continued

| Entry No. | Structure | Name |
|---|---|---|
| 126 | 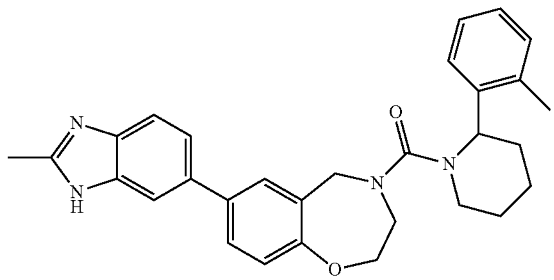 | 7-(2-methyl-1H-benzimidazol-6-yl)-4-{[2-(2-methylphenyl)piperidin-1-yl]carbonyl}-2,3,4,5-tetrahydro-1,4-benzoxazepine |
| 127 | 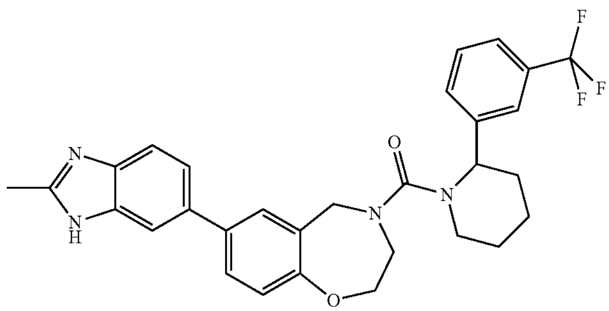 [SMILES: Cc1nc2ccc(-c3ccc4c(c3)CN(C(=O)N3CCCCC3c3cccc(C(F)(F)F)c3)CCO4)cc2[nH]1] | 7-(2-methyl-1H-benzimidazol-6-yl)-4-({2-[3-(trifluoromethyl)phenyl]piperidin-1-yl}carbonyl)-2,3,4,5-tetrahydro-1,4-benzoxazepine |
| 128 | 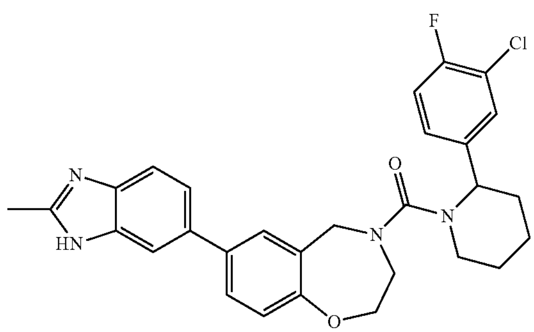 [SMILES: Cc1nc2ccc(-c3ccc4c(c3)CN(C(=O)N3CCCCC3c3ccc(F)c(Cl)c3)CCO4)cc2[nH]1] | 4-{[2-(3-chloro-4-fluorophenyl)piperidin-1-yl]carbonyl}-7-(2-methyl-1H-benzimidazol-6-yl)-2,3,4,5-tetrahydro-1,4-benzoxazepine |
| 129 | 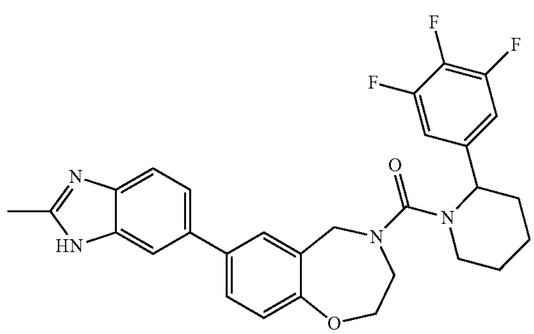 [SMILES: Cc1nc2ccc(-c3ccc4c(c3)CN(C(=O)N3CCCCC3c3cc(F)c(F)c(F)c3)CCO4)cc2[nH]1] | 7-(2-methyl-1H-benzimidazol-6-yl)-4-{[2-(3,4,5-trifluorophenyl)piperidin-1-yl]carbonyl}-2,3,4,5-tetrahydro-1,4-benzoxazepine |
| 130 | 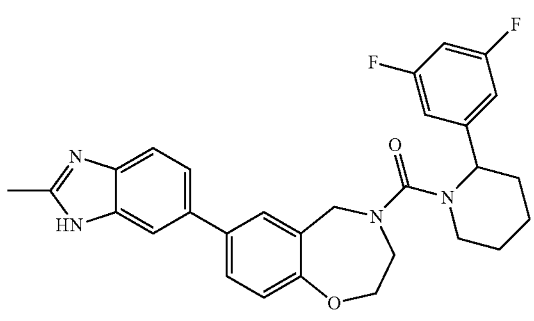 [SMILES: Cc1nc2ccc(-c3ccc4c(c3)CN(C(=O)N3CCCCC3c3cc(F)cc(F)c3)CCO4)cc2[nH]1] | 4-{[2-(3,5-difluorophenyl)piperidin-1-yl]carbonyl}-7-(2-methyl-1H-benzimidazol-6-yl)-2,3,4,5-tetrahydro-1,4-benzoxazepine |

TABLE 1-continued

| Entry No. | Structure | Name |
|---|---|---|
| 131 | 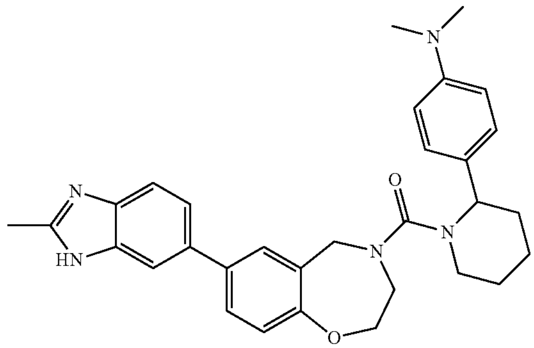 [SMILES: Cc1nc2ccc(-c3ccc4c(c3)CN(C(=O)N3CCCCC3c3ccc(N(C)C)cc3)CCO4)cc2[nH]1] | N,N-dimethyl-4-(1-{[7-(2-methyl-1H-benzimidazol-6-yl)-2,3-dihydro-1,4-benzoxazepin-4(5H)-yl]carbonyl}piperidin-2-yl)aniline |
| 132 | 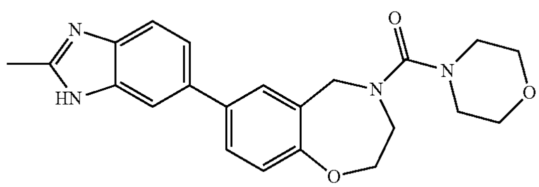 [SMILES: Cc1nc2ccc(-c3ccc4c(c3)CN(C(=O)N3CCOCC3)CCO4)cc2[nH]1] | 7-(2-methyl-1H-benzimidazol-6-yl)-4-(morpholin-4-ylcarbonyl)-2,3,4,5-tetrahydro-1,4-benzoxazepine |
| 133 | 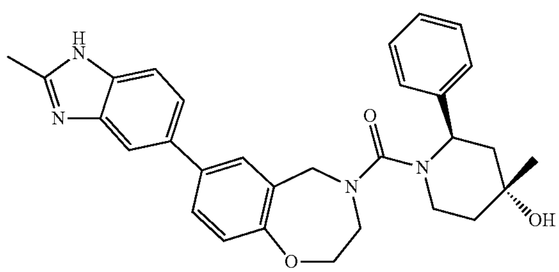 [SMILES: Cc1nc2cc(-c3ccc4c(c3)CN(C(=O)N3CC[C@@](C)(O)C[C@@H]3c3ccccc3)CCO4)ccc2[nH]1] | (±)-(2R,4R)-4-methyl-1-{[7-(2-methyl-1H-benzimidazol-5-yl)-2,3-dihydro-1,4-benzoxazepin-4(5H)-yl]carbonyl}-2-phenylpiperidin-4-ol |
| 134 | 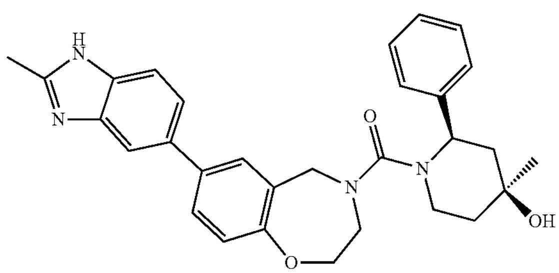 [SMILES: Cc1nc2cc(-c3ccc4c(c3)CN(C(=O)N3CC[C@](C)(O)C[C@@H]3c3ccccc3)CCO4)ccc2[nH]1] | (±)-(2R,4S)-4-methyl-1-{[7-(2-methyl-1H-benzimidazol-5-yl)-2,3-dihydro-1,4-benzoxazepin-4(5H)-yl]carbonyl}-2-phenylpiperidin-4-ol |
| 135 | 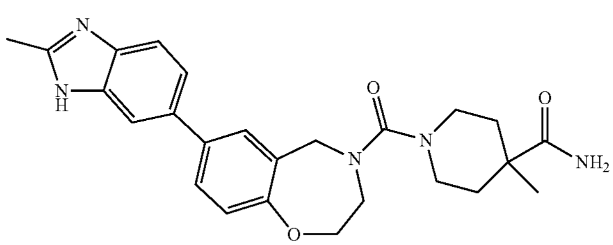 [SMILES: Cc1nc2ccc(-c3ccc4c(c3)CN(C(=O)N3CCC(C)(C(N)=O)CC3)CCO4)cc2[nH]1] | 4-methyl-1-{[7-(2-methyl-1H-benzimidazol-6-yl)-2,3-dihydro-1,4-benzoxazepin-4(5H)-yl]carbonyl}piperidine-4-carboxamide |

TABLE 1-continued

| Entry No. | Structure | Name |
|---|---|---|
| 136 | 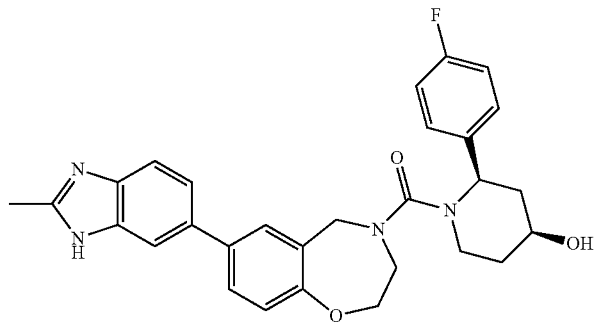 [SMILES: Cc1nc2ccc(-c3ccc4c(c3)CN(C(=O)N3CC[C@H](O)C[C@@H]3c3ccc(F)cc3)CCO4)cc2[nH]1] | (±)-(2R,4S)-2-(4-fluorophenyl)-1-{[7-(2-methyl-1H-benzimidazol-6-yl)-2,3-dihydro-1,4-benzoxazepin-4(5H)-yl]carbonyl}piperidin-4-ol |
| 137 | 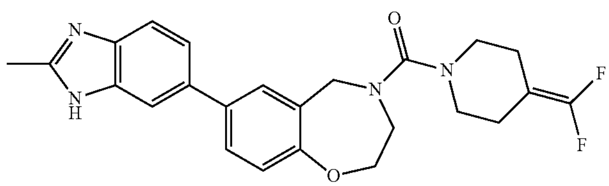 [SMILES: Cc1nc2ccc(-c3ccc4c(c3)CN(C(=O)N3CCC(=C(F)F)CC3)CCO4)cc2[nH]1] | 4-{[4-(difluoromethylidene)piperidin-1-yl]carbonyl}-7-(2-methyl-1H-benzimidazol-6-yl)-2,3,4,5-tetrahydro-1,4-benzoxazepine |
| 138 | 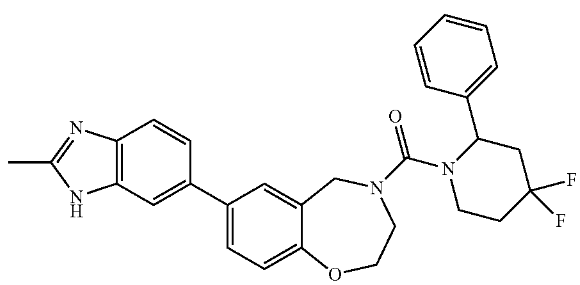 [SMILES: Cc1nc2ccc(-c3ccc4c(c3)CN(C(=O)N3CCC(F)(F)CC3c3ccccc3)CCO4)cc2[nH]1] | 4-[(4,4-difluoro-2-phenylpiperidin-1-yl)carbonyl]-7-(2-methyl-1H-benzimidazol-6-yl)-2,3,4,5-tetrahydro-1,4-benzoxazepine |
| 139 | 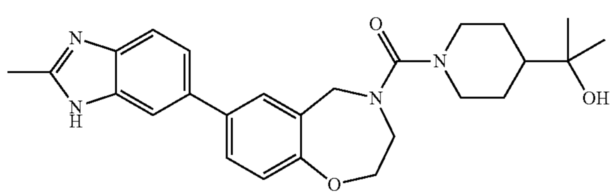 [SMILES: Cc1nc2ccc(-c3ccc4c(c3)CN(C(=O)N3CCC(C(C)(C)O)CC3)CCO4)cc2[nH]1] | 2-(1-{[7-(2-methyl-1H-benzimidazol-6-yl)-2,3-dihydro-1,4-benzoxazepin-4(5H)-yl]carbonyl}piperidin-4-yl)propan-2-ol |
| 140 | 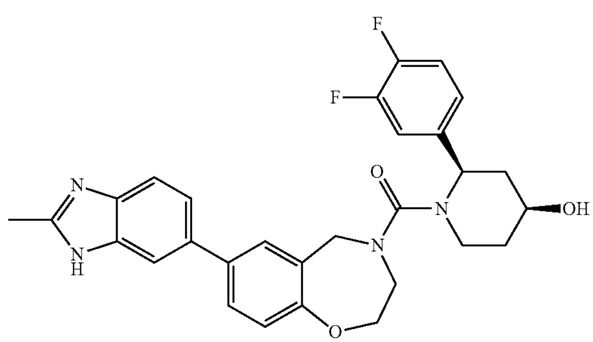 [SMILES: Cc1nc2ccc(-c3ccc4c(c3)CN(C(=O)N3CC[C@H](O)C[C@@H]3c3ccc(F)c(F)c3)CCO4)cc2[nH]1] | (±)-(2R,4S)-2-(3,4-difluorophenyl)-1-{[7-(2-methyl-1H-benzimidazol-6-yl)-2,3-dihydro-1,4-benzoxazepin-4(5H)-yl]carbonyl}piperidin-4-ol |
| 141 | 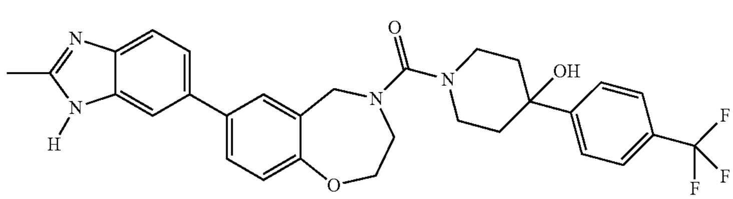 [SMILES: Cc1nc2ccc(-c3ccc4c(c3)CN(C(=O)N3CCC(O)(c5ccc(C(F)(F)F)cc5)CC3)CCO4)cc2[nH]1] | 1-{[7-(2-methyl-1H-benzimidazol-6-yl)-2,3-dihydro-1,4-benzoxazepin-4(5H)-yl]carbonyl}-4-[4-(trifluoromethyl)phenyl]piperidin-4-ol |

TABLE 1-continued

| Entry No. | Structure | Name |
|---|---|---|
| 142 | 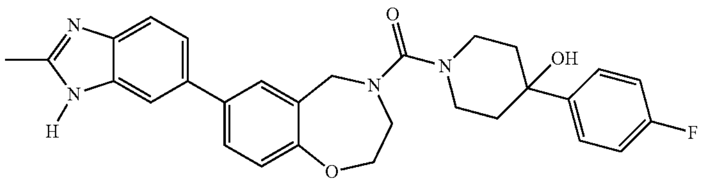 [SMILES: Cc1nc2ccc(-c3ccc4c(c3)CN(C(=O)N3CCC(O)(c5ccc(F)cc5)CC3)CCO4)cc2[nH]1] | 4-(4-fluorophenyl)-1-{[7-(2-methyl-1H-benzimidazol-6-yl)-2,3-dihydro-1,4-benzoxazepin-4(5H)-yl]carbonyl}piperidin-4-ol |
| 143 | 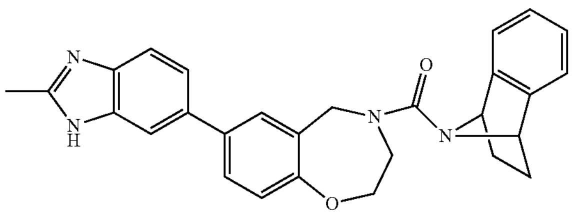 [SMILES: Cc1nc2ccc(-c3ccc4c(c3)CN(C(=O)N3C5CCC3c3ccccc35)CCO4)cc2[nH]1] | 9-{[7-(2-methyl-1H-benzimidazol-6-yl)-2,3-dihydro-1,4-benzoxazepin-4(5H)-yl]carbonyl}-1,2,3,4-tetrahydro-1,4-epiminonaphthalene |
| 144 | 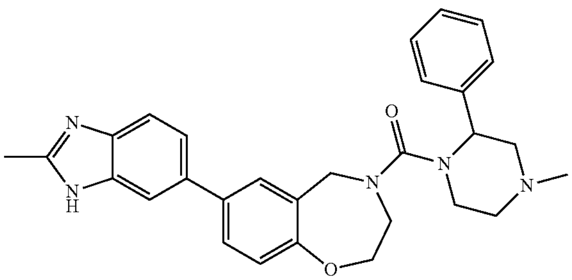 | 7-(2-methyl-1H-benzimidazol-6-yl)-4-[(4-methyl-2-phenylpiperazin-1-yl)carbonyl]-2,3,4,5-tetrahydro-1,4-benzoxazepine |
| 145 | 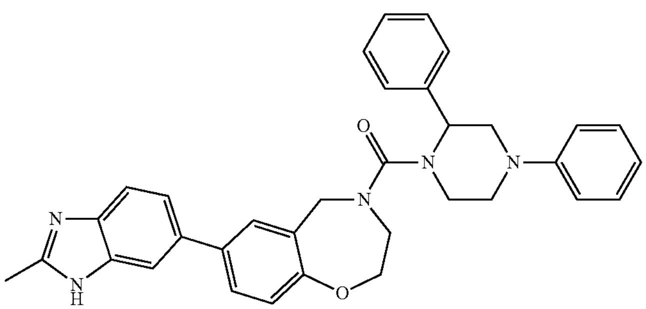 [SMILES: Cc1nc2ccc(-c3ccc4c(c3)CN(C(=O)N3CCN(c5ccccc5)CC3c3ccccc3)CCO4)cc2[nH]1] | 4-[(2,4-diphenylpiperazin-1-yl)carbonyl]-7-(2-methyl-1H-benzimidazol-6-yl)-2,3,4,5-tetrahydro-1,4-benzoxazepine |
| 146 | 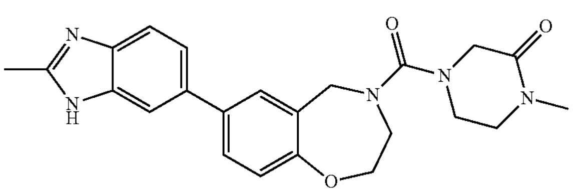 | 1-methyl-4-{[7-(2-methyl-1H-benzimidazol-6-yl)-2,3-dihydro-1,4-benzoxazepin-4(5H)-yl]carbonyl}piperazin-2-one |
| 147 | 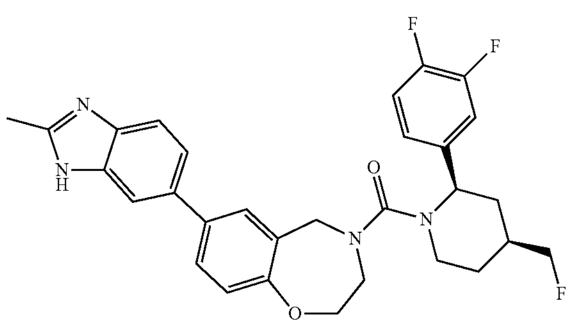 [SMILES: Cc1nc2ccc(-c3ccc4c(c3)CN(C(=O)N3CC[C@H](CF)C[C@@H]3c3ccc(F)c(F)c3)CCO4)cc2[nH]1] | (±)-4-{[(2R,4S)-2-(3,4-difluorophenyl)-4-(fluoromethyl)piperidin-1-yl]carbonyl}-7-(2-methyl-1H-benzimidazol-6-yl)-2,3,4,5-tetrahydro-1,4-benzoxazepine |

TABLE 1-continued

| Entry No. | Structure | Name |
|---|---|---|
| 148 | 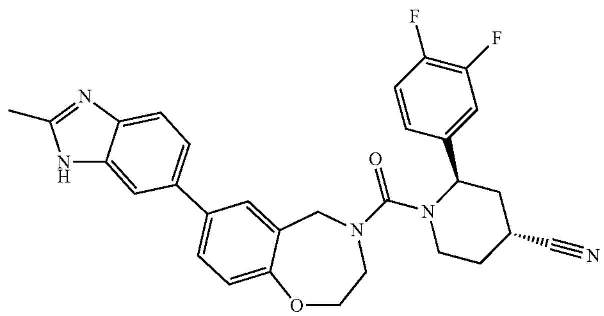 [SMILES: Cc1nc2ccc(-c3ccc4c(c3)CN(C(=O)N3CC[C@@H](C#N)C[C@@H]3c3ccc(F)c(F)c3)CCO4)cc2[nH]1] | (±)-(2R,4R)-2-(3,4-difluorophenyl)-1-{[7-(2-methyl-1H-benzimidazol-6-yl)-2,3-dihydro-1,4-benzoxazepin-4(5H)-yl]carbonyl}piperidine-4-carbonitrile |
| 149 | 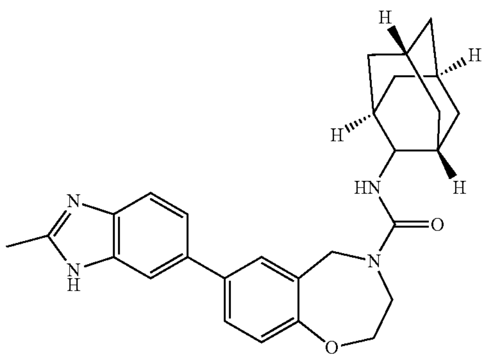 [SMILES: Cc1nc2ccc(-c3ccc4c(c3)CN(C(=O)NC3[C@H]5C[C@@H]6C[C@@H](C[C@H]3C6)C5)CCO4)cc2[nH]1] | 7-(2-methyl-1H-benzimidazol-6-yl)-N-[(1r,3r,5R,7R)-tricyclo[3.3.1.1~3,7~]dec-2-yl]-2,3-dihydro-1,4-benzoxazepine-4(5H)-carboxamide |
| 150 | 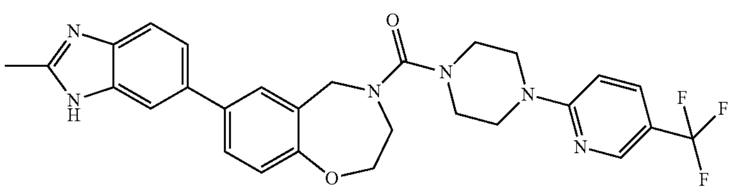 [SMILES: Cc1nc2ccc(-c3ccc4c(c3)CN(C(=O)N3CCN(c5ccc(C(F)(F)F)cn5)CC3)CCO4)cc2[nH]1] | 7-(2-methyl-1H-benzimidazol-6-yl)-4-({4-[5-(trifluoromethyl)pyridin-2-yl]piperazin-1-yl}carbonyl)-2,3,4,5-tetrahydro-1,4-benzoxazepine |
| 151 | 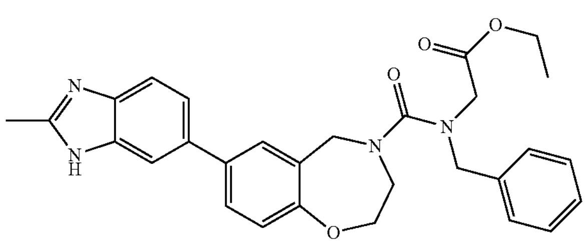 [SMILES: CCOC(=O)CN(Cc1ccccc1)C(=O)N1CCOc2ccc(-c3ccc4nc(C)[nH]c4c3)cc2C1] | ethyl N-{[7-(2-methyl-1H-benzimidazol-6-yl)-2,3-dihydro-1,4-benzoxazepin-4(5H)-yl]carbonyl}-N-(phenylmethyl)glycinate |
| 152 | 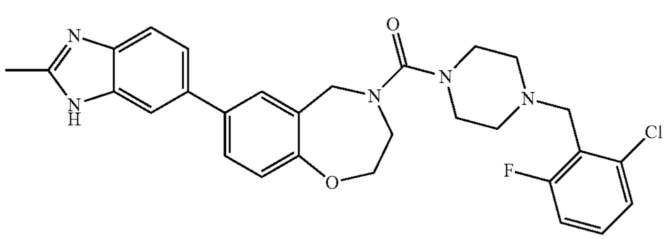 [SMILES: Cc1nc2ccc(-c3ccc4c(c3)CN(C(=O)N3CCN(Cc5c(F)cccc5Cl)CC3)CCO4)cc2[nH]1] | 4-({4-[(2-chloro-6-fluorophenyl)methyl]piperazin-1-yl}carbonyl)-7-(2-methyl-1H-benzimidazol-6-yl)-2,3,4,5-tetrahydro-1,4-benzoxazepine |
| 153 | 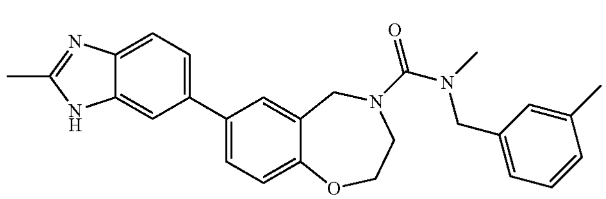 | N-methyl-7-(2-methyl-1H-benzimidazol-6-yl)-N-[(3-methylphenyl)methyl]-2,3-dihydro-1,4-benzoxazepine-4(5H)-carboxamide |

TABLE 1-continued

| Entry No. | Structure | Name |
|---|---|---|
| 154 | 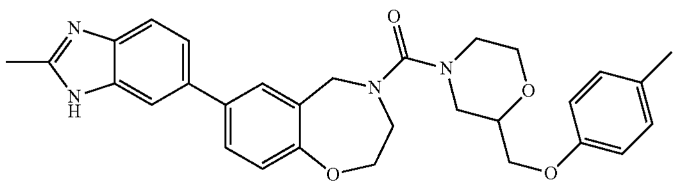 | 7-(2-methyl-1H-benzimidazol-6-yl)-4-[(2-{[(4-methylphenyl)oxy]methyl}morpholin-4-yl)carbonyl]-2,3,4,5-tetrahydro-1,4-benzoxazepine |
| 155 | 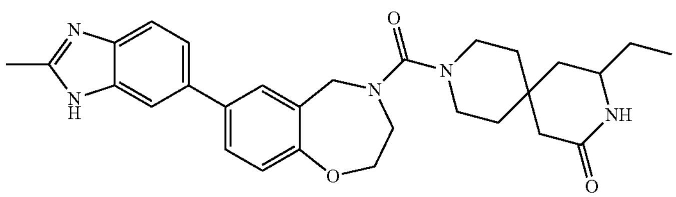 [SMILES: CCC1CC2(CCN(C(=O)N3CCOc4ccc(-c5ccc6nc(C)[nH]c6c5)cc4C3)CC2)CC(=O)N1] | 4-ethyl-9-{[7-(2-methyl-1H-benzimidazol-6-yl)-2,3-dihydro-1,4-benzoxazepin-4(5H)-yl]carbonyl}-3,9-diazaspiro[5.5]undecan-2-one |
| 156 | 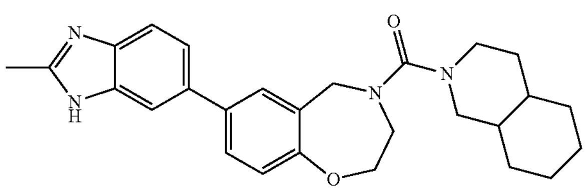 [SMILES: Cc1nc2ccc(-c3ccc4c(c3)CN(C(=O)N3CCC5CCCCC5C3)CCO4)cc2[nH]1] | 7-(2-methyl-1H-benzimidazol-6-yl)-4-(octahydroisoquinolin-2(1H)-ylcarbonyl)-2,3,4,5-tetrahydro-1,4-benzoxazepine |
| 157 | 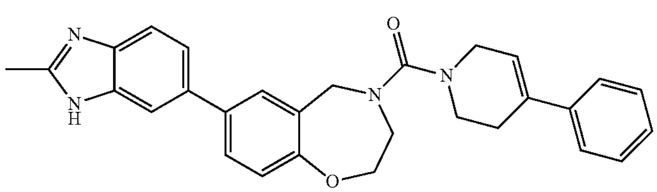 [SMILES: Cc1nc2ccc(-c3ccc4c(c3)CN(C(=O)N3CC=C(c5ccccc5)CC3)CCO4)cc2[nH]1] | 7-(2-methyl-1H-benzimidazol-6-yl)-4-[(4-phenyl-3,6-dihydropyridin-1(2H)-yl)carbonyl]-2,3,4,5-tetrahydro-1,4-benzoxazepine |
| 158 | 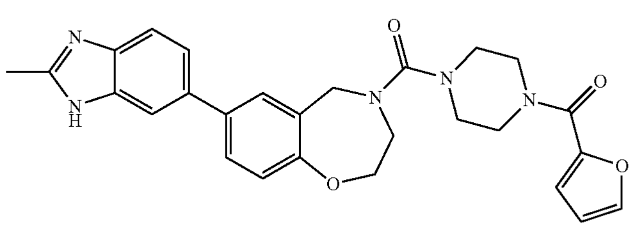 [SMILES: Cc1nc2ccc(-c3ccc4c(c3)CN(C(=O)N3CCN(C(=O)c5ccco5)CC3)CCO4)cc2[nH]1] | 4-{[4-(furan-2-ylcarbonyl)piperazin-1-yl]carbonyl}-7-(2-methyl-1H-benzimidazol-6-yl)-2,3,4,5-tetrahydro-1,4-benzoxazepine |
| 159 | 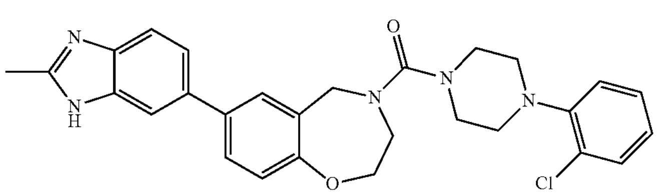 [SMILES: Cc1nc2ccc(-c3ccc4c(c3)CN(C(=O)N3CCN(c5ccccc5Cl)CC3)CCO4)cc2[nH]1] | 4-{[4-(2-chlorophenyl)piperazin-1-yl]carbonyl}-7-(2-methyl-1H-benzimidazol-6-yl)-2,3,4,5-tetrahydro-1,4-benzoxazepine |
| 160 | 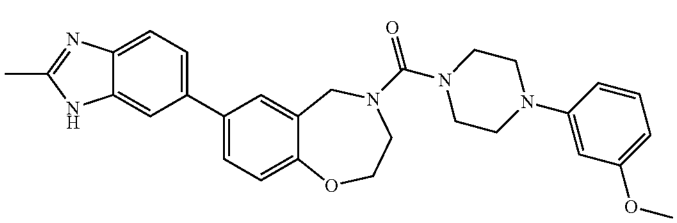 | 7-(2-methyl-1H-benzimidazol-6-yl)-4-({4-[3-(methyloxy)phenyl]piperazin-1-yl}carbonyl)-2,3,4,5-tetrahydro-1,4-benzoxazepine |

TABLE 1-continued

| Entry No. | Structure | Name |
|---|---|---|
| 161 | 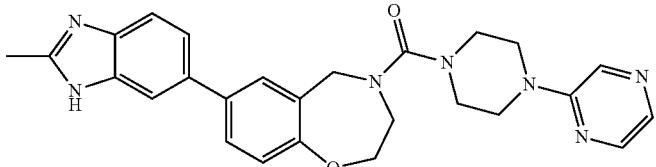 | 7-(2-methyl-1H-benzimidazol-6-yl)-4-[(4-pyrazin-2-ylpiperazin-1-yl)carbonyl]-2,3,4,5-tetrahydro-1,4-benzoxazepine |
| 162 | 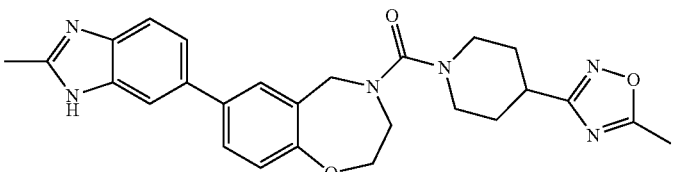 | 7-(2-methyl-1H-benzimidazol-6-yl)-4-{[4-(5-methyl-1,2,4-oxadiazol-3-yl)piperidin-1-yl]carbonyl}-2,3,4,5-tetrahydro-1,4-benzoxazepine |
| 163 | 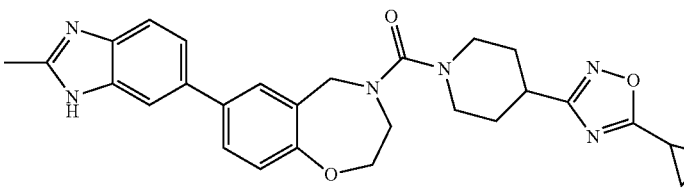 | 4-{[4-(5-cyclopropyl-1,2,4-oxadiazol-3-yl)piperidin-1-yl]carbonyl}-7-(2-methyl-1H-benzimidazol-6-yl)-2,3,4,5-tetrahydro-1,4-benzoxazepine |
| 164 | 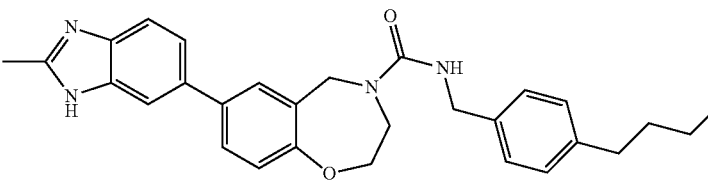 | 7-(2-methyl-1H-benzimidazol-6-yl)-N-(4-pentylphenyl)-2,3-dihydro-1,4-benzoxazepine-4(5H)-carboxamide |
| 165 | 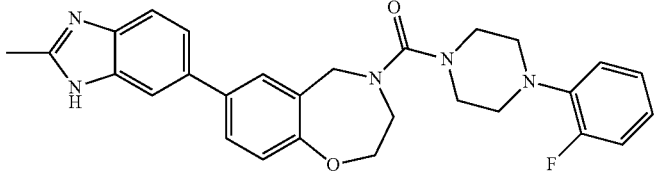 [SMILES: Cc1nc2ccc(-c3ccc4c(c3)CN(C(=O)N3CCN(c5ccccc5F)CC3)CCO4)cc2[nH]1] | 4-{[4-(2-fluorophenyl)piperazin-1-yl]carbonyl}-7-(2-methyl-1H-benzimidazol-6-yl)-2,3,4,5-tetrahydro-1,4-benzoxazepine |
| 166 | 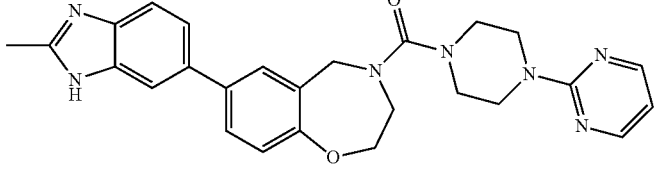 | 7-(2-methyl-1H-benzimidazol-6-yl)-4-[(4-pyrimidin-2-ylpiperazin-1-yl)carbonyl]-2,3,4,5-tetrahydro-1,4-benzoxazepine |
| 167 | 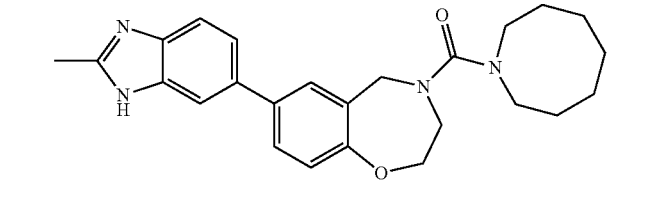 [SMILES: Cc1nc2ccc(-c3ccc4c(c3)CN(C(=O)N3CCCCCCC3)CCO4)cc2[nH]1] | 4-(azocan-1-ylcarbonyl)-7-(2-methyl-1H-benzimidazol-6-yl)-2,3,4,5-tetrahydro-1,4-benzoxazepine |
| 168 | 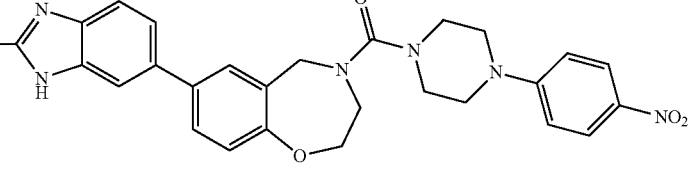 | 7-(2-methyl-1H-benzimidazol-6-yl)-4-{[4-(4-nitrophenyl)piperazin-1-yl]carbonyl}-2,3,4,5-tetrahydro-1,4-benzoxazepine |

US 8,637,499 B2

TABLE 1-continued

| Entry No. | Structure | Name |
|---|---|---|
| 169 | 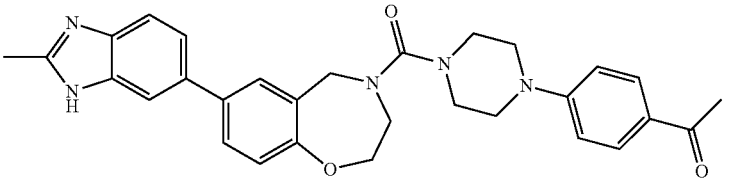 [SMILES: CC(=O)c1ccc(N2CCN(C(=O)N3CCOc4ccc(-c5ccc6nc(C)[nH]c6c5)cc4C3)CC2)cc1] | 1-[4-(4-{[7-(2-methyl-1H-benzimidazol-6-yl)-2,3-dihydro-1,4-benzoxazepin-4(5H)-yl]carbonyl}piperazin-1-yl)phenyl]ethanone |
| 170 | 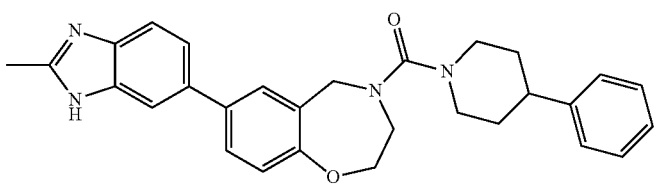 [SMILES: Cc1nc2ccc(-c3ccc4c(c3)CN(C(=O)N3CCC(c5ccccc5)CC3)CCO4)cc2[nH]1] | 7-(2-methyl-1H-benzimidazol-6-yl)-4-[(4-phenylpiperidin-1-yl)carbonyl]-2,3,4,5-tetrahydro-1,4-benzoxazepine |
| 171 | 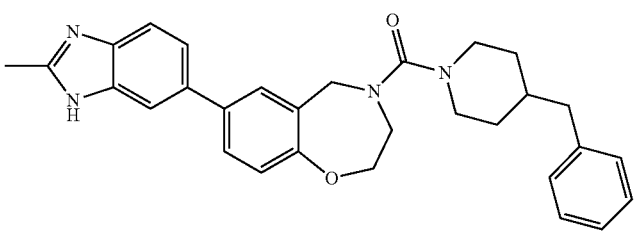 [SMILES: Cc1nc2ccc(-c3ccc4c(c3)CN(C(=O)N3CCC(Cc5ccccc5)CC3)CCO4)cc2[nH]1] | 7-(2-methyl-1H-benzimidazol-6-yl)-4-{[4-(phenylmethyl)piperidin-1-yl]carbonyl}-2,3,4,5-tetrahydro-1,4-benzoxazepine |
| 172 | 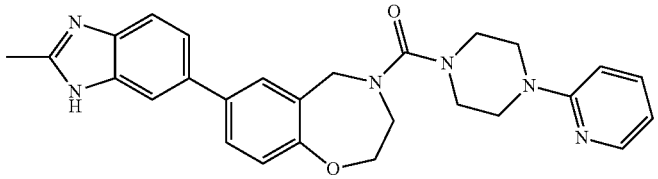 [SMILES: Cc1nc2ccc(-c3ccc4c(c3)CN(C(=O)N3CCN(c5ccccn5)CC3)CCO4)cc2[nH]1] | 7-(2-methyl-1H-benzimidazol-6-yl)-4-[(4-pyridin-2-ylpiperazin-1-yl)carbonyl]-2,3,4,5-tetrahydro-1,4-benzoxazepine |
| 173 | 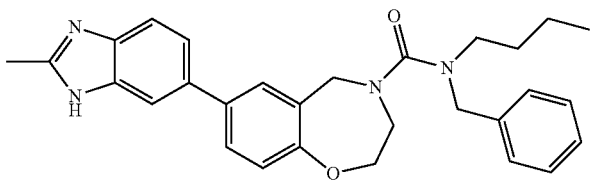 [SMILES: CCCCN(Cc1ccccc1)C(=O)N1CCOc2ccc(-c3ccc4nc(C)[nH]c4c3)cc2C1] | N-butyl-7-(2-methyl-1H-benzimidazol-6-yl)-N-(phenylmethyl)-2,3-dihydro-1,4-benzoxazepine-4(5H)-carboxamide |
| 174 | 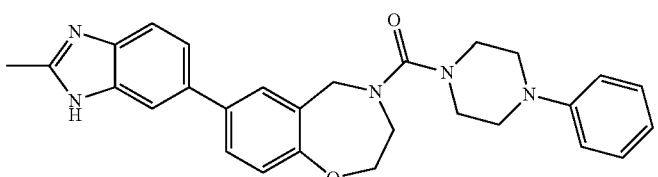 | 7-(2-methyl-1H-benzimidazol-6-yl)-4-[(4-phenylpiperazin-1-yl)carbonyl]-2,3,4,5-tetrahydro-1,4-benzoxazepine |
| 175 | 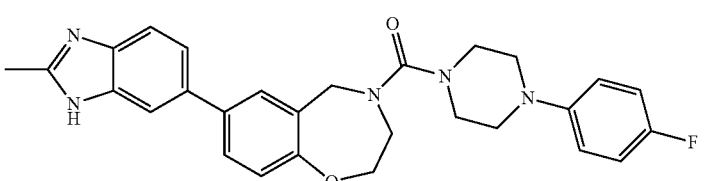 | 4-{[4-(4-fluorophenyl)piperazin-1-yl]carbonyl}-7-(2-methyl-1H-benzimidazol-6-yl)-2,3,4,5-tetrahydro-1,4-benzoxazepine |

TABLE 1-continued

| Entry No. | Structure | Name |
|---|---|---|
| 176 | 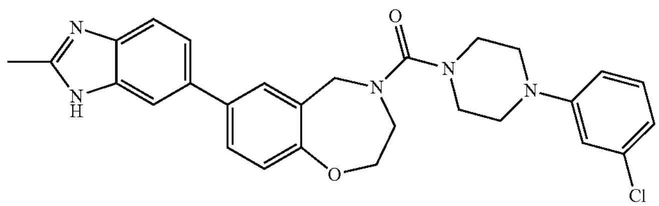 [SMILES: Cc1nc2ccc(-c3ccc4c(c3)CN(C(=O)N3CCN(c5cccc(Cl)c5)CC3)CCO4)cc2[nH]1] | 4-{[4-(3-chlorophenyl)piperazin-1-yl]carbonyl}-7-(2-methyl-1H-benzimidazol-6-yl)-2,3,4,5-tetrahydro-1,4-benzoxazepine |
| 177 | 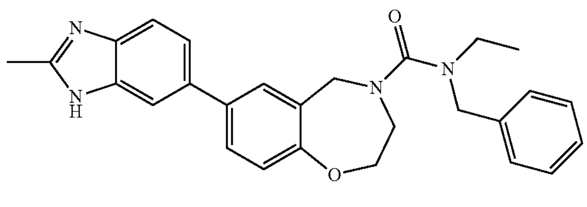 [SMILES: CCN(Cc1ccccc1)C(=O)N1CCOc2ccc(-c3ccc4nc(C)[nH]c4c3)cc2C1] | N-ethyl-7-(2-methyl-1H-benzimidazol-6-yl)-N-(phenylmethyl)-2,3-dihydro-1,4-benzoxazepine-4(5H)-carboxamide |
| 178 | 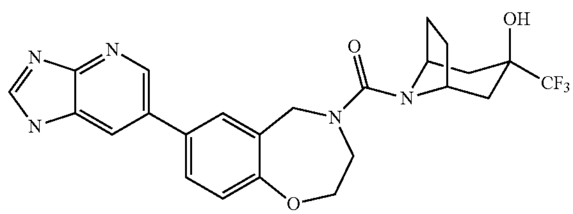 [SMILES: O=C(N1CCOc2ccc(-c3cnc4nc[nH]c4c3)cc2C1)N1C2CCC1CC(O)(C(F)(F)F)C2] | 8-{[7-(1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-(endo)-ol |
| 179 | 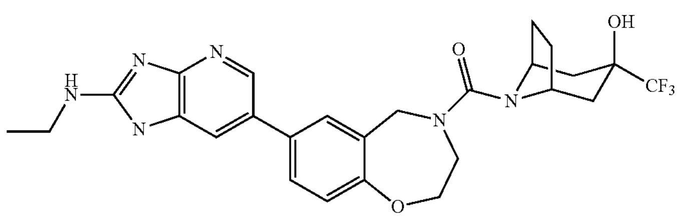 [SMILES: CCNc1nc2ncc(-c3ccc4c(c3)CN(C(=O)N3C5CCC3CC(O)(C(F)(F)F)C5)CCO4)cc2[nH]1] | 8-({7-[2-(ethylamino)-1H-imidazo[4,5-b]pyridin-6-yl]-2,3-dihydro-1,4-benzoxazepin-4(5H)-yl}carbonyl)-3-(trifluoromethyl)-8-azabicyclo[3.2.1]octan-3-(endo)-ol |
| 180 | 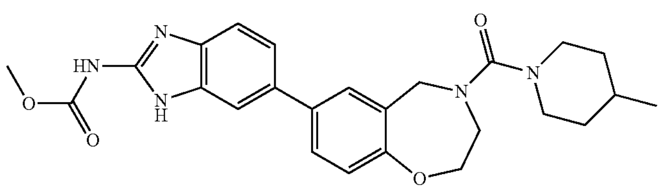 | 8-{[7-{6-amino-5-[(3-aminoazetidin-1-yl)sulfonyl]pyridin-3-yl}-2,3-dihydro-1,4-benzoxazepin-4(5H)-yl]carbonyl}-3-(trifluoromethyl)-8-azabicyclo[3.2.1]octan-3-ol |
| 181 | 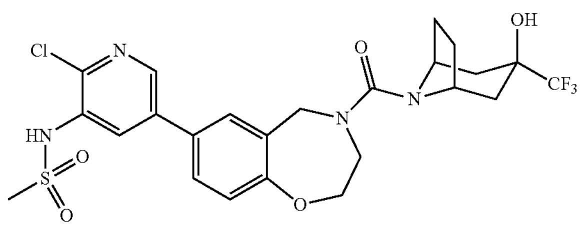 [SMILES: CS(=O)(=O)Nc1cc(-c2ccc3c(c2)CN(C(=O)N2C4CCC2CC(O)(C(F)(F)F)C4)CCO3)cnc1Cl] | N-[2-chloro-5-(4-{[3-hydroxy-3-(trifluoromethyl)-8-azabicyclo[3.2.1]oct-8-yl]carbonyl}-2,3,4,5-tetrahydro-1,4-benzoxazepin-7-yl)pyridin-3-yl]methanesulfonamide |

General Administration

In one aspect, the invention provides pharmaceutical compositions comprising an inhibitor of PI3K and/or mTOR according to the invention and a pharmaceutically acceptable carrier, excipient, or diluent. In certain other specific embodiments, administration is by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semisolid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Utility

Compounds of the Invention have activity for PI3K-alpha, mTOR, or for both. Compounds of this invention have been tested using the assays described in Biological Examples 1 and 3 and have been determined to be inhibitors of PI3K-alpha, mTOR, or for both. Suitable in vitro assays for measuring PI3K, mTORc1, and mTORc2 activity and the inhibition thereof by compounds are known in the art. For further details of an in vitro assay for measuring PI3K and mTOR activity see Biological Examples, Example 1, 2, and 3 infra. Cell-based assays for measurement of in vitro efficacy in treatment of cancer are known in the art. In addition, assays are described in Biological Examples, Example 5 and 6, infra. Suitable in vivo models for cancer are known to those of ordinary skill in the art. For further details of in vivo models for prostate adenocarcinoma, glioblastoma, lung carcinoma, and melanoma, see Biological Examples 7, 8, 9, 10, 11, 12, and 13, infra. Following the examples disclosed herein, as well as that disclosed in the art, a person of ordinary skill in the art can determine the activity of a compound of this invention.

Compounds of Formula I are useful for treating diseases, particularly cancer in which activity against PI3K-alpha, mTOR, or both contributes to the pathology and/or symptomatology of the disease. For example, cancer in which activity against PI3K-alpha, mTOR, or both contributes to its pathology and/or symptomatology include breast cancer, mantle cell lymphoma, renal cell carcinoma, acute myelogenous leukemia, chronic myelogenous leukemia, NPM/ALK-transformed anaplastic large cell lymphoma, diffuse large B cell lymphoma, rhabdomyosarcoma, ovarian cancer, endometrial cancer, cervical cancer, non small cell lung carcinoma, small cell lung carcinoma, adenocarcinoma, colon cancer, rectal cancer, gastric carcinoma, hepatocellular carcinoma, melanoma, pancreatic cancer, prostate carcinoma, thyroid carcinoma, anaplastic large cell lymphoma, hemangioma, glioblastoma, or head and neck cancer.

Compounds of the invention are also useful as inhibitors of PI3Kα and/or mTOR in vivo for studying the in vivo role of PI3Kα and/or mTOR in biological processes, including the diseases described herein. Accordingly, the invention also comprises a method of inhibiting PI3Kα and/or mTOR in vivo comprising administering a compound or composition of the invention to a mammal.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, $4^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of the Invention that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Some of the compounds of the invention contain an active ketone —$C(O)CF_3$ and may exist in part or in whole as the —C(OH$_2$)CF$_3$ form. Regardless of whether the compound is drawn as the —C(O)CF$_3$ or —C(OH$_2$)CF$_3$ form, both are included within the scope of the Invention. Although an individual compound may be drawn as the —C(O)CF$_3$ form, one of ordinary skill in the art would understand that the compound may exist in part or in whole as the —C(OH$_2$)CF$_3$ form and that the ratio of the two forms may vary depending on the compound and the conditions in which it exists.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. Further, for example, in this application R$^1$ can be 5-oxo-1H-1,2,4-triazol-3-yl, depicted structurally below:

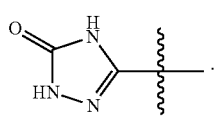

100

Both 5-oxo-1H-1,2,4-triazol-3-yl and the above structure 1 include, and are equivalent to, 3-hydroxy-4H-1,2,4-triazol-5-yl and its structure 2:

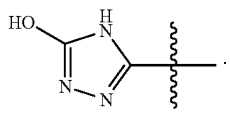

200

Regardless of which structure or which terminology is used, each tautomer is included within the scope of the Invention.

The present invention also includes N-oxide derivatives and protected derivatives of compounds of the Invention. For example, when compounds of the Invention contain an oxidizable nitrogen atom, the nitrogen atom can be converted to an N-oxide by methods well known in the art. When compounds of the Invention contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of the Invention can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. The following examples illustrate but do not limit the invention. All references cited herein are incorporated by reference in their entirety.

An intermediate of formula 4 where PG is a nitrogen-protecting group, R$^{5a}$ and R$^{5c}$ are independently hydrogen or alkyl, R$^{5h}$ is hydrogen or halo, R$^{5b}$ is hydrogen, amino, or halo, and R$^{5d}$, R$^{5e}$, R$^{5f}$, and R$^{5g}$ are hydrogen can be prepared according to Scheme 1.

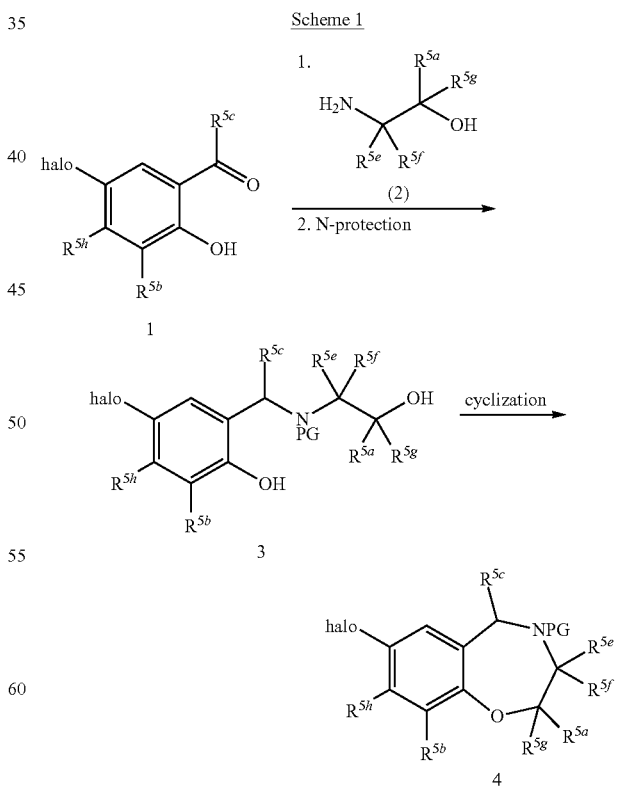

In particular, an intermediate of formula 4a can be prepared according to Scheme a.

Scheme 1a

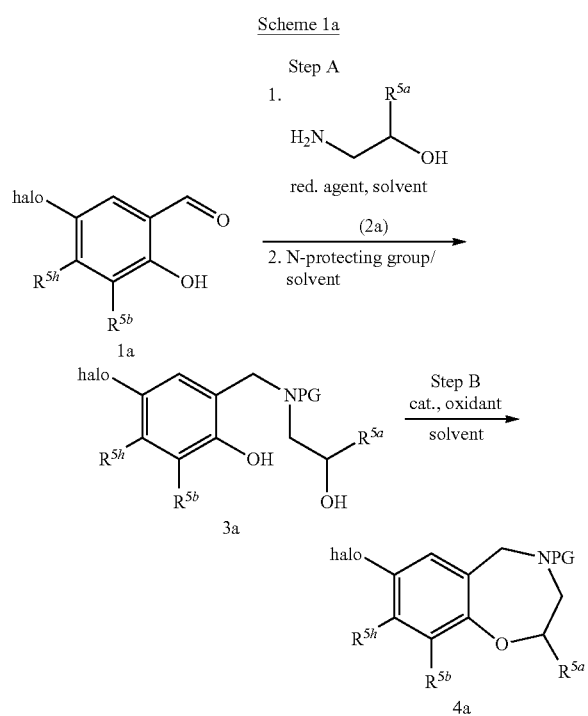

An intermediate of formula Ia is commercially available or can be prepared using methods known to one of ordinary skill in the art. In particular an intermediate of formula 1a where $R^{5b}$ is hydrogen and $R^{5h}$ is hydrogen, bromo, or chloro is commercially available. An intermediate of formula 1a where $R^{5h}$ is hydrogen and $R^{5b}$ is bromo, chloro, iodo, or fluoro is commercially available. An intermediate of formula 1a where $R^{5h}$ is fluoro and $R^{5b}$ is hydrogen can be prepared using procedures described in *J. of Med. Chem.*, 2004, 47(12), 3163-3179. An intermediate of formula 1a where $R^{5h}$ is hydrogen and $R^{5b}$ is amino can be prepared from the corresponding, commercially-available nitro intermediate using procedures known to one of ordinary skill in the art.

An intermediate of formula 2a where $R^{5a}$ is hydrogen or methyl is commercially available. The intermediate of formula 1a is treated with an intermediate of formula 2a in the presence of a reducing agent such as sodium borohydride, in a solvent(s) such as tetrahydrofuran and/or methanol and allowed to react at a temperature of about 40° C. for approximately 4 hours. The solvent is then removed and the reaction is taken up in a solvent(s) such as ethyl acetate and/or saturated sodium bicarbonate. To this suspension a nitrogen-protecting group precursor, such as di-tert-butyl dicarbonate, is added and the mixture is allowed to stir at room temperature overnight to yield an intermediate of formula 3a where PG is a nitrogen-protecting group.

Intermediate 3a is then treated with a catalyst, such as triphenylphosphine, in the presence of a dehydrating agent such as diisopropyl azodicarboxylate, in a solvent such as DCM. The reaction is allowed to proceed at room temperature for approximately 12 hours and the resulting product is optionally purified by column chromatography to yield an intermediate of formula 4a. Alternatively, the intermediate of formula 4a can be prepared by treating the intermediate of formula 3a with Burgess' reagent.

An intermediate of formula 5 where PG is a nitrogen-protecting group, $R^{5a}$ and $R^{5c}$ are independently hydrogen or alkyl, $R^{5h}$ is hydrogen or halo, $R^{5b}$ is hydrogen, amino, or halo, $R^{5e}$, $R^{5f}$, and $R^{5g}$ are hydrogen, and $R^1$ is as defined in the Summary of the Invention for a Compound of Formula I can be prepared according to Scheme 2.

Scheme 2

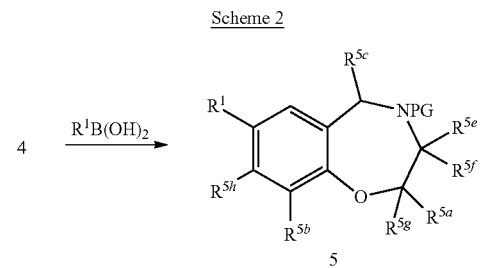

where the intermediate of formula 4 is prepared as described in Scheme 1.

In particular, an intermediate of formula 5a where $R^{5a}$ is hydrogen or alkyl, $R^{5h}$ is hydrogen or halo, $R^{5b}$ is hydrogen, amino, or halo, and $R^1$ is as defined in the Summary of the Invention for a Compound of Formula I, can be prepared according to Scheme 2a.

Scheme 2a

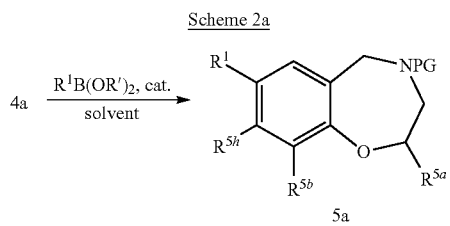

The intermediate of formula 4a, prepared as described in Scheme 1a, is treated with a boronic acid of formula —B(OR')$_2$ (where both R' are hydrogen or the two R' together form a boronic ester), which is commercially available or can be prepared using procedures known to one of ordinary skill in the art. The reaction is carried out in the presence of a catalyst such as Pd(dppf)$_2$Cl$_2$, a base such as potassium carbonate, and in a solvent such as DME at about 80° C. for about 2 hours. The product can then be purified by chromatography to yield an intermediate of formula 5a.

Alternatively, an intermediate of formula 5, as defined above, can be prepared as described in Scheme 4.

Scheme 4

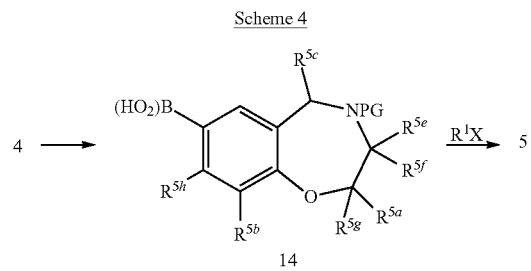

In particular, an intermediate of formula 5b where PG is a nitrogen-protecting group and $R^1$ is as defined in the Summary of the Invention for a Compound of Formula I can be prepared according to Scheme 4a.

Scheme 4a

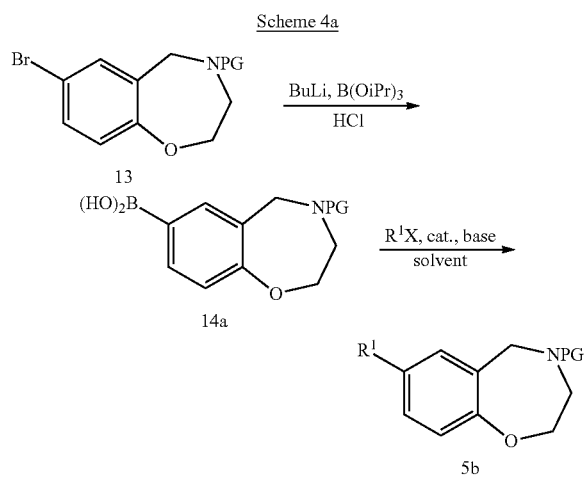

An intermediate of formula 13, where PG is a nitrogen-protecting group, is prepared as described in Scheme 1a. 13 is treated with triisopropylborate in a solvent such as THF at a temperature of about −60° C., followed by dropwise addition of a base such as n-butyllithium in tetrahydrofuran. The reaction was allowed to proceed for about 30 minutes, was treated with an acid such as hydrochloric acid, and allowed to warm to room temperature to yield an intermediate of formula 14a. Intermediate 14a is then treated with an intermediate of formula $R^1X$ (where X is a halide, and which is commercially available or can be prepared using procedures known to one of ordinary skill in the art), in the presence of a base such as potassium carbonate, in the presence of a catalyst such as tetrakis(triphenylphosphine)palladium(0), and in a solvent(s) such as 1,2-dimethoxyethane and/or water. The reaction is allowed to proceed under nitrogen and stirred at reflux for about 3 hours to yield an intermediate of formula 5b.

A Compound of the Invention of Formula I where $R^{5a}$ and $R^{5c}$ are independently hydrogen or alkyl, $R^{5h}$ is hydrogen or halo, $R^{5b}$ is hydrogen, amino, or halo, $R^{5e}$, $R^{5f}$, and $R^{5g}$ are hydrogen, and $R^1$ and $R^2$ are as defined in the Summary of the Invention for a Compound of Formula I can be prepared as described in Scheme 5,

Scheme 5

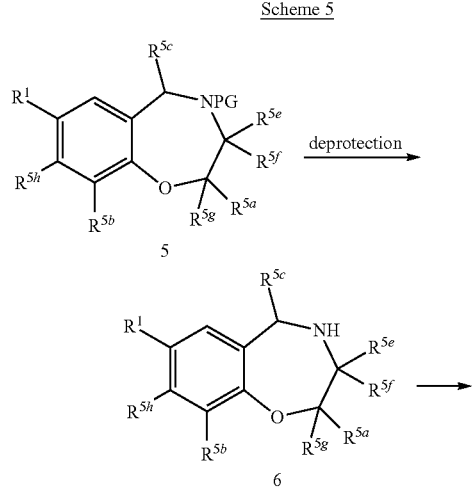

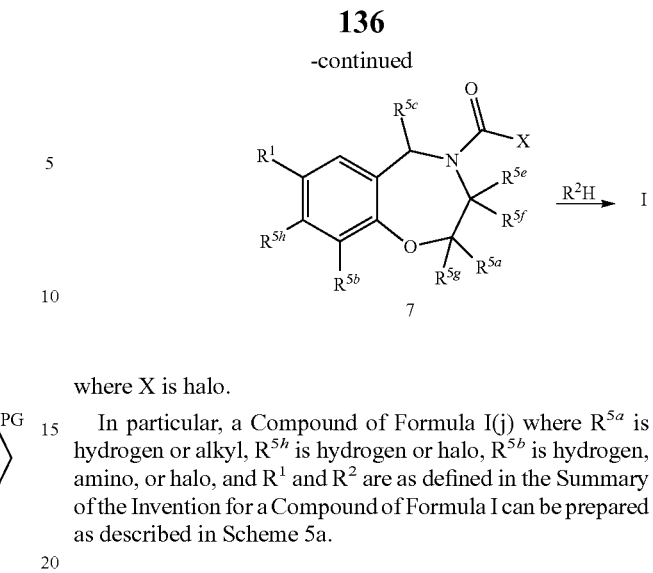

where X is halo.

In particular, a Compound of Formula I(j) where $R^{5a}$ is hydrogen or alkyl, $R^{5h}$ is hydrogen or halo, $R^{5b}$ is hydrogen, amino, or halo, and $R^1$ and $R^2$ are as defined in the Summary of the Invention for a Compound of Formula I can be prepared as described in Scheme 5a.

Scheme 5a

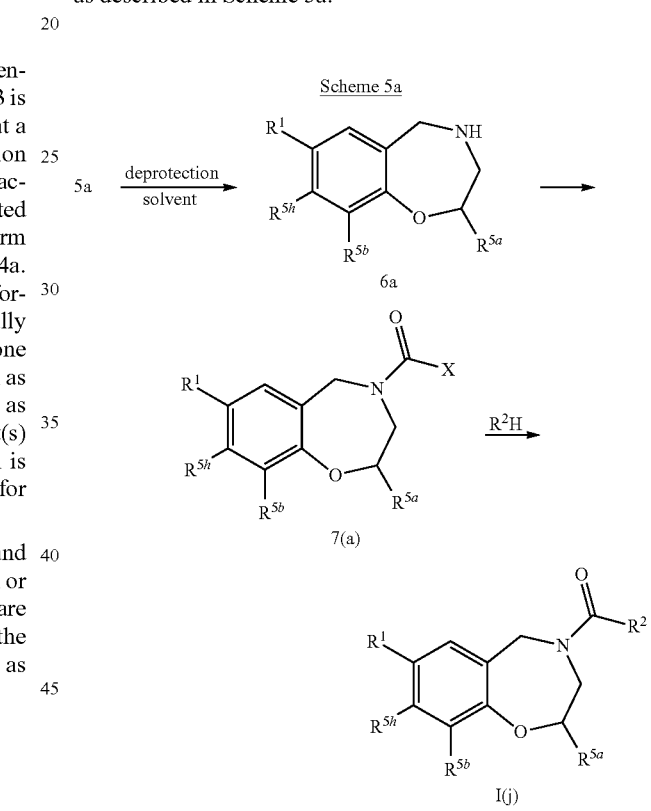

The protecting group on the intermediate of formula 5a is removed. When the protecting group is Boc, it can be removed with HCl to yield an intermediate of formula 6a. The intermediate of formula 7(a) where X is halo is prepared using procedures known to one of ordinary skill in the art. The intermediate of formula $R^2H$ is commercially available or can be prepared using procedures described herein or procedures known to one of ordinary skill in the art. The intermediate of formula 6a is then treated with $R^2H$, in the presence of a base such as Hünig's base, in a solvent such as DMF, at a temperature of about 50° C. The product can be purified by column chromatography to yield an intermediate of Formula I(j).

In particular, a Compound of Formula I(k) where $R^1$ and $R^2$ are as defined in the Summary of the Invention for a Compound of Formula I can be prepared according to Scheme 5b.

137

Scheme 5b

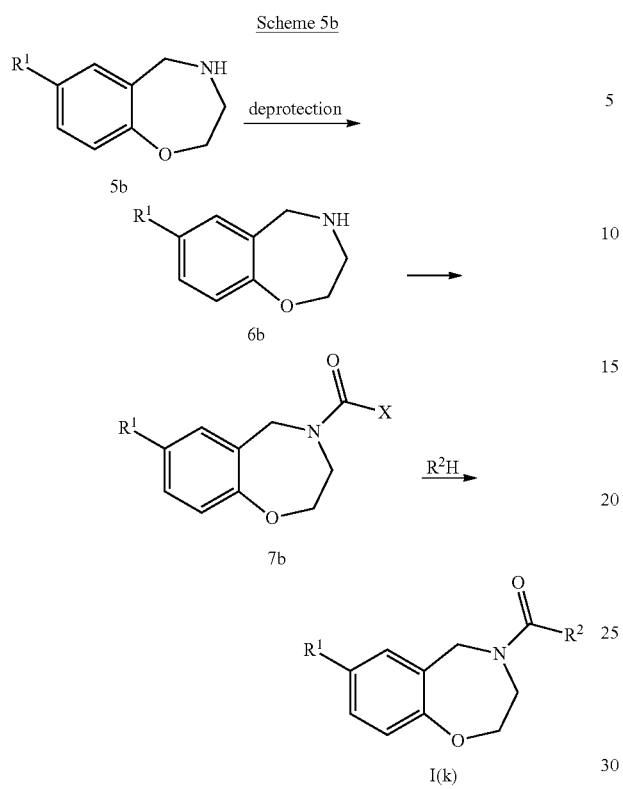

The protecting group on intermediate of formula 5b, prepared as described in Scheme 4a, is removed. When the protecting group is Boc, it can be removed with HCl to yield an intermediate of formula 6b. Intermediate 7b is then prepared using procedures known to one of ordinary skill in the art. Intermediate 7b is then treated with an intermediate of R²H using conditions known to one or ordinary skill in the art to yield a Compound of Formula I(k).

A compound of the invention where $R^{5a}$, $R^{5b}$, $R^{5c}$, $R^{5d}$, $R^{5e}$, $R^{5f}$, $R^{5g}$, and $R^{5h}$ are hydrogen; $R^1$ is benzimidazol-6-yl substituted at the 2-position with one $R^7$; $R^7$ is alkyl; and $R^2$ is as defined in the Summary of the Invention for a Compound of Formula I can be prepared according to Scheme 6.

Scheme 6

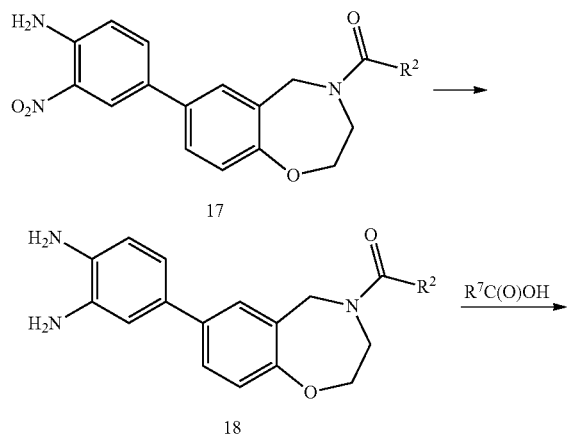

138

-continued

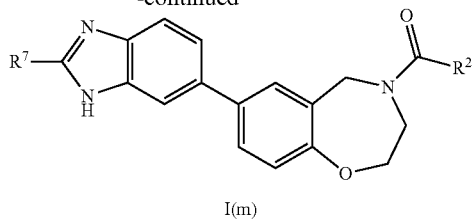

A Compound of Formula I(y) where and $R^2$ is as defined in the Summary of the Invention for a Compound of Formula I can be prepared according to Scheme 7a.

Scheme 7a

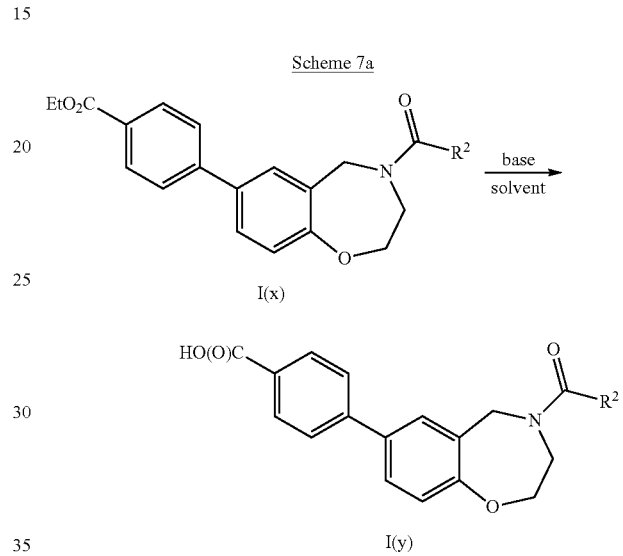

The Compound of Formula I(x), prepared using procedures according to Scheme 5b, is treated with a base such as LiOH, in a solvent(s) such as THF and/or water to yield the hydrolyzed Compound of Formula I(y).

A Compound of Formula I where $R^1$, $R^2$, $R^{5a}$, $R^{5b}$, $R^{5c}$, $R^{5d}$, $R^{5e}$, $R^{5f}$, $R^{5g}$, and $R^{5h}$ are as defined in the Summary of the Invention for a Compound of Formula I can be prepared according to the following scheme (where X is halo) using procedures known to one of ordinary skill in the art.

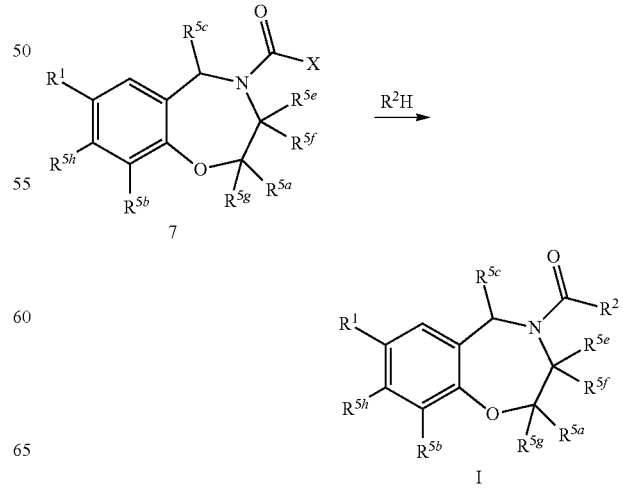

A Compound of Formula I where $R^1$, $R^2$, $R^{5a}$, $R^{5b}$, $R^{5c}$, $R^{5d}$, $R^{5e}$, $R^{5f}$, $R^{5g}$ and $R^{5h}$ are as defined in the Summary of the Invention for a Compound of Formula I can be prepared according to the following scheme where R is —B(OR')$_2$ (where both R' are hydrogen or the two R' together form a boronic ester) and Y is halo, or R is halo and Y is —B(OR')$_2$ (where both R' are hydrogen or the two R' together form a boronic ester) using Suzuki coupling procedures known to one of ordinary skill in the art.

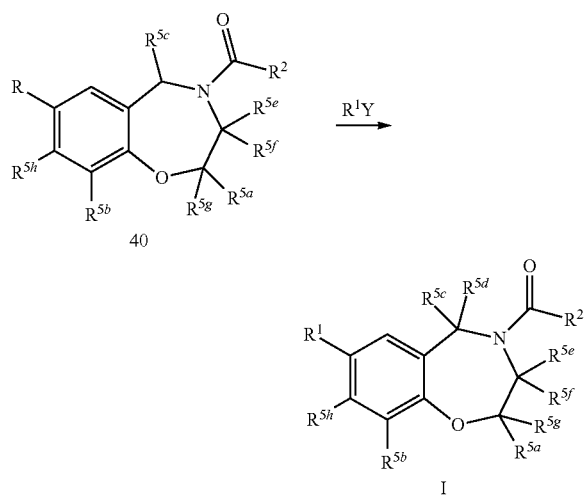

Synthetic Examples

Reagent Preparation 1

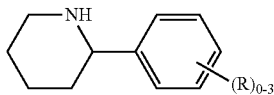

STEP 1: To a solution of tert-butyl 2-oxopiperidine-1-carboxylate (0.30 g, 1.51 mmol) in tetrahydrofuran (8 mL) cooled to −78° C. was added slowly over 15 minutes 0.3 M 3,4,5-trifluorophenylmagnesium bromide in tetrahydrofuran (3.30 mL, 1.66 mmol) and the mixture was then allowed to warm to 25° C. over 30 minutes. The reaction mixture was poured slowly into an ice cold solution of 0.5 N hydrochloric acid (100 mL), and extracted twice with ethyl acetate (2×50 mL). The combined organic extracts were dried over anhydrous sodium sulfate then filtered and concentrated. The residue was purified by silica gel column chromatography (diethyl ether/hexanes 1:4) to give tert-butyl 5-oxo-5-(3,4,5-trifluorophenyl)pentylcarbamate (0.18 g, 36% yield). MS (EI) for $C_{16}H_{20}F_3NO_3$: 332 (MH$^+$).

STEP 2: Tert-butyl 5-oxo-5-(3,4,5-trifluorophenyl)pentylcarbamate (0.18 g, 0.54 mmol) was stirred in trifluoroacetic acid/dichloromethane 1:1 (8 mL) for 1 hour then concentrated. The residue was dissolved in ethyl acetate (40 mL) and washed with saturated sodium chloride/2M aqueous sodium hydroxide 10:1 (11 mL), then dried over anhydrous sodium sulfate, filtered and concentrated to provide 5-amino-1-(3,4,5-trifluorophenyl)pentan-1-one (0.11 g, 88% yield) as an oil. MS (EI) for $C_{11}H_{12}F_3NO$: 232 (MH$^+$).

STEP 3: To 5-amino-1-(3,4,5-trifluorophenyl)pentan-1-one (0.11 g, 0.48 mmol) in tetrahydrofuran/methanol 4:1 (10 mL) was added in portions over 20 minutes solid sodium borohydride (0.20 g, 5.0 mmol) and stirring was continued 18 hours at 25° C. The reaction mixture was concentrated then taken into ethyl acetate (40 mL), washed with saturated sodium chloride/2 N aqueous sodium hydroxide 10:1 (11 mL) then dried over anhydrous sodium sulfate, filtered and concentrated. The residue was purified by silica gel column chromatography (ethyl acetate/hexanes, 1:1) to give 2-(3,4,5-trifluorophenyl)piperidine (0.70 g, 68% yield) as an oil. $^1$H NMR (400 MHz, CDCl$_3$): 7.01 (m, 2H), 3.52 (m, 1H), 3.17 (m, 1H) 2.77 (m, 1H), 2.07 (br s, 1H), 1.88 (m, 1H), 1.74 (m, 1H), 1.64 (m, 1H), 1.55-1.35 (m, 3H).

Using analogous synthetic techniques and substituting with alternative starting materials in step 1 the following reagents were prepared. Alternative starting materials were purchased from commercial sources unless otherwise indicated.

2-(3-chloro-4-fluorophenyl)piperidine. Prepared according to the method of reagent preparation 1 using 3-chloro-4-fluorphenylmagnesium bromide in step 1. MS (EI) for $C_{11}H_{13}ClFN$: 214 (MH$^+$).

2-(3,5-difluorophenyl)piperidine. Prepared according to the method of reagent preparation 1 using 3,4-difluorphenylmagnesium bromide in step 1. MS (EI) for $C_{11}H_{13}F_2N$: 198 (MH$^+$).

2-(4-fluoro-3-methylphenyl)piperidine. Prepared according to the method of reagent preparation 1 using 4-fluoro-3-methylphenylmagnesium bromide in step 1. $^1$H NMR (400 MHz, CDCl$_3$): 7.19 (dd, 1H), 7.11 (m, 1H), 6.92 (t, 1H), 3.54 (m, 1H), 3.17 (m, 1H), 2.76 (m, 1H), 2.25 (d, 3H), 1.89 (m, 2H), 1.75 (m, 1H), 1.66 (m, 1H), 1.48 (m, 2H).

2-(4-chlorophenyl)piperidine. Synthesized according to the method of reagent preparation 1 using 4-chlorophenylmagnesium bromide in step 1. MS (EI) for $C_{11}H_{14}ClN$: 196 (MH$^+$).

2-(3,4-difluorophenyl)piperidine. Synthesized according to the method of reagent preparation 1 using 3,4-difluorophenylmagnesium bromide in step 1. $^1$H NMR (400 MHz, CDCl$_3$): 7.64 (m, 1H), 7.49 (m, 1H), 7.15 (m, 1H), 3.83 (m, 2H), 2.57 (m, 2H), 1.84 (m, 2H), 1.67 (m, 2H).

2-(4-chloro-3-fluorophenyl)piperidine. Synthesized according to the method of reagent preparation 1 using 4-chloro-3-fluorophenylmagnesium bromide in step 1. $^1$H NMR (400 MHz, CDCl$_3$): 7.59 (dd, 1H), 7.49 (dd, 1H), 7.38 (tr, 1H), 3.84 (m, 2H), 2.56 (m, 2H), 1.84 (m, 2H), 1.67 (m, 2H).

2-(3,5-bis(trifluoromethyl)phenyl)piperidine. Synthesized according to the method of reagent preparation 1 using 3,5-bis(trifluoromethyl)phenylmagnesium bromide in step 1. MS (EI) for $C_{13}H_{13}F_6N$: 298 (MH$^+$).

2-(3-chloro-5-fluorophenyl)piperidine. Synthesized according to the method of reagent preparation 1 using 3-chloro-5-fluorophenylmagnesium bromide in step 1. MS (EI) for $C_{11}H_{13}ClFN$: 214 (MH$^+$).

2-(4-(trifluoromethoxy)phenyl)piperidine. Synthesized according to the method of reagent preparation 1 using 4-trifluoromethoxyphenylmagnesium bromide in step 1. MS (EI) for $C_{12}H_{14}F_3NO$: 246 (MH$^+$).

2-(3-fluoro-4-methoxyphenyl)piperidine. Synthesized according to the method of reagent preparation 1 using 3-fluoro-4-methoxyphenylmagnesium bromide in step 1. MS (EI) for $C_{12}H_{16}FNO$: 210 (MH$^+$).

2-(2-fluorophenyl)piperidine. Synthesized according to the method of reagent preparation 1 using 2-fluorophenylmagnesium bromide in step 1. MS (EI) for $C_{11}H_{14}FN$: 180 (MH$^+$).

2-(4-(trifluoromethyl)phenyl)piperidine. Synthesized according to the method of reagent preparation 1 using 4-trifluorophenylmagnesium chloride in step 1. MS (EI) for $C_{12}H_{14}F_3N$: 230 (MH$^+$).

2-(3-fluoro-4-methylphenyl)piperidine. Synthesized according to the method of reagent preparation 1 using 3-fluoro-4-methylphenylmagnesium bromide in step 1. MS (EI) for $C_{12}H_{16}FN$: 194 (MH$^+$).

2-(3,4-dichlorophenyl)piperidine. Synthesized according to the method of reagent preparation 1 using 3,4-dichlorophenylmagnesium bromide in step 1. MS (EI) for $C_{11}H_{13}Cl_2N$: 230 MH$^+$).

2-(4-fluoro-2-methylphenyl)piperidine. Synthesized according to the method of reagent preparation 1 using 4-fluoro-2-methylphenylmagnesium bromide in step 1. MS (EI) for $C_{12}H_{16}FN$: 194 (MH$^+$).

Reagent Preparation 2

(±)-(2R,4S)-2-phenylpiperidin-4-ylmethanol

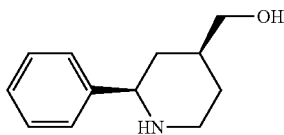 [SMILES: OC[C@H]1CCN[C@@H](c2ccccc2)C1]

STEP 1: A suspension of potassium tert-butoxide (1.25 g, 11.1 mmol) and methyltriphenylphosphonium bromide (3.86 g, 1.1 mmol) in tetrahydrofuran (100 mL) was stirred at 40° C. for 30 minutes. The mixture was then cooled to room temperature and a solution of tert-butyl 4-oxo-2-phenylpiperidine-1-carboxylate (2.35 g, 8.5 mmol) in tetrahydrofuran (30 mL) was added slowly. The reaction mixture was stirred at 40° C. for 24 hours. The mixture was cooled to room temperature and quenched by the addition of water and diluted with ethyl acetate (250 mL), The organic layer was separated then washed with water, 10% aqueous citric acid and brine, dried over anhydrous sodium sulfate, filtered and concentrated. Column chromatography on silica gel (hexane:ethyl acetate 95:5 to 9:1) provided tert-butyl 4-methylene-2-phenylpiperidine-1-carboxylate (2.24 g, 96%). $^1$H NMR (400 MHz, CDCl$_3$): 7.31 (m, 4H), 7.21 (m, 1H), 5.48 (br d, 1H), 4.84 (dd, 2H), 4.07 (br dd, 1H), 2.85 (br, t, 1H), 2.78 (dtr, 1H), 2.64 (dd, 1H), 2.28 (dtr, 1H), 2.20 (br d, 1H), 1.42 (s, 9H). GC/MS (EI) for $C_{17}H_{23}NO_2$: 273 (M$^+$).

STEP 2: To solution of tert-butyl 4-methylene-2-phenylpiperidine-1-carboxylate (2.20 g, 8.04 mmol) in tetrahydrofuran (50 mL) at 0° C. was added borane-tetrahydrofuran complex (1M solution in tetrahydrofuran) (12.1 mL, 12.1 mmol) and the reaction mixture was stirred at 0° C. for 1 hour. The reaction mixture was allowed to warm to room temperature then stirred for an additional 2 hours. It was cooled to 0° C. and 2M aqueous sodium hydroxide (8.0 mL, 16.0 mmol) was added slowly followed by the slow addition of 30% aqueous hydrogen peroxide (5.5 mL, 48.4 mmol). The mixture was stirred for another hour then diluted with water (100 mL) and partitioned with ethyl acetate (250 mL). The organic layer was separated and washed with 2M aqueous sodium thiosulfate (100 mL), brine, dried over anhydrous sodium sulfate, filtered and concentrated. Column chromatography in silica gel (chloroform:methanol 9:1 to 4:1) provided tert-butyl 4-(hydroxymethyl)-2-phenylpiperidine-1-carboxylate (1.86 g, 79%). $^1$H NMR (400 MHz, CDCl$_3$): 7.30 (m, 2H), 7.20 (m, 3H), 4.86 (dd, 1H), 4.04 (m, 1H), 3.62 (m, 0.5H), 3.44 (m, 3H), 3.24 (m, 1H), 2.12 (m, 0.5H), 1.93 (m, 1H), 1.64 (m, 2H), 1.42 (m, 1H), 1.26 (s, 9H). GC/MS (EI) for $C_{17}H_{25}NO_3$: 235 (M-tBu$^+$).

STEP 3: To a solution of tert-butyl 4-(hydroxymethyl)-2-phenylpiperidine-1-carboxylate (0.29 g, 1.00 mmol) in dichloromethane (50 mL) was added trifluoroacetic acid (10 mL) and the reaction mixture was heated to reflux. After cooling to room temperature the solvent was evaporated. The residue was twice taken into 50% ethyl acetate in toluene then concentrated (2×100 mL) and the resulting solid then dried to give (±)-(2R,4S)-2-phenylpiperidin-4-ylmethanol as the trifluoroacetic acid salt (0.26 g, quantitative). MS (EI) for $C_{12}H_{17}NO$: 192 (MH$^+$).

Reagent Preparation 3

2-(trifluoromethyl)piperidine

A mixture of 2-(trifluoromethyl)pyridine (0.38 g, 2.60 mmol) and platinum oxide (0.04 g, 0.18 mmol) in acetic acid (15 mL) and concentrated hydrochloric acid (2 mL) was hydrogenated in a Parr apparatus at 40 psi for 3 d. Filtration through celite and concentration of the filtrate provided 2-(trifluoromethyl)piperidine as hydrochloride salt which was used without further purification. $^1$H NMR (400 MHz, methanol-d$_4$): 4.18 (m, 1H), 3.50 (m, 1H), 3.15 (m, 1H), 2.16 (m, 1H), 1.99 (m, 2H), 1.71 (m, 3H).

Using analogous synthetic techniques and substituting with alternative starting reagents the following reagents were prepared. Alternative starting materials were obtained commercially unless otherwise indicated.

4-cyclopropylpiperidine. Prepared as hydrochloride salt according to reagent preparation 3 by using 4-cyclopropylpyridine. MS (EI) for $C_8H_{15}N$: 125 (M$^+$).

Reagent Preparation 4 tert-butyl 8-azabicyclo[3.2.1]octan-3-(endo)-ylcarbamate

STEP 1: To a 5 L round-bottom flask was added 8-methyl-8-azabicyclo[3.2.1]octan-3-endo-amine (432 g, 3.1 mol), 2 L of dry 1,4-dioxane, 675 mL of deionized water and 468 g of dry triethylamine. Di-tert-butyl dicarbonate (solution in 1.2 L of dioxane) was added dropwise to the stirring solution at room temperature over 16 h. The reaction mixture was concentrated and the resulting residue suspended in 2.5 L of methylene chloride. then washed twice with 1 L of water, dried with anhydrous magnesium sulfate, filtered, and volatile organics removed by rotary evaporation to yield 617 g (83%) of tert-butyl 8-methyl-8-azabicyclo[3.2.1]octan-3-ylcarbamate (mp 79-81° C.).

STEP 2: To a 5 L round-bottom flask was added 480 g (2.0 mol) of tert-butyl 8-methyl-8-azabicyclo[3.2.1]octan-3-endo-ylcarbamate, 2 L of toluene, and 69 g (0.5 mol) of potassium carbonate. 2,2,2-Trichloroethyl chloroformate (347 mL, 2.4 mol) was added dropwise at room temperature over 6 h and the reaction heated at reflux temperature for 8 h. After the solution was cooled to room temperature, 1.2 L of water was added to the reaction solution and stirred 0.5 h. The organic layer was separated and washed with 1 L of brine, dried with anhydrous magnesium sulfate, filtered, and concentrated to yield a cloudy oil. The oil was titurated with 700 mL of a 3:2 ethyl ether/hexanes solution to yield 280 g (mp 131-135° C.) of 2,2,2-trichloroethyl 3-endo-(tert-butoxycarbonylamino)-8-azabicyclo[3.2.1]octane-8-carboxylate as a solid that was collected by filtration. The mother liquor was concentrated and titrated further to yield a less pure sample of the Troc protected diamine (129 g, mp 116-118° C.).

STEP 3: To a 5 L round-bottom flask was added 360 g (0.9 mol) of 2,2,2-trichloroethyl 3-endo-(tert-butoxycarbonylamino)-8-azabicyclo[3.2.1]octane-8-carboxylate, 2.8 L of methanol and 675 g (12.6 mol) of ammonium chloride. The solution was heated to reflux and 387 g (7.5 mol) of zinc dust was carefully added in small portions over 0.5 h. Upon complete addition of the zinc dust, the reaction was heated at reflux temperature for 2 h then cooled to room temperature. The reaction filtered through a thin pad a Celite 545, and the methanol removed by rotary evaporation. The resulting solid was dissolved in 800 mL of methylene chloride and stirred with 600 mL of concentrated ammonium hydroxide for 0.5 h. The organic layer was separated, washed with 600 mL of water, dried with anhydrous magnesium sulfate, filtered, and concentrated to yield an oil. The residue was dissolved in 200 ml, of methylene chloride and 1 L of ethyl ether then filtered. The resulting solution was chilled to 0° C. and 215 mL of 4 N hydrogen chloride in dioxane was added slowly, dropwise over 0.5 h, being sure to maintain the reaction solution temperature close to 0° C. After the addition was complete, 200 mL of methylene chloride and 1.4 L of ethyl ether were added to the cooled solution and a pale white precipitate formed. The resulting solid was collected by filtration to yield 173 g (85%) of tert-butyl 8-azabicyclo[3.2.1]octan-3-endo-ylcarbamate hydrochloride salt.

Reagent Preparation 5

4-methylpiperidin-4-ol

STEP 1: To a solution of methyl magnesium bromide (6.00 mmol) in ethyl ether (27 mL) was added 1-benzyl-piperidin-4-one (0.53 g, 0.28 mmol) at 0° C. followed by tetrahydrofuran (10 mL). The reaction mixture was warmed to room temperature and stirred for 18 h. Saturated ammonium chloride was added and the aqueous layer was extracted with ethyl acetate (3×). The combined organic extracts were dried over sodium sulfate, filtered and concentrated. Column chromatography on silica (2-10% methanol in dichloromethane) afforded 1-benzyl-4-methylpiperidin-4-ol (0.42 g, 72% yield).

STEP 2: A mixture of 1-benzyl-4-methylpiperidin-4-ol (0.20 g, 0.97 mmol) and 10% palladium on carbon in methanol was hydrogenated in a Parr apparatus at 35 psi for 18 h. Then a solution of 4M hydrochloric acid in dioxane (0.1 mL) was added and the mixture was filtered through celite. The filtrate was concentrated and dried to give 4-methylpiperidin-4-ol as hydrochloride salt (0.10 g, 89% yield). $^1$H NMR (400 MHz, methanol-$d_4$): 3.23 (m, 4H), 1.77 (m, 4H), 1.29 (s, 3H).

Reagent Preparation 6

4-(difluoromethyl)piperidine

STEP 1: To a solution of tert-butyl (4-hydroxymethyl)piperidine-1-carboxylate (0.52 g, 2.40 mmol, (J. Labelled Compounds and Radiopharmaceuticals 1999, 42, 1289-1300) in dichloromethane (20 mL) was added Dess-Martin-periodinane (1.13 g, 2.66 mmol), and the mixture was stirred at room temperature for 2 h. A 10% aqueous solution of sodium thiosulfate (20 mL) was added followed by saturated sodium bicarbonate (20 mL), and the biphasic mixture was stirred at room temperature for 45 min. The layers were separated and the aqueous layer was extracted with dichloromethane (2×). The combined organic layers were washed with saturated sodium bicarbonate, brine, dried over sodium sulfate then filtered and concentrated to afford tert-butyl 4-formylpiperidine-1-carboxylate. $^1$H NMR (400 MHz, CDCl$_3$): 9.67 (s, 1H), 3.99 (m, 2H), 2.93 (m, 2H), 2.42 (m, 1H), 1.89 (m, 2H), 1.55 (m, 2H), 1.46 (s, 9H).

STEP 2: To a solution of DAST (1.16 g, 7.20 mmol) in dichloromethane (30 mL) was added a solution of tert-butyl 4-formylpiperidine-1-carboxylate (0.51 g, 2.40 mmol) in dichloromethane (5 mL) at 0° C. The reaction mixture was warmed to room temperature and stirred for 18 h. A 5% aqueous solution of sodium bicarbonate was added, the layers were separated, the organic layer was washed with saturated sodium bicarbonate, and brine, dried over sodium sulfate, filtered and concentrated to provide tert-butyl 4-(difluoromethyl)piperidine-1-carboxylate. $^1$H NMR (400 MHz, CDCl$_3$): 5.59 (m, 1H), 4.20 (m, 2H), 2.69 (m, 2H), 1.91 (m, 1H), 1.74 (m, 2H), 1.46 (s, 9H), 1.34 (m, 2H).

STEP 3: A solution of tert-butyl 4-(difluoromethyl)piperidine-1-carboxylate in trifluoroacetic acid was stirred at room temperature for 1 h then concentrated and dried to give 4-(difluoromethyl)piperidine as the trifluoroacetate salt. $^1$H NMR (400 MHz, CDCl$_3$): 5.67 (m, 1H), 3.55 (m, 2H), 2.96 (m, 2H), 2.04 (m, 3H), 1.80 (m, 2H).

Reagent Preparation 7

4-(fluoromethyl)piperidine

A solution of tert-butyl 4-(fluoromethyl)piperidine-1-carboxylate (J. Labelled Compounds and Radiopharmaceuticals 1999, 42, 1289-1300) in trifluoroacetic acid was stirred at room temperature for 1 h and then concentrated and dried to give 4-(fluoromethyl)-piperidine as the trifluoroacetate salt. $^1$H NMR (400 MHz, CDCl$_3$): 4.33 (dd, 2H), 3.49 (m, 2H), 2.92 (m, 2H), 2.07 (m, 1H), 1.97 (m, 2H), 1.64 (m, 2H).

Reagent Preparation 8

4-fluoro-4-methylpiperidine

STEP 1: To a solution of 1-benzyl-4-methylpiperidine-4-ol (0.16 g, 0.76 mmol) (reagent preparation 5, step 1) in dichloromethane (10 mL) was added DAST (0.37 g, 2.30 mmol) at 0° C. The reaction mixture was warmed to room temperature and stirred for 16 h. A 5% aqueous solution of sodium bicarbonate was added, the layers were separated, the organic layer was washed with saturated sodium bicarbonate, and brine, dried over sodium sulfate, filtered and concentrated to provide a mixture of 1-benzyl-4-fluoro-4-methylpiperidine and 1-benzyl-4-methyl-1,2,3,6-tetrahydropyridine. The mixture was dissolved in acetone (15 mL) and water (3 mL) then osmium tetroxide (0.25 mL of a 4% aqueous solution, 0.04 mmol) and N-methylmorpholine N-oxide (0.11 g, 0.91 mmol) were added at 0° C. The solution was kept in a freezer at −20° C. for 3 d then warmed to room temperature and 10% aqueous sodium thiosulfate was added. The biphasic mixture was stirred for 90 min at room temperature. Dichloromethane was added, the mixture was filtered through celite and the organic layer was washed with 1M hydrochloric acid, dried over sodium sulfate, filtered and concentrated to give a 1-benzyl-4-fluoro-4-methylpiperidine.

STEP 2: A suspension of 1-benzyl-4-fluoro-4-methylpiperidine as obtained in step 1 and 10% palladium on carbon in methanol was hydrogenated in a Parr apparatus at 40 psi for 18 h. The mixture was filtered through celite and the filtrate concentrated to give 4-fluoro-4-methylpiperidine which was used without further purification. MS (EI) for $C_6H_{12}FN$: 118 (MH$^+$)

Reagent Preparation 9

4-(1,1-difluoroethyl)piperidine

STEP 1: To a solution of DAST (1.83 g, 11.35 mmol) in dichloromethane (30 mL) was added 4-acetylpyridine (1.00 g, 8.25 mmol) at 0° C. The reaction mixture was warmed to room temperature and stirred for 2 d. More DAST (0.61 g, 3.78 mmol) was added and stirring was continued for 1 d. A 5% aqueous solution of sodium bicarbonate was added, the layers were separated and the organic layer was washed with saturated sodium bicarbonate, and brine then dried over sodium sulfate, filtered and concentrated to provide a 5:1 mixture of 4-(1,1-difluoroethyl)pyridine and 4-acetylpyridine.

STEP 2: The mixture was dissolved in methanol (10 mL) and 1 M hydrochloric acid (10 mL) then catalytic platinum oxide was added and the resulting suspension was hydrogenated in a Parr apparatus at 40 psi for 3 d. Filtration through celite and concentration of the filtrate gave a complex mixture containing 20% of the desired 4-(1,1-difluoroethyl)piperidine as the hydrochloride salt which was used without further purification.

Reagent Preparation 10

(3aR,6aS)-5-methyloctahydrocyclopenta[c]pyrrole

STEP 1: (3aR,6aS)-tent-Butyl 5-methylenehexahydrocyclopenta[c]pyrrole-2(1H)-carboxylate (Tetrahedron 1993, 49(23), 5047-54) (107 mg, 0.48 mmol) was taken into methanol (1 mL) followed by addition of platinum oxide (10 mg) and the mixture was sparged with hydrogen gas at 1 atm for 10 minutes then allowed to stir under an atmosphere of hydrogen for 12 h. The mixture was filtered through a celite pad and the filtrate concentrated. The residue was taken into a minimum of ethyl acetate then filtered through a silica gel pad using 100% ethyl acetate. The filtrate was concentrated and dried to give (3aR,6aS)-tert-butyl 5-methyl hexahydrocyclopenta[c]pyrrole-2(1H)-carboxylate as a colorless oil, 5-methyl endo/exo isomer mixture (98.6 mg, 92% yield). GC-MS (EI) for $C_{13}H_{23}NO_2$: 225 (M$^+$)

STEP 2: (3aR,6aS)-tert-butyl 5-methyl hexahydrocyclopenta[c]pyrrole-2(1H)-carboxylate (98.6 mg, 0.44 mmol) was taken into a minimum of neat TFA and the solution was allowed to stand for 30 minutes at room temperature. The mixture was then concentrated and the residue taken into methanol and concentrated again then dried. The residue thus obtained was taken into methanol (5 mL) and basified using Bio-Rad AG-1X hydroxide form resin. The mixture was then filtered and concentrated and dried to give (3aR,6aS)-5-methyloctahydrocyclopenta[c]pyrrole (27.9 mg, 55%) as an amorphous residue.

Reagent Preparation 11

(±)-(3aR,6aS)-5-methyl-1,2,3,3a,4,6a-hexahydrocyclopenta[c]pyrrole

STEP 1: (3aR,6aS)-tert-Butyl 5-methylenehexahydrocyclopenta[c]pyrrole-2(1H)-carboxylate (Tetrahedron 1993, 49(23), 5047-54) (114 mg, 0.51 mmol) was taken into a minimum of neat TFA and the solution was allowed to stand for 30 minutes at room temperature. The mixture was then concentrated and the residue taken into methanol and concentrated again then dried. The residue thus obtained was taken into methanol (5 mL) and basified using Bio-Rad AG-1X hydroxide form resin. The mixture was then filtered and concentrated and dried to give impure (±)-(3aR,6aS)-5-methyl-1,2,3,3a,4,6a-hexahydrocyclopenta[c]pyrrole (93 mg) as an amorphous residue that was used without further purification.

Reagent Preparation 12

4-(methylthio)piperidine

STEP 1: To a solution of tert-butyl 4-hydroxypiperidine-1-carboxylate (4.0 g, 20.0 mmol) and triethylamine (4.0 g, 40 mmol) in dichloromethane (50 mL) was added methanesulfonyl chloride (2.8 g, 24.4 mmol) at 0° C. The solution was stirred at 0° C. for 10 min, then at room temperature for 2 h. The reaction mixture was partitioned between 10% citric acid and ethyl acetate. The organic layer was washed with sodium bicarbonate, and brine, dried over sodium sulfate, filtered and concentrated to give tert-butyl 4-(methylsulfonyloxy)piperidine-1-carboxylate (6.4 g, quantitative yield). MS (EI) for $C_{11}H_{21}NO_5S$: 279 (M$^+$).

STEP 2: A solution of tert-butyl 4-(methylsulfonyloxy)piperidine-1-carboxylate (2.0 g, 7.2 mmol) and sodium thiomethoxide (1.0 g, 14.4 mmol) in methanol (30 mL) was refluxed for 15 h and then concentrated. The residue was partitioned between water and ethyl acetate. The aqueous layer was extracted twice with ethyl acetate and the combined organic extracts washed with brine, dried over sodium sulfate, filtered and concentrated. Column chromatography on silica (3% ethyl acetate in hexanes) afforded tert-butyl 4-(methylthio)piperidine-1-carboxylate (0.98 g, 58% yield) as a colorless oil. MS (EI) for $C_{11}H_{21}NO_2S$: 231 (M$^+$).

STEP 3: A solution of tert-butyl 4-(methylthio)piperidine-1-carboxylate (63 mg, 0.27 mmol) in methanol (1 mL) and 4 N hydrogen chloride in dioxane (4 mL) was refluxed for 2 min and then concentrated and dried to provide 4-(methylthio)piperidine hydrochloride as a colorless oil.

Reagent Preparation 13 thiomorpholine-1-oxide

Thiomorpholine-1-oxide was prepared according to the literature procedure given in J. Med. Chem. (1983), 26, 916-922. MS (EI) for $C_4H_9NOS$: 119 (M$^+$).

Reagent Preparation 14

4-(methylsulfonyl)piperidine

STEP 1: To a solution of tert-butyl 4-(methylthio)piperidine-1-carboxylate (280 mg, 1.2 mmol) (reagent preparation 12, step 2) in dichloromethane (8 mL) was added m-chloroperbenzoic acid (835 mg, 4.8 mmol) at 0° C. The solution was warmed to room temperature and stirred for 15 h. The reaction mixture was partitioned between 1N sodium hydroxide and ethyl acetate. The organic layer was washed with brine, dried over sodium sulfate, filtered and concentrated to give tert-butyl 4-(methylsulfonyl)piperidine-1-carboxylate (290 mg, 92% yield). MS (EI) for $C_{11}H_{21}NO_4S$: 206 (M-tBu$^+$).

STEP 2: A solution tert-butyl 4-(methylsulfonyl)piperidine-1-carboxylate (100 mg, 0.38 mmol) in methanol (1 mL) and 4 N hydrogen chloride in dioxane (4 mL) was refluxed for 2 min and then concentrated to provide 4-(methylthio)piperidine hydrochloride salt as a colorless solid. MS (EI) for $C_6H_{13}NO_2S$: 163 ($M^+$).

Reagent Preparation 15

3-(trifluoromethyl)-8-azabicyclo[3.2.1]octan-3-(endo)-ol

Step 1: Trimethyl(trifluoromethyl)silane (0.32 g, 2.25 mmol) was added to a mixture of tert-butyl 3-oxo-8-azabicyclo[3.2.1]octane-8-carboxylate (0.50 g, 2.2 mmol), cesium carbonate (1.1 g, 3.4 mmol) in N,N-dimethylformamide (5 mL) at 0° C. The resulting mixture was warmed to room temperature and stirred for two hours. The mixture was diluted with ethyl acetate (80 mL), washed with water (3×50 mL) then brine (50 mL), dried over sodium sulfate, filtered, and concentrated. The residue was taken into methanol (20 mL) and potassium carbonate (0.62 g, 4.5 mmol) was added then stirred at room temperature for 18 hours. The mixture was diluted with ethyl acetate (150 mL) then filtered and concentrated. The residue was purified by silica gel chromatography (10% to 25% ethyl acetate in hexanes gradient) to give tert-butyl 3-(endo)-hydroxy-3-(trifluoromethyl)-8-azabicyclo[3.2.1]octane-8-carboxylate (0.36 g, 55% yield), GC-MS (EI) for $C_{13}H_{20}F_3NO_3$: 295 ($M^+$).

Step 2: tert-Butyl 3-(endo)-hydroxy-3-(trifluoromethyl)-8-azabicyclo[3.2.1]octane-8-carboxylate 1 (0.36 g, 1.2 mmol) was taken into acetonitrile (2 mL) and 4 M hydrogen chloride in 1,4-dioxane (2 mL) then stirred at 70° C. for 15 minutes. The reaction mixture was concentrated and dried to give 3-(trifluoromethyl)-8-azabicyclo[3.2.1]octan-3-(endo)-ol hydrochloride (0.28 g, 100% yield). MS (EI) for $C_8H_{12}F_3NO$: 196 ($M^+$).

Reagent Preparation 16

3-methyl-8-azabicyclo[3.2.1]octan-3-(endo)-ol

Step 1: Methylmagnesium bromide (3 M solution in ether, 2.7 mmol) was added to a solution of tert-butyl 3-oxo-8-azabicyclo[3.2.1]octane-8-carboxylate (0.50 g, 2.2 mmol), in tetrahydrofuran (20 mL) at 0° C. and the resulting mixture was stirred one hour. The reaction mixture was quenched with saturated aqueous ammonium chloride solution (20 mL) then partitioned with ethyl acetate (80 mL). The organic portion was separated, washed with water, then brine, dried over sodium sulfate, filtered and concentrated. The residue was purified by silica gel chromatography (5% to 35% ethyl acetate in hexanes gradient) to give tert-butyl 3-(endo)-hydroxy-3-methyl-8-azabicyclo[3.2.1]octane-8-carboxylate (0.22 g, 41% yield), GC-MS (EI) for $C_{13}H_{23}NO_3$: 241 ($MH^+$).

Step 2: tert-Butyl 3-(endo)-hydroxy-3-methyl-8-azabicyclo[3.2.1]octane-8-carboxylate (0.22 g, 1.2 mmol) was taken into acetonitrile (1 mL), and 4 M hydrogen chloride in 1,4-dioxane (1 mL) then stirred at 70° C. for 15 minutes. The reaction mixture was concentrated and dried to give 3-methyl-8-azabicyclo[3.2.1]octan-3-(endo)-ol hydrochloride salt (0.16 g, 100% yield). MS (EI) for $C_8H_{12}F_3NO$: 142 ($MH^+$).

Reagent Preparation 17

3-fluoro-3-(endo)-methyl-8-azabicyclo[3.2.1]octane

Step 1: Dimethylaminosulfur trifluoride (81 mg, 0.61 mmol) was added to a solution of tert-butyl 3-(endo)-(hydroxymethyl)-8-azabicyclo[3.2.1]octane-8-carboxylate (50 mg, 0.21 mmol) (reagent preparation 18, step 2) in dichloromethane (2 mL) at 0° C., and the resulting mixture was stirred one hour. The reaction mixture was quenched with saturated aqueous sodium bicarbonate solution (10 mL) then partitioned with dichloromethane (20 mL). The organic portion was separated, washed with water, then brine, dried over sodium sulfate, filtered and concentrated. The residue was purified by silica gel chromatography (5% to 35% ethyl acetate in hexanes gradient) to give tert-butyl 3-fluoro-3-(endo)-methyl-8-azabicyclo[3.2.1]octane-8-carboxylate (28 mg, 56% yield), GC-MS (EI) for $C_{13}H_{22}FNO_2$: 243 ($M^+$).

Step 2: A mixture of tert-butyl 3-fluoro-3-(endo)-methyl-8-azabicyclo[3.2.1]octane-8-carboxylate (0.22 g, 1.2 mmol), acetonitrile (1 mL) and 4 M hydrogen chloride in 1,4-dioxane (1 mL) was stirred at 70° C. for 15 minutes. The reaction mixture was concentrated and dried to give 3-fluoro-3-(endo)-methyl-8-azabicyclo[3.2.1]octane hydrochloride salt (20 mg, 100% yield). MS (EI) for $C_8H_{14}FN$: 144 ($MH^+$)

Reagent Preparation 18

8-azabicyclo[3.2.1]octan-3-(endo)-ylmethanol

Step 1: Potassium tert-butoxide (0.62 g, 5.5 mmol) was added to a suspension of methyltriphenylphosphonium bromide (1.98 g, 5.5 mmol) in tetrahydrofuran (20 mL) and the resulting mixture was stirred at room temperature for one hour. A solution of tert-butyl 3-oxo-8-azabicyclo[3.2.1]octane-8-carboxylate (0.50 g, 2.2 mmol) in tetrahydrofuran (5 mL) was then added and the resulting mixture was stirred at 35° C. for two hours. The mixture was cooled, diluted with hexane (100 mL), filtered, and the filtrate was washed with water then brine, dried over sodium sulfate, filtered and concentrated. The residue was purified by silica gel chromatography (20% ethyl acetate in hexanes) to give tert-butyl 3-methylene-8-azabicyclo[3.2.1]octane-8-carboxylate (0.45 g, 91% yield). GC-MS (EI) for $C_{13}H_{21}NO_2$: 223 ($M^+$).

Step 2: Borane (1 M solution in tetrahydrofuran, 1.79 mL) was added to a solution of tert-butyl 3-methylene-8-azabicyclo[3.2.1]octane-8-carboxylate (0.20 g, 0.87 mmol) in tetrahydrofuran (20 mL) at 0° C. The reaction mixture was slowly warmed to room temperature and stirred for 18 hours. It was then cooled to 0° C., followed by sequential addition of 2 M sodium hydroxide solution (1 mL) and hydrogen peroxide solution (30% in water, 0.46 mL). The mixture was warmed to room temperature and stirred for 1.5 hours. The reaction mixture was quenched with saturated sodium bicarbonate solution (10 mL), diluted with water (20 mL) and partitioned with ethyl acetate (20 mL). The organic portion was separated and washed twice with saturated sodium bisulfite solution (20 mL), water then brine, dried over sodium sulfate, filtered and concentrated. The residue was purified by silica gel chromatography (20% to 90% ethyl acetate hexanes gradient) to give tert-butyl 3-(endo)-(hydroxymethyl)-8-azabicyclo[3.2.1]octane-8-carboxylate (0.19 g, 88% yield), GC-MS (EI) for $C_{13}H_{23}NO_3$: 241 ($M^+$).

Step 3: A mixture of tert-butyl 3-(endo)-(hydroxymethyl)-8-azabicyclo[3.2.1]octane-8-carboxylate (50 mg, 0.21 mmol), acetonitrile (1 mL), and 4 M hydrogen chloride in 1,4-dioxane (1 mL) was stirred at 70° C. for 15 minutes. The reaction mixture was concentrated and dried to give 8-azabicyclo[3.2.1]octan-3-(endo)-ylmethanol hydrochloride salt (36 mg, 100% yield). MS (EI) for $C_8H_{15}NO$: 142 ($MH^+$).

Reagent Preparation 19

3-(endo)-(fluoromethyl)-8-azabicyclo[3.2.1]octane

Step 1: Methanesulfonyl chloride (154 mg, 1.35 mmol) was added to a mixture of tert-butyl 3-(endo)-(hydroxymethyl)-8-azabicyclo[3.2.1]octane-8-carboxylate (325 mg, 1.4 mmol) (reagent preparation 18, step 2), triethylamine (136 mg, 1.4 mmol), and 1,4-diazabicyclo[2.2.2]octane (31 mg, 0.28 mmol) in toluene (10 mL) at 0° C. The resulting mixture was stirred at 0° C. for 15 minutes, and at room temperature for another 15 minutes. The reaction mixture was quenched with a cold mixture of water and ethyl acetate. The organic portion was separated, washed with water, then brine, dried over sodium sulfate, filtered and concentrated. The residue was purified by silica gel chromatography (5% to 25% ethyl acetate in hexanes gradient) to give tert-butyl 3-((endo-methylsulfonyloxy)methyl)-8-azabicyclo[3.2.1]octane-8-carboxylate (330 mg, 77% yield), GC-MS (EI) for $C_{14}H_{25}NO_5S$: 319 ($M^+$).

Step 2: A mixture of tert-butyl 3-((endo)-methylsulfonyloxy)methyl)-8-azabicyclo[3.2.1]octane-8-carboxylate (330 mg, 1.0 mmol), triethylamine (136 mg, 1.4 mmol), and tetrabutylammonium fluoride hexahydrate (489 mg, 1.3 mmol) in tetrahydrofuran (10 mL) was stirred at 60° C. for 18 hours. The reaction mixture was cooled, concentrated and the residue purified by silica gel chromatography (5% to 15% ethyl acetate in hexanes gradient) to give tert-butyl 3-(endo)-(fluoromethyl)-8-azabicyclo[3.2.1]octane-8-carboxylate (120 mg, 36% yield), GC-MS (EI) for $C_{13}H_{22}FNO_2$: 243 ($M^+$).

Step 3: A mixture of tert-butyl 3-(endo)-(fluoromethyl)-8-azabicyclo[3.2.1]octane-8-carboxylate (50 mg, 0.21 mmol), acetonitrile (1 mL), and 4 M hydrogen chloride in 1,4-dioxane (1 mL) was stirred at 70° C. for 15 minutes. The reaction mixture was concentrated and dried to give 3-(endo)-(fluoromethyl)-8-azabicyclo[3.2.1]octane hydrochloride salt (37 mg, 100% yield). MS (EI) for $C_8H_{15}FN$: 144 ($MH^+$)

Reagent Preparation 20

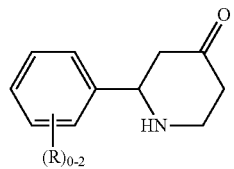

STEP 1: Benzyl 2-(4-fluorophenyl)-4-oxo-3,4-dihydropyridine-1(2H)-carboxylate was prepared according to the method in (Tetrahedron Lett., 1986, 27, 4549-4552) using 4-methoxypyridine (29.8 mL, 290 mmol), benzyl chloroformate (50.0 mL, 350 mmol) and 4-fluorophenyl magnesium bromide (0.8 M solution in THF), (450 mL, 0.36 mmol), to yield (81 g, 86% yield) of the title compound. MS (EI) for $C_{19}H_{16}FNO_3$: 326 ($MH^+$).

STEP 2: Benzyl 2-(4-fluorophenyl)-4-oxopiperidine-1-carboxylate was prepared according to the method described in (J. Am. Chem. Soc., 2001, 66, 2181-2182) using benzyl 2-(4-fluorophenyl)-4-oxo-3,4-dihydropyridine-1(2H)-carboxylate (16.5 g, 50.7 mmol) and zinc dust (9.8 g, 150 mmol) to afford (16.0 g, 96% yield) of the title compound. $^1$H NMR (400 MHz, CDCl$_3$): 7.39-7.32 (m, 5H), 7.21 (m, 2H), 7.00 (t, 2H), 5.82 (br s, 1H), 5.21 (dd, 2H), 4.28 (br s, 1H), 3.15 (m, 1H), 2.92 (m, 1H), 2.88 (dd, 1H), 2.54 (m, 1H), 2.37 (m, 1H). MS (EI) for $C_{19}H_{18}FNO_3$: 328 ($MH^+$).

STEP 3: A solution of benzyl 2-(4-fluorophenyl)-4-oxopiperidine-1-carboxylate (4.75 g, 14.50 mmol) in a mixture of ethyl acetate and tetrahydrofuran (1:1, 100 mL) was hydrogenated in the presence of 10% Pd/C at atmospheric pressure over 12 h. The catalyst was filtered off and the filtrate was concentrated. The residue was dissolved in ethyl acetate (250 mL) and washed twice with saturated aqueous bicarbonate (100 mL), brine, then dried over anhydrous sodium sulfate, filtered and concentrated. The residue was dried to give 2-(4-fluorophenyl)piperidin-4-one (2.8 g, quantitative). MS (EI) for $C_{11}H_{12}FNO$: 194 ($MH^+$).

Using analogous synthetic techniques and substituting with alternative starting reagents in step 1 the following reagents were prepared. Alternative starting materials were obtained commercially unless otherwise indicated.

2-(3,4-difluorophenyl)piperidin-4-one. Synthesized according to the method of reagent preparation 20 using 3,4-difluorophenylmagnesium bromide in step 1. MS (EI) for $C_{11}H_{12}F_2NO$: 212 ($MH^+$).

2-(3-fluorophenyl)piperidin-4-one. Synthesized according to the method of reagent preparation 20 using 3-fluorophenylmagnesium bromide in step 1. MS (EI) for $C_{11}H_{12}FNO$: 194 ($MH^+$)

Reagent Preparation 21

2-(3,4-difluorophenyl)-4-(trifluoromethyl)piperidin-4-ol

STEP 1: To a solution of benzyl 2-(3,4-difluorophenyl)-4-oxopiperidine-1-carboxylate (0.21 g, 0.60 mmol) (reagent preparation 20, step 2) in dimethylformamide (4.0 mL) at 0° C. was added cesium carbonate (0.30 g, 0.90 mmol), followed by the addition of trimethyl(trifluoromethyl)silane (0.35 mL, 2.40 mmol). The reaction mixture was stirred at room temperature for 12 hours then partitioned between ethyl acetate and water. The organic layer was separated, washed with brine, dried over anhydrous magnesium sulfate then filtered and concentrated. To a solution of the residue in methanol was added potassium carbonate (0.16 g, 1.19 mmol) and the reaction mixture was stirred at room temperature for 24 hours. The mixture was diluted with ethyl acetate and washed with 1M aqueous hydrochloric acid, brine, dried over anhydrous magnesium sulfate then filtered and concentrated to give benzyl 2-(3,4-difluorophenyl)-4-hydroxy-4-(trifluoromethyl)piperidine-1-carboxylate (0.24 g, quantitative).

STEP 2: A solution of benzyl 2-(3,4-difluorophenyl)-4-hydroxy-4-(trifluoromethyl)piperidine-1-carboxylate (0.24 g, 0.60 mmol) in methanol (100 mL) was hydrogenated in the presence of catalytic 10% palladium on carbon at atmospheric pressure for 12 h. The catalyst was filtered off and the filtrate was concentrated and dried to give 2-(3,4-difluorophenyl)-4-(trifluoromethyl)piperidin-4-ol (0.13 g, 78%). MS (EI) for $C_{12}H_{12}F_5NO$: 282 (MI-1').

Reagent Preparation 22

4-(2,2-difluoroethyl)piperidine

STEP 1: To a solution of tert-butyl 4-(2-hydroxyethyl)piperidine-1-carboxylate (0.6 g, 2.6 mmol) in dichloromethane (30 mL) was added Dess-Martin-periodinane (1.2 g, 2.8 mmol), and the mixture was stirred at room temperature for 90 min. A 10% aqueous solution of sodium thiosulfate (15 mL) was added followed by saturated sodium bicarbonate (15 mL), and the biphasic mixture was stirred at room temperature for 1 h. The layers were separated, the aqueous layer was extracted twice with dichloromethane. The combined organic layers were washed with saturated sodium bicarbonate, and brine, dried over sodium sulfate, filtered and concentrated to afford tert-butyl 4-(oxoethyl)piperidine-1-carboxylate that was used directly without further purification.

STEP 2: To a solution of tert-butyl 4-(oxoethyl)piperidine-1-carboxylate as obtained in step 1 in dichloromethane (50 mL) was added DAST (1.2 g, 7.8 mmol) at 0° C. The reaction mixture was warmed to room temperature and stirred for 17 h. A 5% aqueous solution of sodium bicarbonate was added and the layers were separated. The organic layer was washed with saturated sodium bicarbonate, and brine, dried over sodium sulfate, filtered and concentrated to provide tert-butyl 4-(2,2-difluoroethyl)piperidine-1-carboxylate that was used directly without further purification.

STEP 3: tert-Butyl 4-(2,2-difluoroethyl)piperidine-1-carboxylate as obtained in step 2 was dissolved in a minimum of trifluoroacetic acid and the resulting solution was stirred at room temperature for 2 h. The solution was then concentrated to give 4-(2,2-difluoroethyl)piperidine as the trifluoroacetate salt. MS (EI) for $C_7H_{13}F_2N$: 150 (MH$^+$).

Reagent Preparation 23

(±)-(2R,4R)-4-methyl-2-phenylpiperidin-4-ol and (±)-(2R,4S)-4-methyl-2-phenylpiperidin-4-ol STEP 1: Methylmagnesium bromide (3 M solution in ether, 1.2 mL, 3.6 mmol) was added to a solution of tert-butyl 4-oxo-2-phenylpiperidine-1-carboxylate (328 mg, 1.2 mmol), in tetrahydrofuran (20 mL) at 0° C. and the resulting mixture was stirred at this temperature one hour. The reaction mixture was then quenched with saturated aqueous ammonium chloride solution (20 mL) and diluted with ethyl acetate (80 mL). The organic portion was separated, washed with water, then brine solution, dried over sodium sulfate, filtered and concentrated. The residue purified by silica gel chromatography (25% to 70% ethyl acetate in hexane gradient) to give the first eluting isomer assigned as (±)-tert-butyl (2R,4S)-4-methyl-2-phenylpiperidin-4-ol-1-carboxylate (100 mg, 29% yield), LC-MS for $C_{17}H_{25}NO_3$: 292 (MH$^+$); and the second eluting isomer assigned as (±)-tert-butyl (2R,4R)-4-methyl-2-phenylpiperidin-4-ol-1-carboxylate (120 mg, 35% yield), MS (EI) for $C_{17}H_{25}NO_3$: 292 (MH$^+$).

STEP 2: (±)-tert-butyl (2R,4S)-4-methyl-2-phenylpiperidin-4-ol-1-carboxylate (37 mg, 0.13 mmol) was taken into a minimum of neat TFA and allowed to stand at room temperature for 15 minutes. The solution was concentrated and taken into ethanol (5 mL) then concentrated and the residue dried to give (2R,4S)-4-methyl-2-phenylpiperidin-4-ol trifluoroacetate salt as an amorphous residue. MS (EI) for $C_{12}H_{17}NO$: 192 (MH$^+$).

In the same manner (±)-(2R,4R)-4-methyl-2-phenylpiperidin-4-ol trifluoroacetate salt was prepared. MS (EI) for $C_{12}H_{17}NO$: 192 (MH$^+$).

Reagent Preparation 24

4-(trifluoromethyl)piperidin-4-ol

STEP 1: To a solution of tert-butyl 4-oxopiperidine-1-carboxylate (0.6 g, 3.0 mmol) and cesium carbonate (1.1 g, 3.3 mmol) in dimethylformamide (10 mL) was added dropwise trimethyl(trifluoromethyl)silane (2 mL, 13.5 mmol) at 0° C. The resulting mixture was stirred at room temperature for 2 hours. The reaction mixture was diluted with diethyl ether (100 ml) washed with water (50 mL) and brine (50 mL). The organic layer was dried over anhydrous sodium sulfate, filtered and concentrated to afford tert-butyl 4-(trifluoromethyl)-4-(trimethylsilyloxy)piperidine-1-carboxylate (0.512 g, 50% yield) as an orange residue that was used without further purification. MS (EI) for $C_{14}H_{26}F_3NO_3Si$: 341 (MH$^+$).

STEP 2: To a solution of tert-butyl 4-(trifluoromethyl)-4-(trimethylsilyloxy)piperidine-1-carboxylate (0.512 g, 1.50 mmol), in methanol (10 mL) was potassium carbonate (0.25 g, 1.81 mmol). The resulting mixture was stirred at room temperature for 12 hours. Filtration and concentration provided an orange residue that was purified by silica gel chromatography (97:3 dichloromethane:methanol) to give tert-butyl 4-hydroxy-4-(trifluoromethyl)piperidine-1-carboxylate (0.07 g, 14% yield). MS (EI) for $C_{11}H_{18}F_3NO_3$: 269 (MH$^+$).

STEP 3: To a solution of tert-butyl 4-hydroxy-4-(trifluoromethyl)piperidine-1-carboxylate (0.07 g, 0.26 mmol) in dichloromethane (1 mL) was added trifluoroacetic acid (1 mL). The resulting mixture was stirred at room temperature for 30 minutes. Concentration and drying afforded 4-(trifluoromethyl)piperidin-4-ol (0.044 g, 100%). MS (EI) for $C_6H_{10}F_3NO$: 269 (MH$^+$).

Reagent Preparation 25

4-methylpiperidine-4-carbonitrile

STEP 1: Trifluoroacetic acid anhydride (75 uL, 0.82 mmol) was added to a mixture of tert-butyl 4-carbamoyl-4-methylpiperidine-1-carboxylate (100 mg, 0.41 mmol) and pyridine (118 uL, 1.6 mmol) in tetrahydrofuran (2 mL), and the resulting mixture was stirred at room temperature for one hour. The mixture was concentrated then taken into ethyl acetate (20 mL) and partitioned with 0.5 M hydrochloric acid. The organic layer was washed with water then brine, dried over sodium sulfate, filtered, and concentrated to provide a 1:1 mixture of tert-butyl 4-cyano-4-methylpiperidine-1-carboxylate and tert-butyl 4-carbamoyl-4-methylpiperidine-1-carboxylate (100 mg) that was carried forward without further purification. GC-MS (EI) for $C_{12}H_{20}N_2O_2$ (tert-butyl 4-cyano-4-methylpiperidine-1-carboxylate): 224 (M$^+$).

STEP 2: tert-Butyl 4-cyano-4-methylpiperidine-1-carboxylate as obtained in step 1 (100 mg, 0.21 mmol), acetonitrile (1 mL), and 4 M hydrogen chloride in 1,4-dioxane (1 mL) were combined and stirred at 70° C. for 15 minutes. The reaction mixture was concentrated and dried to give 4-methylpiperidine-4-carbonitrile hydrochloride salt (56 mg) contaminated with 4-methylpiperidine-4-carboxamide hydrochloride salt. MS (EI) for $C_7H_{12}N_2$ (4-methylpiperidine-4-carbonitrile): 125 (MH$^+$).

Reagent Preparation 26

8-azabicyclo[3.2.1]octan-3-ol

STEP 1: Sodium borohydride (178 mg, 4.7 mmol) was added to a solution of tert-butyl 3-oxo-8-azabicyclo[3.2.1]octane-8-carboxylate (0.50 g, 2.2 mmol) in ethanol (10 mL), and the resulting mixture was stirred at room temperature for one hour. The mixture was quenched with saturated ammonium chloride solution (30 mL), and extracted with ethyl acetate (3×20 mL). The combined extract was washed with water then brine, dried over sodium sulfate, filtered and concentrated to give tert-butyl 3-hydroxy-8-azabicyclo[3.2.1]octane-8-carboxylate (463 mg, 92% yield) as a mixture of endo and exo stereoisomers. GC-MS (EI) for $C_{12}H_{21}NO_3$: 227 (M+).

STEP 2: tent-Butyl 3-hydroxy-8-azabicyclo[3.2.1]octane-8-carboxylate as obtained in step 1 (100 mg, 2.0 mmol), acetonitrile (2 mL) and 4 M hydrogen chloride in 1,4-dioxane (2 mL) were combined and stirred at 70° C. for 15 minutes. The reaction mixture was concentrated and dried to give 8-azabicyclo[3.2.1]octan-3-ol hydrochloride salt (71 mg, 100% yield). MS (EI) for $C_7H_{13}NO$: 128 (MH+).

Reagent Preparation 27

3-(endo)-methyl-8-azabicyclo[3.2.1]octane

STEP 1: A mixture of tert-butyl 3-methylene-8-azabicyclo[3.2.1]octane-8-carboxylate (0.10 g, 0.44 mmol) (reagent preparation 18), 10% palladium on charcoal (10 mg) and ethanol (15 mL) was hydrogenated in a Parr apparatus at 40 psi for 18 hours. The mixture was filtered and concentrated then dried to give tert-butyl 3-(endo)-methyl-8-azabicyclo[3.2.1]octane-8-carboxylate (96 mg, 95% yield); GC-MS (EI) for $C_{13}H_{23}NO_2$: 225 (M+).

STEP 2: A mixture of tert-butyl 3-(endo)-methyl-8-azabicyclo[3.2.1]octane-8-carboxylate (96 mg, 0.43 mmol), acetonitrile (1 mL), and 4 M hydrogen chloride in 1,4-dioxane (1 mL) was stirred at 70° C. for 15 minutes. The reaction mixture was concentrated and dried to give 3-(endo)-methyl-8-azabicyclo[3.2.1]octane hydrochloride salt (68 mg, 100% yield). MS (EI) for $C_8H_{15}N$: 126 (MH+).

Reagent Preparation 28

(±)-(2R,4S)-2-(3,4-difluorophenyl)piperidin-4-ol

STEP 1: A solution of benzyl 2-(3,4-difluorophenyl)-4-oxo-3,4-dihydropyridine-1(2H)-carboxylate (6.70 g, 19.50 mmol) (reagent preparation 20) in methanol (100 mL) was hydrogenated with catalytic 10% palladium on carbon in a Parr shaker at 35 psi. The catalyst was filtered off and the filtrate was concentrated then dried to give (±)-(2R,4S)-2-(3,4-difluorophenyl)piperidin-4-ol (4.2 g, quantitative). $^1$H NMR (400 MHz, $d_6$-DMSO): 7.33 (m, 1H), 7.28 (m, 1H), 7.02 (m, 1H), 5.00 (t, 1H), 4.49 (d, 1H), 3.91 (m, 1H), 3.77 (m, 1H), 3.21 (m, 1H), 2.11 (2t, 1H), 1.95 (2q, 1H), 1.70 (m, 1H), 1.50 (m, 1H). MS (EI) for $C_{11}H_{13}F_2NO$: 214 (MH+).

Using analogous synthetic techniques and substituting with alternative starting reagents in step 1 the following reagents were prepared. Alternative starting materials were obtained commercially unless otherwise indicated.

(±)-(2R,4S)-2-(4-fluorophenyl)piperidin-4-ol. Synthesized according to the method of reagent preparation 28 starting with benzyl 6-(4-fluorophenyl)-4-oxo-3,4-dihydropyridine-1(2H)-carboxylate (reagent preparation 20). MS (EI) for $C_{11}H_{14}FNO$: 194 (M−).

Reagent Preparation 29

4,4-difluoro-2-phenylpiperidine

STEP 1: To a solution of tert-butyl 4-oxo-2-phenylpiperidine-1-carboxylate (0.20 g, 0.73 mmol), in dichloromethane (50 mL) at 0° C. was slowly added bis(2-methoxyethyl)aminosulfur trifluoride (0.16 mL, 0.87 mmol) and the reaction mixture was allowed to warm to room temperature. The mixture was stirred for 12 hours, then quenched by the addition of saturated aqueous ammonium chloride and partitioned with ethyl acetate. The organic layer was separated, washed with brine, dried over anhydrous magnesium sulfate, filtered and concentrated. Silica gel chromatography of the residue (hexanes:ethyl acetate 4:1) provided tert-butyl 4,4-difluoro-2-phenylpiperidine-1-carboxylate (0.17 g, 81%). GC-MS (EI) for $C_{16}H_{21}F_2NO_2$: 241 (M-tBu+).

STEP 2: To a solution of tert-butyl 4,4-difluoro-2-phenylpiperidine-1-carboxylate (0.17 g, 0.57 mmol) in methanol (5 mL) was added 4M hydrogen chloride in dioxane (5 mL). The reaction mixture was stirred at room temperature for 4 hours then concentrated and the residue was triturated with diethyl ether. The white solid was collected by filtration and dried to give 4,4-difluoro-2-phenylpiperidine as the hydrochloride salt (93 mg, 70%). GC-MS (EI) for $C_{11}H_{13}F_2N$: 197 (MH+).

Reagent Preparation 30

1,3-diphenylpiperizine

STEP 1: A solution of tert-butyl 3-phenylpiperazine-1-carboxylate (0.95 g, 3.6 mmol), benzyl chloroformate (0.85 g, 5.0 mmol) and diisopropylethylamine (1.0 g, 7.7 mmol) in dioxane (20 mL) was heated to 95° C. for 3 hours. After cooling, the reaction mixture was diluted with ethyl acetate (100 mL), and washed with saturated aqueous sodium bicarbonate (50 mL) and brine (25 mL). After drying over anhydrous sodium sulfate, filtration and concentration, the residue was purified by silica gel column chromatography (ethyl acetate/hexanes, 1:8) to give 1-benzyl 4-tert-butyl 2-phenylpiperazine-1,4-dicarboxylate (0.84 g, 59% yield).

STEP 2: To 1-benzyl 4-tert-butyl 2-phenylpiperazine-1,4-dicarboxylate (0.84 g, 2.12 mmol) in dichloromethane (5.0 mL) added drop wise trifluoroacetic acid (5.0 mL) and maintained at 25° C. for 90 minutes. The reaction mixture was concentrated, and the residue dissolved in ethyl acetate (60 mL). The solution was washed with saturated aqueous sodium carbonate (30 mL) and brine (20 mL), and then dried over anhydrous sodium sulfate, filtered and concentrated to yield benzyl 2-phenylpiperazine-1-carboxylate (0.59 g, 94% yield). MS (EI) for $C_{18}H_{20}N_2O_2$: 297 (MH+).

STEP 3: A solution of benzyl 2-phenylpiperazine-1-carboxylate (0.17 g, 0.58 mmol), bromobenzene (0.37 g, 2.37 mmol), tris(dibenzylideneacetone)dipalladium(0) (0.06 g, 0.06 mmol), sodium tert-butoxide (0.20 g, 2.0 mmol) and 2-dicyclohexylphosphino-2'-(N,N-dimethylamino)biphenyl (0.25 g, 0.64 mmol) in benzene (20 mL) was heated to 80° C. for 4.5 hours. After cooling, the reaction was diluted with ethyl acetate (60 mL), and washed with water (2×30 mL), then dried over anhydrous sodium sulfate, filtered and concentrated. The residue was purified by silica gel column chromatography (ethyl acetate/hexanes, 1:4) to give benzyl 2,4-diphenylpiperazine-1-carboxylate (0.17 g, 79% yield) as an oil. MS (EI) for $C_{24}H_{24}N_2O_2$: 373 (MH+).

STEP 4: A solution of benzyl 2,4-diphenylpiperazine-1-carboxylate (0.17 g, 0.45 mmol) and 5% Pd on carbon (0.1 g) in tetrahydrofuran/methanol 5:1 (10 mL) was stirred under hydrogen (1 atm) for 4.5 hours. The reaction was filtered through celite and concentrated to give the title compound 1,3-diphenylpiperizine (0.10 g, 93% yield) as an oil. MS (EI) for $C_{16}H_{18}N_2$: 239 (MH+).

Reagent Preparation 31

(±)-(2R,4R)-2-(4-fluorophenyl)piperidin-4-ol

STEP 1: A mixture of benzyl 2-(4-fluorophenyl)-4-oxo-3,4-dihydropyridine-1(2H)-carboxylate (1.00 g, 3.07 mmol)

(reagent preparation 20) and 5% Pd on carbon (0.1 g) in acetic acid:methanol 1:10 (20 mL) was hydrogenated at 45 psi using a Parr apparatus for 16 hours. The catalyst was removed by filtering through Celite, and the filtrate concentrated to give (±)-(2S,4R)-2-(4-fluorophenyl)piperidin-4-ol as an oil. The material was taken into chloroform (100 mL) and di-tert-butyl dicarbonate (0.74 g, 3.4 mmol) was added, followed by the dropwise addition of diisopropylethylamine (1.5 g, 12 mmol). The reaction was warmed to reflux for 10 minutes, then allowed to cool to 25° C. over 30 minutes. The organic solution was washed with 0.1M aqueous hydrochloric acid (45 mL), water (50 mL) and saturated sodium bicarbonate (50 mL), then dried over anhydrous sodium sulfate, filtered and concentrated. The residue was purified by silica gel column chromatography (ethyl acetate:hexanes, 1:1) to give (±)-(2S, 4R)-tert-butyl 2-(4-fluorophenyl)-4-hydroxypiperidine-1-carboxylate (0.59 g, 65% yield). $^1$H NMR (400 MHz, $d_6$-DMSO): 7.25 (m, 2H), 7.10 (m, 2H), 4.96 (t, 1H), 4.46 (d, 1H), 3.90 (m, 1H), 3.77 (m, 1H), 3.23 (dt, 1H), 2.06 (m, 1H), 1.95 (m, 1H) 1.73 (m, 1H), 1.45 (m, 1H), 1.29 (s, 9H).

STEP 2: To (±)-(2S,4R)-tert-butyl 2-(4-fluorophenyl)-4-hydroxypiperidine-1-carboxylate (0.55 g, 1.90 mmol) in tetrahydrofuran (20 mL) was added methanesulfonyl chloride (0.158 mL, 2.05 mmol), followed by dropwise addition of diisopropylethylamine (0.50 g, 3.9 mmol) and N,N-dimethylpyridin-4-amine (10 mg). After 30 minutes the reaction was diluted with ethyl acetate (50 mL) and washed with 0.1 M hydrochloric acid (25 mL) then saturated sodium bicarbonate (50 mL), dried over anhydrous sodium sulfate, filtered and concentrated. The residue was purified by silica gel chromatography (ethyl acetate:hexanes, 1:4) to give (±)-(2S,4R)-tert-butyl 2-(4-fluorophenyl)-4-(methylsulfonyloxy)piperidine-1-carboxylate (0.62 g, 88% yield). $^1$H NMR (400 MHz, $CDCl_3$): 7.19 (dd, 1H), 7.05 (t, 2H), 5.38 (d, 1H), 5.14 (m, 1H), 4.14 (m, 1H), 3.25 (m, 1H), 2.68 (m, 1H), 2.59 (s, 3H), 2.21 9M, 1H), 1.93 (m, 2H), 1.42 (s, 9H).

STEP 3: A solution of (±)-(2S,4R)-tert-butyl 2-(4-fluorophenyl)-4-(methylsulfonyloxy)piperidine-1-carboxylate (0.30 g, 0.80 mmol) and sodium acetate (0.33 g, 4.0 mmol) in dimethylsulfoxide (15 mL) was heated to 90° C. for 2.5 hours. After cooling, the reaction mixture was diluted with ethyl acetate (40 mL), and washed with water (25 mL) and brine (25 mL). The organic layer was dried over anhydrous sodium sulfate then filtered and concentrated. The residue was purified by silica gel column chromatography (ethyl acetate:hexanes 1:10) to give (±)-(2R,4R)-tert-butyl 4-acetoxy-2-(4-fluorophenyl)piperidine-1-carboxylate (150 mg, 49% yield). $^1$H NMR (400 MHz, $d_6$-DMSO): 7.24 (m, 4H), 5.14 (br s, 1H), 4.63 (m, 1H), 4.00 (br d, 1H), 2.72 (m, 1H), 2.56 (br d, 1H), 1.88 (s, 3H), 1.84 (br d 1H), 1.78 (m, 1H), 1.44 (m, 1H), 1.39 (s, 9H).

STEP 4: A suspension of (±)-(2R,4R)-tert-butyl 4-acetoxy-2-(4-fluorophenyl)piperidine-1-carboxylate (150 mg, 0.40 mmol) and potassium carbonate (1.0 g) in methanol:water 10:1 (11 mL) was stirred for 1 hour then diluted with ethyl acetate (40 mL) and washed with water (25 mL) and brine (25 mL). The organic layer was dried over anhydrous sodium sulfate, filtered and concentrated to give (±)-(2R,4R)-tert-butyl 2-(4-fluorophenyl)-4-hydroxypiperidine-1-carboxylate (117 mg, 99% yield). $^1$H NMR (400 MHz, $d_6$-DMSO): 7.17 (m, 4H), 5.34 (br d, 1H), 4.73 (d, 1H), 4.34 (br d, 1H), 3.41 (m, 1H), 2.67 (m, 1H), 2.42 (br d, 1H), 1.57 (m, 1H), 1.38 (s, 9H).

STEP 5: To (±)-(2R,4R)-tert-butyl 2-(4-fluorophenyl)-4-hydroxypiperidine-1-carboxylate (0.10 g, 0.34 mmol) in dichloromethane (10 mL) added trifluoroacetic acid: dichloromethane 1:4 (5 mL) and the mixture was stirred at 25° C. for 30 minutes. The solution was concentrated and dried to give title compound (±)-(2R,4R)-2-(4-fluorophenyl)piperidin-4-ol (105 mg, 99% yield) as the trifluoracetic acid salt. $^1$H NMR (400 MHz, $d_6$-DMSO): 7.56 (m, 2H), 7.31 (m, 2H), 4.53 (t, 1H), 4.12 (br s, 1H), 3.32 (q, 1H), 3.20 (d, 1H), 2.10 (t, 1H), 1.85 (br d, 2H), 1.79 (dd, 1H). MS (EI) for $C_{11}H_{14}FNO$: 196 (MH$^+$).

Reagent Preparation 32

3-(endo)-(hydroxymethyl)-8-azabicyclo[3.2.1]octan-3-ol

STEP 1: To a solution of tert-butyl 3-methylene-8-azabicyclo[3.2.1]octane-carboxylate (0.9 g, 4.0 mmol) (reagent preparation 18, step 1) in acetone (16 mL) and water (4 mL) was added osmium tetroxide (0.25 mL of a 4% aqueous solution, 0.04 mmol) and N-methylmorpholine N-oxide (1.4 g, 12.0 mmol). The reaction mixture was stirred at room temperature for 15 h, concentrated, and the residue was partitioned between 20% citric acid and ethyl acetate. The organic layer was washed twice with brine, dried over sodium sulfate, filtered and concentrated to give tert-butyl 3-(hydroxy)-3-(endo)-(hydroxymethyl)-8-azabicyclo[3.2.1]octane-carboxylate (1.0 g, quantitative yield). MS (EI) for $C_{13}H_{23}NO_4$: 257 (M$^+$).

STEP 2: A solution of tert-butyl 3-(hydroxy)-3-(endo)-(hydroxymethyl)-8-azabicyclo[3.2.1]octane-carboxylate (50 mg, 0.20 mmol) in dichloromethane (1 mL) and trifluoroacetic acid (1 mL) was stirred at room temperature for 1 h and then concentrated and dried to give 3-(endo)-(hydroxymethyl)-8-azabicyclo[3.2.1]octan-3-ol as the trifluoroacetate salt, which was used without further purification.

Reagent Preparation 33

(±)-(2R,4S)-2-(3,4-difluorophenyl)-4-(fluoromethyl) piperidine

STEP 1: Potassium tert-butoxide (0.81 g, 7.2 mmol) was added to a suspension of methyltriphenylphosphonium bromide (2.58 g, 7.2 mmol) in tetrahydrofuran (20 mL) and the resulting mixture was stirred at room temperature for one hour. A solution of phenylmethyl 2-(3,4-difluorophenyl)-4-oxopiperidine-1-carboxylate (1.00 g, 2.9 mmol) (reagent preparation 20) in tetrahydrofuran (5 mL) was added and the resulting mixture was stirred at 35° C. for two hours. The mixture was cooled, diluted with hexane (100 mL), filtered, and the filtrate washed with water then brine, dried over sodium sulfate, filtered and concentrated. The residue was purified by silica gel chromatography (20% ethyl acetate in hexanes) to give phenylmethyl 2-(3,4-difluorophenyl)-4-methylidenepiperidine-1-carboxylate (0.79 g, 79% yield), MS (EI) for $C_{20}H_{19}F_2NO_2$: 344 (MH$^+$).

STEP 2: A solution of borane (1 M in tetrahydrofuran, 4.58 mL) was added to a solution of phenylmethyl 2-(3,4-difluorophenyl)-4-methylidenepiperidine-1-carboxylate (0.79 g, 2.3 mmol) in tetrahydrofuran (20 mL) at 0° C. The reaction mixture was slowly warmed to room temperature and stirred for 18 hours. The mixture was then cooled to 0° C., and 2M sodium hydroxide solution (2.6 mL, 5.2 mmol) then hydrogen peroxide solution (30% in water, 1.2 mL) were added sequentially. The mixture was warmed to room temperature and stirred for 1.5 hours. The reaction mixture was quenched with saturated sodium bicarbonate solution (10 mL), diluted with water (20 mL), and partitioned with ethyl acetate (20 mL). The organic portion was separated and washed twice with saturated sodium bisulfite solution (20 mL), water, then brine, dried over sodium sulfate, filtered and concentrated. The residue was purified by silica gel chromatography (20% to 90% ethyl acetate in hexanes gradient) to give (±)-phenylmethyl (2R,4S)-2-(3,4-difluorophenyl)-4-(hydroxymethyl)piperidine-1-carboxylate (0.57 g, 69% yield), MS (EI) for $C_{20}H_{21}F_2NO_3$: 362 (MH$^+$).

STEP 3: Methanesulfonyl chloride (74 mg, 0.65 mmol) was added to a mixture of (±)-phenylmethyl (2R,4S)-2-(3,4-difluorophenyl)-4-(hydroxymethyl)piperidine-1-carboxylate (233 mg, 0.64 mmol), triethylamine (233 mg, 1.7 mmol), and 1,4-diazabicyclo[2.2.2]octane (15 mg, 0.13 mmol) in toluene (10 mL) at 0° C., and the resulting mixture was stirred at 0° C. for 15 minutes, and at room temperature for another 15 minutes. The reaction mixture was then quenched with a cold mixture of water and ethyl acetate. The organic portion was separated, washed with water, then brine, dried over sodium sulfate, filtered and concentrated. The residue was purified by silica gel chromatography (5% to 25% ethyl acetate in hexanes gradient) to give (±)-phenylmethyl (2R,4S)-2-(3,4-difluorophenyl)-4-{[(methylsulfonyl)oxy]methyl}piperidine-1-carboxylate (271 mg, 96% yield). MS (EI) for $C_{21}H_{23}F_2NO_5S$: 440 (MH$^+$).

STEP 4: A mixture of (±)-phenylmethyl (2R,4S)-2-(3,4-difluorophenyl)-4-{[(methylsulfonyl)oxy]methyl}piperidine-1-carboxylate (200 mg, 0.46 mmol), and cesium fluoride (190 mg, 1.3 mmol) in dimethyl sulfoxide (2 mL) was stirred at 100° C. for 18 hours. The reaction mixture was cooled and purified directly by silica gel chromatography (5% to 25% ethyl acetate in hexanes gradient) to give (±)-phenylmethyl (2R,4S)-2-(3,4-difluorophenyl)-4-(fluoromethyl)piperidine-1-carboxylate (85 mg, 51% yield). MS (EI) for $C_{20}H_{20}F_3NO_2$: 364 (MH$^+$).

STEP 5: A mixture of (±)-phenylmethyl (2R,4S)-2-(3,4-difluorophenyl)-4-(fluoromethyl)piperidine-1-carboxylate (85 mg, 0.23 mmol), 10% palladium on carbon (85 mg) and ethyl acetate (5 mL) in a 100 mL flask was stirred under 1 atmosphere of hydrogen at room temperature for three days. The mixture was filtered and the filtrate concentrated and dried to give (±)-(2R,4S)-2-(3,4-difluorophenyl)-4-(fluoromethyl)piperidine (39 mg, 73% yield), MS (EI) for $C_{12}H_{14}F_3N$: 230 (MH$^+$).

Reagent Preparation 34

(±)-(2R,4R)-2-(3,4-difluorophenyl)piperidine-4-carbonitrile

Step 1: Methanesulfonyl chloride (1.0 g, 3.2 mmol) was added to a mixture of (±)-1,1-dimethylethyl (2R,4S)-2-(3,4-difluorophenyl)-4-hydroxypiperidine-1-carboxylate (1.00 g, 3.0 mmol) (obtained by conducting reagent preparation 28 in the presence of di-tert-butyl dicarbonate) and triethylamine (0.70 g, 7.0 mmol), in tetrahydrofuran (25 mL) at 0° C., and the resulting mixture was at room temperature for two hours. The reaction mixture was then quenched with a cold mixture of water and ethyl acetate. The organic portion was separated, washed with 5% sodium hydroxide, 0.5M hydrochloric acid, water then brine, dried over sodium sulfate, filtered and concentrated. The residue was purified by silica gel chromatography (5% to 75% ethyl acetate in hexanes gradient) to give (±)-1,1-dimethylethyl (2R,4S)-2-(3,4-difluorophenyl)-4-[(methylsulfonyl)oxy]piperidine-1-carboxylate (1.2 g, 88% yield). MS (EI) for $C_{17}H_{23}F_2NO_5S$: 392 (MH$^+$).

STEP 2: A mixture of (±)-1,1-dimethylethyl (2R,4S)-2-(3,4-difluorophenyl)-4-[(methylsulfonyl)oxy]piperidine-1-carboxylate (0.72 g, 1.8 mmol), and potassium cyanide (0.33 g, 3.7 mmol) in N,N-dimethylformamide (3.3 mL) was stirred at 90° C. for 18 hours. The reaction mixture was cooled, diluted with ethyl acetate (50 mL), washed twice with 5% lithium chloride solution (30 mL), then brine, dried over sodium sulfate, filtered and concentrated. The residue was purified by silica gel chromatography (5% to 25% ethyl acetate in hexanes gradient) to give (±)-1,1-dimethylethyl (2R,4R)-4-cyano-2-(3,4-difluorophenyl)piperidine-1-carboxylate (165 mg, 30% yield). MS (EI) for $C_{17}H_{23}F_2N_2O_2$: 323 (MH$^+$).

STEP 3: A mixture of (±)-1,1-dimethylethyl (2R,4R)-4-cyano-2-(3,4-difluorophenyl)piperidine-1-carboxylate (65 mg, 0.20 mmol), acetonitrile (2 mL), and 4 M hydrogen chloride in 1,4-dioxane (2 mL) was stirred at 70° C. for 15 minutes. The reaction mixture was concentrated and dried to give (±)-(2R,4R)-2-(3,4-difluorophenyl)piperidine-4-carbonitrile hydrochloride salt (50 mg, 96% yield); MS (EI) for $C_{12}H_{12}F_2N_2$: 223 (MH$^+$).

Reagent Preparation 35 tert-butyl 6-bromo-2-(tert-butoxycarbonyl(methoxycarbonyl)amino)-1H-benzo[d]imidazole-1-carboxylate STEP 1: To a slurry of 4-bromobenzene-1,2-diamine (2.1 g, 11 mmol), 1,2-dimethoxyethane (20 mL) and methanol (5 mL) was added 1,3-bis(methoxycarbonyl)-2-methyl-2-thiopseudourea (4.0 g, 19 mmol). The reaction mixture was heated (105° C.) for 12 h and then diluted with ethyl ether (100 mL). The resulting precipitate was collected by filtration and rinsed with ethyl ether (2×25 mL) to provide methyl 6-bromo-1H-benzo[d]imidazol-2-ylcarbamate (2.3 g, 77% yield). MS (EI) for $C_9H_8BrN_3O_2$: 271 (MH$^+$).

STEP 2: To a cooled (0° C.) slurry of 6-bromo-1H-benzo[d]imidazol-2-ylcarbamate (2.3 g, 8.5 mmol), di-tert-butyl dicarbonate (4.5 g, 20 mmol), DIPEA (5.9 mL, 34 mmol) and chloroform (30 mL) was added DMAP (0.36 g, 2.9 mmol). The reaction mixture was stirred for 2 h at ambient temperature and then partitioned between dichloromethane (50 mL) and saturated aqueous ammonium chloride (50 mL). The organic layer was then washed with brine (25 mL), dried over anhydrous magnesium sulfate, filtered and concentrated. Column chromatography on silica (10-25% ethyl acetate in hexanes) provided tert-butyl 6-bromo-2-(tert-butoxycarbonyl(methoxycarbonyl)amino)-1H-benzo[d]imidazole-1-carboxylate (2.3 g, 58% yield) as a red-brown solid. MS (EI) for $C_{19}H_{24}BrN_3O_6$: 471 (MH$^+$).

Reagent Preparation 36

3-(4-bromophenyl)-1-(tetrahydro-2H-pyran-2-yl)-1H-pyrazole

STEP 1: To a heated (80° C.) solution of 3-(4-bromophenyl)-1H-pyrazole (1.0 g, 4.5 mmol) and trifluoroacetic acid (0.02 mL, 0.23 mmol) in toluene (5 mL) was added 3,4-dihydro-2H-pyran (0.43 mL, 4.7 mol) over 1 hour. The reaction mixture was stirred for an additional hour and was then concentrated and dried to provide 3-(4-bromophenyl)-1-(tetrahydro-2H-pyran-2-yl)-1H-pyrazole (1.3 g, 94% yield). MS (EI) for $C_{14}H_{15}BrN_2O$: 308 (MH$^+$).

Reagent Preparation 37

4-(fluoromethyl)-4-hydroxypiperidine-1-carbonyl chloride

STEP 1: To a solution of tert-butyl 4-hydroxy-4-(hydroxymethyl)piperidine-1-carboxylate (Bioorganic &

Medicinal Chemistry Letters 2008, 18(21), 5804-5808) (400 mg, 1.73 mmol) and DIPEA (1.2 mL, 7.0 mmol) in THF (10 mL) cooled to 0° C. was added thionyl chloride (0.65 mL, 8.6 mmol) in a dropwise manner and the mixture was stirred at this temperature for 1 h. The mixture was then partioned with saturated aqueous sodium bicarbonate and ethyl acetate. The organic phase was extracted with ethyl acetate (3×) and the combined organic layers were washed with brine then dried over anhydrous sodium sulfate, filtered and concentrated to afford 1,1-dimethylethyl 1,3-dioxa-2-thia-8-azaspiro[4.5]decane-8-carboxylate 2-oxide (562 mg) as an amber oil that was used without further purification. GC-MS (EI) for $C_{11}H_{19}NO_5S$: 277 (M$^+$).

STEP 2: 1,1-dimethylethyl 1,3-dioxa-2-thia-8-azaspiro[4.5]decane-8-carboxylate 2-oxide as obtained in step 1 (555 mg) was taken into acetonitrile (20 mL) followed by addition of sodium periodate (642 mg, 3.0 mmol), water (5 mL), and ruthenium (III) chloride hydrate (5 mg) and the mixture was stirred for 3 h at room temperature. The mixture was then concentrated and the residue partitioned with ethyl acetate and water. The organic phase was washed with water (2×) and brine followed by drying over anhydrous sodium sulfate, filtration and concentration. The residue was purified by silica gel chromatography (30% ethyl acetate in hexanes) to give 1,1-dimethylethyl 1,3-dioxa-2-thia-8-azaspiro[4.5]decane-8-carboxylate 2,2-dioxide (500 mg, 98% yield) as a yellow crystalline solid. $^1$H NMR (400 mHz, CDCl$_3$): 4.44 (s, 2H), 4.03 (br, 2H), 3.16 (br tr, 2H), 2.21 (d, 2H), 1.76 (m, 2H), 1.46 (s, 9H).

STEP 3: 1,1-dimethylethyl 1,3-dioxa-2-thia-8-azaspiro[4.5]decane-8-carboxylate 2,2-dioxide (500 mg, 1.7 mmol) was taken into THF (5 mL) followed by addition of TBAF (1M in THF, 1.8 mL) and the resulting solution was stirred for 3 h at 40° C. The mixture was then cooled and partitioned with ethyl acetate and 20% aqueous citric acid. The organic solution was washed with brine then dried over anhydrous sodium sulfate, filtered and concentrated to afford tert-butyl 4-(fluoromethyl)-4-hydroxypiperidine-1-carboxylate (350 mg, 88% yield). GC-MS (EI) for $C_{11}H_{20}FNO_3$: 233 (M$^+$). BOC-group deprotection was carried out in a manner well established in the literature (see, Greene and Wuts, Protective Groups in Organic Synthesis, Wiley-Interscience) to give 4-(fluoromethyl)piperidin-4-ol hydrochloride salt as a colorless solution.

STEP 4: 4-(Fluoromethyl)piperidin-4-ol hydrochloride (233 mg, 1.37 mmol) was suspended in dichloromethane (3 mL) followed by addition of DIPEA (0.6 mL, 3.4 mmol) and the slurry obtained added in portions over several minutes to a solution of phosgene (20W % in toluene, 0.75 mL) diluted into dichloromethane (5 mL) and the mixture was allowed to stir at this temperature for 15 minutes. The mixture was then concentrated and the residue partitioned with ethyl acetate and water. The organic solution was washed 0.5M hydrochloric acid, brine then dried over anhydrous sodium sulfate, filtered and concentrated. The residue was purified by silica gel chromatography (3:1 ethyl ether:hexanes) to give 4-(fluoromethyl)-4-hydroxypiperidine-1-carbonyl chloride (100 mg, 37% yield) as a colorless amorphous residue. GC-MS (EI) for $C_7H_{11}FNO_2Cl$: 196 (M$^+$).

Using analogous synthetic techniques and substituting with alternative starting materials in step 4 the following reagents were prepared. Alternative starting materials were purchased from commercial sources unless otherwise indicated.

4-methylpiperidine-1-carbonyl chloride. Synthesized according to the method of reagent preparation 37 by using 4-methylpiperidine in step 4. $^1$H NMR (400 MHz, CDCl$_3$): 4.28, (d, 1H), 2.95 (dt, 2H), 1.75 to 1.56 (m, 3H), 1.27 to 1.10 (m, 2H), 0.97 (d, 3H), GC-MS for $C_7H_{12}ClNO$: 161 (M$^+$).

4-cyanopiperidine-1-carbonyl chloride. Synthesized according to the method of reagent preparation 37 by using piperidine-4-carbonitrile in step 4. GC-MS for $C_7H_9ClN_2O$: 172 (M$^+$).

4-(trifluoromethyl)piperidine-1-carbonyl chloride. Synthesized according to reagent preparation 37 by using 4-(trifluoromethyl)piperidine in step 4. GC-MS (EI) for $C_7H_9ClF_3NO$: 215 (M$^+$).

4-(1,1-difluoroethyl)piperidine-1-carbonyl chloride. Synthesized according to reagent preparation 37 by using 4-(1,1-difluoroethyl)piperidine (reagent preparation 9) in step 4. GC-MS (EI) for $C_8H_{12}ClF_2NO$: 211 (M$^+$).

4-(2-fluoroethyl)piperidine-1-carbonyl chloride. Synthesized according to reagent preparation 37 by using 4-(2-fluoroethyl)piperidine (WO 9746553) in step 4. GC-MS (EI) for $C_8H_{13}ClFNO$: 193 (M$^+$).

3-(endo)-hydroxy-3-(trifluoromethyl)-8-azabicyclo[3.2.1]octane-8-carbonyl chloride. Synthesized according to the method of reagent preparation 37 using 3-(trifluoromethyl)-8-azabicyclo[3.2.1]octan-3-ol hydrochloride salt (reagent preparation 15) in step 4. GC-MS (EI) for $C_9H_{11}ClF_3NO_2$: 257 (M$^+$)

2-(4-fluorophenyl)piperidine-1-carbonyl chloride. Synthesized according to the method of reagent preparation 37 using 2-(4-fluorophenyl)piperidine in step 4. GC-MS (EI) for $C_{12}H_{13}ClFNO$: 241 (M$^+$).

2-(3-fluorophenyl)-4-oxopiperidine-1-carbonyl chloride. Synthesized according to the method of reagent preparation 37 using 2-(3-fluorophenyl)piperidin-4-one (reagent preparation 20) in step 4. $^1$H NMR (400 MHz, CDCl$_3$): 7.37 (dd, 1H), 7.07 (d, 1H), 7.02 (t, 1H), 5.98 (br s, 1H), 4.40 (m, 1H), 3.36 (br d, 1H), 3.04 (t, 1H), 2.98 (dd, 1H), 2.64 (m, 1H), 2.46 (br d, 1H). GC-MS (EI) for $C_{12}H_{11}ClFNO_2$: 255 (M$^+$).

2-(4-fluorophenyl)-4-oxopiperidine-1-carbonyl chloride. Synthesized according to the method of reagent preparation 37 using 2-(4-fluorophenyl)piperidin-4-one (reagent preparation 20) in step 4. GC-MS (EI) for $C_{12}H_{11}ClFNO_2$: 255 (M$^+$).

2-(3,4-difluorophenyl)-4-oxopiperidine-1-carbonyl chloride. Synthesized according to the method of reagent preparation 37 using 2-(3,4-fluorophenyl)piperidin-4-one (reagent preparation 20) in step 4. $^1$H NMR (400 MHz, CDCl$_3$): 7.18 (dd, 1H), 7.13 (m, 1H), 7.02 (m, 1H), 5.94 (br s, 1H), 4.42 (m, 1H), 3.33 (br d, 1H), 2.98 (m, 2H), 2.65 (m, 1H), 2.46 (br d, 1H). GC/MS (EI) for $C_{12}H_{11}ClFNO_2$: 255 (M$^+$). GC-MS (EI) for $C_{12}H_{10}ClF_2NO_2$: 273 (M$^+$).

4-(fluoromethyl)piperidine-1-carbonyl chloride. Synthesized according to the method of reagent preparation 37 using 4-(fluoromethyl)piperidine (reagent preparation 7) in step 4. GC-MS (EI) for $C_7H_{11}ClFNO$: 180 (M$^+$).

Reagent Preparation 38: 6-bromo-N-ethyl-3-(methoxymethyl)-3H-imidazo[4,5-b]pyridin-2-amine and 6-bromo-N-ethyl-N,3-bis(methoxymethyl)-3H-imidazo[4,5-b]pyridin-2-amine Step 1: To a cooled (0° C.) solution of 5-bromopyridine-2, 3-diamine (5.0 g, 27 mmol) in NMP (20 mL) was added isothiocyanatoethane (2.3 mL, 26 mmol). The resulting solution was heated (65° C.) for four hours and then cooled to ambient temperature before 1,3-diisopropylcarbodiimide (4.2 mL, 27 mmol) was added. The reaction mixture was stirred for 18 hours, diluted with water and the resulting suspension was collected by filtration. Trituration with ethyl acetate provided 6-bromo-N-ethyl-3H-imidazo[4,5-b]pyridin-2-amine (4.8 g, 75% yield) as a brown solid. $^1$H NMR (400 MHz, $d_6$-DMSO) δ 11.41 (bs, 1H), 7.91 (s, 1H), 7.53 (s, 1H), 7.17 (s, 1H), 3.33 (q, 2H), 1.17 (t, 3H); MS (ES) for $C_8H_9BrN_4$: 241 (MH$^+$).

Step 2: To a cooled (0° C.) solution of 6-bromo-N-ethyl-3H-imidazo[4,5-b]pyridin-2-amine (0.36 g, 1.5 mmol) in DMF was added NaH (60% dispersion in mineral oil, 0.060 g, 1.5 mmol) portionwise over 15 minutes. The reaction mixture was stirred for 15 minutes and then chloro(methoxy)methane (0.12 mL, 1.5 mmol) was added dropwise over 15 minutes. The resulting slurry was allowed to warm to ambient temperature and was stirred for two hours and was partitioned between ethyl acetate and saturated aqueous sodium bicarbonate. The organic layer was washed with brine, dried over magnesium sulfate, filtered and concentrated in vacuo. Purification by silica gel chromatography provided both 6-bromo-N-ethyl-N,3-bis(methoxymethyl)-3H-imidazo[4,5-b]pyridin-2-amine (0.091 g, 18%) and 6-bromo-N-ethyl-3-(methoxymethyl)-3H-imidazo[4,5-b]pyridin-2-amine (0.15 g, 35% yield). Bisprotected product: MS (ES) for $C_{12}H_{17}BrN_4O_2$: 329 (MH$^+$). Monoprotected product: $^1$H NMR (400 MHz, CDCl$_3$) δ 8.03 (d, 1H), 7.73 (d, 1H), 5.42 (s, 2H), 4.98 (s, 1H), 3.59 (q, 2H), 3.36 (s, 3H), 1.34 (t, 3H); MS (ES) for $C_{10}H_{13}BrN_4O$: 285 (MH$^+$).

Reagent Preparation 39:
N-(5-bromo-2-chloropyridin-3-yl)methanesulfonamide

STEP 1: A solution of 5-bromo-2-chloropyridin-3-amine (1.0 g, 4.8 mmol) and diisopropylethylamine (1.85 mL, 10.6 mmol) in dichloromethane (25 mL) was cooled to 0° C., and then methanesulfonyl chloride (750 uL, 9.6 mmol) was added slowly. The reaction mixture was stirred at 0° C. for 15 min and was then warmed to rt. After stirring for 2 h, water was added, and then the biphasic mixture was partitioned. The organic phase was dried over magnesium sulfate, filtered, and concentrated in vacuo. The residue was then dissolved in dioxane (10 mL) and water (10 mL). Potassium carbonate (2.76 g, 20 mmol) was added, and the reaction mixture was stirred for 15 h at rt. Water was then added to the mixture which was subsequently acidified with aqueous citric acid (10%). The aqueous mixture was extracted twice with ethyl acetate. The combined organic extracts were dried over magnesium sulfate, filtered, and concentrated in vacuo. The residue was purified by flash chromatography (gradient, 100% hexanes to 50% hexanes: 50% ethyl acetate) to provide N-(5-bromo-2-chloropyridin-3-yl)methanesulfonamide (520 mg, 1.82 mmol, 38% yield) as a light pink solid. $^1$H NMR (400 MHz, CDCl$_3$) δ 8.27 (d, 1H), 8.14 (d, 1H), 6.83 (br s, 1H), 3.11 (s, 3H); MS (EI) for $C_6H_6BrClN_2O_2S$: 285, 287, 289 (Br+Cl isotopes, MH$^+$).

Reagent Preparation: 40: tert-butyl 1-(2-amino-5-bromopyridin-3-ylsulfonyl)azetidin-3-ylcarbamate To a solution of tert-butyl azetidin-3-ylcarbamate (64 mg, 0.37 mmol) and potassium carbonate (102 mg, 0.74 mmol) in dioxane (2 mL) and water (400 uL) was added 2-amino-5-bromopyridine-3-sulfonyl chloride (100 mg, 0.37 mmol, prepared according to the methods in WO2008144463). The reaction mixture was stirred for 1 h at room temperature then quenched by addition of saturated aqueous sodium bicarbonate, and the aqueous solution was extracted twice with ethyl acetate. The combined organic extracts were dried over magnesium sulfate, filtered and concentrated to provide tert-butyl 1-(2-amino-5-bromopyridin-3-ylsulfonyl)azetidin-3-ylcarbamate (120 mg, 0.30 mmol, 80% yield) as a white solid. $^1$H NMR (400 MHz, CDCl$_3$) δ 8.31 (d, 1H), 8.00 (d, 1H), 5.76 (br s, 2H), 4.80 (br s, 1H), 4.50-4.36 (m, 1H), 4.11 (t, 2H), 3.75 (t, 2H), 1.42 (s, 9H); MS (EI) for $C_{13}H_{19}BrN_4O_4S$: 407, 409 (Br isotopes, MH$^+$).

Synthetic Example 1

4-(azepan-1-ylcarbonyl)-7-(2-methyl-1H-benzimidazol-6-yl)-2,3,4,5-tetrahydro-1,4-benzoxazepine STEP 1: To 5-bromo-2-methylbenzimidazole (38 g, 180 mmol) in THF (400 mL) was added di-tert-butyl dicarbonate (39 g, 189 mmol). The reaction mixture was stirred at room temperature for 24 h and then concentrated. Ethyl acetate (400 mL) was added to the residue, and the solution was washed with 10% aqueous citric acid (2×100 mL), water (100 mL), and brine (100 mL), dried over sodium sulfate, and concentrated. Column chromatography on silica (gradient 20-30% ethyl acetate in hexane) provided 1,1-dimethyl 6-bromo-2-methyl-1H-benzimidazole-1-carboxylate (27 g, 48% yield) as a beige solid. MS (EI) for $C_{13}H_{15}BrN_2O_2$: 312 (MH$^+$).

STEP 2: A solution of 1,1-dimethylethyl 7-bromo-2,3-dihydro-1,4-benzoxazepine-4(5H)-carboxylate (30.0 g, 91.4 mmol) and triisopropyl borate (22.4 g, 119 mmol) in THF (300 mL) was cooled to −78° C., and a 2.5M solution of n-butyllithium in hexanes (47.6 mL, 119 mmol) was added dropwise over 40 min at this temperature. The reaction mixture was stirred at −78° C. for an additional 30 min, then quenched by dropwise addition of 2 N hydrochloric acid (80 ml), and allowed to warm up to room temperature. Ethyl acetate (100 mL) and water (100 mL) were added, the organic layer was separated, and the aqueous layer was extracted with ethyl acetate (100 mL). The combined organic layers were washed with water, dried over sodium sulfate, and concentrated. Hexane (200 mL) was added to the residue and the mixture was stirred overnight. The precipitate was filtered, washed several times with hexane, and dried to give (4-{[(1,1-dimethylethyl)oxy]carbonyl}-2,3,4,5-tetrahydro-1,4-benzoxazepin-7-yl)boronic acid (23.4 g, 87%) as a colorless solid. MS (EI) for $C_{14}H_{20}BNO_5$: 294 (MH$^+$).

STEP 3: A suspension of 1,1-dimethylethyl 6-bromo-2-methyl-1H-benzimidazole-1-carboxylate (11.3 g, 36 mmol), (4-{[(1,1-dimethylethyl)oxy]carbonyl}-2,3,4,5-tetrahydro-1,4-benzoxazepin-7-yl)boronic acid (11.7 g, 40 mmol), dichloro[1,1-bis-(diphenylphosphino]ferrocenepalladium (II) dichloromethane adduct (3.0 g, 10 mol %) in dioxane (115 mL) and water (28.5 mL) was degassed with nitrogen, and then diisopropylethylamine (18.6 g, 144 mmol) was added. The reaction mixture was stirred at 90° C. for 220 min, cooled to room temperature, and concentrated. Column chromatography on silica of the residue (gradient 25-30% ethyl acetate in hexane) afforded 1,1-dimethyl 7-(1-{[(1,1-dimethylethyl)oxy]carbonyl}-2-methyl-1H-benzimidazol-6-yl)-2,3-dihydro-1,4-benzoxazepine-4(5H)-carboxylate (13.2 g, 76% yield) as an amorphous solid. MS (EI) for $C_{27}H_{33}N_3O_5$: 480 (MH$^+$).

STEP 4: A solution of 1,1-dimethyl 7-(1-{[(1,1-dimethylethyl)oxy]carbonyl}-2-methyl-1H-benzimidazol-6-yl)-2,3-dihydro-1,4-benzoxazepine-4(5H)-carboxylate (13.1 g, 27 mmol) in a mixture of methanol (20 mL) and 4 N hydrogen chloride in dioxane (30 mL) was refluxed for 15 min. After cooling to room temperature ethyl ether (100 mL) was added, and the reaction mixture was concentrated. Another portion of ethyl ether (100 mL) was added, the precipitate was filtered off, washed several times with ethyl ether, and dried to give 7-(2-methyl-1H-benzimidazol-6-yl)-2,3,4,5-tetrahydro-1,4- benzoxazepine dihydrochloride (8.9 g, 93% yield) as a light beige solid. $^1$HNMR (400 MHz, CD$_3$OD): 7.93 (s, 1H), 7.86-7.67 (m, 4H), 7.28 (s, 1H), 4.54 (s, 2H), 4.33-4.23 (m, 2H), 3.65-3.54 (m, 2H), 2.91 (s, 3H); MS (EI) for C$_{17}$H$_{17}$N$_3$O: 280 (MH$^+$).

STEP 5: 7-(2-methyl-1H-benzimidazol-6-yl)-2,3,4,5-tetrahydro-1,4-benzoxazepine dihydrochloride (6.95 g, 19.73 mmol) was suspended in dichloromethane (100 mL) and cooled to 0° C. To the resulting mixture was added DIPEA (19 mL, 109 mmol) followed by allyl chloroformate (4.6 mL, 43.4 mmol) and stirring was continued at 0° C. for 30 minutes then warmed to room temperature. The reaction mixture was then charged with additional DIPEA (3.4 mL) and allyl chloroformate (1 mL) then stirred an additional 30 minutes at room temperature. The resulting solution was then concentrated and the residue azeotroped once from methanol (100 mL). The residue was then taken back into methanol (100 mL) followed by portionwise addition of 2 M aqueous sodium hydroxide (20 mL) and the mixture was allowed to stir for 1 h at room temperature. The solution was then concentrated and the residue partitioned with chloroform and dilute brine. The organic phase was then dried over anhydrous sodium sulfate, filtered and concentrated to give prop-2-en-1-yl 7-(2-methyl-1H-benzimidazol-6-yl)-2,3-dihydro-1,4-benzoxazepine-4(5H)-carboxylate as an amorphous residue which was carried forward directly into step 6.

STEP 6: prop-2-en-1-yl 7-(2-methyl-1H-benzimidazol-6-yl)-2,3-dihydro-1,4-benzoxazepine-4(5H)-carboxylate as obtained in step 5 was taken into THF (100 mL) followed by addition of pyridine (2.5 mL, 30 mml) and di-tert-butyl dicarbonate (4.9 g, 22.4 mmol) and the mixture was allowed to stir at room temperature over 12 h. The resulting solution was concentrated and the residue partitioned with ethyl acetate and 10% aqueous citric acid. The organic phase was washed twice with additional 10% aqueous citric acid then brine, dried over anhydrous magnesium sulfate, filtered and concentrated. The residue was purified by silica gel chromatography using 3:2 to 4:1 ethyl acetate in hexanes as eluent to afford 7-[1-[(1,1-dimethylethoxy)carbonyl]-2-methyl-1H-benzimidazol-6-yl]-2,3-dihydro-1,4-benzoxazepine-4(5H)-carboxylic acid 2-propenyl ester (10.2 g) as a pale yellow amorphous residue. MS (EI) for C$_{26}$H$_{29}$N$_3$O$_5$: 465 (MH$^+$).

STEP 7: 7-[1-[(1,1-dimethylethoxy)carbonyl]-2-methyl-1H-benzimidazol-6-yl]-2,3-dihydro-1,4-benzoxazepine-4 (5H)-carboxylic acid 2-propenyl ester (110 mg, 0.27 mmol) was taken into THF (1 mL) followed by addition of sodium triacetoxyborohydride (254 mg, 1.2 mmol) then tetrakis (triphenylphosphine)palladium (0) (6.1 mg, 0.005 mmol) and the mixture was stirred for 1 h at room temperature. The mixture was diluted with chloroform and partitioned with dilute aqueous sodium bicarbonate. The aqueous phase was extracted twice with chloroform and the combined organic layers were dried over anhydrous sodium sulfate then filtered and concentrated to give crude 1,1-dimethylethyl 2-methyl-6-(2,3,4,5-tetrahydro-1,4-benzoxazepin-7-yl)-1H-benzimidazole-1-carboxylate (109.5 mg) as an amorphous residue. MS (EI) for C$_{22}$H$_{25}$N$_3$O$_3$: 380 (MH$^+$).

STEP 8: Phosgene (20 W % in toluene) (190 uL, 0.38 mmol) was added by syringe to a 0° C. cooled solution of pyridine (100 uL, 1.2 mmol) in chloroform (3 mL) followed by addition of 1,1-dimethylethyl 2-methyl-6-(2,3,4,5-tetrahydro-1,4-benzoxazepin-7-yl)-1H-benzimidazole-1-carboxylate as obtained in step 7 as a solution in chloroform (1 mL). The mixture was stirred for 15 minutes at 0° C. then partitioned with 10% aqueous citric acid. The organic phase was dried over anhydrous sodium sulfate then filtered and concentrated. The residue was purified by silica gel chromatography to give 1,1-dimethylethyl 6-[4-(chlorocarbonyl)-2,3,4,5-tetrahydro-1,4-benzoxazepin-7-yl]-1H-benzimidazole-1-carboxylate (62.6 mg, 59% yield) as a yellow amorphous residue. MS (EI) for C$_{23}$H$_{24}$ClN$_3$O$_4$: 442 (MH$^+$).

STEP 9: 1,1-dimethylethyl 6-[4-(chlorocarbonyl)-2,3,4,5-tetrahydro-1,4-benzoxazepin-7-yl]-1H-benzimidazole-1-carboxylate (33 mg, 0.08 mmol), was taken into dichloromethane (1.5 mL) followed by addition of homopiperidine (0.1 mL, 0.89 mmol) and the mixture was allowed to stir for 12 h at room temperature. The mixture was then concentrated and the residue partitioned with ethyl acetate and 10% aqueous citric acid. The organic phase was separated and dried over magnesium sulfate then filtered and concentrated. The residue obtained was taken into trifluoroacetic acid (1 mL) and allowed to stand for 1 h at room temperature. The solution was then concentrated and the residue taken into a minimum of aqueous acetonitrile and purified by preparative reverse phase HPLC. Lyophilization of the combined pure fractions afforded 4-(azepan-1-ylcarbonyl)-7-(2-methyl-1H-benzimidazol-6-yl)-2,3,4,5-tetrahydro-1,4-benzoxazepine (18 mg) as an amorphous solid. $^1$H NMR (400 MHz, d$_6$-DMSO): 7.91 (s, 1H), 7.83 (d, 1H), 7.76 (dd, 1H), 7.64 (d, 1H), 7.55 (dd, 1H), 7.06 (d, 1H), 4.42 (s, 2H), 4.22 (br s, 2H), 3.55 (br s, 2H), 3.29 (tr, 4H), 2.64 (s, 3H), 1.65 (br s, 4H), 1.49 (br s, 4H). MS (EI) for C$_{24}$H$_{28}$N$_4$O$_2$: 406 (MH$^+$).

Using analogous synthetic techniques and substituting with alternative starting reagents in step 9 the following compounds of the invention were prepared. Protecting group introduction and removal steps were conducted as required according to literature techniques appropriate for a given protecting group (see for example: Greene and Wuts, Protective Groups in Organic Synthetic, Wiley-Interscience). Alternative starting materials were obtained commercially unless otherwise indicated.

4-(hexahydrocyclopenta[c]pyrrol-2(1H)-ylcarbonyl)-7-(2-methyl-1H-benzimidazol-6-yl)-2,3,4,5-tetrahydro-1,4-benzoxazepine. Prepared according to the method of example 1 by using octahydrocyclopenta[c]pyrrole in step 9. $^1$H NMR (400 MHz, methanol-d$_4$): 7.64 (m, 1H), 7.54-7.42 (m, 4H), 7.02 (d, 1H), 4.53 (s, 2H), 4.21 (m, 2H), 3.71 (m, 2H), 3.55 (m, 2H), 3.20 (m, 2H), 2.62 (m, 2H), 2.59 (s, 3H), 1.86-1.69 (m, 3H), 1.58 (m, 1H), 1.44 (m, 2H); MS (EI) for C$_{25}$H$_{28}$N$_4$O$_2$: 417 (MH$^+$).

4-(3,4-dihydroquinolin-1(2H)-ylcarbonyl)-7-(2-methyl-1H-benzimidazol-6-yl)-2,3,4,5-tetrahydro-1,4-benzoxazepine. Prepared according to the method of example 1 by using 1,2,3,4-tetrahydroquinoline in step 9. $^1$H NMR (400 MHz, methanol-d$_4$): 7.59 (m, 1H), 7.51 (d, 1H), 7.45 (dd, 1H), 7.38 (dd, 1H), 7.19 (d, 1H), 7.14 (d, 1H), 7.03 (d, 1H), 7.00-6.85 (m, 3H), 4.50 (s, 2H), 4.19 (m, 2H), 3.72 (m, 2H), 3.52 (m, 2H), 2.80 (t, 2H), 2.59 (s, 3H), 1.92 (m, 2H); MS (EI) for C$_{27}$H$_{26}$N$_4$O$_2$: 439 (MH$^+$).

7-(2-methyl-1H-benzimidazol-6-yl)-4-{[2-(phenylmethyl)pyrrolidin-1-yl]carbonyl}-2,3,4,5-tetrahydro-1,4-benzoxazepine. Prepared according to the method of example 1 by using 2-benzylpyrrolidine in step 9. $^1$H NMR (400 MHz, methanol-d$_4$): 7.65 (m, 1H), 7.57-7.42 (m, 4H), 7.21-7.03 (m, 6H), 4.56 (m, 2H), 4.32 (m, 1H), 4.16 (m, 2H), 3.77 (m, 1H), 3.65 (m, 1H), 3.44 (m, 1H), 3.34 (m, 1H), 2.90 (m, 1H), 2.58 (s, 3H), 2.50 (m, 1H), 1.84 (m, 2H), 1.60 (m, 2H); MS (EI) for C$_{29}$H$_{30}$N$_4$O$_2$: 467 (MH$^+$).

7-(2-methyl-1H-benzimidazol-6-yl)-4-[(2-phenylpyrrolidin-1-yl)carbonyl]-2,3,4,5-tetrahydro-1,4-benzoxazepine acetate. Prepared according to the method of example 1 by using 2-phenylpyrrolidine in step 9. $^1$H NMR (400 MHz, methanol-d$_4$): 7.66 (m, 1H), 7.53 (m, 2H), 7.46 (m, 2H), 7.14 (m, 2H), 7.04 (m, 4H), 4.95 (m, 1H), 4.59 (m, 2H), 4.14 (m, 2H), 3.88 (m, 1H), 3.70 (m, 2H), 3.61 (m, 1H), 2.57 (s, 3H), 2.34 (m, 1H), 2.00 (m, 1H), 1.98 (s, 3H), 1.86 (m, 1H), 1.70 (m, 1H); MS (EI) for $C_{28}H_{28}N_4O_2$: 453 (MH$^+$).

7-(2-methyl-1H-benzimidazol-6-yl)-4-[(2-phenylpiperidin-1-yl)carbonyl]-2,3,4,5-tetrahydro-1,4-benzoxazepine. Prepared as the trifluoroacetate salt according to the method of example 1 by using 2-phenylpiperidine in step 9. $^1$H NMR (400 MHz, methanol-d$_4$): 7.80-7.65 (m, 3H), 7.50 (dd, 1H), 7.32 (d, 1H), 7.27-7.11 (m, 5H), 7.07 (d, 1H), 4.65 (m, 1H), 4.57 (s, 2H), 4.20 (m, 2H), 3.78 (m, 2H), 3.37 (m, 1H), 3.16 (m, 1H), 2.86 (s, 3H), 2.05 (m, 1H), 1.87 (m, 1H), 1.75-1.54 (m, 4H); MS (EI) for $C_{29}H_{30}N_4O_2$: 467 (MH$^+$).

7-(2-methyl-1H-benzimidazol-6-yl)-4-[(3-phenylpiperidin-1-yl)carbonyl]-2,3,4,5-tetrahydro-1,4-benzoxazepine. Prepared as the acetate salt according to the method of example 1 by using 3-phenylpiperidine in step 9. $^1$H NMR (400 MHz, methanol-d$_4$): 7.58 (d, 1H), 7.49 (m, 2H), 7.42 (dd, 1H), 7.32 (dd, 1H), 7.16-7.03 (m, 5H), 7.01 (d, 1H), 4.51 (s, 2H), 4.20 (m, 2H), 3.73 (m, 4H), 2.87 (m, 2H), 2.77 (m, 1H), 2.59 (s, 3H), 2.01 (m, 1H), 1.97 (s, 3H), 1.84-1.62 (m, 3H); MS (EI) for $C_{29}H_{30}N_4O_2$: 467 (MH$^+$).

7-(2-methyl-1H-benzimidazol-6-yl)-4-[(3-phenylpyrrolidin-1-yl)carbonyl]-2,3,4,5-tetrahydro-1,4-benzoxazepine. Prepared as the acetate salt according to the method of example 1 by using 3-phenylpyrrolidine in step 9. $^1$H NMR (400 MHz, methanol-d$_4$): 7.04 (s, 1H), 7.50 (m, 2H), 7.46 (dd, 1H), 7.36 (dd, 1H), 7.26-7.12 (m, 5H), 7.04 (d, 1H), 4.61 (m, 1H), 4.58 (s, 2H), 4.31 (m, 1H), 4.15 (m, 1H), 3.85 (m, 1H), 3.66 (m, 2H), 3.61 (m, 2H), 3.35 (m, 1H), 2.60 (s, 3H), 2.26 (m, 1H), 2.01 (m, 1H), 1.97 (s, 3H); MS (EI) for $C_{28}H_{28}N_4O_2$: 453 (MH$^+$).

7-(2-methyl-1H-benzimidazol-6-yl)-4-[(2-methylpyrrolidin-1-yl)carbonyl]-2,3,4,5-tetrahydro-1,4-benzoxazepine. Prepared as the acetate salt according to the method of example 1 by using 2-methylpyrrolidine in step 9. $^1$H NMR (400 MHz, methanol-d$_4$): 7.55 (m, 1H), 7.45-7.32 (m, 4H), 6.94 (d, 1H), 4.44 (m, 2H), 4.19 (m, 1H), 4.04 (m, 1H), 3.87 (m, 1H), 3.65 (m, 1H), 3.59-3.46 (m, 2H), 3.26 (m, 1H), 2.49 (s, 3H), 2.02 (m, 1H), 1.89 (s, 3H), 1.80 (m, 1H), 1.58 (m, 1H), 1.38 (m, 1H), 0.98 (d, 3H); MS (EI) for $C_{23}H_{26}N_4O_2$: 391 (MH$^+$).

7-(2-methyl-1H-benzimidazol-6-yl)-4-{[3-(phenylmethyl)pyrrolidin-1-yl]carbonyl}-2,3,4,5-tetrahydro-1,4-benzoxazepine. Prepared as the acetate salt according to the method of example 1 by using 3-benzylpyrrolidine in step 9. $^1$H NMR (400 MHz, methanol-d$_4$): 7.65 (m, 1H), 7.54-7.42 (m, 4H), 7.16-7.06 (m, 5H), 7.01 (d, 1H), 4.52 (m, 2H), 4.24 (m, 1H), 4.14 (m, 1H), 3.74 (m, 1H), 3.63 (m, 1H), 3.45 (m, 2H), 3.34 (m, 1H), 3.17 (m, 1H), 2.65 (m, 2H), 2.58 (s, 3H), 2.37 (m, 1H), 1.99 (s, 3H), 1.93 (m, 1H), 1.60 (m, 1H); MS (EI) for $C_{29}H_{30}N_4O_2$: 467 (MH$^+$).

7-(2-methyl-1H-benzimidazol-6-yl)-4-[(1-oxidothiomorpholin-4-yl)carbonyl]-2,3,4,5-tetrahydro-1,4-benzoxazepine. Prepared according to the method of example 1 by using 4-(methylsulfinyl)piperidine (synthesized according to reagent preparation 13) in step 9. $^1$H NMR (400 MHz, DMSO-d$_6$): 7.63 (m, 1H), 7.58 (d, 1H), 7.48 (m, 2H), 7.36 (dd, 1H), 7.00 (d, 1H), 4.48 (s, 2H), 4.19 (m, 2H), 3.62 (m, 4H), 3.66 (m, 2H), 2.96 (m, 2H), 2.72 (m, 2H), 1.86 (s, 3H); MS (EI) for $C_{22}H_{24}N_4O_3S$: 425 (MH$^+$).

7-(2-methyl-1H-benzimidazol-6-yl)-4-{[4-(methylsulfonyl)piperidin-1-yl]carbonyl}-2,3,4,5-tetrahydro-1,4-benzoxazepine. Prepared according to the method of example 1 by using 4-(methylsulfonyl)piperidine (synthesized according to reagent preparation 14) in step 9. $^1$H NMR (400 MHz, DMSO-d$_6$): 12.27 (br. s, 1H), 7.64 (m, 1H), 7.55 (m, 1H), 7.48 (m, 2H), 7.37 (m, 1H), 7.01 (m, 1H), 4.46 (s, 2H), 4.19 (m, 2H), 3.68 (m, 2H), 3.62 (m, 2H), 2.94 (m, 3H), 2.81 (m, 2H), 1.99 (m, 2H), 1.91 (m, 1H), 1.60 (m, 2H); MS (EI) for $C_{24}H_{28}N_4O_4S$: 469 (MH$^+$).

7-(2-methyl-1H-benzimidazol-6-yl)-N-(1-methylethyl)-N-(phenylmethyl)-2,3-dihydro-1,4-benzoxazepine-4(5H)-carboxamide. Prepared according to the method of example 1 by using N-benzylpropan-2-amine in step 9. $^1$H NMR (400 MHz, DMSO-d$_6$): 12.27 (br. s, 1H), 7.64 (m, 1H), 7.55 (m, 1H), 7.48 (m, 2H), 7.37 (m, 1H), 7.01 (m, 1H), 4.46 (s, 2H), 4.19 (m, 2H), 3.68 (m, 2H), 3.62 (m, 2H), 2.94 (m, 3H), 2.81 (m, 2H), 1.99 (m, 2H), 1.91 (m, 1H), 1.60 (m, 2H); MS (EI) for $C_{24}H_{28}N_4O_4S$: 469 (MH$^+$).

7-(2-methyl-1H-benzimidazol-6-yl)-4-{[2-(phenylmethyl)piperidin-1-yl]carbonyl}-2,3,4,5-tetrahydro-1,4-benzoxazepine. Prepared as the free base as described in example 1 using racemic 2-benzylpiperidine step 9. $^1$H NMR (400 MHz, methanol-d$_4$): 7.49 (s, 1H), 7.43-7.36 (m, 2H), 7.32-7.27 (m, 2H), 7.08-6.90 (m, 6H), 4.19 (s, 2H), 4.13-4.04 (m, 2H), 3.73-3.66 (m, 1H), 3.45-3.32 (m, 2H), 3.30-3.23 (m, 1H), 3.17-3.07 (m, 1H), 2.89-2.82 (m, 1H), 2.74-2.67 (m, 1H), 2.49 (s, 3H), 1.77-1.38 (m, 6H); MS (EI) for $C_{30}H_{32}N_4O_2$: 481 (MH$^+$).

7-(2-methyl-1H-benzimidazol-6-yl)-4-{[4-(methyloxy)piperidin-1-yl]carbonyl}-2,3,4,5-tetrahydro-1,4-benzoxazepine. Prepared as described in example 1 using 4-methoxypiperidine in step 9. $^1$H NMR (400 MHz, methanol-d$_4$): 7.57 (s, 1H), 7.47-7.34 (m, 4H), 6.96 (d, 1H), 4.41 (s, 2H), 4.12 (t, 2H), 3.61 (t, 2H), 3.48-3.40 (m, 2H), 3.39-3.31 (m, 1H), 3.27 (s, 3H), 2.96 (t, 2H), 1.88-1.81 (m, 2H), 1.53-1.42 (m, 2H); MS (EI) for $C_{24}H_{28}N_4O_3$: 421 (MH$^+$).

7-(2-methyl-1H-benzimidazol-6-yl)-4-{[3-(phenylmethyl)piperidin-1-yl]carbonyl}-2,3,4,5-tetrahydro-1,4-benzoxazepine. Prepared as described in example 1 using racemic 3-benzylpiperidine in step 9. $^1$H NMR (400 MHz, methanol-d$_4$): 7.62 (s, 1H), 7.51-7.38 (m, 4H), 7.13-7.04 (m, 3H), 7.01-6.96 (m, 3H), 4.45-4.34 (m, 2H), 4.07 (t, 2H), 3.60-3.43 (m, 4H), 2.80-2.72 (m, 1H), 2.57 (s, 3H), 2.50-2.42 (t, 1H), 2.37 (d, 2H), 1.80-1.61 (m, 3H), 1.55-1.46 (m, 1H), 1.15-1.05 (m, 1H); MS (EI) for $C_{30}H_{32}N_4O_2$: 481 (MH$^+$).

4-(2-azabicyclo[2.2.1]hept-2-ylcarbonyl)-7-(2-methyl-1H-benzimidazol-6-yl)-2,3,4,5-tetrahydro-1,4-benzoxazepine. Prepared as the free base as described in example 1 using 2-azabicyclo[2.2.1]heptane in step 9. $^1$H NMR (400 MHz, d$_6$-DMSO): 12.26 (br s, 1H), 7.72-7.43 (m, 4H), 7.35 (d, 1H), 6.99 (d, 1H), 4.47 (s, 2H), 4.24 (m, 1H), 4.12 (m, 1H), 3.96 (s, 1H), 3.71-3.43 (m, 4H), 2.81 (d, 1H), 2.51 (s, 3H), 1.84-1.75 (m, 1H), 1.62-1.52 (m, 2H), 1.48-1.41 (d, 2H), 1.39-1.28 (m, 2H); MS (EI) for $C_{24}H_{26}N_4O_2$: 403 (WO.

1-{[7-(2-methyl-1H-benzimidazol-6-yl)-2,3-dihydro-1,4-benzoxazepin-4(5H)-yl]carbonyl}piperidin-3-ol. Prepared as described in example 1 using racemic 3-hydroxypiperidine step 9. $^1$H NMR (400 MHz, methanol-d$_4$): 7.65 (s, 1H), 7.55-7.50 (m, 2H), 7.48-7.42 (m, 2H), 7.03 (d, 1H), 4.50 (s, 2H), 4.19 (m, 2H), 3.75-3.66 (m, 3H), 3.55 (m, 1H), 3.37 (m, 1H), 2.99 (m, 1H), 2.87 (m, 1H), 2.58 (s, 3H), 1.93 (m, 1H), 1.82 (m, 1H), 1.60-1.44 (m, 2H); MS (EI) for $C_{23}H_{26}N_4O_3$: 407 (MH$^+$).

N-methyl-7-(2-methyl-1H-benzimidazol-6-yl)-N-[(1R)-1-phenylethyl]-2,3-dihydro-1,4-benzoxazepine-4(5H)-carboxamide. Prepared as the free base as described in example 1 using (R)—N-methyl-1-phenylethanamine step 9. $^1$H NMR (400 MHz, methanol-d$_4$): 7.60 (s, 1H), 7.53-7.45 (m, 2H), 7.38-7.32 (m, 2H), 7.30-7.17 (m, 5H), 7.05 (d, 1H), 5.11 (q, 1H), 4.62 (s, 2H), 4.51 (br s, 2H), 4.25 (m, 1H), 3.70 (m, 1H), 2.65 (s, 3H), 2.59 (s, 3H), 1.54 (d, 3H); MS (EI) for $C_{27}H_{28}N_4O_2$: 441 (MH$^+$).

7-(2-methyl-1H-benzimidazol-6-yl)-4-(piperidin-1-ylcarbonyl)-2,3,4,5-tetrahydro-1,4-benzoxazepine. Synthesized according to the method of example 1 using piperidine in step 9. MS (EI) for $C_{23}H_{26}N_4O_2$: 391 (MH$^+$).

7-(2-methyl-1H-benzimidazol-6-yl)-4-(pyrrolidin-1-ylcarbonyl)-2,3,4,5-tetrahydro-1,4-benzoxazepine. Synthesized according to the method of example 1 using pyrrolidine in step 9. MS (EI) for $C_{22}H_{24}N_4O_2$: 377 (MH$^+$).

7-(2-methyl-1H-benzimidazol-6-yl)-4-[(3-methylpiperidin-1-yl)carbonyl]-2,3,4,5-tetrahydro-1,4-benzoxazepine. Synthesized according to the method of example 1 using racemic 3-methylpiperidine in step 9. MS (EI) for $C_{24}H_{28}N_4O_2$: 406 (MH$^+$).

7-(2-methyl-1H-benzimidazol-5-yl)-4-{[(3aR,6aS)-5-methylhexahydrocyclopenta[c]pyrrol-2(1H)-yl]carbonyl}-2,3,4,5-tetrahydro-1,4-benzoxazepine. Synthesized as a 4:1 mixture of 5-methyl isomers according to the method of example 1 using (3aR,6aS)-5-methyloctahydrocyclopenta[c]pyrrole (reagent preparation 10) in step 9. $^1$H NMR (400 MHz, methanol-d$_4$): 7.85 (s, 1H), 7.76-7.75 (d, 2H), 7.54 (s, 1H), 7.48 (dd, 1H), 7.05 (dd, 1H), 4.56 (s, 2H), 4.24 (m, 2H), 3.75 (m, 2H), 3.59 (minor isomer, dd, 0.5H), 3.40 (major isomer, dd, 1.5H), 3.32 (major isomer, dd, 1.5H), 3.14 (minor isomer, dd, 0.5H), 2.71 (minor isomer, br, 0.5H), 2.59 (major isomer, br, 1.5H), 2.06-1.98 (m, 2H), 1.97-1.88 (m, 1H), 1.62 (minor isomer, dd, 0.5H), 1.01-0.9 (m, 4.5H). MS (EI) for $C_{26}H_{30}N_4O_2$: 432 (MH$^+$).

(±)-7-(2-methyl-1H-benzimidazol-5-yl)-4-{[(3aS,6aR)-5-methyl-3,3a,4,6a-tetrahydrocyclopenta[c]pyrrol-2(1H)-yl]carbonyl}-2,3,4,5-tetrahydro-1,4-benzoxazepine. Synthesized according to the method of example 1 using (±)-(3aR,6aS)-5-methyl-1,2,3,3a,4,6a-hexahydrocyclopenta[c]pyrrole (reagent preparation 11) in step 9. $^1$H NMR (400 MHz, d$_6$-DMSO): 7.91 (s, 1H), 7.82 (d, 1H), 7.75 (dd, 1H), 7.59 (d, 1H), 7.54 (dd, 1H), 7.04 (dd, 1H), 5.19 (s, 1H), 4.49 (s, 2H), 4.21 (m, 2H), 3.61 (m, 2H), 3.21 (br, 1H), 3.18 (d, 1H), 3.04 (dd, 1H), 2.74 (tr, 1H), 2.44 (dd, 1H), 2.01 (d, 1H), 1.65 (s, 3H). MS (EI) for $C_{26}H_{28}N_4O_2$: 430 (MH$^+$).

4-[(4,4-difluoropiperidin-1-yl)carbonyl]-7-(2-methyl-1H-benzimidazol-6-yl)-2,3,4,5-tetrahydro-1,4-benzoxazepine. Prepared according to the method of example 1 by using 4,4-difluoropiperidine in step 9. $^1$H NMR (400 MHz, methanol-d$_4$): 7.65 (d, 1H), 7.54 (d, 1H), 7.52 (d, 1H), 7.47 (dd, 1H), 7.44 (dd, 1H), 7.04 (d, 1H), 4.54 (s, 2H), 4.22 (m, 2H), 3.73 (m, 2H), 3.38 (m, 4H), 2.59 (s, 3H), 2.02 (m, 4H); MS (EI) for $C_{23}H_{24}F_2N_4O_2$: 427 (MH$^+$).

1-{[7-(2-methyl-1H-benzimidazol-6-yl)-2,3-dihydro-1,4-benzoxazepin-4(5H)-yl]carbonyl}piperidin-4-ol. Prepared according to the method of example 1 by using 4-piperidin-4-ol in step 9. $^1$H NMR (400 MHz, CDCl$_3$): 7.60 (s, 1H), 7.53 (d, 1H), 7.41 (m, 2H), 7.35 (m, 1H), 7.07 (d, 1H), 4.45 (s, 2H), 4.21 (m, 2H), 3.89 (m, 1H), 3.72 (m, 2H), 3.63 (m, 2H), 3.00 (m, 2H), 2.64 (m, 3H), 1.96 (m, 2H), 1.61 (m, 2H); MS (EI) for $C_{23}H_{26}N_4O_3$: 407 (MH$^+$).

4-({4-[(4-chlorophenyl)methyl]piperidin-1-yl}carbonyl)-7-(2-methyl-1H-benzimidazol-6-yl)-2,3,4,5-tetrahydro-1,4-benzoxazepine. Prepared according to the method of example 1 by using 4-(4-chlorobenzyl)piperidine in step 9. $^1$H NMR (400 MHz, methanol-d$_4$): 7.64 (s, 1H), 7.52 (d, 1H), 7.50 (d, 1H), 7.46 (dd, 1H), 7.41 (dd, 1H), 7.21 (d, 2H), 7.12 (d, 2H), 7.03 (d, 1H), 4.48 (s, 2H), 4.19 (m, 2H), 3.67 (m, 4H), 2.76 (m, 2H), 2.59 (s, 3H), 2.55 (d, 2H), 1.71 (m, 1H), 1.61 (m, 2H), 1.27 (m, 2H); MS (EI) for $C_{30}H_{31}ClN_4O_2$: 515 (MH$^+$).

4-({4-[(4-chlorophenyl)oxy]piperidin-1-yl}carbonyl)-7-(2-methyl-1H-benzimidazol-6-yl)-2,3,4,5-tetrahydro-1,4-benzoxazepine. Prepared according to the method of example 1 by using 4-(4-chlorophenoxy)piperidine in step 9. $^1$H NMR (400 MHz, methanol-d$_4$): 7.64 (s, 1H), 7.51 (m, 2H), 7.47 (dd, 1H), 7.42 (dd, 1H), 7.23 (m, 2H), 7.04 (d, 1H), 6.93 (m, 2H), 4.55 (m, 1H), 4.52 (s, 2H), 4.21 (m, 2H), 3.71 (m, 2H), 3.54 (m, 2H), 3.20 (m, 2H), 2.58 (s, 3H), 2.01 (m, 2H), 1.76 (m, 2H); MS (EI) for $C_{29}H_{29}ClN_4O_3$: 517 (MH$^+$).

1-{[7-(2-methyl-1H-benzimidazol-6-yl)-2,3-dihydro-1,4-benzoxazepin-4(5H)-yl]carbonyl}-4,4'-bipiperidine. Prepared as the acetate salt according to the method of example 1 by using 4,4'-bipiperidine in step 9. $^1$H NMR (400 MHz, methanol-d$_4$): 7.64 (s, 1H), 7.51 (m, 2H), 7.47 (dd, 1H), 7.42 (d, 1H), 7.04 (d, 1H), 4.50 (s, 2H), 4.20 (m, 2H), 3.74 (m, 2H), 3.68 (m, 2H), 3.37 (m, 2H), 2.92 (m, 2H), 2.81 (m, 2H), 2.58 (s, 3H), 1.95 (m, 2H), 1.37 (m, 2H), 1.52-1.23 (m, 6H); MS (EI) for $C_{28}H_{35}N_5O_2$: 474 (MH$^+$).

4-[(3-ethylpiperidin-1-yl)carbonyl]-7-(2-methyl-1H-benzimidazol-6-yl)-2,3,4,5-tetrahydro-1,4-benzoxazepine. Prepared according to the method of example 1 by using racemic 3-ethylpiperidine in step 9. $^1$H NMR (400 MHz, methanol-d$_4$): 7.64 (s, 1H), 7.51 (m, 2H), 7.47 (dd, 1H), 7.42 (dd, 1H), 7.04 (d, 1H), 4.50 (s, 2H), 4.21 (m, 2H), 3.67 (m, 2H), 3.62 (m, 2H), 2.79 (m, 1H), 2.58 (s, 3H), 2.46 (m, 1H), 1.90 (m, 1H), 1.70 (m, 1H), 1.56 (m, 1H), 1.42 (m, 1H), 1.17 (m, 2H), 1.07 (m, 1H), 0.80 (t, 3H); MS (EI) for $C_{25}H_{30}N_4O_2$: 419 (MH$^+$).

4-{[2-(4-fluorophenyl)piperidin-1-yl]carbonyl}-7-(2-methyl-1H-benzimidazol-6-yl)-2,3,4,5-tetrahydro-1,4-benzoxazepine. Prepared according to the method of example 1 by using racemic 2-(4-fluorophenyl)piperidine in step 9. MS (EI) for $C_{29}H_{29}N_4O_2$: 485 (MH$^+$).

ethyl (3S)-1-{[7-(2-methyl-1H-benzimidazol-6-yl)-2,3-dihydro-1,4-benzoxazepin-4(5H)-yl]carbonyl}piperidine-3-carboxylate. Prepared according to the method of example 1 by using (S)-ethyl piperidine-3-carboxylate in step 9. $^1$H NMR (400 MHz, methanol-d$_4$): 7.67 (s, 1H), 7.53 (m, 2H), 7.47 (m, 2H), 7.04 (d, 1H), 4.51 (s, 2H), 4.20 (m, 2H), 3.96 (m, 2H), 3.69 (m, 3H), 3.49 (m, 1H), 3.09 (m, 1H), 2.97 (m, 1H), 2.61 (m, 1H), 2.60 (s, 3H), 2.01 (m, 1H), 1.81-1.53 (m, 3H), 1.10 (t, 3H); MS (EI) for $C_{26}H_{30}N_4O_4$: 463 (MH$^+$).

ethyl 1-{[7-(2-methyl-1H-benzimidazol-6-yl)-2,3-dihydro-1,4-benzoxazepin-4(5H)-yl]carbonyl}piperidine-2-carboxylate. Prepared according to the method of example 1 by using racemic ethyl piperidine-2-carboxylate in step 9. $^1$H NMR (400 MHz, methanol-d$_4$): 7.65 (s, 1H), 7.51 (m, 2H), 7.44 (m, 2H), 7.04 (d, 1H), 4.52 (s, 2H), 4.28 (m, 1H), 4.21 (m, 1H), 4.08 (m, 2H), 3.70 (m, 2H), 2.58 (s, 3H), 2.05 (m, 1H), 1.81 (m, 1H), 1.64 (m, 2H), 1.49 (m, 1H), 1.13 (t, 3H); MS (EI) for $C_{26}H_{30}N_4O_4$: 463 (MH$^+$).

4-[(5-ethyl-2-methylpiperidin-1-yl)carbonyl]-7-(2-methyl-1H-benzimidazol-6-yl)-2,3,4,5-tetrahydro-1,4-benzoxazepine. Prepared according to the method of example 1 by using racemic 5-ethyl-2-methylpiperidine in step 9. $^1$H NMR (400 MHz, methanol-d$_4$): 7.64 (s, 1H), 7.50 (m, 2H), 7.43 (m, 2H), 7.04 (d, 1H), 4.46 (s, 2H), 4.21 (m, 2H), 4.06 (m, 1H), 3.65 (m, 2H), 3.42 (m, 1H), 2.68 (m, 1H), 2.58 (s, 3H), 1.77 (m, 1H), 1.70 (m, 1H), 1.56 (m, 1H), 1.39 (m, 1H), 1.31 (m, 1H), 1.18 (d, 3H), 0.81 (t, 3H); MS (EI) for $C_{26}H_{32}N_4O_2$: 433 (MH$^+$).

8-{[7-(2-methyl-1H-benzimidazol-6-yl)-2,3-dihydro-1,4-benzoxazepin-4 (5H)-yl]carbonyl}-8-azabicyclo[3.2.1]octan-3-(endo)-amine. Prepared as the acetate salt according to the method of example 1 by using tert-butyl 8-azabicyclo [3.2.1]octan-3-(endo)-ylcarbamate (synthesized according to reagent preparation 4) in step 9. $^1$H NMR (400 MHz, methanol-d$_4$): 7.64 (s, 1H), 7.50 (m, 2H), 7.44 (m, 2H), 7.03 (d, 1H), 4.62 (s, 2H), 4.24 (m, 2H), 4.15 (m, 2H), 3.77 (m, 2H), 3.46

(m, 1H), 2.58 (s, 3H), 2.55 (m, 2H), 2.05 (m, 2H), 1.92 (s, 3H), 1.75 (m, 2H), 1.60 (m, 2H); MS (EI) for $C_{25}H_{29}N_5O_2$: 432 (MH$^+$).

(3R)-1-{[7-(2-methyl-1H-benzimidazol-6-yl)-2,3-dihydro-1,4-benzoxazepin-4(5H)-yl]carbonyl}pyrrolidin-3-ol. Prepared according to the method of example 1 by using (R)-pyrrolidin-3-ol in step 9. $^1$H NMR (400 MHz, methanol-d$_4$): 7.64 (s, 1H), 7.51 (m, 2H), 7.44 (m, 2H), 7.03 (d, 1H), 4.56 (s, 2H), 4.36 (m, 1H), 4.28 (m, 1H), 4.17 (m, 1H), 3.80-3.60 (m, 4H), 3.38 (m, 2H), 2.58 (s, 3H), 1.90 (m, 2H); MS (EI) for $C_{22}H_{24}N_4O_3$: 393 (MH$^+$).

4-methyl-1-{[7-(2-methyl-1H-benzimidazol-6-yl)-2,3-dihydro-1,4-benzoxazepin-4(5H)-yl]carbonyl}piperidin-4-ol. Prepared according to the method of example 1 by using 4-methylpiperidin-4-ol (synthesized according to reagent preparation 5) in step 9. $^1$H NMR (400 MHz, methanol-d$_4$): 7.64 (s, 1H), 7.50 (m, 2H), 7.43 (m, 2H), 7.03 (d, 1H), 4.49 (s, 2H), 4.20 (m, 1H), 3.68 (m, 2H), 3.39 (m, 2H), 3.24 (m, 2H), 2.58 (s, 3H), 1.61 (m, 4H), 1.23 (s, 3H); MS (EI) for $C_{24}H_{28}N_4O_3$: 421 (MH$^+$).

(±)-7-(2-methyl-1H-benzimidazol-6-yl)-4-[(4aS,8aR)-octahydroisoquinolin-2(1H)-ylcarbonyl]-2,3,4,5-tetrahydro-1,4-benzoxazepine. Prepared according to the method of example 1 by using racemic (4aS,8aR)-decahydroisoquinoline in step 9. $^1$H NMR (400 MHz, methanol-d$_4$): $^1$H NMR (400 MHz, methanol-d$_4$): 7.66 (s, 1H), 7.52 (m, 2H), 7.48 (dd, 1H), 7.44 (dd, 1H), 7.05 (d, 1H), 4.73 (d, 1H), 4.62 (d, 1H), 4.13 (m, 2H), 3.95 (m, 1H), 3.82 (m, 1H), 3.21 (m, 1H), 2.66 (m, 1H), 2.58 (s, 3H), 2.44 (m, 1H), 1.83 (m, 1H), 1.78-1.54 (m, 6H), 1.35 (m, 1H), 1.21 (m, 2H), 1.06 (m, 2H), 0.87 (m, 1H); MS (EI) for $C_{27}H_{32}N_4O_2$: 445 (MH$^+$).

4-{[2-(3-fluorophenyl)piperidin-1-yl]carbonyl}-7-(2-methyl-1H-benzimidazol-6-yl)-2,3,4,5-tetrahydro-1,4-benzoxazepine. Prepared according to the method of example 1 by using racemic 2-(3-fluorophenyl)piperidine in step 9. $^1$H NMR (400 MHz, methanol-d$_4$): 7.59 (s, 1H), 7.50 (d, 1H), 7.47 (d, 1H), 7.35 (m, 2H), 7.20 (m, 1H), 7.05 (d, 1H), 7.03 (d, 1H), 6.97 (m, 1H), 6.86 (m, 1H), 4.60 (m, 2H), 4.56 (m, 1H), 4.21 (m, 1H), 4.12 (m, 2H), 3.76 (m, 2H), 3.23 (m, 2H), 2.58 (s, 3H), 1.99 (m, 1H), 1.88 (m, 1H), 1.70 (m, 2H), 1.60 (m, 2H); MS (EI) for $C_{29}H_{29}N_4O_2$: 485 (MH$^+$).

(3S)-1-{[7-(2-methyl-1H-benzimidazol-6-yl)-2,3-dihydro-1,4-benzoxazepin-4(5H)-yl]carbonyl}pyrrolidin-3-ol. Prepared according to the method of example 1 by using (S)-pyrrolidin-3-ol in step 9. $^1$H NMR (400 MHz, methanol-d$_4$): 7.64 (s, 1H), 7.51 (m, 2H), 7.44 (m, 2H), 7.03 (d, 1H), 4.56 (m, 2H), 4.36 (m, 1H), 4.28 (m, 1H), 4.18 (m, 1H), 3.81-3.60 (m, 4H), 3.38 (m, 1H), 3.24 (m, 1H), 2.58 (s, 3H), 1.92 (m, 2H); MS (EI) for $C_{22}H_{24}N_4O_3$: 393 (MH$^+$).

4-[(4-fluoro-4-methylpiperidin-1-yl)carbonyl]-7-(2-methyl-1H-benzimidazol-6-yl)-2,3,4,5-tetrahydro-1,4-benzoxazepine. Prepared according to the method of example 1 by using 4-fluoro-4-methylpiperidine (synthesized according to reagent preparation 8) in step 9. $^1$H NMR (400 MHz, methanol-d$_4$): 7.69 (s, 1H), 7.58 (d, 1H), 7.50 (m, 3H), 7.04 (d, 1H), 4.51 (s, 2H), 4.20 (m, 2H), 3.70 (m, 2H), 3.49 (m, 2H), 3.15 (m, 2H), 2.65 (s, 3H), 1.75 (m, 4H), 1.36 (d, 3H); MS (EI) for $C_{24}H_{27}FN_4O_2$: 423 (MH$^+$).

7-(2-methyl-1H-benzimidazol-6-yl)-4-{[(2R)-2-phenylpiperidin-1-yl]carbonyl}-2,3,4,5-tetrahydro-1,4-benzoxazepine. Prepared by chiral preparative HPLC separation of racemic 7-(2-methyl-1H-benzimidazol-6-yl)-4-[(2-phenylpiperidin-1-yl)carbonyl]-2,3,4,5-tetrahydro-1,4-benzoxazepine (example 1) using a SHIMADZU LC-20AD apparatus equipped with a Chiralpak AD-H, 25 cm×4.6 mm column using a mobile phase of ethanol:methanol 1:1 and flow rate of 18.0 mL/min and detection at 220 nm. The isomer with retention time 11.20 min. was assigned as the (R)-enantiomer. Chiral analytical HPLC was carried out using a SHIMADZU LC-20AD apparatus equipped with a Chiralpak AD-H, 25 cm×4.6 mm column using a mobile phase of ethanol:methanol 1:1 and flow rate of 0.7 mL/min with detection at 254/220 nm. This isomer gave a retention time 9.51 min and ee>99%. MS (EI) $C_{29}H_{30}N_4O_2$: 467 (MH$^+$).

7-(2-methyl-1H-benzimidazol-6-yl)-4-{[(2S)-2-phenylpiperidin-1-yl]carbonyl}-2,3,4,5-tetrahydro-1,4-benzoxazepine. Prepared by chiral preparative HPLC separation of racemic 7-(2-methyl-1H-benzimidazol-6-yl)-4-[(2-phenylpiperidin-1-yl)carbonyl]-2,3,4,5-tetrahydro-1,4-benzoxazepine (example 1) using a SHIMADZU LC-20AD apparatus equipped with a Chiralpak AD-H, 25 cm×4.6 mm column using a mobile phase of ethanol:methanol 1:1 and flow rate of 18.0 mL/min and detection at 220 nm. The isomer with retention time 11.20 min. was assigned as the (5)-enantiomer. Chiral analytical HPLC was carried out using a SHIMADZU LC-20AD apparatus equipped with a Chiralpak AD-H, 25 cm×4.6 mm column using a mobile phase of ethanol:methanol 1:1 and flow rate of 0.7 mL/min with detection at 254/220 nm. This isomer gave a retention time 13.30 min and ee>99%. MS (EI) $C_{29}H_{30}N_4O_2$: 467 (MH$^+$).

7-(2-Methyl-1H-benzimidazol-6-yl)-4-[(5-phenylhexahydropyrrolo[3,4-c]pyrrol-2(1H)-yl)carbonyl]-2,3,4,5-tetrahydro-1,4-benzoxazepine. Prepared according to the method of example 1 by using commercially available 2-phenyl-octahydro-pyrrolo[3,4-c]pyrrole in step 9. (400 MHz, methanol-d$_4$): 7.61 (br, 1H), 7.50 to 7.45 (m, 2H), 7.44 (dd, 1H), 7.37 (dd, 1H), 7.12 (t, 2H), 7.03 (d, 1H), 6.62 (t, 1H), 6.55 (d, 2H), 4.54 (s, 2H), 4.21 (m, 2H), 3.77 to 3.69 (m, 4H), 3.48 to 3.66 (m, 2H), 3.19 (dd, 2H), 3.04 to 2.95 (2H), 2.57 (s, 3H); MS (EI) for $C_{30}H_{31}N_5O_2$: 494 (MH$^+$).

1-{[7-(2-Methyl-1H-benzimidazol-6-yl)-2,3-dihydro-1,4-benzoxazepin-4(5H)-yl]carbonyl}-2-phenylpiperidin-4-one. Prepared according to the method of example 1 by using 2-phenylpiperidin-4-one in step 9. 400 MHz, methanol-d$_4$): 7.61 (s, 1H), 7.50 (d, 1H), 7.47 (dd, 1H), 7.40 (d, 1H), 7.35 (dd, 1H), 7.28 to 7.17 (m, 5H), 7.04 (d, 1H), 5.23 (t, 1H), 4.61 (s, 2H), 4.22 (m, 2H), 3.80 (m, 4H), 3.37 (m, 2H), 2.93 (m, 2H), 2.66 (m, 1H), 2.58 (s, 3H), 2.34 (dd, 1H); MS (EI) for Molecular Formula $C_{29}H_{28}N_4O_3$: 481 (MH$^+$).

(8-{[7-(2-Methyl-1H-benzimidazol-6-yl)-2,3-dihydro-1,4-benzoxazepin-4(5H)-yl]carbonyl}-8-azabicyclo[3.2.1]oct-3-(endo)-yl)methanol. Prepared according to the method of example 1 using 8-azabicyclo[3.2.1]octan-3-(endo)-yl-methanol hydrochloride (reagent preparation 18) in step 9. (400 MHz, methanol-d$_4$): 7.64 (br, 1H), 7.54 to 7.50 (m, 2H), 7.45 (dd, 1H), 7.43 (dd, 1H), 7.05 (d, 1H), 4.60 (s, 2H), 4.22 (m, 2H), 4.07 (br, 2H), 3.77 (m, 2H), 3.55 (d, 2H), 2.58 (s, 3H), 2.24 to 2.15 (m, 2H), 1.95 to 1.87 (m, 2H), 1.66 to 1.54 (m, 4H); MS (EI) for $C_{26}H_{30}N_4O_3$: 447 (MH$^+$).

Synthetic Example 2

5-{4-[(4-methylpiperidin-1-yl)carbonyl]-2,3,4,5-tetrahydro-1,4-benzoxazepin-7-yl}pyrimidin-2-amine STEP 1: 1,1-dimethylethyl 7-bromo-2,3-dihydro-1,4-benzoxazepine-4 (5H)-carboxylate (10 g, 30.5 mmol) was taken into hot ethanol (10 mL) followed by addition of 4M hydrogen chloride in dioxane solution (2.1 eq, 16 mL) and the resulting solution was allowed to slowly cool to ambient temperature over one hour. An excess of ethyl ether was then added and the resulting slurry was filtered. The filter cake was washed with ethyl ether and dried to give 7-bromo-2,3,4,5- tetrahydro-1,4-benzoxazepine hydrochloride (7.9 g, 98% yield) as a colorless crystalline solid. MS (EI) for $C_9H_{10}NOBr$: 229 (MH+).

STEP 2: 7-bromo-2,3,4,5-tetrahydro-1,4-benzoxazepine hydrochloride (3.0 g, 11.34 mmol) was suspended in dichloromethane (30 mL) followed by addition of DIPEA (3 mL, 34 mmol) and pyridine (4 mL, 49 mmol) and the resulting partially heterogeneous mixture was added portionwise over 5 minutes to a 0° C. cooled solution of phosgene (20 W % in toluene, 15 mL, 28 mmol) in dichloromethane (15 mL). The resulting mixture was then allowed to slowly warm to room temperature over 30 minutes then concentrated. The residue was partitioned with ethyl acetate and water and the organic phase washed twice with 1M aqueous hydrochloric acid then brine, dried over anhydrous magnesium sulfate, filtered and concentrated to give 7-bromo-2,3-dihydro-1,4-benzoxazepine-4(5H)-carbonyl chloride (3.35 g) as a pale yellow oil. MS (EI) for $C_{10}H_9BrClNO_2$: 292 (MH+).

STEP 3: 7-bromo-2,3-dihydro-1,4-benzoxazepine-4(5H)-carbonyl chloride as obtained in step 2 was taken into dichloromethane (35 mL) followed by portionwise addition of 4-methylpiperidine (3.5 mL, 28.4 mmol) over 5 minutes. The resulting mixture was stirred an additional 5 minutes then concentrated. The residue was partitioned with ethyl acetate and water and the organic phase washed with 1 M aqueous hydrochloric acid then brine, dried over anhydrous magnesium sulfate, filtered and concentrated to give 7-bromo-4-[(4-methylpiperidin-1-yl)carbonyl]-2,3,4,5-tetrahydro-1,4-benzoxazepine (3.91 g) as a clear oil. MS (EI) for $C_{16}H_{21}BrN_2O_2$: 292 (MH+).

STEP 4: 7-bromo-4-[(4-methylpiperidin-1-yl)carbonyl]-2,3,4,5-tetrahydro-1,4-benzoxazepine as obtained in step 3 (3.91 g, 11.07 mmol) was azeotroped twice from warm heptane then taken into anhydrous THF and cooled to −78° C. under nitrogen. Triisopropyl borate (3.3 mL, 14.4 mmol) was added by syringe followed by dropwise addition of n-butyllithium (2.5M in hexane, 5.8 mL, 14.4 mmol) over 30 minutes. The mixture was allowed to stir an additional 30 minutes at −78° C. then quenched by careful addition of 2M aqueous hydrochloric acid (10 mL) and warmed to room temperature. The mixture was stirred for 1 h at room temperature then concentrated to remove THF. The resulting aqueous mixture was then diluted with additional water and basified to pH greater than 12 by addition of 50% aqueous sodium hydroxide. The aqueous mixture was extracted once with ethyl ether then acidified to pH 1 by addition of concentrated aqueous hydrochloric acid. The acidic mixture was extracted once with ethyl acetate then washed with brine, dried over anhydrous sodium sulfate, filtered and concentrated to afford {4-[4(4-methylpiperidin-1-yl)carbonyl]-2,3,4,5-tetrahydro-1,4-benzoxazepine-7-yl}boronic acid (2.86 g, 81% yield). MS (EI) for $C_{16}H_{23}BrN_2O_4$: 319 (MH+).

STEP 5: To a mixture of 2-amino-5-bromopryimidine (65 mg, 0.37 mmol), {4-[(4-methylpiperidin-1-yl)carbonyl]-2,3,4,5-tetrahydro-1,4-benzoxazepine-7-yl}boronic acid (100 mg, 0.31 mmol) and potassium carbonate (215 mg, 1.6 mmol) in DMA (5.0 mL) and water (0.5 mL) was added dichloro[1,1-bis(diphenylphosphino)ferrocenepalladium (II) dichloromethane adduct (23 mg, 0.03 mmol). The reaction mixture was stirred at 95° C. for 2.5 hours and then partitioned between dichloromethane (10 mL) and 1M aqueous sodium hydroxide (10 mL). The organic layer was separated and washed with brine (10 mL) then dried over anhydrous magnesium sulfate, filtered and concentrated. The residue was chromatographed on silica gel using 2% methanol in dichloromethane as eluent and the combined product containing fractions were concentrated. The residue thus obtained was taken into a minimum of acetonitrile and purified by preparative reverse phase HPLC to afford 5-{4-[(4-methylpiperidin-1-yl)carbonyl]-2,3,4,5-tetrahydro-1,4-benzoxazepin-7-yl}pyrimidin-2-amine (24 mg) as an amorphous solid. $^1$H NMR (400 mHz, DSMO-$d_6$): 8.51 (s, 2H), 7.47 (d, 1H), 7.42 (dd, 1H), 6.98 (d, 1H), 6.75 (s, 2H), 4.39 (s, 2H), 4.12-4.18 (m, 2H), 3.46-3.59 (m, 4H), 2.70 (t, 2H), 1.42-1.61 (m, 3H), 1.04-1.18 (m, 2H), 0.91 (d, 3H); MS (EI) for $C_{20}H_{25}N_5O_2$: 368 (MH+).

Using analogous synthetic techniques and substituting with alternative starting reagents in step 5 then conducting protecting group removal as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

5-{4-[(4-methylpiperidin-1-yl)carbonyl]-2,3,4,5-tetrahydro-1,4-benzoxazepin-7-yl}pyrazin-2-amine. Synthesized according to the method of example 2 using 5-bromopyrazin-2-amine in step 5. $^1$H NMR (400 MHz, $d_6$-DMSO): 8.44 (s, 1H), 7.99 (s, 1H), 7.79 (d, 1H), 7.71 (dd, 1H), 6.97 (d, 1H), 4.39 (s, 2H), 4.17 (br s, 2H), 3.57 (br s, 2H), 3.51 (d, 2H), 2.68 (tr, 2H), 1.56 (d, 2H), 1.49 (m, 1H), 1.11 (q, 2H), 0.92 (d, 3H). MS (EI) for $C_{20}H_{25}N_5O_2$: 368 (MIT).

6-{4-[(4-methylpiperidin-1-yl)carbonyl]-2,3,4,5-tetrahydro-1,4-benzoxazepin-7-yl}pyridazin-3-amine. Synthesized according to the method of example 2 using 6-bromopyridazin-3-amine in step 5. $^1$H NMR (400 MHz, $d_6$-DMSO): 8.49 (br s, 2H), 8.33 (d, 1H), 7.84 (d, 1H), 7.76 (dd, 1H), 7.49 (d, 1H), 7.05 (d, 1H), 4.44 (s, 2H), 4.24 (m, 2H), 3.60 (m, 2H), 3.47 (d, 2H), 2.68 (t, 2H), 1.56 (d, 2H), 1.48 (m, 1H), 1.08 (m, 2H), 0.91 (d, 2H). MS (EI) $C_{20}H_{25}N_5O_2$: 368 (MH+).

methyl (6-{4-[(4-methylpiperidin-1-yl)carbonyl]-2,3,4,5-tetrahydro-1,4-benzoxazepin-7-yl}-1H-benzimidazol-2-yl)carbamate. Synthesized according to the method of example 2 using tert-butyl 6-bromo-2-(tert-butoxycarbonyl(methoxycarbonyl)amino)-1H-benzo[d]imidazole-1-carboxylate (reagent preparation 35) in step 5. $^1$H NMR (400 mHz, $CD_3OD$): 7.61 (s, 1H), 7.44-7.51 (m, 3H), 7.38 (d, 1H), 7.02 (d, 1H), 4.90 (s, 3H), 4.48-4.63 (m, 2H), 4.17-4.21 (m, 2H), 3.64-3.72 (m, 2H), 3.5 (d, 2H), 2.82 (t, 2H), 1.51-1.70 (m, 3H), 1.15-1.52, (m, 2H), 0.94 (d, 3H); MS (EI) for $C_{25}H_{29}N_5O_4$: 464 (MH+).

Synthetic Example 3

N-(5-{4-[(4-methylpiperidin-1-yl)carbonyl]-2,3,4,5-tetrahydro-1,4-benzoxazepin-7-yl}-1,3-thiazol-2-yl)acetamide STEP 1: A mixture of N-(5-bromothiazol-2-yl)acetamide (1.00 g, 4.52 mmol), (4-{[(1,1-dimethylethyl)oxy]carbonyl}-2,3,4,5-tetrahydro-1,4-benzoxazepin-7-yl)boronic acid (example 1, step 2) (1.54 g, 5.43 mmol), [1,1′-bis(diphenylphosphino)ferrocene]dichloropalladium(II), complex with dichloromethane (0.33 g, 0.40 mmol), potassium carbonate (2.50 g, 18.1 mmol) in 1,4-dioxane (20 mL) and water (2 mL) was degassed with nitrogen for 5 minutes and then stirred at 93° C. for 18 hours. The reaction mixture was cooled to room temperature, diluted with ethyl acetate (80 mL), filtered over celite. The filtrate was washed with brine (2×50 mL), dried over sodium sulfate, filtered, concentrated. The residue was purified by flash chromatography (20% to 80% ethyl acetate-hexane gradient) to give 1,1-dimethylethyl 7-[2-(acetylamino)-1,3-thiazol-5-yl]-2,3-dihydro-1,4-benzoxazepine-4

(5H)-carboxylate (0.99 g, 2.54 mmol, 56.2% yield); MS (EI) for $C_{19}H_{23}N_3O_4S$: 390 (MH$^+$).

STEP 2: A mixture 1,1-dimethylethyl 7-[2-(acetylamino)-1,3-thiazol-5-yl]-2,3-dihydro-1,4-benzoxazepine-4(5H)-carboxylate (0.29 g, 0.75 mmol), in methanol (2 mL) and 4 M hydrogen chloride in 1,4-dioxane (2 mL) was stirred at 70° C. for 15 minutes. The reaction mixture was cooled and concentrated, and dried in vacuum to give the de-protected product N-[5-(2,3,4,5-tetrahydro-1,4-benzoxazepin-7-yl)-1,3-thiazol-2-yl]acetamide hydrochloride (0.24 g, 0.24 mmol, 99% yield); MS (EI) for $C_{14}H_{15}N_3O_2S$: 290 (MH$^+$).

STEP 3: 4-Methylpiperidine-1-carbonyl chloride (reagent preparation 37) (103 mg, 0.64 mmol) was added to a mixture of N-[5-(2,3,4,5-tetrahydro-1,4-benzoxazepin-7-yl)-1,3-thiazol-2-yl]acetamide hydrochloride, (173 mg, 0.53 mmol) and potassium carbonate (374 mg, 2.7 mmol) in N,N-dimethylformamide (2 mL). The resulting mixture was stirred at room temperature for 18 hours, then methanol (2 mL) was added and concentrated. The residue was diluted with ethyl ether (40 mL), a solid was collected by filtration, and washed with ether and water to give N-(5-{4-[(4-methylpiperidin-1-yl)carbonyl]-2,3,4,5-tetrahydro-1,4-benzoxazepin-7-yl}-1,3-thiazol-2-yl)acetamide (140 mg, 0.34 mol, 63% yield), $^1$H NMR (400 MHz, DMSO-d$_6$): 7.58 (s, 1H), 7.35 to 7.32 (m, 2H), 6.91 (d, 1H), 4.36 (s, 2H), 4.12 (br, 2H), 3.54 to 3.47 (m, 4H), 2.71 to 2.65 (m, 2H), 2.00 (s, 3H), 1.60 to 1.43 (m, 3H), 1.16 to 1.067 (m, 2H), 0.92 (d, 3H); MS (EI) for $C_{21}H_{26}N_4O_3S$: 415 (MH$^+$).

Synthetic Example 4

7-[4-(1H-imidazol-2-yl)phenyl]-4-{[4-(trifluoromethyl)piperidin-1-yl]carbonyl}-2,3,4,5-tetrahydro-1,4-benzoxazepine STEP 1: 1,1-Dimethylethyl 7-bromo-2,3-dihydro-1,4-benzoxazepine-4(5H)-carboxylate (5.0 g, 20.1 mmol), bis(pinacolato)diboron (5.6 g, 22.1 mmol), potassium acetate (5.9 g, 60.2 mmol) and [1,1'-bis(diphenylphosphino)ferrocene]dichloropalladium(II) (440 mg, 0.62 mmol) were heated in DMSO (5 mL) solution at 80° C. for 1.5 h. The mixture was then cooled to room temperature and diluted with an excess of ethyl acetate and filtered through a bed of celite. The filtrate was partitioned with 1M aqueous hydrochloric acid and the organic phase washed with brine and dried over anhydrous sodium sulfate. The mixture was filtered and concentrated and the residue purified by silica chromatography using 4:1 hexanes:ethyl acetate as eluent to give tert-butyl 7-(4,4,5,5-tetramethyl-1,3,2-dioxaborolan-2-yl)-2,3-dihydrobenzazepine-4(5)-carboxylate (7.6 g, 100%). $^1$H NMR (400 MHz, CDCl$_3$): 7.77 (s, 0.4H), 7.67 (s, 1H), 7.65 (s, 0.6H), 7.04-6.98 (m, 1H), 4.54 (s, 0.7H), 4.43 (s, 1.3H), 4.09-4.01 (m, 2H), 3.79 (dd, 2H), 1.40 (br s, 9H), 1.26 (s, 12H). MS (EI) for $C_{20}H_{30}BNO_5$: 376 (MH$^+$).

STEP 2: To a solution of 1,1-dimethylethyl 7-(4,4,5,5-tetramethyl-1,3,2-dioxaboralan-2-yl)-2,3-dihydro-1,4-benzoxazepine benzoxazepin-4(5H)-carboxylate (3.0 g, 8.00 mmol) in dichloromethane (90 mL) was added trifluoroacetic acid (10 mL) and the reaction mixture was heated to reflux. After cooling to room temperature the solvent was evaporated and the residue was taken into ethyl acetate (250 mL). The solution was partitioned with saturated aqueous sodium bicarbonate (200 mL) and the organic layer was separated. It was washed again with saturated aqueous bicarbonate (150 mL) then brine. The combined aqueous phase was extracted once with ethyl acetate (200 mL). The combined organic phases were then washed with brine, dried over anhydrous sodium sulfate, filtered and concentrated to give 7-(4,4,5,5-tetramethyl-1,3,2-dioxaboralan-2-yl)-2,3,4,5-tetrahydro-1,4-benzoxazepine (2.1 g, 96%). MS (EI) for $C_{23}H_{25}N_3O_3$: 276 (MH$^+$).

STEP 3: 7-(4,4,5,5-tetramethyl-1,3,2-dioxaboralan-2-yl)-2,3,4,5-tetrahydro-1,4-benzoxazepine (2.2 g, 8.0 mmol) was taken into dichloromethane (30 mL) followed by addition of DIPEA (3.2 mL, 17.1 mmol) and the resulting solution was added dropwise to a 0° C. cooled solution of phosgene (20W % in toluene, 4.2 mL, 8.0 mmol) in dichloromethane (25 mL). The mixture was then allowed to warm to room temperature over 30 minutes and concentrated. The residue was partitioned with dilute aqueous hydrochloric acid and ethyl acetate. The organic phase was washed with brine, dried over anhydrous sodium sulfate then filtered and concentrated to give 7-(4,4,5,5-tetramethyl-1,3,2-dioxaboralan-2-yl)-2,3-dihydro-1,4-benzoxazepine-4(5H)-carbonyl chloride (3.0 g) as a pale yellow amorphous residue. MS (EI) for $C_{16}H_{21}BNO_4Cl$: 356 (M+H$_2$O$^+$).

STEP 4: 7-(4,4,5,5-Tetramethyl-1,3,2-dioxaboralan-2-yl)-2,3-dihydro-1,4-benzoxazepine-4(5H)-carbonyl chloride (3.0 g) as obtained in step 3 was taken into dichloromethane (50 mL) followed by addition of DIPEA (40 mmol, 7 mL) then 4-trifluoromethylpiperidine hydrochloride salt (1.55 g, 8.2 mmol). The mixture was allowed to stir 30 minutes at room temperature then concentrated. The residue was partitioned with ethyl acetate and 5% aqueous citric acid. The organic phase was washed with brine, dried over anhydrous sodium sulfate then filtered and concentrated to give 7-(4,4,5,5-tetramethyl-1,3,2-dioxaboralan-2-yl)-4-{[4-(trifluoromethyl)piperidin-1-yl]carbonyl}2,3,4,5-tetrahydro-1,4-benzoxazepine. MS (EI) for $C_{22}H_{30}BF_3N_2O_4Cl$: 455 (MH$^+$).

STEP 5: 2-(4-bromophenyl)imidazole (5.3 g, 23.76 mmol) was taken into THF (100 mL) followed by addition of DIPEA (5 mL, 28.5 mmol) and isobutyl chloroformate (3.4 mL, 26.1 mmol) and the resulting solution was stirred for 30 minutes at room temperature. The solution was then concentrated and the residue partitioned with ethyl acetate and water. The organic phase was washed once with 10% aqueous citric acid, brine then dried over anhydrous magnesium sulfate, filtered and concentrated. The residue was purified by silica gel chromatography (2.5:1 hexanes:ethyl acetate) to give isobutyl 2-(4-bromophenyl)-1H-imidazole-1-carboxylate (3.5 g, 46% yield) as an amorphous residue.

STEP 6: To a solution of 7-(4,4,5,5-tetramethyl-1,3,2-dioxaborolan-2-yl)-4-{[4-(trifluoromethyl)piperidin-1-yl]carbonyl}-2,3,4,5-tetrahydro-1,4-benzoxazepine (0.4 g, 0.88 mmol) and isobutyl 2-(4-bromophenyl)-1H-imidazole-1-carboxylate (0.6 g, 1.86 mmol) in dioxane (4 mL) and water (0.5 ml) was added diisopropylethylamine (0.34 g, 2.64 mmol). The solution was sparged with N$_2$(g) for ten minutes before the addition of dichloro[1,1-bis-(diphenylphosphino]ferrocenepalladium (II) dichloromethane adduct (0.072 g, 10 mol %). The resulting suspension was heated at 120° C. for 2 hours in a sealed tube on a CEM Explorer microwave synthesizer. On cooling to room temperature the mixture was diluted with ethyl acetate (100 mL), washed with saturated sodium bicarbonate (70 mL), brine (50 mL) then dried over anhydrous sodium sulfate, filtered and concentrated. The resulting residue was purified by silica gel chromatography (97:3 dichloromethane/methanol) then preparative reverse phase HPLC of the combined product containing fractions (0.1% aqueous ammonium acetate-acetonitrile) to afford 7-[4-(1H-imidazol-2-yl)phenyl]-4-{[4-(trifluoromethyl)piperidin-1-yl]carbonyl}-2,3,4,5-tetrahydro-1,4-benzoxazepine (0.058 g, 12% yield) as a white solid. $^1$H NMR (400 MHz, methanol-d$_4$): 7.92 (d, 2H), 7.70 (d, 2H), 7.58-7.50 (m, 2H), 7.15 (s, 2H), 7.05 (d, 1H), 4.52 (s, 2H), 4.22 (t, 2H), 3.77 (d, 2H), 3.71 (t, 2H), 2.87 (t, 2H), 2.39 (m, 1H), 1.86 (d, 2H), 1.59 (m, 2H); MS (EI) for $C_{25}H_{25}F_3N_4O_2$: 471 (MH$^+$).

Using analogous synthetic techniques and substituting with alternative starting reagents in step 6 and conducting subsequent protecting group removal as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

5-(4-{[4-(trifluoromethyl)piperidin-1-yl]carbonyl}-2,3,4,5-tetrahydro-1,4-benzoxazepin-7-yl)pyrazin-2-amine. Synthesized according to the method of example 4 using 5-bromopyrazin-2-amine in step 6. $^1$H NMR (400 MHz, d$_6$-DMSO): 8.43 (d, 1H), 7.92 (d, 1H), 7.78 (d, 1H), 7.70 (dd, 1H), 6.95 (d, 1H), 6.53 (br s, 2H), 4.42 (s, 2H), 4.18 (m, 2H), 3.58 (m, 4H), 2.74 (t, 2H), 1.74 (d, 2H), 1.46 (m, 2H). MS (EI) for $C_{20}H_{22}F_3N_5O_2$: 422 (MH$^+$).

Synthetic Example 5

4-[(4-methylpiperidin-1-yl)carbonyl]-7-(1,3-thiazol-5-yl)-2,3,4,5-tetrahydro-1,4-benzoxazepine STEP 1: A solution of tert-butyl 7-(4,4,5,5-tetramethyl-1,3,2-dioxaborolan-2-yl)-2,3-dihydrobenzo[f][1,4]oxazepine-4(5H)-carboxylate (73 mg, 0.19 mol), 5-bromothiazole (40 mg, 0.26 mmol), 1,1'-Bis(diphenylphosphino)ferrocene] dichloropalladium(II) (22 mg, 0.03 mmol) and potassium carbonate (0.14 g, 1.0 mmol) in N,N-dimethylacetamide/water 5:1 (5.5 mL) was heated to 90° C. for 1 hour. The cooled reaction mixture was diluted with ethyl acetate (50 mL) and washed with water (30 mL) and brine (20 mL), and then dried over anhydrous sodium sulfate and concentrated. Purified by silica gel column chromatography (ethyl acetate/hexanes, 1:2) to give tert-butyl 7-(thiazol-5-yl)-2,3-dihydrobenzo[f][1,4]oxazepine-4(5H)-carboxylate (44 mg, 70% yield). MS (EI) for $C_{17}H_{20}N_2O_3S$: 333 (MH$^+$).

STEP 2: To tert-butyl 7-(thiazol-5-yl)-2,3-dihydrobenzo[f][1,4]oxazepine-4(5H)-carboxylate (41 mg, 0.12 mmol) in methanol (5.0 mL) added 4.0 M hydrogen chloride in dioxane (3.0 mL) and the mixture stirred at 25° C. for 20 minutes then concentrated to give 7-(thiazol-5-yl)-2,3,4,5-tetrahydrobenzo[f][1,4]oxazepine as the hydrochloride salt.

STEP 3: To a suspension of 7-(thiazol-5-yl)-2,3,4,5-tetrahydrobenzo[f][1,4]oxazepine hydrochloride as obtained in step 2 in dichloromethane (20 mL) at −20° C. added 20% phosgene in toluene (0.25 mL, 0.50 mmol) followed by addition of triethylamine (0.35 mL, 25 mmol). The reaction was allowed to warm to 25° C. and stand for 18 h. The mixture was then concentrated to give 7-(thiazol-5-yl)-2,3-dihydrobenzo[f][1,4]oxazepine-4(5H)-carbonyl chloride.

STEP 4: 7-(thiazol-5-yl)-2,3-dihydrobenzo[f][1,4]oxazepine-4(5H)-carbonyl chloride as obtained in step 3 was taken into dichloromethane (15 mL) and cooled to −10° C. 4-Methylpiperidine (0.25 g, 29 mmol) was then added and stirring continued at 25° C. for 2 hours. The reaction mixture was concentrated and the residue taken into ethyl acetate (50 mL) then washed with saturated aqueous sodium bicarbonate (25 mL) and brine (20 mL). The organic solution was dried over anhydrous sodium sulfate then filtered and concentrated. The residue was purified by preparative reverse phase HPLC (0.1% aqueous ammonium acetate-acetonitrile). Pure fractions were concentrated and the residue was taken up in acetonitrile (2 mL) and 4.0 M hydrochloric acid (0.05 mL) then concentrated and dried to afford 4-[(4-methylpiperidin-1-yl)carbonyl]-7-(1,3-thiazol-5-yl)-2,3,4,5-tetrahydro-1,4-benzoxazepine (3.9 mg, 6.5% yield) as the hydrochloride salt. $^1$H NMR (400 MHz, CDCl$_3$): 8.83 (br s, 1H), 8.03 (br s, 1H), 7.43 (s, 1H), 7.41 (d, 1H), 7.06 (d, 1H), 4.39 (s, 2H), 4.19 (m, 2H), 3.79-3.60 (m, 4H), 2.76 (t, 2H), 1.65 (d, 2H), 1.56 (br s, 1H), 1.22 (m, 2H), 0.98 (d, 3H)); MS (EI) for $C_{19}H_{23}N_3O_2S$: 358 (MH$^+$).

Synthetic Example 6

3-{4-[(4-methylpiperidin-1-yl)carbonyl]-2,3,4,5-tetrahydro-1,4-benzoxazepin-7-yl}-N-(phenylmethyl)-1H-pyrazol-5-amine STEP 1: n-Butyllithium (2.5 Min hexane, 2.31 mL, 5.8 mmol) was added to a solution of 1,1-dimethylethyl 7-bromo-2,3-dihydro-1,4-benzoxazepine-4(5H)-carboxylate (1.56 g, 4.76 mmol) in tetrahydrofuran (20 mL) and the resulting mixture was stirred at −78° C. for one hour. A solution of N-methoxy-N-methylacetamide (0.97 g, 9.4 mmol) in tetrahydrofuran (5 mL) was added to the reaction mixture dropwise then warmed to room temperature and stirred for an additional hour. Water (50 mL) was added and the resulting mixture was extracted with ethyl acetate (3×40 mL). The combined organic extract was washed with water, then brine solution (80 mL each), dried over sodium sulfate, filtered, concentrated to give 1,1-dimethylethyl 7-acetyl-2,3-dihydro-1,4-benzoxazepine-4(5H)-carboxylate (1.34 g, 97% yield); MS (EI) for $C_{16}H_{21}NO_4$: 292 (MH$^+$).

STEP 2: A solution of 1,1-dimethylethyl 7-acetyl-2,3-dihydro-1,4-benzoxazepine-4(5H)-carboxylate (1.34 g, 4.60 mmol) in tetrahydrofuran (5 mL) was added to a suspension of sodium hydride (60% oil suspension, 0.80 g, 13.3 mmol) in tetrahydrofuran (20 mL) and the resulting mixture was stirred at room temperature for 5 minutes. Dimethyl carbonate (5 mL) was added and the resulting mixture was stirred at 65° C. for twenty minutes. Then the reaction mixture was cooled, quenched with ice (20 g) and aqueous ammonium chloride (20 mL) then extracted with ethyl acetate (3×40 mL). The combined organic extract was washed with water, then brine solution (80 mL each), dried over sodium sulfate, filtered, concentrated, and purified by silica gel chromatography (25% ethyl acetate in hexanes) to give 1,1-dimethylethyl 7-[3-(methyloxy)-3-oxopropanoyl]-2,3-dihydro-1,4-benzoxazepine-4(5H)-carboxylate (0.94 g, 59% yield). MS (EI) for $C_{18}H_{23}NO_6$: 350 (MH$^+$).

STEP 3: A mixture of 1,1-dimethylethyl 7-[3-(methyloxy)-3-oxopropanoyl]-2,3-dihydro-1,4-benzoxazepine-4(5H)-carboxylate (300 mg, 0.86 mmol) and benzylamine (92 mg, 0.86 mmol) in o-xylene (3 mL) was stirred at 150° C. for one hour. The reaction mixture was cooled and purified directly by silica gel chromatography (50% ethyl acetate in hexanes) to give 1,1-dimethylethyl 7-{3-oxo-3-[(phenylmethyl)amino]propanoyl}-2,3-dihydro-1,4-benzoxazepine-4(5H)-carboxylate (220 mg, 60% yield). MS (EI) for $C_{24}H_{28}N_2O_5$: 425 (MH$^+$).

STEP 4: A mixture of 1,1-dimethylethyl 7-{3-oxo-3-[(phenylmethyl)amino]propanoyl}-2,3-dihydro-1,4-benzoxazepine-4(5H)-carboxylate (180 mg, 0.42 mmol) and Lawesson's reagent (177 mg, 0.44 mmol) in 1,4-dioxane (2 mL) was stirred at 65° C. for two hours. The reaction mixture was cooled and purified directly by silica gel chromatography (25% ethyl acetate in hexanes) to give 1,1-dimethylethyl 7-{3-[(phenylmethyl)amino]-3-thioxopropanoyl}-2,3-dihydro-1,4-benzoxazepine-4(5H)-carboxylate (155 mg, 83% yield). MS (EI) for $C_{24}H_{28}N_2O_4S$: 441 (MH$^+$).

STEP 5: A mixture of 1,1-dimethylethyl 7-{3-[(phenylmethyl)amino]-3-thioxopropanoyl}-2,3-dihydro-1,4-benzoxazepine-4(5H)-carboxylate (155 mg, 0.35 mmol), hydrazine monohydrate (66 mg, 0.59 mmol), acetic acid and Lawesson's reagent (63 mg, 1.0 mmol) in ethanol (5 mL) was stirred at 78° C. for one hour. The reaction mixture was cooled, concentrated and the residue purified directly by silica gel chromatography (5% methanol in dichlomethane) to give 1,1-dimethylethyl 7-{5-[(phenylmethyl)amino]-1H-pyrazol-3-yl}-2,3-dihydro-1,4-benzoxazepine-4(5H)-carboxylate (92 mg, 62% yield). MS (EI) for $C_{24}H_{28}N_4O_3$: 421 (MH$^+$).

STEP 6 A mixture of 1,1-dimethylethyl 7-{5-[(phenylmethyl)amino]-1H-pyrazol-3-yl}-2,3-dihydro-1,4-benzoxazepine-4(5H)-carboxylate (92 mg, 0.22 mmol) in acetonitrile (2 mL) and 4 M hydrogen chloride in 1,4-dioxane (2 mL) was stirred at 70° C. for 10 minutes. The reaction mixture was allowed to cool then concentrated and the residue suspended in N,N-dimethylformamide (2 mL). Triethylamine (123 mg, 1.21 mmol), then 4-methylpiperidine-1-carbonyl chloride (reagent preparation 37) (35 mg, 0.22 mmol) were added and the resulting mixture was stirred at room temperature for 18 hours. The crude mixture diluted with methanol (6 mL) and purified by preparative reverse phase HPLC to give 3-{4-[(4-methylpiperidin-1-yl)carbonyl]-2,3,4,5-tetrahydro-1,4-benzoxazepin-7-yl}-N-(phenylmethyl)-1H-pyrazol-5-amine (56 mg, 57% yield), (400 MHz, methanol-$d_4$): 7.49 (br, 1H), 7.45 (dd, 1H), 7.39 (d, 2H), 7.30 (t, 2H), 7.22 (dd, 1H), 6.96 (d, 1H), 5.81 (s, 1H), 4.43 (s, 2H), 4.33 (s, 2H), 4.17 (m, 2H), 3.66 to 3.59 (m, 4H), 2.80 (t, 2H), 1.67 to 1.50 (m, 3H), 1.24 to 1.12 (m, 2H), 0.96 (d, 3H); MS (EI) for $C_{26}H_{31}N_5O_2$: 446 (MH$^+$).

Synthetic Example 7

3-{4-[(4-methylpiperidin-1-yl)carbonyl]-2,3,4,5-tetrahydro-1,4-benzoxazepin-7-yl}-1H-pyrazol-5-amine A mixture of 3-{4-[(4-methylpiperidin-1-yl)carbonyl]-2,3,4,5-tetrahydro-1,4-benzoxazepin-7-yl}-N-(phenylmethyl)-1H-pyrazol-5-amine (example 6) (39 mg, 0.088 mmol), 10% palladium on charcoal (37 mg) and methanol (15 mL) was hydrogenated in a Parr apparatus at 45 psi for 18 hours. The suspension was filtered, concentrated and the residue purified by preparative reverse phase HPLC to give 3-{4-[(4-methylpiperidin-1-yl)carbonyl]-2,3,4,5-tetrahydro-1,4-benzoxazepin-7-yl}-1H-pyrazol-5-amine (17 mg, 55% yield). $^1$H NMR (400 MHz, methanol-$d_4$): 7.50 (br, 1H), 7.46 (dd, 1H), 6.98 (d, 1H), 5.86 (s, 1H), 4.44 (s, 2H), 4.18 (m, 2H), 3.68 to 3.60 (m, 4H), 2.80 (t, 2H), 1.67 to 1.51 (m, 3H), 1.23 to 1.15 (m, 2H), 0.97 (d, 2H); MS (EI) for $C_{19}H_{25}N_5O_2$: 356 (MH$^+$).

Synthetic Example 8 methyl [6-(4-{[4-(fluoromethyl)piperidin-1-yl]carbonyl}-2,3,4,5-tetrahydro-1,4-benzoxazepin-7-yl)-1H-benzimidazol-2-yl]carbamate STEP 1: (4-{[(1,1-dimethylethyl)oxycarbonyl}-2,3,4,5-tetrahydro-1,4-benzoxazepin-7-yl)boronic acid (example 1, step 2) (2.22 g, 7.57 mmol) and 4-bromo-2-nitroaniline (1.56 g, 7.20 mmol) were taken into dioxane (20 mL), water (4 mL) and DIPEA (5.4 mL, 31 mmol) followed by addition of dichloro[1,1-bis(diphenylphosphino]ferrocenepalladium (II) dichloromethane adduct (322 mg, 0.39 mmol) and the mixture was heated to 95° C. for 2 h. The mixture was cooled to room temperature and partitioned with ethyl acetate and 10% aqueous citric acid. The biphasic mixture was filtered through a celite pad and the organic filtrate was washed once with 0.5M aqueous hydrochloric acid, brine then dried over anhydrous magnesium sulfate, filtered and concentrated. The residue was purified by silica gel chromatography to give 1,1-dimethylethyl 7-(4-amino-3-nitrophenyl)-2,3-dihydro-1,4-benzoxazepine-4(5H)-carboxylate (2.01 g, 69% yield) as a yellow crystalline solid.

STEP 2: 1,1-Dimethylethyl 7-(4-amino-3-nitrophenyl)-2,3-dihydro-1,4-benzoxazepine-4(5H)-carboxylate (3.3 g, 8.56 mmol) and 10% palladium on carbon (300 mg) were suspended in ethanol (100 mL) and the mixture was hydrogenated at 50 psi using a Parr apparatus for 12 h. The mixture was filtered through a celite pad and the filtrate concentrated. The residue was taken into acetic acid (25 mL) followed by addition of 1,3-bis(methoxycarbonyl)-2-methyl-2-thiopseudourea (2.3 g, 11.15 mmol) and the resulting mixture heated to 80° C. for 30 minutes. The mixture was cooled to room temperature then concentrated and partitioned with ethyl ether (60 mL) and dilute aqueous sodium bicarbonate. The biphasic mixture was allowed to stand for several minutes until a precipitate formed. The solid was collected by filtration, washed with water then ethyl ether and dried to give 1,1-dimethylethyl 7-(2-{[(methyloxy)carbonyl]amino}-1H-benzimidazol-6-yl)-2,3-dihydro-1,4-benzoxazepine-4(5H)-carboxylate (2.98 g, 80% yield) as a white solid. MS (EI) for $C_{23}H_{26}N_4O_5$: 439 (MH$^+$).

STEP 3: 1,1-Dimethylethyl 7-(2-{[(methyloxy)carbonyl]amino}-1H-benzimidazol-6-yl)-2,3-dihydro-1,4-benzoxazepine-4(5H)-carboxylate (517 mg, 1.18 mmol) was taken into methanol (2 mL) and 4M hydrogen chloride in dioxane (2 mL) and the mixture was allowed to stand at room temperature for 30 minutes. The suspension obtained was diluted with excess ethyl ether and the solid collected by filtration to give methyl [6-(2,3,4,5-tetrahydro-1,4-benzoxazepin-7-yl)-1H-benzimidazol-2-yl]carbamate dihydrochloride salt (462 mg, 95% yield) as a white solid. MS (EI) for $C_{18}H_{18}N_4O_3$: 339 (MH$^+$).

STEP 4: Methyl [6-(2,3,4,5-tetrahydro-1,4-benzoxazepin-7-yl)-1H-benzimidazol-2-yl]carbamate dihydrochloride salt (51.7 mg, 0.13 mmol) was taken into DMF (1 mL) and dichloromethane (1 mL) followed by addition of DIPEA (88 uL, 0.52 mmol) and the mixture was cooled to 0° C. 4-(Fluoromethyl)piperidine-1-carbonyl chloride (reagent preparation 37) (33 mg, 0.13 mmol) was added to the mixture in a minimum of dichloromethane then stirred for 30 minutes. The mixture was partitioned with ethyl acetate and water and the organic phase washed twice with water, dried over anhydrous sodium sulfate, filtered and concentrated. The residue was purified by silica gel chromatography (4:1 ethyl acetate:hexanes) to give methyl [6-(4-{[4-(fluoromethyl)piperidin-1-yl]carbonyl}-2,3,4,5-tetrahydro-1,4-benzoxazepin-7-yl)-1H-benzimidazol-2-yl]carbamate (40.3 mg, 66% yield) as a white solid. $^1$H NMR (400 MHz, $d_6$-DMSO): 7.58 (s, 1H), 7.47 (s, 1H), 7.45-7.42 (m, 2H), 7.31 (dd, 1H), 7.02 (d, 1H), 4.42 (s, 2H), 4.37 (d, 1H), 4.26 (d, 1H), 4.17 (br s, 1H), 3.77 (s, 3H), 3.60 (br m, 4H), 2.75 (tr, 2H), 1.85 (br, 1H), 1.63 (d, 2H), 1.25 (q, 2H). MS (EI) for $C_{25}H_{18}FN_5O_4$: 483 (MH$^+$).

Using analogous synthetic techniques and substituting with alternative starting reagents in step 4 the following compounds of the invention were prepared. Alternative starting materials were obtained commercially unless otherwise indicated.

methyl [6-(4-{[2-(4-fluorophenyl)piperidin-1-yl]carbonyl}-2,3,4,5-tetrahydro-1,4-benzoxazepin-7-yl)-1H-benzimidazol-2-yl]carbamate. Synthesized according to the method of example 8 using 2-(4-fluorophenyl)-piperidine-1- carbonyl chloride (reagent preparation 37) in step 4. $^1$H NMR (400 MHz, d$_6$-DMSO): 11.70 (br s 1H), 7.57 (d, 1H), 7.45 (m, 2H), 7.40 (d, 1H), 7.28-7.22 (m, 3H), 7.08-7.01 (m, 3H), 4.59 (m, 1H), 4.52 (dd, 2H), 4.14 (m, 2H), 3.76 (s, 3H), 3.63 (t, 2H), 3.22 (m, 1H), 3.02 (m, 1H), 1.98 (m, 1H), 1.79 (m, 1H), 1.57 (m, 2H), 1.48 (m, 2H). MS (EI) C$_{30}$H$_{30}$FN$_5$O$_4$: 544 (MH$^+$).

methyl [6-(4-{[2-(3-fluorophenyl)-4-oxopiperidin-1-yl]carbonyl}-2,3,4,5-tetrahydro-1,4-benzoxazepin-7-yl)-1H-benzimidazol-2-yl]carbamate. Synthesized according to the method of example 8 using 2-(3-fluorophenyl)-4-oxopiperidine-1-carbonyl chloride (reagent preparation 37) in step 4. $^1$H NMR (400 MHz, d$_6$-DMSO): 11.58 (br d, 1H), 7.55 (d, 1H), 7.50 (d, 1H), 7.42 (dd, 1H), 7.41 (d, 1H), 7.27 (m, 2H), 7.11-7.02 (m, 3H), 6.99 (d, 1H), 5.19 (t, 1H), 4.56 (s, 2H), 4.18 (m, 2H), 3.76 (s, 3H), 3.66 (m, 4H), 2.82 (m, 2H), 2.58 (m, 1H), 2.31 (m 1H). MS (EI) for C$_{30}$H$_{28}$FN$_5$O$_5$: 558 (MH$^+$).

methyl [6-(4-{[2-(4-fluorophenyl)-4-oxopiperidin-1-yl]carbonyl}-2,3,4,5-tetrahydro-1,4-benzoxazepin-7-yl)-1H-benzimidazol-2-yl]carbamate. Synthesized according to the method of example 8 using 2-(4-fluorophenyl)-4-oxopiperidine-1-carbonyl chloride (reagent preparation 37) in step 4. $^1$H NMR (400 MHz, d$_6$-DMSO): 7.58 (d, 1H), 7.51 (s, 1H), 7.44 (dd, 2H), 7.30-7.26 (m, 3H), 7.04 (q, 3H), 5.20 (tr, 1H), 4.57 (dd AB, 2H), 4.26-4.16 (m, 2H), 3.76 (s, 3H), 3.71-3.65 (m, 3H), 3.34-3.28 (m, 1H), 2.86 (d q, 2H), 2.65-2.57 (m, 1H), 2.30 (d, 1H). MS (EI) for C$_{30}$H$_{28}$FN$_5$O$_5$: 559 (MH$^+$).

methyl [6-(4-{[4-(fluoromethyl)-4-hydroxypiperidin-1-yl]carbonyl}-2,3,4,5-tetrahydro-1,4-benzoxazepin-7-yl)-1H-benzimidazol-2-yl]carbamate. Synthesized according to the method of example 8 using 4-(fluoromethyl)-4-hydroxypiperidine-1-carbonyl chloride (reagent preparation 37) in step 4. $^1$H NMR (400 MHz, d$_6$-DMSO): 7.69 (d, 1H), 7.58 (d, 1H), 7.50 (d, 1H), 7.49 (dd, 1H), 7.44 (dd, 1H), 7.03 (d, 1H), 4.44 (s, 2H), 4.19 (br s, 2H), 4.16 (d, 2H), 3.84 (s, 3H), 3.60 (br s, 2H), 3.36 (d, 2H), 3.07 (tr, 2H), 2.71 (dd, 1H), 1.56 (d tr, 2H), 1.43 (d, 2H). MS (EI) for C$_{25}$H$_{28}$FN$_5$O$_5$: 499 (MH$^+$).

methyl [6-(4-{[2-(3,4-difluorophenyl)-4-oxopiperidin-1-yl]carbonyl}-2,3,4,5-tetrahydro-1,4-benzoxazepin-7-yl)-1H-benzimidazol-2-yl]carbamate. Synthesized according to the method of example 8 using 2-(3,4-difluorophenyl)-4-oxopiperidine-1-carbonyl chloride (reagent preparation 37) in step 4. $^1$H NMR (400 MHz, d$_6$-DMSO): 7.58 (s, 1H), 7.53 (s, 1H), 7.44 (d, 2H), 7.35-7.25 (m, 3H), 7.11 (br, 1H), 7.01 (d, 1H), 5.16 (tr, 1H), 4.58 (dd AB, 2H), 4.26-4.15 (m, 2H), 3.76 (s, 3H), 3.73-3.63 (m, 3H), 3.45 (m, 1H), 2.83 (d, 2H), 2.64-2.55 (m, 1H), 2.35 (d, 1H). MS (EI) for C$_{30}$H$_{27}$F$_2$N$_5$O$_5$: 578 (MH$^+$).

Synthetic Example 9

(±)-methyl [5-(4-{[(2R,4S)-2-(4-fluorophenyl)-4-hydroxypiperidin-1-yl]carbonyl}-2,3,4,5-tetrahydro-1,4-benzoxazepin-7-yl)-1H-benzimidazol-2-yl]carbamate STEP 1: Methyl [6-(2,3,4,5-tetrahydro-1,4-benzoxazepin-7-yl)-1H-benzimidazol-2-yl]carbamate dihydrochloride salt (example 8, step 3) (503 mg, 1.2 mmol) was suspended in dichloromethane (15 mL) followed by addition of DIPEA (1.2 mL, 6.9 mmol) and the mixture was stirred for 5 minutes. Phosgene (20 W % in toluene, 0.7 mL, 1.3 mmol) was then added and the mixture was stirred at room temperature an additional 1 h. The mixture was then concentrated and partitioned with ethyl acetate and 10% aqueous citric acid. The bisphasic mixture was filtered and the organic filtrate was washed with brine, dried over anhydrous sodium sulfate then filtered and concentrated. The residue thus obtained was triturated with ethyl ether and the resulting suspension was filtered and the filter cake washed with additional ethyl ether and dried to give methyl 5-[4-(chlorocarbonyl)-2,3,4,5-tetrahydro-1,4-benzoxazepin-7-yl]-1H-benzimidazol-2-carboxylate (133 mg, 27% yield) as a light tan solid that was carried forward without further purification. MS (EI) for C$_{19}$H$_{17}$ClN$_4$O$_4$: 401 (MH$^+$).

STEP 2: Methyl 5-[4-(chlorocarbonyl)-2,3,4,5-tetrahydro-1,4-benzoxazepin-7-yl]-1H-benzimidazol-2-carboxylate (133 mg, 0.33 mmol) as obtained in step 1 was taken in to N,N-dimethylacetamide (1 mL) followed by addition of DIPEA (0.23 mL, 1.32 mmol) and racemic (2R,4S)-2-(4-fluorophenyl)piperidin-4-ol hydrochloride salt (reagent preparation 28) (76.5 mg, 0.33 mmol) and the mixture was stirred for 1 h at room temperature. Racemic (2R,4S)-2-(4-fluorophenyl)piperidin-4-ol hydrochloride salt (80 mg) was added to the mixture at this point and the mixture was stirred an additional 1 h followed then by addition of another aliquot of the piperidine reagent (56 mg) and the mixture was allowed to stir an additional 12 h. The mixture was partitioned with ethyl acetate and 10% aqueous citric acid. The bisphasic mixture was filtered and the organic filtrate was washed with brine, dried over anhydrous sodium sulfate then filtered and concentrated. The residue was chromatographed on silica gel (7.5% ethanol in ethyl acetate) to give 26 mg of residue after concentration of product containing fractions. Purification of the residue by preparative reverse phase HPLC afforded (±)-methyl [5-(4-{[(2R,4S)-2-(4-fluorophenyl)-4-hydroxypiperidin-1-yl]carbonyl}-2,3,4,5-tetrahydro-1,4-benzoxazepin-7-yl)-1H-benzimidazol-2-yl]carbamate (6.4 mg) as a colorless solid. $^1$H NMR (400 MHz, d$_4$-methanol): 7.68 (s, 1H), 7.56 (s, 2H), 7.45 (s, 1H), 7.43 (d, 1H), 7.02-6.96 (m, 3H), 6.65 (tr, 2H), 4.60 (dd AB, 2H), 4.04 (m, 2H), 3.92 (dd, 1H), 3.86 (s, 3H), 3.81 (br, 1H), 3.69-3.63 (m, 2H), 3.40-3.36 (m, 1H), 2.75 (tr, 1H), 1.94-1.88 (m, 2H), 1.44 (q, 1H). MS (EI) for C$_{29}$H$_{29}$FN$_4$O$_3$: 502 (MH$^+$).

Synthetic Example 10 methyl {6-[4-({4-hydroxy-4-[3-(trifluoromethyl)phenyl]piperidin-1-yl}carbonyl)-2,3,4,5-tetrahydro-1,4-benzoxazepin-7-yl]-1H-benzimidazol-2-yl}carbamate STEP 1: A solution of 7-bromo-2,3-dihydro-1,4-benzoxazepine-4(5H)-carbonyl chloride (example 2) (0.400 g, 1.38 mmol), 4-(3-(trifluoromethyl)phenyl)piperidin-4-ol (0.371 g, 1.51 mmol), and diisopropylethylamine (0.535 g, 4.14 mmol) in dichloromethane (3 mL) was stirred at room temperature for 1 hour. The reaction mixture was diluted with ethyl acetate (50 mL), washed with 10% citric acid (20 mL) and brine (20 mL). The organic layer was dried over sodium sulfate. Filtration and concentration afforded 1-[(7-bromo-2,3-dihydro-1,4-benzoxazepin-4(5H)-yl)carbonyl]-4-[3-(trifluoromethyl)phenyl]piperidin-4-ol (0.688 g, 100%) as a white solid that was used without further purification. MS (EI) for C$_{22}$H$_{22}$BrF$_3$N$_2$O$_3$: 500 (MH$^+$).

STEP 2: To a solution of 1-[(7-bromo-2,3-dihydro-1,4-benzoxazepin-4(5H)-yl)carbonyl]-4-[3-(trifluoromethyl)phenyl]piperidin-4-ol (0.688 g, 1.38 mmol) and 2-nitro-4-(4,4,5,5-tetramethyl-1,3,2-dioxaborolan-2-yl)aniline (0.365 g, 1.38 mmol) in dioxane (24 mL) and water (3.00 ml) was added tribasic potassium phosphate (0.413 g, 1.79 mmol). The solution was sparged with N$_2$(g) for ten minutes before the addition of dichloro[1,1-bis-(diphenylphosphino]ferrocenepalladium (II) dichloromethane adduct (0.023 g, 10 mol %). The resulting suspension was heated at 90° C. for 2 hours in a sealed tube vessel. On cooling to room temperature the mixture was diluted with ethyl acetate (50 mL), washed with water (50 mL) and then dried over anhydrous sodium sulfate. Filtration and concentration afforded a crude orange oil that was purified by silica gel chromatography (7:3 hexanes/ethyl acetate) to provide 1-{[7-(4-amino-3-nitrophenyl)-2,3-dihydro-1,4-benzoxazepin-4(5H)-yl]carbonyl}-4-[3-(trifluoromethyl)phenyl]piperidin-4-ol (0.200 g, 26% yield) as an orange oil. MS (EI) for $C_{28}H_{27}F_3N_4O_5$: 557 (MH$^+$).

STEP 3: To a solution of 1-{[7-(4-amino-3-nitrophenyl)-2,3-dihydro-1,4-benzoxazepin-4(5H)-yl]carbonyl}-4-[3-(trifluoromethyl)phenyl]piperidin-4-ol (0.200 g, 0.359 mmol) in methanol (40 mL) was added 10% palladium on carbon (0.200 g). The solution was sparged with $N_2$(g) for five minutes before being placed on a Parr shaker and degassed. The resulting suspension was shaken for 3 hours under $H_2$(g) at 30 psi. Filtration and concentration afforded 1-{[7-(3,4-diaminophenyl)-2,3-dihydro-1,4-benzoxazepin-4 (5H)-yl]carbonyl}-1-[3-(trifluoromethyl)phenyl]piperidin-4-ol (0.156 g, 84% yield) as crude brown oil that was used without further purification. MS (EI) for $C_{28}H_{29}F_3N_4O_3$: 527 (MH$^+$).

STEP 4: To a solution of 1-{[7-(3,4-diaminophenyl)-2,3-dihydro-1,4-benzoxazepin-4(5H)-yl]carbonyl}-1-[3-(trifluoromethyl)phenyl]piperidin-4-ol (0.156 g, 0.148 mmol) in glacial acetic acid (3 mL) was added 1,3-bis(methoxycarbonyl)-2-methyl-2-thiopseudourea (0.040 g, 0.193 mmol). The reaction mixture was stirred at 80° C. for 3 h and then concentrated. Ethyl acetate (50 mL) was added to the residue, and the solution was washed with saturated sodium bicarbonate (50 mL) and then dried over anhydrous sodium sulfate. Filtration and concentration afforded a brown residue that was purified by silica gel chromatography (95:5 dichloromethane/methanol). Product containing fractions were combined and concentrated and the residue taken up in a 1:1 solution of methanol and acetonitrile (4 mL). The resulting precipitate was collected by filtration, washed with diethyl ether and dried to give methyl {6-[4-({4-hydroxy-4-[3-(trifluoromethyl)phenyl]piperidin-1-yl}carbonyl)-2,3,4,5-tetrahydro-1,4-benzoxazepin-7-yl]-1H-benzimidazol-2-yl}carbamate (0.042 g, 52% yield) as a white solid. $^1$H NMR (400 MHz, d$_6$-DMSO): 12.01-11.77 (br s, 1H), 11.43-11.19 (br s, 1H), 7.87-7.84 (s, 1H), 7.80-7.76 (d, 1H), 7.62-7.52 (m, 4H), 7.46-7.39 (m, 2H), 7.33-7.29 (d, 1H), 7.03-6.99 (d, 1H), 5.33-5.31 (s, 1H), 4.50-4.47 (s, 2H), 4.22-4.17 (s, 2H), 3.77-3.74 (s, 3H), 3.67-3.62 (s, 2H), 3.52-3.45 (d, 2H), 3.25-3.15 (t, 2H), 2.06-1.95 (t, 2H), 1.63-1.55 (d, 2H); MS (EI) for $C_{31}H_{30}F_3N_5O_5$: 610 (MH$^+$).

Using analogous synthetic techniques and substituting with alternative starting reagents in step 1 the following compounds of the invention were prepared. Alternative starting materials were obtained commercially unless otherwise indicated.

methyl [6-(4-{[4-(difluoromethyl)piperidin-1-yl]carbonyl}-2,3,4,5-tetrahydro-1,4-benzoxazepin-7-yl)-1H-benzimidazol-2-yl]carbamate. Prepared according to the method of example 10 by using 4-(difluoromethyl)piperidine (reagent preparation 6) in step 1. $^1$H NMR (400 MHz, DMSO-d$_6$): 11.72 (br. s, 1H), 7.58 (s, 1H), 7.48 (s, 1H), 7.43 (d, 2H), 7.31 (d, 1H), 7.00 (d, 1H), 5.93 (m, 1H), 4.43 (s, 2H), 4.17 (m, 2H), 3.76 (s, 2H), 3.60 (m, 4H), 2.75 (m, 2H), 1.99 (m, 1H), 1.65 (m, 2H), 1.36 (m, 2H); MS (EI) for $C_{25}H_{27}F_2N_5O_4$: 500 (MH$^+$).

Synthetic Example 11

Methyl (6-{4-[(4-cyanopiperidin-1-yl)carbonyl]-2,3,4,5-tetrahydro-1,4-benzoxazepin-7-yl}-1H-benzimidazol-2-yl)carbamate STEP 1: 1,1-dimethylethyl 7-(4-amino-3-nitrophenyl)-2,3-dihydro-1,4-benzoxazepine-4(5H)-carboxylate (example 8, step 1) (6.0 g, 15.6 mmol) was taken into warm methanol (50 mL) followed by addition of 4M hydrogen chloride in dioxane (50 mL) in portions and the warm solution was allowed to slowly cool to room temperature over 1 h. The mixture was diluted with ethyl ether (100 mL) and the yellow solid was collected by filtration and dried to give 2-nitro-4-(2,3,4,5-tetrahydro-1,4-benzoxazepin-7-yl)aniline hydrochloride salt (3.61 g, 72% yield) as a yellow solid. $^1$H NMR (400 MHz, D$_2$O): 7.79 (s, 1H), 7.44 (d, 1H), 7.29 (s, 1H), 7.26 (d, 1H), 7.02 (d, 1H), 6.82 (d, 1H), 4.34 (s, 2H), 4.32 (br m, 2H), 3.67 (br m, 2H).

STEP 2: 2-nitro-4-(2,3,4,5-tetrahydro-1,4-benzoxazepin-7-yl)aniline hydrochloride salt (3.61 g, 11.2 mmol) and DIPEA (5.2 mL, 30 mmol) were taken into dichloromethane (50 mL) followed by dropwise addition of allyl chloroformate (1.23 mL, 11.2 mmol) over 5 minutes. The mixture was allowed to stir 30 minutes at room temperature then concentrated. The residue was partitioned with ethyl acetate and 10% aqueous citric acid and the organic solution washed with brine then dried over anhydrous sodium sulfate, filtered and concentrated to give prop-2-en-1-yl 7-(4-amino-3-nitrophenyl)-2,3-dihydro-1,4-benzoxazepine-4(5H)-carboxylate (4.2 g, 100% yield) as a red amorphous residue. MS (EI) for $C_{19}H_{19}N_3O_5$: 370 (MH$^1$).

STEP 3: Prop-2-en-1-yl 7-(4-amino-3-nitrophenyl)-2,3-dihydro-1,4-benzoxazepine-4(5H)-carboxylate (4.2 g, 11.2 mmol) was taken into glacial acetic acid (25 mL) and the solution was warmed to 45° C. Tin (II) chloride (8.51 g, 44.8 mmol) was added in portions over 5 minutes and the mixture was allowed to stir at this temperature for 6 h. The mixture was then cooled to room temperature and diluted with MTBE (100 mL). 50% aqueous sodium hydroxide was then added in small portions with stirring until complete precipitation of tin salts occurred. Anhydrous sodium sulfate was then added in portions until the precipitated salts formed a fine granular solid and the mixture was filtered. The filter cake was washed with additional MTBE and the combined organic filtrate was concentrated. The residue was partitioned with ethyl acetate and saturated aqueous sodium bicarbonate. 50% aqueous sodium hydroxide was added to the biphasic mixture in portions until the aqueous pH was 9-10. The layers were then separated and the organic solution washed with brine then dried over anhydrous sodium sulfate, filtered and concentrated to provide prop-2-en-1-yl 7-(3,4-diaminophenyl)-2,3-dihydro-1,4-benzoxazepine-4(5H)-carboxylate (2.7 g, 71% yield) as a yellow solid. MS (EI) for $C_{19}H_{21}N_3O_3$: 340 (MH$^+$).

STEP 4: Prop-2-en-1-yl 7-(3,4-diaminophenyl)-2,3-dihydro-1,4-benzoxazepine-4(5H)-carboxylate (2.7 g, 7.96 mmol) was taken into glacial acetic acid (15 mL) followed by addition of 1,3-(dimethoxycarbonyl)-2-methyl-2-thiopseudourea (1.81 g, 8.8 mmol) and the mixture was heated to 80° C. for 30 minutes then concentrated to a thick residue. The residue was treated with saturated aqueous sodium bicarbonate and the aqueous mixture basified with portionwise addition of solid sodium bicarbonate with pH 8-9. The aqueous mixture was then partitioned with hexanes then filtered. The filter cake was washed with water then hexanes and dried to give prop-2-en-1-yl 7-(2-{[(methyloxy)carbonyl]amino}-

1H-benzimidazol-5-yl)-2,3-dihydro-1,4-benzoxazepine-4 (5H)-carboxylate (3.46 g, 100% yield) as a pale yellow solid.

STEP 5: Prop-2-en-1-yl 7-(2-{[(methyloxy)carbonyl]amino}-1H-benzimidazol-5-yl)-2,3-dihydro-1,4-benzoxazepine-4(5H)-carboxylate (3.46 g, 7.96 mmol) was suspended in THF (75 mL) followed by addition of di-tert-butyl dicarbonate (4.3 g, 19.9 mmol) and pyridine (2 mL, 23.9 mmol). The mixture was stirred at room temperature 1 h then warmed to reflux for an additional hour. The solution was then cooled to room temperature and concentrated. The residue was partitioned with ethyl acetate and 10% aqueous citric acid and the organic solution washed with brine then dried over anhydrous sodium sulfate, filtered and concentrated. The residue was chromatographed on silica gel (ethyl acetate:hexanes 1:1) to provide N,N'-di-BOC prop-2-en-1-yl 7-(2-{[(methyloxy)carbonyl]amino}-1H-benzimidazol-5-yl)-2,3-dihydro-1,4-benzoxazepine-4(5H)-carboxylate (3.3 g, 67% yield) as an impure amorphous residue. MS (EI) for $C_{32}H_{38}N_4O_9$: 624 (MH).

STEP 6: N,N'-di-BOC prop-2-en-1-yl 7-(2-{[(methyloxy)carbonyl]amino}-1H-benzimidazol-5-yl)-2,3-dihydro-1,4-benzoxazepine-4(5H)-carboxylate (3.3 g, 5.3 mmol) was taken into THF (30 mL) followed by addition of sodium triacetoxyborohydride (5.6 g, 26.5 mmol) and palladium tetrakis-triphenylphosphine (612 mg) and the mixture was stirred for 30 minutes at room temperature. The mixture was concentrated and the residue partitioned with chloroform and saturated aqueous sodium bicarbonate. The biphasic mixture was saturated with solid sodium chloride and the aqueous phase extracted twice with chloroform. The combined organic solution was then dried over anhydrous sodium sulfate, filtered and concentrated. The residue was chromatographed on silica gel (100% ethyl acetate to 10% methanol in chloroform) to afford N,N'-di-BOC methyl [5-(2,3,4,5-tetrahydro-1,4-benzoxazepin-7-yl)-1H-benzimidazol-2-yl]carbamate (830 mg, 29% yield) as an amorphous residue. MS (EI) for $C_{28}H_{34}N_4O_7$: 540 (MH+).

STEP 7: To a solution of triphosgene (137 mg, 0.56 mmol) in THF (5 mL) was added a solution of N,N'-di-BOC methyl [5-(2,3,4,5-tetrahydro-1,4-benzoxazepin-7-yl)-1H-benzimidazol-2-yl]carbamate (830 mg, 1.54 mmol), DIPEA (0.4 mL, 2.3 mmol) and pyridine (15 uL, 0.15 mmol) in THF (10 mL) in a dropwise manner over 5 minutes. The mixture was stirred an addition 10 minutes then concentrated. The residue was partitioned with ethyl acetate and 10% aqueous citric acid and the organic solution washed with brine then dried over anhydrous sodium sulfate, filtered and concentrated. The residue was chromatographed on silica gel (ethyl acetate:hexanes 2:3) to provide N,N'-di-BOC methyl {5-[4-(chlorocarbonyl)-2,3,4,5-tetrahydro-1,4-benzoxazepin-7-yl]-1H-benzimidazol-2-yl}carbamate (384 mg, 41% yield). MS (EI) for $C_{29}H_{33}ClN_4O_8$: 602 (MH+).

STEP 8: A mixture of N,N'-di-BOC methyl {5-[4-(chlorocarbonyl)-2,3,4,5-tetrahydro-1,4-benzoxazepin-7-yl]-1H-benzimidazol-2-yl}carbamate (40 mg, 0.07 mmol), 4-cyanopiperidine hydrochloride (20 mg, 0.14 mmol), and diisoproylethylamine (0.13 mL, 0.14 mmol), in dichloromethane (2 mL) was stirred at room temperature for one hour. The mixture was concentrated and purified directly by silica gel chromatography (0-15% methanol-dichlomethane) to give N,N'-di-BOC methyl (6-{4-[(4-cyanopiperidin-1-yl)carbonyl]-2,3,4,5-tetrahydro-1,4-benzoxazepin-7-yl}-1H-benzimidazol-2-yl)carbamate as an amorphous residue.

STEP 9: A solution of N,N'-di-BOC methyl (6-{4-[(4-cyanopiperidin-1-yl)carbonyl]-2,3,4,5-tetrahydro-1,4-benzoxazepin-7-yl}-1H-benzimidazol-2-yl)carbamate as obtained in step 8 was taken into trifluoroacetic acid (0.2 mL) and dichloroethane (1.8 mL) was stirred at room temperature for one hour. The reaction mixture was concentrated and purified by preparative reverse phase HPLC to give methyl (6-{4-[(4-cyanopiperidin-1-yl)carbonyl]-2,3,4,5-tetrahydro-1,4-benzoxazepin-7-yl}-1H-benzimidazol-2-yl)carbamate (4.6 mg) as an amorphous solid. $^1$H NMR (400 MHz, methanol-$d_4$): 7.57 (br, 1H), 7.51 (br, 1H), 7.43 (dd, 2H), 7.31 (dd, 1H), 7.01 (d, 1H), 4.44 (s, 2H), 4.17 (m, 2H), 3.75 (s, 3H), 3.59 (m, 2H), 3.40 to 3.27 (m, 2H), 3.10 to 2.96 (m, 3H), 1.93 to 1.86 (m, 2H), 1.79 to 1.69 (m, 2H); MS (EI) for $C_{25}H_{26}N_6O_4$: 475 (MH+).

Using analogous synthetic techniques and substituting with alternative starting reagents in step 8 the following compounds of the invention were prepared. Alternative starting materials were obtained commercially unless otherwise indicated.

Methyl [6-(4-{[3-(endo)-hydroxy-3-(trifluoromethyl)-8-azabicyclo[3.2.1]oct-8-yl]carbonyl}-2,3,4,5-tetrahydro-1,4-benzoxazepin-7-yl)-1H-benzimidazol-2-yl]carbamate. Prepared according to the method of example 11 by using 3-(trifluoromethyl)-8-azabicyclo[3.2.1]octan-3-(endo)-ol hydrochloride (reagent preparation 15) in step 8. $^1$H NMR (400 MHz, methanol-$d_4$): 7.60 (br, 1H), 7.48 to 7.43 (m, 3H), 7.37 (dd, 1H), 7.02 (d, 1H), 4.58 (s, 2H), 4.22 (m, 2H), 4.16 (br, 2H), 3.85 (s, 3H), 3.75 (m, 2H), 2.21 to 2.11 (m, 4H), 1.92 to 1.85 (m, 2H), 1.79 (d, 2H); MS (EI) for $C_{27}H_{28}F_3N_5O_5$: 560 (MH+).

Methyl [6-(4-{[4-hydroxy-4-(trifluoromethyl)piperidin-1-yl]carbonyl}-2,3,4,5-tetrahydro-1,4-benzoxazepin-7-yl)-1H-benzimidazol-2-yl]carbamate. Prepared according to the method of example 11 by using 4-(trifluoromethyl)piperidine-4-ol hydrochloride (reagent preparation 24) in step 8. $^1$H NMR (400 MHz, methanol-$d_4$): 7.61 (d, 1H), 7.52 (d, 1H), 7.48 to 7.44 (m, 2H), 7.38 (dd, 1H), 7.02 (d, 1H), 4.51 (s, 2H), 4.20 (m, 2H), 3.85 (s, 3H), 3.70 (m, 2H), 3.61 (d, 2H), 3.18 (dd, 2H), 1.84 (dt, 2H), 1.70 (d, 2H); MS (EI) for $C_{25}H_{26}F_3N_5O_5$: 534 (MH+).

1-{[7-(2-amino-1H-benzimidazol-6-yl)-2,3-dihydro-1,4-benzoxazepin-4 (5H)-yl]carbonyl}-4-methylpiperidin-4-ol. Prepared according to the method of example 11 by using 4-methylpiperidin-4-ol (reagent preparation 5) in step 8. Isolated as a co-product in step 9. $^1$H NMR (400 MHz, methanol-$d_4$): 7.46 (d, 1H), 7.44 to 7.41 (m, 2H), 7.32 (dd, 1H), 7.28 (d, 1H), 7.02 (d, 1H), 4.48 (s, 2H), 4.19 (m, 2H), 3.68 (m, 2H), 3.43 to 3.21 (m, 4H), 1.66 to 1.53 (m, 4H), 1.23 (s, 3H); MS (EI) for $C_{23}H_{27}N_5O_3$: 422 (MH+).

Methyl (6-{4-[(4-hydroxy-4-methylpiperidin-1-yl)carbonyl]-2,3,4,5-tetrahydro-1,4-benzoxazepin-7-yl}-1H-benzimidazol-2-yl)carbamate. Prepared according to the method of example 11 by using 4-methylpiperidin-4-ol hydrochloride (reagent preparation 5) in step 8. $^1$H NMR (400 MHz, methanol-$d_4$): 7.43 (d, 1H), 7.48 to 7.44 (m, 3H), 7.38 (dd, 1H), 7.03 (d, 1H), 4.48 (s, 2H), 4.19 (m, 2H), 3.85 (s, 3H), 3.64 (m, 2H), 3.43 to 3.22 (m, 4H), 1.67 to 1.53 (m, 4H), 1.23 (s, 3H); MS (EI) for $C_{25}H_{29}N_5O_5$: 480 (MH+).

Methyl (6-{4-[(3-oxo-8-azabicyclo[3.2.1]oct-8-yl)carbonyl]-2,3,4,5-tetrahydro-1,4-benzoxazepin-7-yl}-1H-benzimidazol-2-yl)carbamate. Prepared according to the method of example 11 by using 8-azabicyclo[3.2.1]octan-3-one hydrochloride in step 8. $^1$H NMR (400 MHz, methanol-$d_4$): 7.60 (br, 1H), 7.53 (br, 1H), 7.47-7.43 (m, 2H), 7.37 (d, 1H), 7.04 (d, 1H), 4.68 (s, 2H), 4.38 to 4.31 (m, 2H), 4.28 to 4.20 (m, 2H), 3.87 (s, 3H), 3.86 to 3.84 (m, 2H), 2.86 (dd, 2H), 2.30 (d, 2H), 2.08-2.01 (m, 2H), 1.70 to 1.63 (m, 2H); MS (EI) for $C_{26}H_{27}N_5O_5$: 490 (MH+).

Synthetic Example 12

6-(4-{[4-(fluoromethyl)piperidin-1-yl]carbonyl}-2,3,4,5-tetrahydro-1,4-benzoxazepin-7-yl)-1H-benzimidazol-2-amine STEP 1: To a solution of methyl [6-(4-{[4-(fluoromethyl)piperidin-1-yl]carbonyl}-2,3,4,5-tetrahydro-1,4-benzoxazepin-7-yl)-1H-benzimidazol-2-yl]carbamate (example 8) (181 mg, 0.38 mmol, in methanol (6 mL) was added a 2 M aqueous solution of potassium hydroxide (6 mL), and the resulting mixture was stirred at 65° C. overnight. The pH was adjusted to 9 with 1 N aqueous hydrochloric acid, ethyl acetate was added (50 mL), and the organic layer was washed with brine (2×25 mL), dried over sodium sulfate, filtered and concentrated. Purification by preparative reverse phase HPLC (0.1% aqueous ammonium acetate-acetonitrile) provided the title compound as the acetate salt (56 mg, 31% yield) as a colorless solid. $^1$H NMR (400 MHz, methanol-d$_4$): 7.47 (m, 1H), 7.43 (m, 2H), 7.30 (m, 2H), 7.02 (d, 1H), 4.48 (s, 2H), 4.29 (dd, 2H), 4.19 (m, 2H), 3.71 (m, 4H), 2.85 (m, 2H), 1.95 (s, 3H), 1.87 (m, 1H), 1.72 (m, 2H), 1.36 (m, 2H); MS (EI) for $C_{23}H_{26}FN_5O_2$: 424 (MH$^+$).

Synthetic Example 13

1-{[7-(2-amino-1H-benzimidazol-6-yl)-2,3-dihydro-1,4-benzoxazepin-4(5H)-yl]carbonyl}-2-(3,4-difluorophenyl)piperidin-4-one STEP 1: A solution of 1,1-dimethylethyl 7-(4-amino-3-nitrophenyl)-2,3-dihydro-1,4-benzoxazepine-4(5H)-carboxylate (example 8, step 1) (2.3 g, 6.0 mmol), in acetic acid (20 mL) and ethyl acetate (20 mL) was hydrogenated at 45 psi over 10% Pd—C (1.0 g) for 1 h using a Parr apparatus. The catalyst was filtered off and the filtrate was concentrated to give 1,1-dimethylethyl 7-(3,4-diaminophenyl)-2,3-dihydro-1,4-benzoxazepine-4(5H)-carboxylate (2.0 g, 94% yield) as a light yellow oil. MS (EI) for $C_{20}H_{25}N_3O_3$: 356 (MH$^+$).

STEP 2: To a solution of 1,1-dimethylethyl 7-(3,4-diaminophenyl)-2,3-dihydro-1,4-benzoxazepine-4(5H)-carboxylate (2.0 g, 5.6 mmol) in acetic acid (20 mL) was added 1,3-bis(benzyloxycarbonyl)-2-methyl-2-thiopseudourea (2.4 g, 6.7 mmol) and the resulting mixture was heated (60° C.). After 12 h the reaction mixture was partitioned between ethyl acetate (50 mL) and water (50 mL). The organic layer was then washed with brine (50 mL), dried over anhydrous magnesium sulfate, filtered and concentrated. Column chromatography on silica (0 to 50% ethyl acetate/hexanes) provided 1,1-dimethylethyl 7-[2-({[(phenylmethyl)oxy]carbonyl}amino)-1H-benzimidazol-6-yl]-2,3-dihydro-1,4-benzoxazepine-4(5H)-carboxylate (1.3 g, 45% yield) as a brown solid. MS (EI) for $C_{29}H_{30}N_4O_5$: 515 (MH$^+$).

STEP 3: TFA (3 mL) was added to 1,1-dimethylethyl 7-[2-({[(phenylmethyl)oxy]carbonyl}amino)-1H-benzimidazol-6-yl]-2,3-dihydro-1,4-benzoxazepine-4(5H)-carboxylate (0.95 g, 1.9 mmol) and the resulting solution was heated (50° C.). After 1 h the reaction mixture was concentrated and azeotroped with ethyl acetate (3×30 mL) to afford phenylmethyl [6-(2,3,4,5-tetrahydro-1,4-benzoxazepin-7-yl)-1H-benzimidazol-2-yl]carbamate bis-trifluoroacetate salt (0.48 g, 49% yield) as a brown solid. MS (EI) for $C_{24}H_{22}N_4O_3$: 415 (MH$^+$).

STEP 4: To a solution of phenylmethyl [6-(2,3,4,5-tetrahydro-1,4-benzoxazepin-7-yl)-1H-benzimidazol-2-yl]carbamate bis-trifluoroacetate salt (0.40 g, 0.95 mmol) and DIPEA (0.66 mL, 3.8 mmol) in DMF (3 mL) was added 2-(3,4-difluorophenyl)-4-oxopiperidine-1-carbonyl chloride (reagent preparation 37) (0.26 g, 0.95 mmol), and the resulting mixture was heated (50° C.). After 2 h, the reaction mixture was partitioned between ethyl acetate (30 mL) and water (30 mL). The organic layer was washed with brine (30 mL), dried over anhydrous magnesium sulfate, filtered and concentrated. Column chromatography on silica with 1-10% (8% reagent ammonium hydroxide in methanol):dichloromethane yielded phenylmethyl [6-(4-{[2-(3,4-difluorophenyl)-4-oxopiperidin-1-yl]carbonyl}-2,3,4,5-tetrahydro-1,4-benzoxazepin-7-yl)-1H-benzimidazol-2-yl]carbamate (0.35 g, 57% yield) as a waxy solid. MS (EI) for $C_{36}H_{31}F_2N_5O_5$: 652 (MH$^+$).

STEP 5: A solution of phenylmethyl [6-(4-{[2-(3,4-difluorophenyl)-4-oxopiperidin-1-yl]carbonyl}-2,3,4,5-tetrahydro-1,4-benzoxazepin-7-yl)-1H-benzimidazol-2-yl]carbamate (0.11 g, 0.17 mmol) in acetic acid (5 mL) was hydrogenated at 1 atm over 10% Pd—C (0.1 g) for 2 h. The catalyst was filtered off and the filtrate was concentrated. The resulting brown residue was dissolved in methanol and purified by preparative reverse phase HPLC to afford 1-{[7-(2-amino-1H-benzimidazol-6-yl)-2,3-dihydro-1,4-benzoxazepin-4(5H)-yl]carbonyl}-2-(3,4-difluorophenyl)piperidin-4-one (0.007 g, 8% yield) as a pale yellow solid. $^1$H NMR (400 MHz, CDCl$_3$): 7.02-7.29 (m, 8H), 6.98 (d, 1H), 6.94 (d, 1H), 5.27 (t, 1H), 4.43-4.46 (m, 2H), 4.16-4.30 (m, 2H), 3.70-3.85 (m, 3H), 3.21-3.31 (m, 1H), 2.79-2.99 (m, 2H), 2.51-2.61 (m, 1H), 2.32 (d, 1H); MS (EI) for $C_{28}H_{25}F_2N_5O_3$: 518 (MH$^+$).

Using analogous synthetic techniques and substituting with alternative starting reagents in step 4 the following compounds of the invention were prepared. Alternative starting materials were obtained commercially unless otherwise indicated.

1-{[7-(2-amino-1H-benzimidazol-6-yl)-2,3-dihydro-1,4-benzoxazepin-4 (5H)-yl]carbonyl}-2-(3-fluorophenyl)piperidin-4-one. Synthesized according to the method of example 13 using 2-(3-fluorophenyl)-4-oxopiperidine-1-carbonyl chloride in step 4. $^1$H NMR (400 mHz, DSMO-d6): δ 6.85-7.30 (m, 10H), 5.33 (t, 1H), 4.50 (s, 2H), 4.16-4.31 (m, 2H), 3.73-3.86 (m, 3H), 3.23 (t, 1H), 2.82-3.01 (m, 2H), 2.52-2.65 (m, 1H), 2.31 (d, 1H); MS (EI) for $C_{28}H_{26}FN_5O_3$: 500 (MH$^+$).

Synthetic Example 14

1-{[7-{2-[(2-fluoroethyl)amino]-1H-benzimidazol-5-yl}-2,3-dihydro-1,4-benzoxazepin-4(5H)-yl]carbonyl}-2-(3-fluorophenyl)piperidin-4-one STEP 1: 2-Fluoroethylamine hydrochloride salt (282.4 mg, 2.83 mmol) was suspended in 1:1 THF:DCM (6 mL) followed by addition of DIPEA (2.5 mL, 14.35 mmol). The mixture was cooled to 0° C. followed by slow addition of thiophosgene (217 uL, 2.8 mmol) by syringe over five minutes then allowed to slowly warm to room temperature over 30 minutes. 4-Bromobenzene-1,2-diamine (530 mg, 2.8 mmol) was then added and the reaction mixture was allowed to stir at room temperature over an additional 12 h. The mixture was concentrated and the residue partitioned with ethyl acetate and 10% aqueous citric acid. The organic phase was washed twice with additional 10% aqueous citric acid then brine, dried over anhydrous sodium sulfate, filtered and concentrated. The crude mixture of thiourea thus obtained was taken into THF (15 mL) followed by addition of mercury (II) oxide (640 mg, 2.95 mmol). The mixture was brought to reflux for 6 h then stirred an additional 60 h at room temperature. The crude mixture was filtered through a bed of celite with ethyl acetate washing and the filtrate concentrated then taken back into ethyl acetate. The organic solution was washed once with 1M aqueous hydrochloric acid and the organic phase discarded. The aqueous phase was filtered to remove trace insoluble residue and the filtrate basified to pH 9-10 by dropwise addition of 50% aqueous sodium hydroxide. The aqueous phase was then extracted once with ethyl acetate and the organic solution was washed with brine then dried over anhydrous sodium sulfate, filtered and concentrated to afford crude 5-bromo-N-(2-fluoroethyl)-1H-benzo[d]imidazol-2-amine (390 mg, 53% yield) which was carried forward without further purification. MS (EI) for $C_9H_9BrFN_3$: 258, 260 (MH$^+$).

STEP 2: 5-bromo-N-(2-fluoroethyl)-1H-benzo[d]imidazol-2-amine (390 mg, 1.51 mmol) thus obtained in step 1 was taken into THF (15 mL) followed by addition of DIPEA (600 uL, 3.4 mmol) and isobutyl chloroformate (400 uL, 3.06 mmol) and the mixture was stirred at room temperature for 1 h. The mixture was concentrated and the residue partitioned with ethyl acetate and 10% aqueous citric acid. The organic phase was washed with brine, dried over anhydrous sodium sulfate, filtered and concentrated. The residue was purified by silica gel chromatography to afford isobutyl 5-bromo-2-(2-fluoroethylamino)-1H-benzo[d]imidazole-1-carboxylate (290 mg, 54% yield) as a colorless crystalline solid. MS (EI) for $C_{14}H_{17}BrFN_3O_2$: 358, 360 (MH$^+$).

STEP 3: Isobutyl 5-bromo-2-(2-fluoroethylamino)-1H-benzo[d]imidazole-1-carboxylate (55 mg, 0.15 mmol) and (4-{[(1,1-dimethylethyl)oxy]carbonyl}-2,3,4,5-tetrahydro-1,4-benzoxazepin-7-yl)boronic acid (example 1, step 2) (50 mg, 0.17 mmol) were taken into dioxane (1 mL) and water (0.2 mL) followed by addition of dichloro[1,1-bis-(diphenylphosphino]ferrocenepalladium (II) dichloromethane adduct (8.5 mg) and DIPEA (0.11 mL, 0.6 mmol) and the mixture was heated to 85° C. for 12 h. The mixture was then cooled and diluted with ethyl acetate then dried over anhydrous sodium sulfate and filtered through a plug of silica gel with an ethyl acetate wash. The organic solution was then concentrated to an oil. The residue was taken into THF (2 mL) followed by sequential addition of DIPEA (0.05 mL, 0.29 mmol) and isobutyl chloroformate (0.01 mL, 0.08 mmol) then the mixture was stirred for 30 minutes. The mixture was concentrated and the residue purified by silica gel chromatography (1.5:1 hexanes:ethyl acetate) to give 1,1-dimethylethyl 7-(2-[(2-fluoroethyl)amino]-1-{[(2-methylpropyl)oxy]carbonyl}-1H-benzimidazol-5-yl)-2,3-dihydro-1,4-benzoxazepine-4(5H)-carboxylate (59.4 mg, 75% yield) as a colorless amorphous residue. MS (EI) for $C_{28}H_{35}FN_4O_5$: 528 (MH$^+$).

STEP 4: 1,1-Dimethylethyl 7-(2-[(2-fluoroethyl)amino]-1-{[(2-methylpropyl)oxy]carbonyl}-1H-benzimidazol-5-yl)-2,3-dihydro-1,4-benzoxazepine-4 (5H)-carboxylate (59.4 mg, 0.11 mmol) was taken into neat TFA (1 mL) and allowed to stand for 1 h at room temperature then concentrated and dried. The residue was taken into THF (5 mL) followed by addition of DIPEA (0.2 mL, 1.1 mmol) followed by addition of 2-(3-fluorophenyl)-4-oxopiperidine-1-carbonyl chloride (reagent preparation 37) (29 mg, 0.11 mmol) in a minimum of THF and the resulting solution was stirred at room temperature for 30 minutes. The mixture was then concentrated and taken up into methanol (5 mL) followed by addition of solid potassium carbonate (80 mg, 0.56 mmol) and stirring was continued for 30 minutes. The mixture was then concentrated and partitioned with ethyl acetate and brine. The organic solution was dried over anhydrous sodium sulfate, filtered and concentrated. The residue thus obtained was triturated with ethyl ether and the solid collected by filtration and dried to afford 1-{[7-{2-[(2-fluoroethyl)amino]-1H-benzimidazol-5-yl}-2,3-dihydro-1,4-benzoxazepin-4(5H)-yl]carbonyl}-2-(3-fluorophenyl)piperidin-4-one (46.4 mg, 75% yield). $^1$H NMR (400 MHz, d$_6$-DMSO): 7.51 (s, 1H), 7.42 (d, 1H), 7.36 (s, 1H), 7.31 (q, 1H), 7.18 (d, 1H), 7.12-7.03 (m, 4H), 6.99 (d, 1H), 5.20 (tr, 1H), 4.66 (tr, 1H), 4.57 (dd AB, 2H), 4.54 (tr, 1H), 4.20 (br m, 2H), 3.75-3.56 (br m, 6H), 2.86 (m, 2H), 2.60 (m, 1H), 2.33 (br d, 1H). MS (EI) for $C_{30}H_{29}F_2N_5O_3$: 547 (MH$^+$).

Using analogous synthetic techniques and substituting with alternative starting reagents in steps 1 and/or 4 the following compounds of the invention were prepared. Alternative starting materials were obtained commercially unless otherwise indicated.

2-(3-fluorophenyl)-1-{[7-{2-[(2,2,2-trifluoroethyl)amino]-1H-benzimidazol-5-yl}-2,3-dihydro-1,4-benzoxazepin-4(5H)-yl]carbonyl}piperidin-4-one. Synthesized according to the method of example 14 using 2,2,2-trifluoroethylamine hydrochloride salt in step 1. $^1$H NMR (400 MHz, d$_6$-DMSO): 7.52 (d, 1H), 7.44-7.35 (m, 3H), 7.30 (q, 1H), 7.25-7.20 (m, 1H), 7.17-7.03 (m, 4H), 6.99 (d, 1H), 5.20 (br s, 1H), 4.58 (dd AB, 2H), 4.25-4.14 (m, 4H), 3.68 (br d, 3H), 2.91-2.80 (m, 2H), 2.64-2.56 (m, 1H), 2.33 (d, 1H). MS (EI) for $C_{30}H_{27}F_4N_5O_3$: 583 (MH$^+$).

N-ethyl-6-(4-{[4-(fluoromethyl)piperidin-1-yl]carbonyl}-2,3,4,5-tetrahydro-1,4-benzoxazepin-7-yl)-1H-benzimidazol-2-amine. Synthesized according to the method of example 14 using ethyl isothiocyanate in step 1 and 4-(fluoromethyl)piperidine-1-carbonyl chloride (reagent preparation 37) in step 4. MS (EI) $C_{25}H_{30}FN_5O_2$: 452 (MH$^+$).

1-({7-[2-(ethylamino)-1H-benzimidazol-6-yl]-2,3-dihydro-1,4-benzoxazepin-4(5H)-yl}carbonyl)-2-(3-fluorophenyl)piperidin-4-one. Prepared as the acetate salt according to the method of example 14 using ethyl isothiocyanate in step 1. $^1$H NMR (400 MHz, DMSO-d$_6$): 10.78 (br.s, 1H), 7.50 (br.s, 1H), 7.41 (d, 1H), 7.30 (m, 2H), 7.16-7.02 (m, 5H), 6.98 (d, 1H), 6.59 (t, 1H), 5.19 (t, 1H), 4.57 (m, 2H), 4.19 (m, 2H), 3.67 (m, 3H), 2.85 (m, 2H), 2.60 (m, 1H), 2.33 (m, 1H), 1.91 (s, 3H), 1.17 (t, 3H); MS (EI) for $C_{30}H_{30}FN_5O_3$: 528 (MH$^+$).

6-(4-{[4-(1,1-difluoroethyl)piperidin-1-yl]carbonyl}-2,3,4,5-tetrahydro-1,4-benzoxazepin-7-yl)-N-ethyl-1H-benzimidazol-2-amine. Prepared as the acetate salt according to the method of example 14 by using ethyl isothiocyanate in step 1 and 4-(1,1-difluoroethyl)piperidine-1-carbonyl chloride (reagent preparation 37) in step 4. $^1$H NMR (400 MHz, methanol-d$_4$): 7.47 (d, 1H), 7.45-7.41 (m, 2H), 7.33 (dd, 1H), 7.29 (d, 1H), 7.02 (d, 1H), 4.49 (s, 2H), 4.20 (m, 2H), 3.77 (m, 2H), 3.69 (m, 2H), 3.44 (q, 2H), 2.82 (m, 2H), 1.96 (s, 3H), 1.80 (m, 2H), 1.55 (t, 3H), 1.48 (m, 2H), 1.32 (t, 3H); MS (EI) for $C_{26}H_{31}F_2N_5O_2$: 484 (MH$^+$).

Synthetic Example 15

Methyl [6-(4-{[4-(fluoromethyl)piperidin-1-yl]carbonyl}-2,3,4,5-tetrahydro-1,4-benzoxazepin-7-yl)-1H-imidazo[4,5-b]pyridin-2-yl]carbamate STEP 1: A mixture of 2-amino-5-bromo-3-nitropyridine (0.70 g, 3.2 mmol), (4-{[(1,1-dimethylethyl)oxy]carbonyl}-2,3,4,5-tetrahydro-1,4-benzoxazepin-7-yl)boronic acid (example 1, step 2) (1.0 g, 3.1 mmol), [1,1'-bis(diphenylphosphino)ferrocene]dichloropalladium(II) complex with dichloromethane (0.15 mg, 0.2 mmol), diisopropylethylamine (1.8 g, 14 mmol) in 50% aqueous 1,4-dioxane (40 mL) was degassed with nitrogen for 5 minutes and then stirred at 90° C. for one hour. The reaction mixture was cooled to room temperature, diluted with ethyl acetate (80 mL) then filtered over celite. The filtrate was washed twice with brine (50 mL), filtered and the filtrate dried over sodium sulfate, filtered again and concentrated. The residue was purified by silica gel chromatography (25% to 95% ethyl acetate in hexanes gradient) to give 1,1-dimethylethyl 7-(6-amino-5-nitropyridin-3-yl)-2,3-dihydro-1,4-benzoxazepine-4(5H)-carboxylate (0.58 g, 48% yield); MS (EI) for $C_{19}H_{22}N_4O_5$: 389 (MH$^+$).

STEP 2: A mixture of 1,1-dimethylethyl 7-(6-amino-5-nitropyridin-3-yl)-2,3-dihydro-1,4-benzoxazepine-4(5H)-carboxylate (0.58 g, 1.5 mmol), palladium (10% on charcoal, 0.50 g) and methanol (30 mL) was hydrogenated in a Parr apparatus at 45 psi for 18 hours. The mixture was filtered then concentrated and dried to give 1,1-dimethylethyl 7-(5,6-diaminopyridin-3-yl)-2,3-dihydro-1,4-benzoxazepine-4(5H)-carboxylate (0.51 g, 96% yield), MS (EI) for $C_{19}H_{24}N_4O_3$: 357 (MH$^+$).

STEP 3: To a solution of 1,1-dimethylethyl 7-(5,6-diaminopyridin-3-yl)-2,3-dihydro-1,4-benzoxazepine-4(5H)-carboxylate (0.51 g, 1.4 mmol) in acetic acid (5 mL) was added 1,3-bis(methoxycarbonyl)-2-methyl-2-thiopseudourea (0.3 g, 1.4 mmol). The reaction mixture was heated 65° C. for 18 h and then concentrated. The resulting residue was suspended in water and basified with portion wise addition of solid sodium bicarbonate. After complete neutralization of the aqueous mixture the insoluble solid was collected by filtration and washed with water then 50% ethyl acetate in hexanes and the filter cake dried to give 1,1-dimethylethyl 7-(2-{[(methyloxy)carbonyl]amino}-1H-imidazo[4,5-b]pyridin-6-yl)-2,3-dihydro-1,4-benzoxazepine-4(5H)-carboxylate (0.52 g, 83% yield), MS (EI) for $C_{22}H_{25}N_5O_5$: 440 (MH$^+$).

STEP 4: To a mixture of 1,1-dimethylethyl 7-(2-{[(methyloxy)carbonyl]amino}-3H-imidazo[4,5-b]pyridin-6-yl)-2,3-dihydro-1,4-benzoxazepine-4(5H)-carboxylate (0.52 g, 1.2 mmol) was taken into acetonitrile (5 mL) followed by addition of 4M hydrogen chloride in 1,4-dioxane (5 mL) and the mixture was stirred at room temperature for 10 minutes. The reaction mixture was concentrated to give a white solid. It was washed with ether then dried to give methyl [6-(2,3,4,5-tetrahydro-1,4-benzoxazepin-7-yl)-1H-imidazo[4,5-b]pyridin-2-yl]carbamate hydrochloride salt (0.40 g, 100% yield), MS (EI) for $C_{17}H_{17}N_5O_3$: 340 (MH$^+$).

STEP 5: A mixture of 4-(fluoromethyl)piperidine-1-carbonyl chloride (reagent preparation 37) (24 mg, 0.13 mmol), methyl [6-(2,3,4,5-tetrahydro-1,4-benzoxazepin-7-yl)-1H-imidazo[4,5-b]pyridin-2-yl]carbamate hydrochloride (34 mg, 0.091 mmol), and diisoproylethylamine (59 mg, 0.45 mmol) in dichloromethane (0.5 mL) and N,N-dimethylformamide (0.5 mL) was stirred at room temperature for one hour. The reaction mixture was concentrated then dissolved in methanol (2 mL) and purified directly by preparative reverse phase HPLC to give methyl [6-(4-{[4-(fluoromethyl)piperidin-1-yl]carbonyl}-2,3,4,5-tetrahydro-1,4-benzoxazepin-7-yl)-1H-imidazo[4,5-b]pyridin-2-yl]carbamate, (21 mg, 48% yield), (400 MHz, DMSO-d$_6$): 8.41 (br, 1H), 7.87 (s, 1H), 7.54 to 7.44 (m, 2H), 7.05 (d, 1H), 4.45 (s, 2H), 4.31 (dd, 2H), 4.19 (m, 2H), 3.67 to 3.55 (m, 4H), 2.74 (t, 2H), 1.84 (br, 1H), 1.67 to 1.58 (m, 2H), 1.29 to 1.18 (m, 2H); MS (EI) for $C_{24}H_{27}FN6O_4$: 483 (MH$^+$).

Using analogous synthetic techniques and substituting with alternative starting reagents in step 5 the following compounds of the invention were prepared. Alternative starting materials were obtained commercially unless otherwise indicated.

methyl [6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-yl]carbamate. Prepared as the trifluoroacetate salt according to the method of example 15 by using 4-(1,1-difluoroethyl)piperidine-1-carbonyl chloride (reagent preparation 37) in step 4. $^1$H NMR (400 MHz, DMSO-d$_6$): 8.48 (s, 1H), 7.99 (s, 1H), 7.56 (s, 1H), 7.49 (d, 1H), 7.06 (d, 1H), 4.46 (s, 2H), 4.21 (m, 2H), 3.80 (s, 3H), 3.62 (m, 4H), 2.73 (m, 2H), 1.70 (m, 2H), 1.56 (t, 3H), 1.35 (m, 2H); MS (EI) for $C_{25}H_{28}F_2N_6O_4$: 515 (MH$^+$).

methyl [6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-yl]carbamate. Prepared as the acetate salt according to the method of example 15 by using 4-(2-fluoroethyl)piperidine-1-carbonyl chloride (reagent preparation 37) in step 4. $^1$H NMR (400 MHz, DMSO-d$_6$): 8.40 (s, 1H), 7.86 (s, 1H), 7.52 (s, 1H), 7.46 (d, 1H), 7.04 (d, 1H), 4.57 (m, 1H), 4.44 (m, 3H), 4.19 (m, 2H), 3.77 (s, 3H), 3.56 (m, 4H), 2.71 (m, 3H), 1.62 (m, 4H), 1.19 (m, 2H); MS (EI) for $C_{25}H_{29}FN_6O_4$: 497 (MH$^+$).

methyl [6-(4-{[2-(4-fluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate. Prepared according to the method of example 15 by using 2-(4-fluorophenyl)-4-oxopiperidine-1-carbonyl chloride (reagent preparation 37) in step 4. $^1$H NMR (400 MHz, DMSO-d$_6$): 8.39 (br, 1H), 7.87 (s, 1H), 7.57 (d, 1H), 7.48 (d, 1H), 7.28 (m, 2H), 7.07 (m, 2H), 5.20 (t, 1H), 4.59 (dd, 2H), 4.22 (m, 2H), 3.74, (s, 3H), 3.68 (m, 4H), 2.92 to 2.79 (m, 2H), 2.66 to 2.55 (m, 2H), 2.31 (dd, 2H); MS (EI) for $C_{29}H_{27}FN_6O_5$: 559 (MH$^+$).

methyl [6-(4-{[4-(fluoromethyl)-4-hydroxypiperidin-1-yl]carbonyl}-2,3,4,5-tetrahydro-1,4-benzoxazepin-7-yl)-1H-imidazo[4,5-b]pyridin-2-yl]carbamate. Prepared according to the method of example 15 by using 4-(fluoromethyl)-4-hydroxypiperidine-1-carbonyl chloride (reagent preparation 37) in step 4. $^1$H NMR (400 MHz, DMSO-d$_6$): 8.41 (br, 1H), 7.88 (s, 1H), 7.53 (br 1H), 7.47 (dd, 2H), 7.05 (d, 1H), 4.45 (s, 2H), 4.19 (m, 2H), 4.15 (d, 2H), 3.78 (s, 3H), 3.59 (m, 2H), 3.41 (m, 2H), 3.08 (t, 2H), 1.62 to 1.50 (m, 2H), 1.46 to 1.41 (m, 2H); MS (EI) for $C_{24}H_{27}FN_6O_5$: 499 (MH$^+$).

methyl [6-(4-{[2-(3,4-difluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate. Prepared according to the method of example 15 by using 2-(3,4-difluorophenyl)-4-oxopiperidine-1-carbonyl chloride (reagent preparation 37) in step 4. $^1$H NMR (400 MHz, DMSO-d$_6$): 8.41 (s, 1H), 7.88 (s, 1H), 7.59 (br, 1H), 7.33 (m, 1H), 7.29 (m, 2H), 7.05 (d, 1H), 5.15 (t, 1H), 4.60 (dd, 2H), 4.22 (m, 2H), 3.77 (s, 3H), 3.75 to 3.61 (m, 4H), 2.82 (m, 2H), 2.59 (m, 1H), 2.39 (dd, 1H); MS (EI) for $C_{29}H_{26}F_2N_6O_5$: 577 (MH$^+$).

methyl (6-{4-[(4-cyanopiperidin-1-yl)carbonyl]-2,3,4,5-tetrahydro-1,4-benzoxazepin-7-yl}-1H-imidazo[4,5-b]pyridin-2-yl)carbamate. Prepared according to the method of example 15 by using 4-cyanopiperidine-1-carbonyl chloride (reagent preparation 37) in step 4. $^1$H NMR (400 MHz, methanol-d$_4$): 8.43 (br, 1H), 7.86 (br, 1H), 7.55 (br, 1H), 7.46 (dd, 1H), 7.04 (d, 1H), 4.47 (s, 2H), 4.20 (m, 2H), 3.78 (s, 3H), 3.60 (m, 2H), 3.44 to 3.27 (m, 2H), 3.06 to 2.97 (m, 3H), 1.93 to 1.85 (m, 2H), 1.79 to 1.69 (m, 2H); MS (EI) for $C_{24}H_{25}N_7O_4$: 476 (MH$^+$).

Synthetic Example 16 methyl (6-{4-[(4-methylpiperidin-1-yl)carbonyl]-2,3,4,5-tetrahydro-1,4-benzoxazepin-7-yl}-1H-imidazo[4,5-b]pyridin-2-yl)carbamate STEP 1: To a mixture of 5-bromo-3-nitropyridin-2-amine (0.69 g, 3.2 mmol), {4-[(4-methylpiperidin-1-yl)carbonyl]-2,3,4,5-tetrahydro-1,4-benzoxazepine-7-yl}boronic acid (1.0 g, 3.2 mmol) (example 2, step 4), potassium bicarbonate (1.3 g, 2.3 mmol) and DIPEA (1.1 mL, 6.3 mmol) in DMA (12 mL) and water (3 mL) was added dichloro[1,1-bis(diphenylphosphino)ferrocenepalladium (II) dichloromethane adduct (0.12 g, 0.16 mmol). The reaction mixture was stirred at 99° C. for 12 hours and then partitioned between ethyl acetate (50 mL) and water (50 mL). The aqueous layer was extracted with ethyl acetate (2×30 mL) and the combined organic layers were dried over anhydrous magnesium sulfate, filtered and concentrated. The resulting brown residue was suspended in methanol (20 mL), filtered and washed with ethyl ether (2×30 mL) to afford 5-{4-[(4-methylpiperidin-1-yl)carbonyl]-2,3,4,5-tetrahydro-1,4-benzoxazepin-7-yl}-3-nitropyridin-2-amine (1.0 g, 77% yield) as a yellow solid. MS (EI) for $C_{21}H_{25}N_5O_4$: 412 (MH$^+$)

STEP 2: To a slurry of 5-{4-[(4-methylpiperidin-1-yl)carbonyl]-2,3,4,5-tetrahydro-1,4-benzoxazepin-7-yl}-3-nitropyridin-2-amine (1.0 g, 2.4 mmol), 10% Pd—C (0.1 g) and ethanol (15 mL) was added ammonium formate (1.5 g, 24 mmol) portionwise over 1 hour. The reaction mixture was stirred for an additional hour and the catalyst was removed by filtration. Concentration of the filtrate followed by purification by silica gel column chromatography (0-5% methanol in dichloromethane) provided 5-{4-[(4-methylpiperidin-1-yl)carbonyl]-2,3,4,5-tetrahydro-1,4-benzoxazepin-7-yl}pyridine-2,3-diamine (0.67 g, 72% yield) as a pale yellow foam. MS (EI) for $C_{21}H_{27}N_5O_2$: 382 (MH$^+$)

STEP 3: To a solution of 5-{4-[(4-methylpiperidin-1-yl)carbonyl]-2,3,4,5-tetrahydro-1,4-benzoxazepin-7-yl}pyridine-2,3-diamine (0.21 g, 0.55 mmol) in acetic acid (5 mL) was added 1,3-bis(methoxycarbonyl)-2-methyl-2-thiopseudourea (0.17 g, 0.82 mmol) and the resulting mixture was heated at 80° C. After 12 h the reaction mixture was diluted with ethyl ether (5 mL) and the resulting precipitate was collected by filtration. The resulting brown filter cake was dissolved in methanol and purified by preparative reverse phase HPLC to afford methyl (6-{4-[(4-methylpiperidin-1-yl)carbonyl]-2,3,4,5-tetrahydro-1,4-benzoxazepin-7-yl}-1H-imidazo[4,5-b]pyridin-2-yl)carbamate (0.030 g, 12% yield) as a pale yellow solid. $^1$H NMR (400 MHz, DMSO-d$_6$): 12.02 (bs, 1H), 8.44 (s, 1H), 7.85 (s, 1H), 7.38-7.55 (m, 2H), 6.96-7.06 (m, 1H), 4.36-4.44 (m, 2H), 4.06-4.22 (m, 2H), 3.76 (s, 3H), 3.44-3.60 (m, 4H), 2.68 (t, 2H) 1.43-1.61 (m, 3H), 1.20 (q, 2H), 0.90 (d, 3H); MS (EI) for $C_{24}H_{28}N_6O_4$: 465 (MH$^+$).

Synthetic Example 17

1-{[7-(2-amino-1H-imidazo[4,5-b]pyridin-6-yl)-2,3-dihydro-1,4-benzoxazepin-4(5H)-yl]carbonyl}piperidine-4-carboxamide and 1-{[7-(2-amino-1H-imidazo[4,5-b]pyridin-6-yl)-2,3-dihydro-1,4-benzoxazepin-4(5H)-yl]carbonyl}piperidine-4-carbonitrile STEP 1: A mixture of methyl (6-{4-[(4-cyanopiperidin-1-yl)carbonyl]-2,3,4,5-tetrahydro-1,4-benzoxazepin-7-yl}-1H-imidazo[4,5-b]pyridin-2-yl)carbamate (example 15) (50 mg, 0.11 mmol) was taken into methanol (1 mL) followed by addition of 1M aqueous potassium hydroxide solution (1 mL) and the mixture was stirred at 70° C. for 18 hours. The reaction mixture was then cooled to room temperature, adjusted to pH 10 with 6 M hydrochloric acid solution then concentrated to remove methanol, diluted with water (10 mL) and extracted with ethyl acetate (3×10 mL). The combined extract was dried over sodium sulfate then filtered and concentrated. The residue, composed of a mixture of the corresponding carbonitrile and carboxamide, was purified by preparative reverse phase HPLC to give 1-{[7-(2-amino-1H-imidazo[4,5-b]pyridin-6-yl)-2,3-dihydro-1,4-benzoxazepin-4(5H)-yl]carbonyl}piperidine-4-carboxamide (2.7 mg, 6% yield); $^1$H NMR (400 MHz, methanol-d$_4$): 8.15 (br, 1H), 7.67 (br, 1H), 7.48 (br, 1H), 7.44 (dd, 1H), 7.04 (d, 1H), 4.50 (s, 2H), 4.21 (m, 2H), 3.75 to 3.69 (m, 4H), 2.84 (t, 2H), 2.45 to 2.38 (m, 1H), 1.83 to 1.67 (m, 4H); MS (EI) for $C_{22}H_{25}N_7O_3$: 436 (MH$^+$); and 1-{[7-(2-amino-1H-imidazo[4,5-b]pyridin-6-yl)-2,3-dihydro-1,4-benzoxazepin-4(5H)-yl]carbonyl}piperidine-4-carbonitrile (3.9 mg, 9% yield); (400 MHz, methanol-d$_4$): 8.16 (br, 1H), 7.66 (br, 1H), 7.48 (br, 1H), 7.43 (dd, 1H), 7.04 (d, 1H), 4.50 (s, 2H), 4.21 (m, 2H), 3.70 (m, 2H), 3.47 (m, 2H), 3.14 (m, 2H), 3.14 (m, 2H), 2.99 (m, 1H), 1.95 (m, 2H), 3.83 (m, 2H), MS (EI) for $C_{22}H_{23}N_7O_2$: 418 (MH$^+$).

Using analogous synthetic techniques and substituting with alternative starting reagents in step 1 the following compounds of the invention were prepared. Alternative starting materials were obtained commercially unless otherwise indicated.

6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-amine. Prepared as the acetate salt according to the method of example 17 by using methyl [6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-yl]carbamate (example 15) in step 1. $^1$H NMR (400 MHz, DMSO-d$_6$): 8.11 (s, 1H), 7.52 (m, 2H), 7.44 (m, 1H), 7.00 (d, 1H), 6.64 (s, 2H), 4.44 (s, 2H), 4.17 (m, 2H), 3.62 (m, 4H), 2.72 (m, 2H), 1.99 (m, 1H), 1.70 (m, 2H), 1.57 (t, 3H), 1.37 (m, 2H); MS (EI) for $C_{23}H_{26}F_2N_6O_2$: 457 (MH$^+$).

6-(4-{[4-(difluoromethyl)piperidin-1-yl]carbonyl}-2,3,4,5-tetrahydro-1,4-benzoxazepin-7-yl)-1H-imidazo[4,5-b]pyridin-2-amine. Prepared as the acetate salt according to the method of example 17 by using methyl [6-(4-{[4-(difluoromethyl)piperidin-1-yl]carbonyl}-2,3,4,5-tetrahydro-1,4-benzoxazepin-7-yl)-1H-imidazo[4,5-b]pyridin-2-yl]carbamate (example 15) in step 1. $^1$H NMR (400 MHz, methanol-d$_4$): 8.15 (d, 1H), 7.65 (d, 1H), 7.48 (d, 1H), 7.43 (dd, 1H), 7.05 (d, 1H), 5.71 (m, 1H), 4.51 (s, 2H), 4.21 (m, 2H), 3.74 (m, 2H), 3.69 (m, 2H), 2.85 (m, 2H), 1.97 (m, 1H), 1.96 (s, 3H), 1.75 (m, 2H), 1.47 (m, 2H); MS (EI) for $C_{22}H_{24}F_2N_6O_2$: 443 (MH$^+$).

6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-amine. Prepared as acetate salt according to the method of example 17 by using methyl [6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-yl]carbamate (example 15) in step 1. $^1$H NMR (400 MHz, methanol-d$_4$): 8.15 (s, 1H), 7.66 (s, 1H), 7.58 (d, 1H), 7.436 (dd, 1H), 7.05 (d, 1H), 4.56 (m, 1H), 4.49 (s, 2H), 4.44 (m, 1H), 3.69 (m, 4H), 2.84 (m, 2H), 1.97 (s, 3H), 1.78-1.59 (m, 5H), 1.28 (m, 2H); MS (EI) for $C_{23}H_{27}FN_6O_2$: 439 (MH$^+$).

6-(4-{[4-(fluoromethyl)piperidin-1-yl]carbonyl}-2,3,4,5-tetrahydro-1,4-benzoxazepin-7-yl)-1H-imidazo[4,5-b]pyridin-2-amine. Synthesized according to the method of example 17 using methyl [6-(4-{[4-(fluoromethyl)piperidin-1-yl]carbonyl}-2,3,4,5-tetrahydro-1,4-benzoxazepin-7-yl)-1H-imidazo[4,5-b]pyridin-2-yl]carbamate (example 15) in step 1. $^1$H NMR (400 MHz, DMSO-d$_6$): 8.12 (br, 1H), 7.53 (s, 1H), 7.49 (br, 1H), 7.44 (dd, 1H), 7.00 (d, 1H), 4.42 (s, 2H), 4.31 (dd, 2H), 4.17 (m, 2H), 3.62 to 3.54 (m, 4H), 2.74 (t, 2H), 1.83 (br, 1H), 1.65 to 1.59 (m, 2H), 1.31 to 1.19 (m, 2H); MS (EI) for $C_{22}H_{25}FN_6O_2$: 425 (MH$^+$)

Synthetic Example 18

1-{[7-(2-amino-1H-imidazo[4,5-b]pyridin-6-yl)-2,3-dihydro-1,4-benzoxazepin-4(5H)-yl]carbonyl}-2-(3-fluorophenyl)piperidin-4-one STEP 1: To a solution of 1,1-dimethylethyl 7-(5,6-diaminopyridin-3-yl)-2,3-dihydro-1,4-benzoxazepine-4(5H)-carboxylate (example 15, step 2) (0.23 g, 0.65 mmol) in acetic acid (10 mL) was added 1,3-bis(benzyloxycarbonyl)-2-methyl-2-thiopseudourea (0.27 g, 0.76 mmol) and the resulting mixture was heated at 50° C. After 4 h the reaction mixture was concentrated then suspended in ethyl acetate (10 mL). Filtration followed by washing the cake with ethyl acetate (2×10 mL) provided 1,1-dimethylethyl 7-[2-({[(phenylmethyl)oxy]carbonyl}amino)-1H-imidazo[4,5-b]pyridin-6-yl]-2,3-dihydro-1,4-benzoxazepine-4(5H)-carboxylate (0.3 g, 91% yield) as a white solid. MS (EI) for $C_{28}H_{29}N_5O_5$: 516 (MH$^+$).

STEP 2: To a solution of 1,1-dimethylethyl 7-[2-({[(phenylmethyl)oxy]carbonyl}amino)-1H-imidazo[4,5-b]pyridin-6-yl]-2,3-dihydro-1,4-benzoxazepine-4(5H)-carboxylate (0.49 g, 1.9 mmol) in dichloromethane (10 mL) was added trifluoroacetic acid (10 mL) and the resulting solution was heated at 50° C. After 1 h the reaction mixture was concentrated and the residue was concentrated three times from ethyl acetate (30 mL) to afford phenylmethyl [6-(2,3,4,5-tetrahydro-1,4-benzoxazepin-7-yl)-1H-imidazo[4,5-b]pyridin-2-yl]carbamate as the bis-trifluoroacetate salt (0.48 g, 95% yield). MS (EI) for $C_{23}H_{21}N_5O_3$: 416 (MH$^+$).

STEP 3: To a solution of phenylmethyl [6-(2,3,4,5-tetrahydro-1,4-benzoxazepin-7-yl)-1H-imidazo[4,5-b]pyridin-2-yl]carbamate bis-trifluoroacetate salt (0.40 g, 0.75 mmol) and DIPEA (1.0 mL, 5.7 mmol) in DMF (10 mL) was added 2-(3-fluorophenyl)-4-oxopiperidine-1-carbonyl chloride (reagent preparation 37) (0.31 g, 1.2 mmol) and the resulting mixture was heated at 50° C. After 12 h, the reaction mixture was partitioned between ethyl acetate (30 mL) and water (30 mL). The organic layer was washed with brine (30 mL), dried over anhydrous magnesium sulfate then filtered and concentrated. Column chromatography on silica (1-10% isopropanol in dichloromethane) yielded phenylmethyl [6-(4-{[2-(3-fluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate (0.15 g, 31% yield) as a waxy solid. MS (EI) for $C_{35}H_{31}FN_6O_5$: 635 (MH$^+$).

STEP 4: A solution of phenylmethyl [6-(4-{[2-(3-fluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate (0.15 g, 0.24 mmol) in acetic acid (5 mL) was hydrogenated at 1 atm over 10% palladium on carbon (0.15 g) for 18 h. The catalyst was removed by filtration and the filtrate was concentrated. The resulting brown residue was dissolved in methanol and purified by preparative reverse phase HPLC to afford 1-{[7-(2-amino-1H-imidazo[4,5-b]pyridin-6-yl)-2,3-dihydro-1,4-benzoxazepin-4(5H)-yl]carbonyl}-2-(3-fluorophenyl)piperidin-4-one (46 mg, 39% yield) as a pale yellow solid. $^1$H NMR (400 MHz, CDCl$_3$): 11.44 (bs, 1H), 8.17 (s, 1H), 6.97-7.60 (m, 7H), 6.75 (s, 1H), 5.18 (t, 1H), 4.51-4.66 (m, 2H), 4.13-4.30 (m, 2H), 3.56-3.78 (m, 3H), 3.21-3.31 (m, 1H), 2.79-2.99 (m, 2H), 2.51-2.61 (m, 1H), 2.32 (d, 1H); MS (EI) for $C_{27}H_{25}FN_6O_3$: 501 (MH$^+$)

Using analogous synthetic techniques and substituting with alternative starting reagents in step 3 the following compounds of the invention were prepared. Alternative starting materials were obtained commercially unless otherwise indicated.

8-{[7-(2-amino-1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-(endo)-ol. Synthesized as the hydrochloride salt according to the method of example 18 using 3-hydroxy-3-(endo)-(trifluoromethyl)-8-azabicyclo[3.2.1]octane-8-carbonyl chloride (reagent preparation 37) in step 3. $^1$H NMR (400 MHz, DMSO-d$_6$): 8.58 (bs, 2H), 8.34 (s, 1H), 7.90 (s, 1H), 7.54 (s, 1H), 7.49 (d, 1H), 7.03 (d, 1H), 5.85 (s, 1H), 4.19-4.27 (m, 2H), 4.00-4.08 (m, 2H), 3.31-3.48 (m, 2H), 1.95-2.10 (m, 4H), 1.67-1.81 (m, 4H); MS (EI) for $C_{24}H_{25}F_3N_6O_3$: 503 (MH$^+$).

Synthetic Example 19

N-[5-(4-{[4-(fluoromethyl)piperidin-1-yl]carbonyl}-2,3,4,5-tetrahydro-1,4-benzoxazepin-7-yl)-1H-benzimidazol-2-yl]acetamide STEP 1: 4-bromobenzene-1,2-diamine (1.02 g, 5.45 mmol) was taken into 50% aqueous methanol (25 mL) followed by slow addition of cyanogen bromide (1.73 g, 16.35 mmol) and the mixture was allowed to stir at room temperature over 12 h. The mixture was then concentrated to approximately 50% volume, diluted with water and brought to neutral pH by addition of 2 M aqueous sodium hydroxide. The aqueous mixture was then partitioned with ethyl acetate and the organic solution washed with brine, dried over anhydrous sodium sulfate, filtered and concentrated to give 6-bromo-1H-benzimidazol-2-amine (1.67 g) as a red amorphous residue. MS (EI) for $C_7H_6BrN_3$: 213 (MH$^+$).

STEP 2: 6-Bromo-1H-benzimidazol-2-amine as obtained in step 1 was taken into THF (40 mL) followed by addition of di-tert-butyl dicarbonate (1.5 g, 6.86 mmol) and the resulting solution was stirred for 30 minutes at room temperature then concentrated. The residue was suspended in hexanes and the crystalline solid collected by filtration and dried to give a mixture of tert-butyl 2-amino-6-bromo-1H-benzimidazole-1-carboxylate and tert-butyl 2-amino-6-bromo-1H-benzimidazole-1-carboxylate (1.17 g, 69% yield over 2 steps). MS (EI) for $C_{12}H_{14}BrN_3O_2$: 256 (M-t-Bu$^+$).

STEP 3: BOC-protected 6-Bromo-1H-benzimidazol-2-amine as obtained in step 2 as a mixture of N1,N3 isomers (52 mg, 0.17 mmol) was taken into THF (2 mL) followed by addition of DIPEA (60 uL, 0.34 mmol) then acetic anhydride (32 uL, 0.34 mmol) and the mixture was brought to reflux for 12 h. The resulting solution was concentrated and the residue taken into TFA then allowed to stand for 1 h at room temperature. The solution was concentrated and the residue partitioned with an ethyl ether/hexane mixture and saturated aqueous sodium bicarbonate. The resulting suspension was filtered and the filter cake washed with water then hexanes and dried to give N-(6-bromo-1H-benzimidazol-2-yl)acetamide (37.2 mg, 88% yield). $^1$H NMR (400 MHz, d$_6$-DMSO): 7.60 (d, 1H), 7.39 (d, 1H), 7.21 (dd, 1H), 2.16 (s, 3H).

STEP 4: (4-{[(1,1-dimethylethyl)oxycarbonyl}-2,3,4,5-tetrahydro-1,4-benzoxazepin-7-yl)boronic acid (Example 1, step 2) (1.07 g, 3.64 mmol) was dissolved into 4M hydrogen chloride in dioxane and the resulting solution was allowed to stir at room temperature for 1.3 h. The heterogeneous mixture was then diluted with ethyl ether (100 mL) and the solid collected by filtration to give 2,3,4,5-tetrahydro-1,4-benzoxazepin-7-ylboronic acid hydrochloride salt (791 mg, 95%). $^1$H NMR (400 MHz, D$_2$O): 7.79 (dd, 1H), 7.74 (d, 1H), 7.21 (d, 1H), 4.47 (s, 2H), 4.36 (m, 2H), 3.69 (m, 2H).

STEP 5: 2,3,4,5-tetrahydro-1,4-benzoxazepin-7-ylboronic acid hydrochloride salt (188 mg, 0.82 mmol) was taken into 50% aqueous THF (2 mL) followed by addition of solid sodium bicarbonate (360 mg, 4.3 mmol) then 4-(fluoromethyl)piperidine-1-carbonyl chloride (reagent preparation 37) (218 mg, 1.21 mmol) in a minimum of THF. The mixture was stirred at room temperature over 1 h then partitioned with 0.5M aqueous hydrochloric acid and ethyl acetate. The organic solution was then brine washed, dried over anhydrous sodium sulfate, filtered and concentrated. The residue obtained was taken into isopropyl acetate and extracted once with 1M aqueous sodium hydroxide. The aqueous solution was then acidified to pH 2 using concentrated hydrochloric acid and extracted once with ethyl acetate then brine washed, dried over anhydrous sodium sulfate, filtered and concentrated to provide (4-{[4-(fluoromethyl)piperidin-1-yl]carbonyl}-2,3,4,5-tetrahydro-1,4-benzoxazepin-7-yl)boronic acid (143 mg, 52% yield) as an amorphous residue. MS (EI) for $C_{16}H_{22}BrFN_2O_4$: 337 (MH$^+$).

STEP 6: (4-{[4-(fluoromethyl)piperidin-1-yl]carbonyl}-2,3,4,5-tetrahydro-1,4-benzoxazepin-7-yl)boronic acid (67.2 mg, 0.2 mmol), N-(6-bromo-1H-benzimidazol-2-yl)acetamide (34.8 mg, 0.14 mmol) and dichloro[1,1-bis(diphenylphosphino)ferrocenepalladium (II) dichloromethane adduct (6 mg) was taken into dioxane (0.5 mL) followed by addition of water (0.1 mL) and DIPEA (0.14 mL). The resulting mixture was heated in a sealable vessel at 85° C. for 12 h then cooled to room temperature. The mixture was diluted with ethyl acetate, dried over anhydrous sodium sulfate and filtered through a silica plug with an ethyl acetate wash. The organic filtrate was washed once with 1M aqueous sodium hydroxide, dried over anhydrous sodium sulfate, filtered and concentrated. The residue was chromatographed on silica gel (100% ethyl acetate to 4:1 ethyl acetate:ethanol) to give N-[5-(4-{[4-(fluoromethyl)piperidin-1-yl]carbonyl}-2,3,4,5-tetrahydro-1,4-benzoxazepin-7-yl)-1H-benzimidazol-2-yl]acetamide as a colorless solid. $^1$H NMR (400 MHz, d$_4$-methanol): 7.64 (dd, 1H), 7.51-7.48 (m, 2H), 7.46 (dd, 1H), 7.40 (dd, 1H), 7.03 (d, 1H), 4.49 (s, 2H), 4.35 (d, 1H), 4.23 (d, 1H), 4.19 (m, 2H), 3.74 (d, 2H), 3.68 (m, 2H), 2.85 (br tr, 2H), 2.25 (s, 3H), 1.88 (br, 1H), 1.71 (d, 2H), 1.36 (d q, 2H). MS (EI) for $C_{25}H_{28}FN_5O_3$: 337 (MH$^+$).

Using analogous synthetic techniques and substituting with alternative starting reagents in steps 5 and 6 then conducting protecting group removal as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

8-({7-[2-(ethylamino)-1H-imidazo[4,5-b]pyridin-6-yl]-2,3-dihydro-1,4-benzoxazepin-4(5H)-yl}carbonyl)-3-(trifluoromethyl)-8-azabicyclo[3.2.1]octan-3-ol. Synthesized according to the method of example 19 using 3-hydroxy-3-(trifluoromethyl)-8-azabicyclo[3.2.1]octane-8-carbonyl chloride (reagent preparation 37) in step 5 and 6-bromo-N-ethyl-1-(methoxymethyl)-1H-imidazo[4,5-b]pyridin-2-amine (reagent preparation 38) in step 6. $^1$H NMR (400 MHz, d$_6$-DMSO) δ 11.03 (s, 1H), 8.08 (d, 1H), 7.49 (m, 3H), 7.11 (s, 1H), 6.99 (d, 1H), 5.83 (s, 1H), 4.51 (s, 2H), 4.19 (m, 2H), 4.05 (m, 2H), 3.66 (m, 2H), 3.34 (q, 2H), 2.04 (m, 4H), 1.74 (m, 4H), 1.18 (t, 3H); MS (ES) for $C_{26}H_{29}F_3N_6O_3$: 531 (MH$^+$).

8-{[7-{6-amino-5-[(3-aminoazetidin-1-yl)sulfonyl]pyridin-3-yl}-2,3-dihydro-1,4-benzoxazepin-4(5H)-yl]carbonyl}-3-(trifluoromethyl)-8-azabicyclo[3.2.1]octan-3-ol. Synthesized according to the method of example 19 using 3-hydroxy-3-(trifluoromethyl)-8-azabicyclo[3.2.1]octane-8-carbonyl chloride (reagent preparation 37) in step 5 and tert-butyl 1-(2-amino-5-bromopyridin-3-ylsulfonyl)azetidin-3-ylcarbamate (reagent preparation 40) in step 6. $^1$H NMR (400 MHz, d$_6$-DMSO) δ 8.56 (d, 1H), 7.93 (d, 1H), 7.47 (d, 1H), 7.44 (dd, 1H), 6.99 (d, 1H), 6.76 (bs, 2H), 5.82 (bs, 1H), 4.52 (s, 2H), 4.21 (m, 2H), 4.04 (m, 2H), 3.88 (t, 2H), 3.67 (m, 2H), 3.57 (m, 1H), 3.38 (t, 2H), 2.04 (m, 4H), 1.73 (m, 4H); MS (ES) for $C_{26}H_{31}F_3N_6O_5S$: 597 (MH$^+$).

N-[2-chloro-5-(4-{[3-hydroxy-3-(trifluoromethyl)-8-azabicyclo[3.2.1]oct-8-yl]carbonyl}-2,3,4,5-tetrahydro-1,4-benzoxazepin-7-yl)pyridin-3-yl]methanesulfonamide. Synthesized according to the method of example 19 using 3-hydroxy-3-(trifluoromethyl)-8-azabicyclo[3.2.1]octane-8-carbonyl chloride (reagent preparation 37) in step 5 and N-(5-bromo-2-chloropyridin-3-yl)methanesulfonamide (reagent preparation 39) in step 6. $^1$H NMR (400 MHz, d$_6$-DMSO) δ 9.84 (s, 1H), 8.49 (s, 1H), 8.01 (s, 1H), 7.58 (s, 1H), 7.53 (d, 1H), 7.04 (d, 1H), 5.82 (s, 1H), 4.54 (s, 2H), 4.25 (s, 2H), 4.03 (s, 2H), 3.68 (s, 2H), 3.15 (s, 3H), 2.02 (m, 4H), 1.72 (m, 4H); MS (ES) for $C_{24}H_{26}ClF_3N_4O_5S$: 575 (MH$^+$).

Synthetic Example 20

2-(3-fluorophenyl)-1-{[7-(3H-imidazo[4,5-b]pyridin-6-yl)-2,3-dihydro-1,4-benzoxazepin-4(5H)-yl]carbonyl}piperidin-4-one STEP 1: A suspension of 5-bromopyridine-2,3-diamine (3.00 g, 15.9 mmol) in trimethoxymethane (20 mL) was heated to 95° C. for one hour. After cooling to room temperature the solid was collected by filtration, and then washed with diethyl ether to give 6-bromo-1H-imidazole[4,5-b]pyridine (3.00 g, 95% yield) as a tan solid.

STEP 2: A solution of 6-bromo-1H-imidazole[4,5-b]pyridine (3.00 g, 15 mmol) and diisopropylethylamine (5.8 g, 45 mmol) in dimethylformamide (20 mL) was cooled to –10° C. followed by dropwise addition of isobutyl chloroformate (2.18 g, 16 mmol) and the mixture was stirred at room temperature for 30 minutes. The mixture was diluted with ethyl acetate (80 mL) and washed with 0.1 N aqueous hydrochloric acid (50 mL), saturated aqueous sodium bicarbonate (50 mL), and brine (25 mL). The organic layer was dried over anhydrous sodium sulfate, filtered and concentrated to give isobutyl 6-bromo-1H-imidazo[4,5-b]pyridine-1-carboxylate (4.3 g, 96% yield) as a tan solid. MS (EI) for $C_{11}H_{12}BrN_3O_2$: 299 (MH$^+$).

STEP 3: A flask was charged with isobutyl 6-bromo-1H-imidazo[4,5-b]pyridine-1-carboxylate (2.00 g, 6.82 mmol), (4-{[(1,1-dimethylethyl)oxy]carbonyl}-2,3,4,5-tetrahydro-1,4-benzoxazepin-7-yl)boronic acid (example 1, step 2) (2.00 g, 6.82 mmol), dichloro[1,1-bis(diphenylphosphino]ferrocenepalladium (II) dichloromethane adduct (0.14 g, 0.17 mmol), and diisopropylethylamine (3.50 g, 27.2 mmol) in dry dioxane (60 mL) and the mixture heated to 95° C. for 24 hours. The resulting mixture was diluted with ethyl acetate (100 mL) then washed with water (50 mL), 10% aqueous citric acid (50 mL) and brine. The organic phase was dried over anhydrous sodium sulfate, filtered and concentrated. The residue was purified by silica gel column chromatography (ethyl acetate/hexane, 1:1) to give 1,1-dimethylethyl 7-(1-{[(2-methylpropyl)oxy]carbonyl}-1H-imidazo[4,5-b]pyridine-6-yl)-2,3-dihydro-1,4-benzoxazepine-4(5H)-carboxylate (1.45 g, 46% yield) as a brown oil. MS (EI) for $C_{25}H_{30}N_4O_5$: 467 (MH$^+$).

STEP 4: To a solution of 1,1-dimethylethyl 7-(1-{[(2-methylpropyl)oxy]carbonyl}-1H-imidazo[4,5-b]pyridine-6-yl)-2,3-dihydro-1,4-benzoxazepine-4(5H)-carboxylate (0.40 g, 0.86 mmol) in chloroform (4 mL) was added dropwise trifluoroacetic acid (5 mL) and the solution then warmed to 80° C. for 45 minutes. After cooling, the solution was concentrated and dried to give 2-methylpropyl 6-(2,3,4,5-tetrahydro-1,4-benzoxazepin-7-yl)-1H-imidazo[4,5-b]pyridine-1-carboxylate (0.37 g, 90% yield) as the trifluoroacetic acid salt. MS (EI) for $C_{20}H_{25}N_4O_3$: 367 (MH$^+$).

STEP 5: A solution of 2-methylpropyl 6-(2,3,4,5-tetrahydro-1,4-benzoxazepin-7-yl)-1H-imidazo[4,5-b]pyridine-1-carboxylate trifluoroacetic acid salt (0.20 g, 0.53 mmol), 2-(3-fluorophenyl)-4-oxopiperidine-1-carbonyl chloride (reagent preparation 37) (0.13 g, 0.51 mmol) and diisopropylethylamine (3.0 g, 23 mmol) in N,N-dimethylformamide (8 mL) was heated to 65° C. for 18 hours. The resulting mixture was diluted with ethyl acetate (50 mL) and washed with water (2×25 mL) and once with brine (15 mL) then dried over anhydrous sodium sulfate, filtered and concentrated. The residue was purified by silica gel column chromatography (acetone/ethyl acetate, 1:4) to give 2-methylpropyl 6-(4-{[2-(3-fluorophenyl)-4-oxopiperidin-1-yl]carbonyl}-2,3,4,5-tetrahydro-1,4-benzoxazepin-7-yl)-1H-imidazo[4,5-b]pyridine-1-carboxylate (0.19 g, 64% yield). MS (EI) for $C_{35}H_{35}FN_5O_5$: 586 (MH$^+$)

STEP 6: 2-methylpropyl 6-(4-{[2-(3-fluorophenyl)-4-oxopiperidin-1-yl]carbonyl}-2,3,4,5-tetrahydro-1,4-benzoxazepin-7-yl)-1H-imidazo[4,5-b]pyridine-1-carboxylate (0.19 g, 0.32 mmol) and potassium carbonate (0.20 g, 1.4 mmol) in methanol (10 mL) was stirred for 45 minutes at 25° C. The mixture was diluted with ethyl acetate (80 mL) washed with water (50 mL) and brine (25 mL), then dried over anhydrous sodium sulfate, filtered and concentrated. The residue was chromatographed on silica gel (methanol/ethyl acetate 1:10). Residue obtained by the concentration of product containing fractions was stirred 18 hours at 25° C. in diethyl ether (20 mL) and the solid product thus formed was isolated by filtration to give 2-(3-fluorophenyl)-1-{[7-(3H-imidazo[4,5-b]pyridin-6-yl)-2,3-dihydro-1,4-benzoxazepin-4(5H)-yl]carbonyl}piperidin-4-one (0.45 g, 27% yield). $^1$H NMR (400 MHz, d$_6$-DMSO): 8.62 (s, 1H), 8.47 (s, 1H), 8.18 (s, 1H), 7.69 (d, 1H), 7.57 (d, 1H), 7.24 (q, 1H), 7.10-7.01 (m, 4H), 5.19 (t, 1H), 4.61 (m, 2H), 4.24 (m, 2H), 3.72 (m, 3H), 3.41 (m, 2H), 2.84 (m, 2H), 2.61 (m, 1H), 2.34 (d, 1H); MS (EI) for $C_{27}H_{24}FN_5O_3$: 486 (MH$^+$).

Using analogous synthetic techniques and substituting with alternative starting reagents in step 1 the following compounds of the invention were prepared.

2-(3-fluorophenyl)-1-{[7-(2-methyl-3H-imidazo[4,5-b]pyridin-6-yl)-2,3-dihydro-1,4-benzoxazepin-4(5H)-yl]carbonyl}piperidin-4-one. Prepared according to the method of example 20 by using triethyl orthoacetate in step 1. $^1$H NMR (400 MHz, d$_6$-DMSO): 12.69 (d, 1H), 8.49 (dd, 1H), 8.00 (dd, 1H), 7.65 (s, 1H), 7.55 (dd, 1H), 7.28 (q, 1H), 7.05 (m, 4H), 5.18 (t, 1H), 4.61 (m, 2H), 4.22 (m, 2H), 3.71 (m, 3H), 3.38 (m, 5H), 2.84 (m, 2H), 2.52 (d, 2H), 2.35 (m, 1H). MS (EI) for $C_{28}H_{26}FN_5O_3$: 500 (MH$^+$).

Synthetic Example 21

1-({7-[4-(1H-imidazol-2-yl)phenyl]-2,3-dihydro-1,4-benzoxazepin-4(5H)-yl}carbonyl)piperidine-4-carbonitrile STEP 1: 2-(4-Bromophenyl)imidazole (330 mg, 1.48 mmol) was suspended in THF (10 mL) and DMAP (194 mg, 1.59 mmol) then di-tert-butyl dicarbonate (366 mg, 1.68 mmol) were sequentially added. The mixture was stirred for 1 h then concentrated and partitioned with ethyl acetate and 10% aqueous citric acid. The organic solution was washed with brine, dried over anhydrous sodium sulfate then filtered and concentrated to afford 1,1-dimethylethyl 2-(4-bromophenyl)-1H-imidazole-1-carboxylate (457 mg, 96% yield) as an oil.

STEP 2: 1,1-Dimethylethyl 2-(4-bromophenyl)-1H-imidazole-1-carboxylate (457 mg, 1.41 mmol) and (4-{[(1,1-dimethylethyl)oxy]carbonyl}-2,3,4,5-tetrahydro-1,4-benzoxazepin-7-yl)boronic acid (example 1, step 2) (456 mg, 1.55 mmol) were taken into dioxane (5 mL) and water (1 mL) followed by addition of DIPEA (1.1 mL, 6.2 mmol) and dichloro[1,1-bis(diphenylphosphino)ferrocenepalladium (II) dichloromethane adduct (58 mg) then the mixture was heated at 80° C. over 12 h. The mixture was cooled then partitioned with ethyl acetate and 10% aqueous citric acid. The organic solution was washed with brine, dried over anhydrous sodium sulfate then filtered and concentrated. The residue thus obtained was taken into methanol (10 mL) followed by addition of sodium hydroxide (180 mg, 4.5 mmol) in water (1 mL). The mixture was stirred at room temperature for 30 minutes then neutralized by addition of 10% aqueous citric acid then concentrated. The aqueous residue was partitioned with ethyl acetate and saturated aqueous sodium bicarbonate and the organic solution was washed with brine, dried over anhydrous sodium sulfate then filtered and concentrated to give 1,1-dimethylethyl 7-[4-(1H-imidazol-2-yl)phenyl]-2,3-dihydro-1,4-benzoxazepine-4(5H)-carboxylate (490 mg, 89% yield). MS (EI) for $C_{23}H_{25}N_3O_3$: 392 (MH$^+$).

STEP 3: 1,1-dimethylethyl 7-[4-(1H-imidazol-2-yl)phenyl]-2,3-dihydro-1,4-benzoxazepine-4(5H)-carboxylate (490 mg, 1.25 mmol) was taken into dichloromethane (20 mL) followed by sequential addition of DIPEA (0.4 mL, 2.3 mmol) and isobutyl chloroformate (0.18 mL, 1.4 mmol) and the mixture was stirred at room temperature for 30 minutes. The mixture was concentrated then partitioned with ethyl acetate and 10% aqueous citric acid. The organic solution was washed with brine, dried over anhydrous sodium sulfate then filtered and concentrated. The residue thus obtained was taken into TFA (5 mL) and allowed to stand for 30 minutes at room temperature. The mixture was concentrated and the residue was partitioned with ethyl acetate and saturated aqueous sodium bicarbonate and the organic solution was washed with brine, dried over anhydrous sodium sulfate then filtered and concentrated to give 2-methylpropyl 2-[4-(2,3,4,5-tetrahydro-1,4-benzoxazepin-7-yl)phenyl]-1H-imidazole-1-carboxylate (361 mg, 65% yield). MS (EI) for $C_{23}H_{25}N_3O_3$: 392 (MH$^+$).

STEP 4: 2-methylpropyl 2-[4-(2,3,4,5-tetrahydro-1,4-benzoxazepin-7-yl)phenyl]-1H-imidazole-1-carboxylate (361 mg, 0.92 mmol) was taken into dichloromethane (5 mL) followed by addition of DIPEA (0.32 mL, 1.84 mmol). The solution thus obtained was added slowly by syringe over several minutes to a solution of phosgene (20 W % in toluene, 0.49 mL, 0.93 mmol) diluted in dichloromethane (5 mL) and cooled to 0° C. The resulting mixture was stirred for 5 minutes then allowed to warm to room temperature and concentrated. The residue was taken back into dichloromethane (5 mL) followed by addition of DIPEA (0.48 mL, 2.76 mmol) and 4-cyanopiperidine hydrochloride salt (156 mg, 1.06 mmol) then stirred for 12 h. The mixture was concentrated then partitioned with ethyl acetate and 10% aqueous citric acid. The organic solution was washed with brine, dried over anhydrous sodium sulfate then filtered and concentrated. The residue was purified by silica gel chromatography (100% ethyl acetate) to give 2-methylpropyl 2-(4-{4-[(4-cyanopiperidin-1-yl)carbonyl]-2,3,4,5-tetrahydro-1,4-benzoxazepin-7-yl}phenyl)-1H-imidazole-1-carboxylate (296 mg, 61% yield) as a crystalline solid. MS (EI) for $C_{30}H_{33}N_5O_4$: 529 (MH$^+$).

STEP 5: 2-Methylpropyl 2-(4-{4-[(4-cyanopiperidin-1-yl)carbonyl]-2,3,4,5-tetrahydro-1,4-benzoxazepin-7-yl}phenyl)-1H-imidazole-1-carboxylate (296 mg, 0.56 mmol) was taken into methanol (10 mL), THF (2 mL) and water (0.5 mL) then warmed to give a homogeneous solution. Potassium carbonate (160 mg, 1.15 mmol) and the mixture was stirred for 30 minutes. The mixture was then concentrated and partitioned with ethyl acetate and 10% aqueous citric acid. The organic solution was washed with brine, dried over anhydrous sodium sulfate then filtered and concentrated. The residue was purified by silica gel chromatography (10% ethanol in ethyl acetate) to give 1-({7-[4-(1H-imidazol-2-yl)phenyl]-2,3-dihydro-1,4-benzoxazepin-4(5H)-yl}carbonyl)piperidine-4-carbonitrile (155 mg, 65% yield). $^1$H NMR (400 MHz, d$_4$-methanol): 7.92 (d, 2H), 7.69 (d, 2H), 7.56 (d, 1H), 7.51 (dd, 1H), 7.15 (s, 2H), 7.04 (d, 1H), 4.51 (s, 2H), 4.21 (tr, 2H), 3.70 (tr, 2H), 3.49-3.43 (m, 2H), 3.13 (m, 2H), 2.97 (m, 1H), 1.98-1.93 (m, 2H), 1.86-1.78 (m, 2H). MS (EI) for $C_{25}H_{25}N_5O_2$: 429 (MH$^+$).

Using analogous synthetic techniques and substituting with alternative starting reagents in step 4 the following compounds of the invention were prepared. Alternative starting materials were obtained commercially unless otherwise indicated.

4-{[4-(fluoromethyl)piperidin-1-yl]carbonyl}-7-[4-(1H-imidazol-2-yl)phenyl]-2,3,4,5-tetrahydro-1,4-benzoxazepine. Synthesized according to the method of example 21 using 4-(fluoromethyl)piperidine (reagent preparation 7) in step 4. $^1$H NMR (400 MHz, d$_4$-methanol): 8.00 (d, 2H), 7.71 (d, 2H), 7.60 (d, 1H), 7.55 (dd, 1H), 7.16 (br, 2H), 7.02 (d, 1H), 4.44 (s, 2H), 4.37 (d, 1H), 4.26 (d, 1H), 4.20 (br s, 2H), 3.59-3.56 (m, 4H), 2.74 (tr, 2H), 1.83 (br, 1H), 1.62 (d, 2H), 1.26 (br q, 2H). MS (EI) for $C_{25}H_{27}N_4O_2$: 435 (MH$^+$).

Synthetic Example 22

2-(4-fluorophenyl)-1-({7-[4-(1H-imidazol-2-yl)phenyl]-2,3-dihydro-1,4-benzoxazepin-4(5H)-yl}carbonyl)piperidin-4-one STEP 1: A solution of isobutyl 2-(4-bromophenyl)-1H-imidazole-1-carboxylate (example 4, step 5) (0.50 g, 1.55 mmol), (4-{[(1,1-dimethylethyl)oxy]carbonyl}-2,3,4,5-tetrahydro-1,4-benzoxazepin-7-yl)boronic acid (example 1, step 2) (0.63 g, 1.70 mmol) and diisopropyethylamine (1.50 mL, 8.50 mmol) in 20% aqueous 1,4-dioxane (10 mL) was deoxygenated for five minutes by bubbling nitrogen gas into it, followed by the addition of 1,1'-bis(diphenylphosphino)ferrocenedichloropalladium(II) complex with dichloromethane (70 mg, 0.085 mmol). The reaction mixture was heated to 80° C. for 2 hours. On cooling to room temperature the mixture was diluted with ethyl acetate (250 mL) then filtered through a pad of Celite. The organic filtrate was washed with 10% aqueous citric acid (50 mL), brine then dried over anhydrous sodium sulfate, filtered and concentrated. Silica gel column chromatography (hexane-ethyl acetate 9:1 to 7:3) provided 1,1-dimethylethyl 7-[4-(1-{[(2-methylpropyl)oxy]carbonyl}-1H-imidazol-2-yl)phenyl]-2,3-dihydro-1,4-benzoxazepine-4(5H)-carboxylate (0.32 g, 43%). $^1$H NMR (400 MHz, d$_6$-DMSO): 7.73 (d, 1H), 7.67 (s, 4H), 7.56 (m, 2H), 7.14 (d, 1H), 7.08 (m, 1H), 4.56 (br s, 1H), 4.51 (br s, 2H), 4.13 (br s, 1H), 4.08 (m, 2H), 3.74 (m, 2H), 1.86 (m, 1H), 1.34 (s, 1H), 1.32 (s, 9H), 0.77 (d, 6H). MS (EI) for $C_{28}H_{33}N_3O_5$: 492 (MH$^+$).

STEP 2: To a solution of 1,1-dimethylethyl 7-[4-(1-{[(2-methylpropyl)oxy]carbonyl}-1H-imidazol-2-yl)phenyl]-2,3-dihydro-1,4-benzoxazepine-4(5H)-carboxylate (0.30 g, 0.61 mmol) in dichloromethane (100 mL) was added trifluoroacetic acid (20 mL) and the reaction mixture was heated to reflux. After cooling to room temperature the solvent was evaporated. The residue was dissolved in ethyl acetate (250 mL). The organic layer was washed with saturated aqueous sodium bicarbonate (2×100 mL), brine, dried over anhydrous sodium sulfate then filtered and concentrated to give 2-methylpropyl 2-[4-(2,3,4,5-tetrahydro-1,4-benzoxazepin-7-yl)phenyl]-1H-imidazole-1-carboxylate (0.22 g, 92%). MS (EI) for $C_{23}H_{25}N_3O_3$: 392 (MH$^+$).

STEP 3: To a solution 2-methylpropyl 2-[4-(2,3,4,5-tetrahydro-1,4-benzoxazepin-7-yl)phenyl]-1H-imidazole-1-carboxylate (0.22 g, 0.56 mmol) and diisopropylethylamine (0.50 mL, 2.81 mmol) in dimethylfomamide (10 mL) at 0° C. a solution of 2-(4-fluorophenyl)-4-oxopiperidine-1-carbonyl chloride (reagent preparation 37) (0.15 g, 0.59 mmol) in tetrahydrofuran (5 mL) was added and the reaction mixture was stirred for 2 hours at room temperature. The mixture was diluted with ethyl acetate (250 mL) and partitioned with water (100 mL). The organic layer was separated and washed with water (50 mL), 10% aqueous citric acid (50 mL), brine then dried over anhydrous sodium sulfate, filtered and concentrated. Column chromatography (hexane-acetone 4:1 to 7:3) provided 2-methylpropyl 2-[4-(4-{[2-(4-fluorophenyl)-4-oxopiperidin-1-yl]carbonyl}-2,3,4,5-tetrahydro-1,4-benzoxazepin-7-yl)phenyl]-1H-imidazole-1-carboxylate (0.28 g, 80%). $^1$H NMR (400 MHz, d$_6$-DMSO): 7.73 (d, 1H), 7.68-7.61 (m, 4H), 7.62 (d, 1H), 7.54 (dd, 1H), 7.30 (m, 1H), 7.15 (d, 1H), 7.10 (m, 3H), 7.04 (d, 2H), 5.20 (t, 1H), 4.62 (s, 2H), 4.24 (m, 2H), 4.04 (d, 2H), 3.68 (m, 3H), 3.40 (m, 1H), 2.86 (m, 2H), 2.61 (m, 1H), 2.32 (2t, 1H), 1.86 (m, 1H), 0.76 (m, 6H). MS (EI) for $C_{35}H_{35}FN_4O_5$: 611 (MH$^+$).

STEP 4: To a solution of 2-methylpropyl 2-[4-(4-{[2-(4-fluorophenyl)-4-oxopiperidin-1-yl]carbonyl}-2,3,4,5-tetrahydro-1,4-benzoxazepin-7-yl)phenyl]-1H-imidazole-1-carboxylate (0.27 g, 0.44 mmol) in methanol (50 mL) was added potassium carbonate (0.37 g, 2.65 mmol) at 0° C. and the reaction mixture was stirred for 2 hours at room temperature. The solid was filtered off and the pH of the resulting solution was adjusted to 6-7 by addition of glacial acetic acid. The solvent was evaporated and the residue was dissolved in ethyl acetate (250 mL), washed with saturated aqueous sodium bicarbonate (2×50 mL), brine and dried over anhydrous sodium sulfate, filtered and concentrated. The precipitating product was collected by filtration, washed with hexane and dried to give 2-(4-fluorophenyl)-1-({7-[4-(1H-imidazol-2-yl)phenyl]-2,3-dihydro-1,4-benzoxazepin-4(5H)-yl}carbonyl)piperidin-4-one (0.19 g, 86%). $^1$H NMR (400 MHz, d$_6$-DMSO): 12.48 (s, 1H), 8.00 (d, 2H), 7.68 (d, 2H), 7.61 (d, 1H), 7.55 (dd, 1H), 7.31-7.26 (m, 3H), 710-6.92 (m, 4H), 5.20 (t, 1H), 4.59 (s, 2H), 4.23 (m, 2H), 3.73-3.63 (m, 3H), 3.31 (m, 1H), 2.85 (m, 2H), 2.61 (m, 1H), 2.30 (2t, 1H). MS (EI) for $C_{30}H_{27}FN_4O_3$: 511 (MH$^+$).

Using analogous synthetic techniques and substituting with alternative starting reagents in step 3 the following compounds of the invention were prepared.

(2R)-2-(4-fluorophenyl)-1-({7-[4-(1H-imidazol-2-yl)phenyl]-2,3-dihydro-1,4-benzoxazepin-4(5H)-yl}carbonyl)piperidin-4-one. Isolated by preparative chiral HPLC separation of the racemate using a SHIMADZU LC-8A apparatus equipped with a Chiralpak AD-H, 25 cm×2.0 cm column using a mobile phase of hexane:2-propanol 4:1 and flow rate of 18.0 mL/min, detection at 220 nm. The isomer with retention time 26.0 min was assigned as the (R)-entantiomer. Chiral Analytical HPLC using a SHIMADZU LC-20AD apparatus equipped with a Chiralpak AD-H, 25 cm×4.6 mm column using a mobile phase of ethanol:methanol 1:1 and flow rate of 0.7 mL/min, detection 254/220 nm gave a retention time 8.76 min and 98% enantiomeric excess. MS (EI) for $C_{30}H_{27}FN_4O_3$: 511 (MH$^+$).

(2S)-2-(4-fluorophenyl)-1-({7-[4-(1H-imidazol-2-yl)phenyl]-2,3-dihydro-1,4-benzoxazepin-4(5H)-yl}carbonyl)piperidin-4-one. Isolated by preparative chiral HPLC separation of the racemate using a SHIMADZU LC-8A apparatus equipped with a Chiralpak AD-H, 25 cm×2.0 cm column using a mobile phase of hexane:2-propanol 4:1 and flow rate of 18.0 mL/min, detection at 220 nm. The isomer with retention time 47.0 min was assigned as the (S)-entantiomer. Chiral Analytical HPLC using a SHIMADZU LC-20AD apparatus equipped with a Chiralpak AD-H, 25 cm×4.6 mm column using a mobile phase of ethanol:methanol 1:1 and flow rate of 0.7 mL/min, detection 254/220 nm gave a retention time 11.20 min and 96% enantiomeric excess. MS (EI) for $C_{30}H_{27}FN_4O_3$: 511 (MH$^+$).

2-(3-fluorophenyl)-1-({7-[4-(1H-imidazol-2-yl)phenyl]-2,3-dihydro-1,4-benzoxazepin-4(5H)-yl}carbonyl)piperidin-4-one. Synthesized according to the method of example 22 using 2-(3-fluorophenyl)-4-oxopiperidine-1-carbonyl chloride (reagent preparation 37) in step 3. $^1$H NMR (400 MHz, d$_6$-DMSO): 12.50 (br s, 1H), 8.00 (d, 2H), 7.67 (d, 2H), 7.61 (d, 1H), 7.55 (dd, 1H), 7.32 (m, 1H), 7.25 (br s, 1H), 7.13-7.04 (m, 4H), 7.02 (d, 1H), 5.20 (t, 1H), 4.60 (s, 2H), 4.23 (m, 2H), 3.68 (m, 3H), 3.40 (m, 1H), 2.85 (m, 2H), 2.60 (m, 1H), 2.33 (2m, 1H). MS (EI) $C_{30}H_{27}FN_4O_3$: 511 (MH$^+$).

8-({7-[4-(1H-imidazol-2-yl)phenyl]-2,3-dihydro-1,4-benzoxazepin-4(5H)-yl}carbonyl)-3-(trifluoromethyl)-8-azabicyclo[3.2.1]octan-3-ol. Prepared according to the method of example 22 by using 3-hydroxy-3-(endo)-(trifluoromethyl)-8-azabicyclo[3.2.1]octane-8-carbonyl chloride (reagent preparation 37) in step 3. $^1$H NMR (400 MHz, methanol-d$_4$): 7.92 (m, 2H), 7.68 (m, 2H), 7.51 (m, 2H), 7.14 (s, 2H), 7.05 (m, 1H), 4.59 (s, 2H), 4.23 (m, 2H), 4.16 (m, 2H), 3.76 (m, 2H), 2.22-2.12 (m, 4H), 1.88 (m, 2H), 1.80 (m, 2H); MS (EI) for $C_{27}H_{27}F_3N_4O_3$: 513 (MH$^+$).

2-(3,4-difluorophenyl)-1-({7-[4-(1H-imidazol-2-yl)phenyl]-2,3-dihydro-1,4-benzoxazepin-4(5H)-yl}carbonyl)piperidin-4-one. Prepared according to the method of example 22 by using 2-(3,4-difluorophenyl)-4-oxopiperidine-1-carbonyl chloride (reagent preparation 37) in step 3. $^1$H NMR (400 MHz, d$_6$-DMSO): 12.55 (s, 1H), 8.00 (d, 2H), 7.70 (d, 2H), 7.63 (d, 1H), 7.55 (m, 1H), 7.35-7.26 (m, 2H), 7.13-7.10 (m, 2H), 7.02 (d, 1H), 5.14 (t, 1H), 4.59 (m, 2H), 4.22 (m, 2H), 3.73-3.64 (m, 3H), 3.46 (m, 1H), 2.83 (d, 2H0, 2.59 (m, 1H), 2.34 (m, 1H). MS (EI) for $C_{30}H_{26}F_2N_4O_3$: 529 (WO.

Synthetic Example 23

4-{[4-(difluoromethyl)piperidin-1-yl]carbonyl}-7-[4-(1H-imidazol-2-yl)phenyl]-2,3,4,5-tetrahydro-1,4-benzoxazepine STEP 1: A suspension of isobutyl 2-(4-bromophenyl)-1-H-imidazole-1-carboxylate (example 4, step 5) (72 mg, 0.22 mmol), bis(pinacolato)diboron (85 mg, 0.33 mmol), potassium acetate (109 mg, 1.11 mmol), and dichloro[1,1-bis(diphenylphosphino)ferrocenepalladium (II) dichloromethane adduct (18 mg, 0.02 mmol) in dimethyl sulfoxide (2 mL) was degassed with nitrogen, and then stirred at 90° C. for 20 h. The reaction mixture was cooled to room temperature, diluted with ethyl acetate, and filtered through celite. The filtrate was washed with water (1×) and brine (1×), dried over sodium sulfate, and concentrated to give crude 2-(4-(4,4,5,5-tetramethyl-1,3,2-dioxaborolan-2-yl)phenyl)-1H-imidazole which was used for the next step without further purification. MS (EI) for $C_{15}H_{19}BN_2O_2$: 271 (WO STEP 2: A mixture of 7-bromo-4-{[4-(difluoromethyl)piperidine-1-yl]carbonyl]-2,3,4,5-tetrahydro-1,4-benzoxazepine (78 mg, 0.20 mmol) (example 2, step 3), 2-(4-(4,4,5,5-tetramethyl-1,3,2-dioxaborolan-2-yl)phenyl)-1H-imidazole (0.20 mmol), cesium carbonate (325 mg, 1.00 mmol), and dichloro[1,1-bis(diphenylphosphino]ferrocenepalladium (II) dichloromethane adduct (16 mg, 0.02 mmol) in dioxane (5.0 mL) and water (0.5 mL) was degassed with nitrogen, and then stirred at 90° C. for 18 h. The reaction mixture was cooled to room temperature, diluted with ethyl acetate, and filtered through celite. The filtrate was washed with water (1×) and brine (1×), dried over sodium sulfate, filtered and concentrated. Purification by preparative reverse phase HPLC (0.1% aqueous trifluoroacetic acid-acetonitrile) provided the title compound (4 mg, 4% yield). $^1$H NMR (400 MHz, methanol-d$_4$): 7.97 (d, 2H), 7.91 (d, 2H), 7.66 (s, 2H), 7.62 (d, 1H), 7.57 (dd, 1H), 7.08 (d, 1H), 5.72 (m, 1H), 4.53 (s, 2H), 4.24 (m, 2H), 3.72 (m, 4H), 2.84 (m, 2H), 2.00 (m, 1H), 1.76 (m, 2H), 1.49 (m, 2H); MS (EI) for $C_{25}H_{26}F_2N_4O_2$: 453 (MH$^+$).

Synthetic Example 24

1-({7-[6-(1H-imidazol-2-yl)pyridin-3-yl]-2,3-dihydro-1,4-benzoxazepin-4(5H)-yl}carbonyl)piperidine-4-carbonitrile STEP 1: A mixture of (4-{[(1,1-dimethylethyl)oxycarbonyl]-2,3,4,5-tetrahydro-1,4-benzoxazepin-7-yl)boronic acid (example 1, step 2) (500 mg, 1.7 mmol), 5-bromopicolinaldehyde (380 mg, 2.0 mmol), cesium carbonate (1.66 g, 5.0 mmol), and dichloro[1,1-bis(diphenylphosphino]ferrocenepalladium (II) dichloromethane adduct (125 mg, 0.17 mmol) in dioxane (5.0 mL) and water (1.0 mL) was degassed with nitrogen, and then stirred at 90° C. with microwave irradiation for 30 min. The reaction mixture was cooled to room temperature, and partitioned between water and ethyl acetate. The aqueous layer was extracted with ethyl acetate (2×), the combined organic layers were washed with brine (1×), dried over sodium sulfate, filtered and concentrated. Column chromatography on silica (hexanes/ethyl acetate 4:1) provided 1,1-dimethylethyl 7-(6-formylpyridin-3-yl)-2,3-dihydro-1,4-benzoxazepin-4(5H)-carboxylate (580 mg, 96% yield) as a colorless solid. MS (EI) for $C_{20}H_{22}N_2O_4$: 355 (MH$^+$).

STEP 2: A solution of 1,1-dimethylethyl 7-(6-formylpyridin-3-yl)-2,3-dihydro-1,4-benzoxazepin-4(5H)-carboxylate (580 mg, 1.6 mmol), ammonium acetate (1.85 g, 24.0 mmol), and glyoxal (0.25 mL of a 40% wt solution in water, 3.2 mmol) in ethanol (10 mL) was stirred at 70° C. for 45 min. The reaction mixture was cooled to room temperature, and partitioned between water and ethyl acetate. The aqueous layer was extracted with ethyl acetate (2×), the combined organic layers were washed with brine (1×), dried over sodium sulfate, filtered and concentrated. Column chromatography on silica chloroform/methanol 9:1 afforded 1,1-dimethylethyl 7-[6-(1H-imidazol-2-yl)pyridin-3-yl]-2,3-dihydro-1,4-benzoxazepin-4(5H)-carboxylate (580 mg, 92% yield) as a brown solid. MS (EI) for $C_{22}H_{24}N_4O_3$: 393 (MH$^+$).

STEP 3: A solution of 1,1-dimethylethyl 7-[6-(1H-imidazol-2-yl)pyridin-3-yl]-2,3-dihydro-1,4-benzoxazepin-4

(5H)-carboxylate (50 mg, 0.13 mmol) in a mixture of methanol (2 mL) and 4N hydrochloric acid in dioxane (2 mL) was refluxed for 5 min. After cooling to room temperature and the reaction mixture was concentrated. The residue was then concentrated from chloroform (3×) and dried to give crude 7-[6-(1H-imidazol-2-yl)pyridin-3-yl]-2,3,4,5-tetrahydro-1,4-benzoxazepine.

STEP 4: The 7-[6-(1H-imidazol-2-yl)pyridin-3-yl]-2,3,4,5-tetrahydro-1,4-benzoxazepine as obtained in step 3 was dissolved in dichloromethane (2 mL), diisopropylethylamine (0.12 mL, 0.65 mmol) was added, followed by addition of phosgene (0.07 mL of a 20% solution in toluene, 0.13 mmol). The reaction mixture was stirred at room temperature for 30 min and then concentrated to afford crude 7-[6-(1H-imidazol-2-yl)pyridin-3-yl]-2,3-dihydro-1,4-benzoxazepin-4 (5H)-carbonyl chloride.

STEP 5: Dichloromethane (2 mL) was added to 7-[6-(1H-imidazol-2-yl)pyridin-3-yl]-2,3-dihydro-1,4-benzoxazepin-4(5H)-carbonyl chloride was obtained in step 4 followed by diisopropylethylamine (0.12 mL, 0.65 mmol) and 4-cyanopiperidine hydrochloride (25 mg, 0.16 mmol). The mixture was stirred at room temperature for 30 min and then concentrated. Purification of the residue by preparative reverse phase HPLC (0.1% aqueous ammonium acetate-acetonitrile) provided the title compound (18 mg, 32% yield) as a colorless solid. $^1$H NMR (400 MHz, DMSO-d$_6$): 12.84 (br. S, 1H), 8.86 (d, 1H), 8.11 (m, 2H), 7.71 (d, 1H), 7.61 (dd, 1H), 7.25 (br. s, 1H), 7.10 (br. s, 1H), 7.06 (d, 1H), 4.49 (s, 2H), 4.23 (m, 2H), 3.61 (m, 2H), 3.30 (m, 2H), 3.00 (m, 3H), 1.87 (m, 2H), 1.73 (m, 2H); MS (EI) for $C_{24}H_{24}N_6O_2$: 429 (MH$^+$).

Example 25

8-{[7-(1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-ol STEP 1: A suspension of 5-bromo-3-nitropyridin-2-amine (4.84 g, 22.2 mmol), (4-{[(1,1-dimethylethyl)oxy]carbonyl}-2,3,4,5-tetrahydro-1,4-benzoxazepin-7-yl)boronic acid (6.51 g, 22.2 mmol), dichloro[1,1-bis(diphenyl)phosphino]ferrocenepalladium (II) dichloromethane adduct (1.60 g, 10 mol %) in dioxane (75 mL) and water (15 mL) was degassed with nitrogen, and then cesium carbonate (14.46 g, 44.4 mmol) was added. The reaction mixture was stirred at 90° C. overnight. The mixture was cooled to room temperature, water (150 mL) was added and stirred for 30 min to give a precipitate. The product 1,1-dimethylethyl 7-(6-amino-5-nitropyridin-3-yl)-2,3-dihydro-1,4-benzoxazepine-4(5H)-carboxylate (8.1 g, 94% yield) was collected by filtration, dried under vacuum. MS (EI) for $C_{19}H_{22}N_4O_5$: 387.1 (MH$^+$).

STEP 2: A mixture of 1,1-dimethylethy 7-(6-amino-5-nitropyridin-3-yl)-2,3-dihydro-1,4-benzoxazepine-4(5H)-carboxylate (3.5 g, 9.1 mmol, example 26, step 1) in methanol (75 mL) and 4N hydrogen chloride in dioxane (11 mL) was stirred at 50° C. for 1.5 h and then concentrated. The resulting residue was triturated with a 10% methanol in diethyl ether solution (50 mL) to provide 3-nitro-5-(2,3,4,5-tetrahydro-1,4-benzoxazepin-7-yl)pyridin-2-amine dihydrochloride (3.1 g, 95%) as a red solid. $^1$H NMR (400 MHz, d$_6$-DMSO) δ 9.76 (bs, 2H), 8.80 (d, 1H), 8.60 (s, 1H), 7.90 (s, 1H), 7.73 (dd, 1H), 7.16 (d, 1H), 4.39 (bs, 2H), 4.25 (bs, 2H), 3.48 (bs, 2H); MS (EI) for $C_{14}H_{14}N_4O_3$: 287 (MH$^+$).

STEP 3: To a solution of 1,1-dimethylethyl 7-(6-amino-5-nitropyridin-3-yl)-2,3-dihydro-1,4-benzoxazepine-4(5H)-carboxylate (1.1 g, 3.1 mmol) and DIPEA (2.7 mL, 16 mmol) in THF (10 mL) and NMP (5 mL) was added 3-hydroxy-3-(trifluoromethyl)-8-azabicyclo[3.2.1]octane-8-carbonyl chloride (reagent preparation 37, 0.81 g, 3.1 mmol). The reaction mixture was heated (50° C.) for four hours and partitioned between dichloromethane and saturated aqueous sodium bicarbonate. The organic layer was washed with brine, dried over magnesium sulfate, filtered and concentrated. Purification by silica gel chromatography provided 8-{[7-(6-amino-5-nitropyridin-3-yl)-2,3-dihydro-1,4-benzoxazepin-4 (5H)-yl]carbonyl}-3-(trifluoromethyl)-8-azabicyclo[3.2.1]octan-3-ol (1.1 g, 69% yield) as red oil. MS (ES) for $C_{23}H_{24}F_3N_5O_5$: 507.2 (MH$^+$).

STEP 4: A slurry of 8-{[7-(6-amino-5-nitropyridin-3-yl)-2,3-dihydro-1,4-benzoxazepin-4(5H)-yl]carbonyl}-3-(trifluoromethyl)-8-azabicyclo[3.2.1]octan-3-ol (1.1 g, 2.2 mmol), Pd/C (5% wt./wt., 0.20 g) and acetic acid (40 mL) was subjected to an atmosphere of hydrogen (45 PSI) using a Parr apparatus. After 2 hours the reaction mixture was filtered through Celite and concentrated to give 8-{[7-(5,6-diaminopyridin-3-yl)-2,3-dihydro-1,4-benzoxazepin-4(5H)-yl]carbonyl}-3-(trifluoromethyl)-8-azabicyclo[3.2.1]octan-3-ol (0.95, 92% yield) as an orange oil. MS (ES) for $C_{23}H_{26}F_3N_5O_3$: 478 (MH$^+$).

STEP 5: A slurry of 8-{[7-(5,6-diaminopyridin-3-yl)-2,3-dihydro-1,4-benzoxazepin-4(5H)-yl]carbonyl}-3-(trifluoromethyl)-8-azabicyclo[3.2.1]octan-3-ol (0.22 g, 0.46 mmol) and trimethyl orthoformate (3.5 mL) was heated (105° C.) for 30 minutes. The reaction mixture was diluted with ethyl ether and the resulting precipitate was collected by filtration. Purification by preparative reverse phase HPLC provided 8-{[7-(1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-ol (64 mg, 29% yield) as a white solid. $^1$H NMR (400 MHz, d$_6$-DMSO) δ 9.39 (s, 1H), 8.87 (s, 1H), 8.44 (s, 1H), 7.66 (s, 1H), 7.62 (dd, 1H), 7.07 (d, 1H), 5.81 (bs, 1H), 4.57 (s, 2H), 4.26 (s, 2H), 4.05 (s, 2H), 3.70 (s, 2H), 2.03 (m, 4H), 1.74 (m, 4H); MS (ES) for $C_{24}H_{24}F_3N_5O_3$: 488 (MH$^+$).

Synthetic Example 26

N-(2,2-difluoroethyl)-4-(4-{[2-(3-fluorophenyl)-4-oxopiperidin-1-yl]carbonyl}-2,3,4,5-tetrahydro-1,4-benzoxazepin-7-yl)benzamide STEP 1: To a solution of 4-(methoxycarbonyl)phenylboronic acid (6.0 g, 33 mmol), potassium bicarbonate (9.1 g, 92 mmol), 1,1-dimethylethyl 7-bromo-2,3-dihydro-1,4-benzoxazepine-4(5H)-carboxylate (10 g, 31 mmol) and DIPEA (16 mL, 92 mmol) in dioxane (27 mL) and water (3 mL) was added dichloro[1,1-bis(diphenylphosphino]ferrocenepalladium (II) dichloromethane adduct (1.3 g, 1.8 mmol). The biphasic mixture was then heated at 90° C. for 2 h then partitioned with ethyl acetate and 1M hydrochloric acid. The organic layer was washed with 1M sodium hydroxide solution then dried over anhydrous magnesium sulfate, filtered and concentrated. The residue was purified by silica gel column chromatography (25% ethyl acetate in hexanes) to provide 1,1-dimethylethyl 7-{4-[(methyloxy)carbonyl]phenyl}-2,3-dihydro-1,4-benzoxazepine-4(5H)-carboxylate (7.5 g, 64% yield) as a pale yellow solid. MS (EI) for $C_{26}H_{23}FN_6O_3$: 384 (MH$^+$).

STEP 2: To a slurry of 1,1-dimethylethyl 7-{4-[(methyloxy)carbonyl]phenyl}-2,3-dihydro-1,4-benzoxazepine-4 (5H)-carboxylate (9.8 g, 26 mmol) in tetrahydrofuran (40 mL) was added a solution of lithium hydroxide (3.1 g, 130 mmol) in water (15 mL). The resulting mixture was heated at 60° C. for 18 h then partitioned between ethyl acetate (100 mL) and 1M hydrochloric acid (50 mL). The organic layer was washed with brine (50 mL), dried over anhydrous magnesium sulfate, filtered and concentrated. Purification by silica gel column chromatography (5% methanol in dichloromethane) provided 4-(4-{[(1,1-dimethylethyl)oxy]carbonyl}-2,3,4,5-tetrahydro-1,4-benzoxazepin-7-yl)benzoic acid (8.1 g, 85% yield). MS (EI) for $C_{21}H_{23}NO_5$: 370 (MH$^+$).

STEP 3: To a cooled (0° C.) solution of 4-(4-{[(1,1-dimethylethyl)oxy]carbonyl}-2,3,4,5-tetrahydro-1,4-benzoxazepin-7-yl)benzoic acid (0.95 g, 2.6 mmol), pyridine (1.3 mL, 15 mmol) and oxalyl chloride (0.44 mL, 5.1 mmol) in toluene (10 mL) was added dimethylformamide (0.01 mL, 0.1 mmol) and the resulting mixture was warmed to room temperature. After 24 h the reaction mixture was concentrated to provide 1,1-dimethylethyl 7-[4-(chlorocarbonyl)phenyl]-2,3-dihydro-1,4-benzoxazepine-4(5H)-carboxylate (1.0 g, 100%) as a brown oil. MS (EI) for $C_{21}H_{22}ClNO_4$: 388 (MH$^+$).

STEP 4: To a solution of 1,1-dimethylethyl 7-[4-(chlorocarbonyl)phenyl]-2,3-dihydro-1,4-benzoxazepine-4(5H)-carboxylate (1.0 g, 2.6 mmol) and DIPEA (2.2 mL, 13 mmol) in tetrahydrofuran (10 mL) was added 2,2-difluoroethylamine (0.21 g, 2.6 mmol). The reaction mixture was stirred for 2 h and then partitioned between ethyl acetate (20 mL) and 1M hydrochloric acid (20 mL). The organic layer was washed with brine (20 mL), dried over anhydrous magnesium sulfate, filtered and concentrated. Purification by column chromatography on silica (30% ethyl acetate in hexanes) provided 1,1-dimethylethyl 7-(4-{[(2,2-difluoroethyl)amino]carbonyl}phenyl)-2,3-dihydro-1,4-benzoxazepine-4 (5H)-carboxylate (0.95 g, 85% yield). MS (EI) for $C_{23}H_{26}F_2N_2O_4$: 433 (MH$^1$).

STEP 5: To a slurry of 1,1-dimethylethyl 7-(4-{[(2,2-difluoroethyl)amino]carbonyl}phenyl)-2,3-dihydro-1,4-benzoxazepine-4(5H)-carboxylate (0.95 g, 2.2 mmol) and methanol (30 mL) was added hydrogen chloride (4 M in dioxane, 3.3 mL, 13 mmol). The reaction mixture was heated (50° C.) for 1.5 hours then concentrated. The resulting residue was suspended in ethyl ether (15 mL) and the solid collected by filtration to give N-(2,2-difluoroethyl)-4-(2,3,4,5-tetrahydro-1,4-benzoxazepin-7-yl)benzamide hydrochloride salt (0.65 g, 80% yield) as a white solid. MS (EI) for $C_{18}H_{18}F_2N_2O_2$: 333 (MH$^+$).

STEP 6: To a slurry of N-(2,2-difluoroethyl)-4-(2,3,4,5-tetrahydro-1,4-benzoxazepin-7-yl)benzamide hydrochloride (0.19 g, 0.51 mmol), DIPEA (0.45 mL, 2.6 mL) and tetrahydrofuran (3 mL) was added 2-(3-fluorophenyl)-4-oxopiperidine-1-carbonyl chloride (reagent preparation 37) (0.13 g, 0.51 mmol). The reaction mixture was heated (50° C.) for 3 h and then concentrated. Purification by preparative reverse phase HPLC provided N-(2,2-difluoroethyl)-4-(4-{[2-(3-fluorophenyl)-4-oxopiperidin-1-yl]carbonyl}-2,3,4,5-tetrahydro-1,4-benzoxazepin-7-yl)benzamide (37 mg, 13% yield) as a white solid. $^1$H NMR (400 MHz, DMSO-d$_6$): 7.82 (d, 2H), 7.55 (d, 2H), 7.47 (dd, 1H), 7.20-7.34 (m, 3H), 7.13 (d, 1H), 6.93-7.06 (m, 3H), 6.43 (t, 1H), 5.99 (tt, 1H), 5.34-5.40 (m, 1H), 4.54 (s, 2H), 4.20-4.30 (m, 2H), 3.73-3.93 (m, 5H), 3.20-3.30 (m, 1H), 2.84-3.06 (m, 2H), 2.54-2.64 (m, 1H), 2.32 (d, 1H); MS (EI) for $C_{30}H_{28}F_3N_3O_4$: 552 (MH$^+$).

Synthetic Example 27

4-{[2-(3-fluoro-4-methylphenyl)piperidin-1-yl]carbonyl}-7-(2-methyl-1H-benzimidazol-6-yl)-2,3,4,5-tetrahydro-1,4-benzoxazepine STEP 1: 7-(2-methyl-1H-benzimidazol-6-yl)-2,3,4,5-tetrahydro-1,4-benzoxazepine dihydrobromide (prepared as in step 5 example 1) (9.16 g, 20.76 mmol) was suspended in dichloromethane (100 mL) followed by addition of DIPEA (12.6 mL, 72.7 mmol) and pyridine (1.7 mL, 20.8 mmol). Di-tert-butyl dicarbonate (10.0 g, 45.7 mmol) and the solution was stirred for 12 h at room temperature. The mixture was concentrated and the residue partitioned with ethyl acetate and 10% aqueous citric acid. The organic phase was washed twice with additional 10% aqueous citric acid then brine, dried over anhydrous sodium sulfate, filtered and concentrated. The residue of 1,1-dimethyl 7-(1-{[(1,1-dimethylethyl)oxy]carbonyl}-2-methyl-1H-benzimidazol-6-yl)-2,3-dihydro-1,4-benzoxazepine-4(5H)-carboxylate was taken into methanol (100 mL) followed by addition of sodium hydroxide (1.0 g, 25 mmol) in water (10 mL). The mixture was stirred for 1 h at room temperature then concentrated. The residue was partitioned with ethyl acetate and 1:1 brine:10% aqueous citric acid. The organic phase was dried over anhydrous sodium sulfate, filtered and concentrated to give 1,1-dimethylethyl 7-(2-methyl-1H-benzimidazol-6-yl)-2,3-dihydro-1,4-benzoxazepine-4(5H)-carboxylate (9.6 g) as an amorphous residue. MS (EI) for $C_{22}H_{25}N_3O_3$: 380 (MH$^+$).

STEP 2: 1,1-dimethylethyl 7-(2-methyl-1H-benzimidazol-6-yl)-2,3-dihydro-1,4-benzoxazepine-4(5H)-carboxylate as prepared in step 1 (9.6 g) was taken into dichloromethane (100 mL) followed by sequential addition of DIPEA (4.3 mL, 24.9 mmol) and isobutyl chloroformate (2.7 mL, 20.8 mmol). The mixture was stirred for 1 h at room temperature then partitioned with 0.5 N aqueous hydrochloric acid. The organic phase was washed with brine, dried over anhydrous sodium sulfate, filtered and concentrated to afford 1,1-dimethylethyl 7-(2-methyl-1-[{(2-methylpropyl)oxy]carbonyl}-1H-benzimidazol-6-yl-2,3-dihydro-1,4-benzoxazepine-4(5H)-carboxylate (10.3 g) as an amorphous residue. MS (EI) for $C_{27}H_{33}N_3O_5$: 480 (MH$^+$).

STEP 3: 1,1-dimethylethyl 7-(2-methyl-1-[{(2-methylpropyl)oxy]carbonyl}-1H-benzimidazol-6-yl-2,3-dihydro-1,4-benzoxazepine-4(5H)-carboxylate as obtained in step 2 (10.3 g) was taken into 1:1 TFA:dichloromethane (100 mL) and the resulting solution was stirred for 1 h at room temperature then concentrated. The residue was treated with saturated aqueous sodium bicarbonate (100 mL) and the aqueous mixture was treated with portion wise solid sodium bicarbonate until pH 8.5. The aqueous mixture was then saturated with sodium chloride and partitioned with ethyl acetate. The organic phase was dried over anhydrous sodium sulfate, filtered and concentrated then dried in vacuo. The residue was taken into 1:1 ethyl acetate:ethyl ether then washed with dilute aqueous sodium bicarbonate, water then brine and dried over anhydrous sodium sulfate. Silica gel was added to the mixture and stirred for 5 minutes then filtered through a celite bed. The filtrate was concentrated to provide 2-methylpropyl 2-methyl-6-(2,3,4,5-tetramethyl-1,4-benzoxazepin-7-yl)-1H-benzimidazole-1-carboxylate (6.8 g, 86% overall yield).

Step 4: Phosgene (20 W % in toluene, 9.5 mL) was diluted into dichloromethane (40 mL) and the resulting solution cooled to 0° C. 2-Methylpropyl 2-methyl-6-(2,3,4,5-tetramethyl-1,4-benzoxazepin-7-yl)-1H-benzimidazole-1-carboxylate as obtained in step 3 (6.8 g, 17.9 mmol)) was taken into dichloromethane (30 mL) followed by addition of DIPEA (7.8 mL, 44.8 mmol) and the resulting solution was slowly added to the cooled phosgene solution over 5 minutes by addition funnel. The mixture was stirred an additional 5 minutes at 0° C. then allowed to warm to room temperature and concentrated. The residue was partitioned with ethyl acetate and 10% aqueous citric acid then washed with brine, dried over anhydrous sodium sulfate, filtered and concentrated. The resulting residue was purified by silica gel chromatography using 50% ethyl acetate in hexanes as eluent to give 2-methylpropyl 6-[4-(chlorocarbonyl)-2,3,4,5-tetrahydro-1,4-benzoxazepin-7-yl)-1H-benzimidazole-1-carboxylate (3.73 g) as an amorphous solid.

STEP 5: 2-Methylpropyl 6-[4-(chlorocarbonyl)-2,3,4,5-tetrahydro-1,4-benzoxazepin-7-yl)-1H-benzimidazole-1-carboxylate (150 mg, 0.38 mmol) and 2-(3-fluoro-4-methylphenyl)piperidine (reagent preparation 1) (80 mg, 0.41 mmol) were taken into THF (3.5 mL) followed by addition of diisopropylethylamine (0.33 mL, 1.9 mmol) and the resulting solution was heated to reflux for 3 h. The mixture was then cooled to room temperature and partitioned with ethyl acetate and 20% aqueous citric acid. The organic phase was separated, dried over sodium sulfate then filtered and concentrated. The residue obtained was taken up into methanol (5 mL) followed by addition of solid potassium carbonate (518 mg, 3.75 mmol) and the mixture was stirred for 12 h at room temperature. The mixture was then concentrated and the residue taken into a minimum of aqueous acetonitrile and purified by preparative reverse phase HPLC. Lyophillization of the combined pure fraction afforded 4-{[2-(3-fluoro-4-methylphenyl)piperidin-1-yl]carbonyl}-7-(2-methyl-1H-benzimidazol-6-yl)-2,3,4,5-tetrahydro-1,4-benzoxazepine (23 mg) as an amorphous solid. $^1$H NMR (400 MHz, $d_6$-DMSO): 12.18 (br s, 1H), 7.59 (br s, 1H), 7.47 (dd, 2H), 7.40 (d, 1H), 7.27 (dd, 1H), 7.12 (t, 1H), 7.01 (d, 1H), 6.96 (d, 2H), 4.59 (m, 1H), 4.40 (dd, 2H), 4.18 (m, 2H), 3.53 (m, 2H), 3.21 (m, 1H), 3.00 (m, 1H), 2.50 (s, 3H), 2.24 (s, 3H), 1.96 (m, 1H), 1.79 (m, 1H), 1.62-1.38 (m, 4H). MS (EI) for $C_{30}H_{31}FN_4O_2$: 499 ($MH^+$).

Using analogous synthetic techniques and substituting with alternative starting reagents in steps 2 and/or 5 the following compounds of the invention were prepared. Protecting group introduction and removal steps were conducted as required according to literature techniques appropriate for a given protecting group (see for example: Greene and Wuts, Protective Groups in Organic Synthetic, Wiley-Interscience). Alternative starting materials were obtained commercially unless otherwise indicated.

7-(2-methyl-1H-benzimidazol-6-yl)-4-{[2-(2-methylphenyl)piperidin-1-yl]carbonyl}-2,3,4,5-tetrahydro-1,4-benzoxazepine. Prepared according to the method of example 27 by using methyl chloroformate in step 2 and racemic 2-o-tolylpiperidine in step 5. $^1$H NMR (400 MHz, $d_6$-DMSO): 7.88 (s, 1H), 7.79 (d, 1H), 7.73 (dd, 1H), 7.63 (m, 1H), 7.56 (dd, 1H), 7.26 (d, 1H), 7.11 (d, 1H), 7.06 (d, 1H), 7.04 (d, 1H), 6.91 (m, 1H), 6.81 (t, 1H), 4.68 (dd, 2H), 4.17-4.10 (m, 3H), 3.87-3.78 (m, 1H), 3.68 (m, 1H), 3.60 (m, 1H), 3.47 (m, 1H), 2.77 (s, 1H), 2.25 (s, 1H), 1.77-1.60 (m, 4H), 1.39 (m, 2H); MS (EI) for $C_{31}H_{33}N_3O_2$: 480 ($MH^+$).

7-(2-methyl-1H-benzimidazol-6-yl)-4-({2-[3-(trifluoromethyl)phenyl]piperidin-1-yl}carbonyl)-2,3,4,5-tetrahydro-1,4-benzoxazepine. Prepared according to the method of example 27 by using methyl chloroformate in step 2 and racemic 2-(3-(trifluoromethyl)phenyl)piperidine in step 5. $^1$H NMR (400 MHz, $d_6$-DMSO): 7.85 (s, 1H), 7.77 (d, 1H) 7.66 (d, 1H), 7.56-7.43 (m, 5H), 7.05 (d, 1H), 4.61 (q, 2H), 4.51 (t, 1H), 4.18 (m, 2H), 3.78-3.44 (m, 5H), 3.10 (br s, 2H), 2.77 (s, 3H), 1.88-1.82 (m, 2H), 1.63 (br s, 2H), 1.52 (br m, 2H); MS (EI) for $C_{30}H_{29}F_3N_4O_2$: 535 (WO.

4-{[2-(3-chloro-4-fluorophenyl)piperidin-1-yl]carbonyl}-7-(2-methyl-1H-benzimidazol-6-yl)-2,3,4,5-tetrahydro-1,4-benzoxazepine. Prepared according to the method of example 27 by using methyl chloroformate in step 2 and racemic 2-(3-chloro-4-fluorophenyl)piperidine in step 5. $^1$H NMR (400 MHz, $d_6$-DMSO): 7.86 (s, 1H), 7.79 (d, 1H), 7.67 (d, 1H), 7.56 (m, 2H), 7.32 (d, 1H), 7.25-7.19 (m, 2H), 7.05 d, 1H), 4.56 (q, 2H), 4.43 (t, 1H), 4.23-4.16 (m, 2H), 3.75-3.64 (m, 3H), 3.09 (t, 2H), 2.78 (s, 3H), 1.84-1.78 (m, 2H), 1.61 (br s, 2H), 1.50 (br m, 2H); MS (EI) for $C_{29}H_{28}ClFN_4O_2$: 519 ($MH^+$).

7-(2-methyl-1H-benzimidazol-6-yl)-4-{[2-(3,4,5-trifluorophenyl)piperidin-1-yl]carbonyl}-2,3,4,5-tetrahydro-1,4-benzoxazepine. Prepared according to the method of example 27 by using methyl chloroformate in step 2 and racemic 2-(3,4,5-trifluorophenyl)piperidine in step 5. $^1$H NMR (400 MHz, $CDCl_3$): 7.61 (br s, 1H), 7.55 (br d, 1H), 7.46 (dd, 1H), 7.37-7.44 (m, 3H), 7.09 (d, 1H), 6.88 (dd, 2H), 4.59-4.47 (m, 3H), 4.22-4.08 (m, 2H), 3.77 (m, 2H), 3.26-3.17 (m, 2H), 2.65 (s, 3H), 1.85 (m, 2H), 1.62 (m, 4H); MS (EI) for $C_{29}H_{27}F_3N_4O_2$: 521 ($MH^+$).

4-{[2-(3,5-difluorophenyl)piperidin-1-yl]carbonyl}-7-(2-methyl-1H-benzimidazol-6-yl)-2,3,4,5-tetrahydro-1,4-benzoxazepine. Prepared according to the method of example 27 by using methyl chloroformate in step 2 and racemic 2-(3,5-difluorophenyl)piperidine in step 5. $^1$H NMR (400 MHz, $d_6$-DMSO): 7.85 (s, 1H), 7.78 (d, 1H), 7.67 (d, 1H), 7.56 (m, 2H), 7.06 (d, 1H), 6.98 (t, 1H), 6.89 (d, 1H), 7.58 (q, 2H), 4.45 (t, 1H), 4.23-4.17 (m, 2H), 3.78-3.65 (m, 3H), 3.11 (bbr s, 2H), 2.78 (s, 3H), 1.81 (m, 2H), 1.61 (br s, 2H), 1.50 (m, 2H); MS (EI) for $C_{29}H_{28}F_2N_4O_2$: 503 ($MH^+$).

N,N-dimethyl-4-(1-{[7-(2-methyl-1H-benzimidazol-6-yl)-2,3-dihydro-1,4-benzoxazepin-4(5H)-yl]carbonyl}piperidin-2-yl)aniline. Prepared according to the method of example 27 by using methyl chloroformate in step 2 and racemic N,N-dimethyl-4-(piperidin-2-yl)aniline in step 5. MS (EI) for $C_{31}H_{35}F_2N_4O_2$: 503 (WO.

7-(2-methyl-1H-benzimidazol-6-yl)-4-(morpholin-4-ylcarbonyl)-2,3,4,5-tetrahydro-1,4-benzoxazepine. Prepared according to the method of example 27 by using methyl chloroformate in step 2 and morpholine in step 5. $^1$H NMR (400 MHz, $d_6$-DMSO): 7.88 (s, 1H), 7.81 (d, 1H), 7.24 (m, 2H), 7.62 (d, 1H), 7.55 (dd, 1H), 7.04 (d, 1H), 4.51 (s, 1H), 4.23 (t, 1H), 3.65-3.58 (m, 6H), 3.12 (t, 4H), 2.74 (s, 3H); MS (EI) for $C_{22}H_{24}N_4O_3$: 393 ($MH^+$).

(±)-(2R,4R)-4-methyl-1-{[7-(2-methyl-1H-benzimidazol-5-yl)-2,3-dihydro-1,4-benzoxazepin-4(5H)-yl]carbonyl}-2-phenylpiperidin-4-ol. Prepared according to the method of example 27 by using methyl chloroformate in step 2 and racemic (2R,4R)-4-methyl-2-phenylpiperidin-4-ol (reagent preparation 23) in step 5. $^1$H NMR (400 MHz, $d_4$-methanol): 7.79 (s, 1H), 7.73 (s, 1H), 7.51-7.49 (m, 2H), 7.13 (d, 2H), 7.07-6.97 (m, 4H), 4.67 (dd AB, 2H), 4.38 (dd, 1H), 4.17 (tr, 2H), 4.03-3.96 (m, 1H), 3.78 (d tr, 1H), 3.29-3.25 (m, 2H), 2.84 (s, 3H), 1.89-1.82 (m, 1H), 1.77-1.62 (m, 3H), 1.17 (s, 3H). MS (EI) for $C_{30}H_{32}N_4O_3$: 498 ($MH^+$).

(±)-(2R,4S)-4-methyl-1-{[7-(2-methyl-1H-benzimidazol-5-yl)-2,3-dihydro-1,4-benzoxazepin-4(5H)-yl]carbonyl}-2-phenylpiperidin-4-ol. Prepared according to the method of example 27 by using methyl chloroformate in step 2 and racemic (2R,4S)-4-methyl-2-phenylpiperidin-4-ol (reagent preparation 23) in step 5. $^1$H NMR (400 MHz, $d_4$-methanol): 7.81 (s, 1H), 7.74 (m, 2H), 7.51 (dd, 1H), 7.38 (d, 1H), 7.18 (d, 2H), 7.12-7.05 (m, 4H), 4.62 (dd AB, 2H), 4.36 (dd, 1H), 4.22-4.10 (m, 2H), 3.22-3.15 (m, 1H), 2.86 (s, 3H), 1.95-1.90 (m, 1H), 1.84-1.72 (m, 3H), 1.70 (s, 3H). MS (EI) for $C_{30}H_{32}N_4O_3$: 498 ($MH^+$).

1-{[7-(2-methyl-1H-benzimidazol-6-yl)-2,3-dihydro-1,4-benzoxazepin-4 (5H)-yl]carbonyl}-4-[4-(trifluoromethyl)phenyl]piperidin-4-ol. Prepared according to the method of example 27 by using 4-(4-(trifluoromethyl)phenyl)piperidin-4-ol in step 5. $^1$H NMR (400 MHz, methanol-$d_4$): 7.66 (s, 1H), 7.65 (d, 1H), 7.55 (m, 3H), 7.51 (d, 1H), 7.47 (dd, 1H), 7.42 (dd, 1H), 7.06 (d, 1H), 4.46 (s, 2H), 4.24 (m, 2H), 3.74 (m, 2H), 3.64 (m, 2H), 3.38-3.24 (m, 2H), 2.58 (s, 3H), 2.11 (m, 2H), 1.70 (m, 2H); MS (EI) for $C_{30}H_{29}F_3N_4O_3$: 551 (MH$^+$).

4-(4-fluorophenyl)-1-{[7-(2-methyl-1H-benzimidazol-6-yl)-2,3-dihydro-1,4-benzoxazepin-4(5H)-yl] carbonyl}piperidin-4-ol. Prepared according to the method of example 27 by using 4-(4-fluorophenyl)piperidin-4-ol in step 5. $^1$H NMR (400 MHz, methanol-d$_4$): 7.64 (s, 1H), 7.55-7.45 (m, 5H), 7.42 (dd, 1H), 7.05 (d, 1H), 6.99 (m, 1H), 4.54 (s, 2H), 4.23 (m, 2H), 3.73 (m, 2H), 3.61 (m, 2H), 3.36 (m, 2H), 2.58 (s, 3H), 2.07 (m, 2H), 1.70 (m, 2H). MS (EI) for $C_{29}H_{29}FN_4O_3$: 501 (MH$^+$).

7-(2-methyl-1H-benzimidazol-6-yl)-4-[(4-methyl-2-phenylpiperazin-1-yl)carbonyl]-2,3,4,5-tetrahydro-1,4-benzoxazepine. Prepared according to the method of example 27 by using racemic 1-methyl-3-phenylpiperazine in step 5. MS (EI) for $C_{29}H_{31}N_5O_2$: 482 (MH$^+$).

4-[(2,4-diphenylpiperazin-1-yl)carbonyl]-7-(2-methyl-1H-benzimidazol-6-yl)-2,3,4,5-tetrahydro-1,4-benzoxazepine. Prepared according to the method of example 27 by using racemic 1,3-diphenylpiperazine in step 5. $^1$H NMR (400 MHz, d$_6$-DMSO): 7.89 (s, 1H), 7.81 (d, 1H), 7.72 (m, 1H), 7.59-7.56 (m, 2H), 7.38 (d, 2H), 7.26-7.17 (m, 5H), 7.07 (d, 1H), 6.92 (d, 2H), 6.78 (t, 1H)), 4.78 (t, 1H), 4.61 (s, 2H), 4.23 (t, 2H), 3.67-3.62 (m, 2H), 3.42-3.27 (m, 4H), 3.13 (m, 1H). MS (EI) for $C_{34}H_{33}N_5O_2$: 544 (MH$^+$).

1-methyl-4-{[7-(2-methyl-1H-benzimidazol-6-yl)-2,3-dihydro-1,4-benzoxazepin-4(5H)-yl]carbonyl}piperazin-2-one. Prepared as described in example 27 using 1-methylpiperazin-2-one in step 5. $^1$H NMR (400 MHz, methanol-d$_4$): 7.65 (s, 1H), 7.54-7.41 (m, 4H), 7.04 (d, 1H), 4.55 (s, 2H), 4.22 (t, 2H), 3.94 (s, 2H), 3.73 (t, 2H), 3.54 (t, 2H), 3.44 (t, 2H), 2.96 (s, 3H), 2.58 (s, 3H); MS (EI) for $C_{23}H_{25}N_5O_3$: 420 (MH$^+$).

2-(1-{[7-(2-methyl-1H-benzimidazol-6-yl)-2,3-dihydro-1,4-benzoxazepin-4(5H)-yl]carbonyl}piperidin-4-yl)propan-2-ol. Prepared according to the method of example 27 by using 2-(piperidin-4-yl)propan-2-ol in step 5. $^1$H NMR (400 MHz, d$_6$-DMSO): 12.30 (br s, 1H), 7.62 (br m, 1H), 7.51 (dd, 1H), 7.46 (dd, 2H), 7.34 (d, 1H), 7.01 (d, 1H), 4.43 (s, 2H), 4.14 (m, 3H), 3.63 (d, 2H), 3.56 (m, 2H), 2.63 (t, 2H), 2.52 (s, 3H), 1.66 (d, 2H), 1.32 (dd, 1H), 1.21 (m, 2H), 1.03 (s, 6H). MS (EI) $C_{26}H_{32}N_4O_3$: 449 (MH$^+$).

(±)-(2R,4S)-2-(3,4-difluorophenyl)-1-{[7-(2-methyl-1H-benzimidazol-6-yl)-2,3-dihydro-1,4-benzoxazepin-4(5H)-yl]carbonyl}piperidin-4-ol. Prepared according to the method of example 27 by using (±)-(2R,4S)-2-(3,4-difluorophenyl)piperidin-4-ol (reagent preparation 28) in step 5. $^1$H NMR (400 MHz, d$_6$-DMSO): 7.62 (s, 1H), 7.60 (d, 1H), 7.47 (d, 1H), 7.38 (d, 1H), 7.08 (d, 1H), 7.04-6.96 (m, 4H), 5.08 (t, 1H), 4.08 (m, 2H), 4.02 (m, 2H), 3.64 (m, 2H), 3.30 (m, 2H), 2.51 (s, 3H), 1.90 (m, 2H), 1.64 (m, 1H), 1.44 (m, 2H). MS (EI) $C_{29}H_{28}F_2N_4O_3$: 519 (MH$^+$).

4-{[2-(3,4-difluorophenyl)piperidin-1-yl]carbonyl}-7-(2-methyl-1H-benzimidazol-6-yl)-2,3,4,5-tetrahydro-1,4-benzoxazepine. Synthesized according to the method of example 27 using methyl chloroformate in step 2 and 2-(3,4-difluorophenyl)piperidine (reagent preparation 1) in step 5. $^1$H NMR (400 MHz, d$_6$-DMSO): 12.24 (s, 1H), 7.67 (s, 0.25H), 7.54 (m, 0.5H), 7.51 (0.25H), 7.49-7.46 (s, 2.5H), 7.44 (d, 0.5H), 7.29 (dt, 1H), 7.26-7.19 (m, 2H), 7.05 (br m, 1H), 7.01 (dd, 1H), 4.58 (dd, 1H), 4.46 (m, 1H), 4.14 (m 1H), 3.66 (m, 1H), 3.30 (m, 1H), 3.10 (m, 2H), 2.51 (s, 3H), 1.89 (m, 1H), 1.78 (m, 1H), 1.60 (m 3H), 1.48 (m, 3H). MS (EI) for $C_{29}H_{28}F_2N_4O_2$: 503 (MH$^+$).

4-({2-[3,5-bis(trifluoromethyl)phenyl]piperidin-1-yl}carbonyl)-7-(2-methyl-1H-benzimidazol-6-yl)-2,3,4,5-tetrahydro-1,4-benzoxazepine. Synthesized according to the method of example 27 using methyl chloroformate in step 2 and 2-(3,5-bis(trifluoromethyl)phenyl)piperidine (reagent preparation 1) in step 5. $^1$H NMR (400 MHz, d$_6$-DMSO): 7.83 (s, 1H), 7.80 (s, 3H), 7.73 (d, 1H), 7.62 (m, 1H), 7.58 (d, 1H), 7.52 (dd, 1H), 7.01 (d, 1H), 4.63 (dd, 2H), 4.42 (m, 1H), 4.18 (m 1H), 3.72 (m 1H), 3.62 (m, 1H), 2.52 (s, 3H), 1.81 (m, 1H), 1.70 (m, 6H), 1.50 (m, 2H). MS (EI) for $C_{31}H_{28}F_6N_4O_2$: 603 (MH$^+$).

4-{[2-(3-chloro-5-fluorophenyl)piperidin-1-yl]carbonyl}-7-(2-methyl-1H-benzimidazol-6-yl)-2,3,4,5-tetrahydro-1,4-benzoxazepine. Synthesized according to the method of example 27 using methyl chloroformate in step 2 and 2-(3-chloro-5-fluorophenyl)piperidine (reagent preparation 1) in step 5. $^1$H NMR (400 MHz, d$_6$-DMSO): 7.85 (d, 1H), 7.78 (d, 1H), 7.67 (dd, 1H), 7.56 (s, 1.5H), 7.53 (d, 0.5H), 7.17 (2t, 1H), 7.08 (s, 1H), 7.05 (d, 1H), 6.99 (br d, 1H), 4.60 (dd, 2H), 4.39 (t, 1H), 4.23 (m, 1H), 4.16 (m, 1H), 3.70 (m, 1H), 3.10 (m, 1H), 2.55 (s, 3H), 1.79 (m, 2H), 1.62 (m, 2H), 1.48 (m, 4H). MS (EI) for $C_{29}H_{28}ClFN_4O_2$: 520 (MH$^+$).

4-{[2-(4-fluoro-2-methylphenyl)piperidin-1-yl]carbonyl}-7-(2-methyl-1H-benzimidazol-6-yl)-2,3,4,5-tetrahydro-1,4-benzoxazepine. Synthesized according to the method of example 27 using methyl chloroformate in step 2 and 2-(4-fluoro-2-methylphenyl)piperidine (reagent preparation 1) in step 5. $^1$H NMR (400 MHz, CDCl$_3$): 9.28 (br s, 1H), 7.69 (br m, 0.5H), 7.49 (d, 2H), 7.46 (br m, 1.5H), 7.40 (d, 1H), 7.08 (d, 1H), 7.04 (t, 1H), 6.70 (d, 1H), 6.49 (t, 1H), 4.67 (dd, 2H), 4.24 (d, 2H), 4.04 (m, 2H), 3.78 (m 2H), 3.46 (m, 1H), 2.89 (m, 1H), 2.63 (s, 3H), 2.34 (s, 3H), 1.72 (m, 3H), 1.48 (m, 2H). MS (EI) for $C_{30}H_{31}FN_4O_2$: 499 (MH$^+$).

4-{[2-(4-fluoro-3-methylphenyl)piperidin-1-yl]carbonyl}-7-(2-methyl-1H-benzimidazol-6-yl)-2,3,4,5-tetrahydro-1,4-benzoxazepine. Synthesized according to the method of example 27 using methyl chloroformate in step 2 and 2-(4-fluoro-3-methylphenyl)piperidine (reagent preparation 1) in step 5. $^1$H NMR (400 MHz, CDCl$_3$): 7.54 (d, 1H), 7.49 (s, 1H), 7.43 (dd, 1H), 7.28 (dd, 1H), 7.19 (br s, 1H), 7.07 (d, 1H), 7.03 (m, 2H), 6.88 (t, 1H), 4.68 (s, 1H), 4.50 (s, 2H), 4.24 (m, 1H), 4.18 (m, 1H), 3.84 (m, 1H), 3.68 (m, 1H), 3.44 (m, 1H), 3.21 (m, 1H), 2.52 (s, 3H), 2.20 (s, 3H), 1.98 (m, 1H), 1.88 (m, 1H), 1.71 (m, 1H), 1.58 (m, 3H). MS (EI) for $C_{30}H_{31}FN_4O_2$: 499 (MH$^+$).

2-(3,4-difluorophenyl)-1-{[7-(2-methyl-1H-benzimidazol-6-yl)-2,3-dihydro-1,4-benzoxazepin-4(5H)-yl]carbonyl}-4-(trifluoromethyl)piperidin-4-ol. Synthesized according to the method of example 27 using methyl chloroformate in step 2 and 2-(3,4-difluorophenyl)-4-(trifluoromethyl)piperidin-4-ol (reagent preparation 21) in step 5. $^1$H NMR (400 MHz, d$_6$-DMSO): 12.22 (br s, 1H), 7.59 (br m, 1H), 7.46 (d, 2H), 7.36 (dd, 1H), 7.33 (s, 1H), 7.26 (m 2H), 7.19 (m, 1H), 7.00 (d, 1H), 5.76 (s, 1H), 4.96 (t, 1H), 4.49 (s, 2H), 4.18 (m, 2H), 3.59 (m, 2H), 2.52 (s, 3H), 2.30 (m, 2H), 2.00 (m. 2H), 1.84 (m, 1H), 1.64 (m, 1H). MS (EI) for $C_{30}H_{27}F_5N_4O_3$: 587 (MH$^+$).

7-(2-methyl-1H-benzimidazol-6-yl)-4-({2-[4-(trifluoromethyl)phenyl]piperidin-1-yl}carbonyl)-2,3,4,5-tetrahydro-1,4-benzoxazepine. Synthesized according to the method of example 27 using methyl chloroformate in step 2 and 2-(4-(trifluoromethyl)phenyl)piperidine (reagent preparation 1) in step 5. $^1$H NMR (400 MHz, d$_4$-methanol): 7.61 (d, 1H), 7.51 (d, 1H), 7.47 (dd, 1H), 7.41 (d, 1H), 7.39 (br s, 4H), 7.34 (dd, 1H), 7.04 (d, 1H), 4.62 (d, 2H), 4.52 (m, 1H), 4.24 (m, 1H), 4.12 (m, 1H), 3.78 (t, 1H), 3.24 (m, 1H), 2.59 (s, 3H), 1.91 (m, 3H), 1.72 (m, 2H), 1.61 (m, 3H). MS (EI) for $C_{30}H_{29}F_3N_4O_2$: 535 (MH$^+$).

2-(3,4-difluorophenyl)-1-{[7-(2-methyl-1H-benzimidazol-6-yl)-2,3-dihydro-1,4-benzoxazepin-4(5H)-yl]carbonyl}piperidin-4-one. Synthesized according to the method of example 27 using methyl chloroformate in step 2 and 2-(3,4-difluorophenyl)piperidin-4-one (reagent preparation 20) in step 5. $^1$H NMR (400 MHz, d$_4$-methanol): 7.64 (d, 1H), 7.51 (t, 1H), 7.48 (m, 2H), 7.39 (dd, 1H), 7.18 (m, 1H), 7.07-7.01 (m, 3H), 5.18 (t, 1H), 4.90 (dd, 2H), 4.23 (m, 2H), 3.79 (t 2H), 3.78 (m, 1H), 3.50 (m, 1H), 2.86 (d, 2H), 2.67 (m, 1H), 2.58 (s, 3H), 2.42 (2t, 1H). MS (EI) for $C_{29}H_{26}F_2N_4O_3$: 517 (MH$^+$).

(±)-(2R,4S)-2-(4-fluorophenyl)-1-{[7-(2-methyl-1H-benzimidazol-6-yl)-2,3-dihydro-1,4-benzoxazepin-4(5H)-yl]carbonyl}piperidin-4-ol. Synthesized according to the method of example 27 using (±)-(2R,4S)-2-(4-fluorophenyl)piperidin-4-ol (reagent preparation 28) in step 5. $^1$H NMR (400 MHz, d$_4$-MeOH): 7.65 (s, 1H), 7.56 (d, 1H), 7.52 (t, 1H), 7.49 (d, 1H), 7.43 (dd, 1H), 7.11 (dd, 2H), 7.04 (d, 1H), 6.75 (t, 2H), 4.62 (s, 2H), 4.10 (m, 1H), 4.01 (dd, 2H), 3.84 (m, 1H), 3.74 (m 2H), 3.48 (2t, 1H), 2.82 (t, 1H), 2.58 (s, 3H). MS (EI) for $C_{29}H_{29}FN_4O_3$: 501 (MH$^+$).

4-{[4-(difluoromethylidene)piperidin-1-yl]carbonyl}-7-(2-methyl-1H-benzimidazol-6-yl)-2,3,4,5-tetrahydro-1,4-benzoxazepine. Synthesized according to the method of example 27 using 4-(difluoromethylene)piperidine (see, WO2005009943) in step 5. $^1$H NMR (400 MHz, d$_4$-MeOH): 7.64 (m, 1H), 7.52 (d and s, 2H), 7.45 (m, 2H), 7.03 (d, 1H), 4.52 (s, 2H), 4.20 (m, 2H), 3.70 (m, 2H), 3.24 (m, 2H), 2.58 (s, 3H), 2.24 (m, 6H). MS (EI) for $C_{24}H_{24}F_2N_4O_2$: 439 (MH$^+$).

4-[(4,4-difluoro-2-phenylpiperidin-1-yl)carbonyl]-7-(2-methyl-1H-benzimidazol-6-yl)-2,3,4,5-tetrahydro-1,4-benzoxazepine. Synthesized according to the method of example 27 using 4,4-difluoro-2-phenylpiperidine (reagent preparation 29) in step 5. $^1$H NMR (400 MHz, d$_4$-MeOH): 7.49 (br s, 1H), 7.41 (d, 1H), 7.38 (dd, 1H), 7.25 (d, 1H), 7.24 (t, 1H), 7.17 (d, 1H), 7.15 (d, 1H), 7.09-7.03 (m, 3H), 6.93 (d, 1H), 4.56 (s, 2H), 4.49 (m, 1H), 4.09 (m, 1H), 3.99 (m, 1H), 3.69 (m, 2H), 3.30 (m, 2H), 2.49 (s, 3H), 2.28 (m, 1H), 2.08 (m, 3H). MS (EI) for $C_{29}H_{28}F_2N_4O_2$: 503 (MH$^+$).

7-(2-methyl-1H-benzimidazol-5-yl)-4-[(2-phenylazepan-1-yl)carbonyl]-2,3,4,5-tetrahydro-1,4-benzoxazepine. Synthesized according to the method of example 27 using methyl chloroformate in step 2 and 2-phenylazepane in step 5. $^1$H NMR (400 MHz, d$_6$-DMSO): 12.22 (br s, 1H), 7.62 (br s, 0.5 H), 7.50 (br m, 1H), 7.44 (dd, 1H), 7.30-7.23 (m, 5.5H), 7.18 (m, 2H), 6.97 d, 1H), 5.06 (m, 1H), 4.34 (s, 2H), 4.10 (m, 2H), 3.78 (dd, 1H), 3.49 (m, 2H), 3.10 (m, 1H), 2.49 (s, 3H), 2.34 (m, 1H), 1.66 (m, 5H), 1.40 (dd, 1H), 1.29 (m, 1H). MS (EI) for $C_{30}H_{32}N_4O_2$: 481 (MH$^+$).

4-{[2-(3-chlorophenyl)piperidin-1-yl]carbonyl}-7-(2-methyl-1H-benzimidazol-6-yl)-2,3,4,5-tetrahydro-1,4-benzoxazepine. Synthesized according to the method of example 27 using methyl chloroformate in step 2 and 2-(3-chlorophenyl)piperidine in step 5. MS (EI) for $C_{29}H_{29}ClN_4O_2$: 502 (MH$^+$).

2-(3-fluorophenyl)-1-{[7-(2-methyl-1H-benzimidazol-6-yl)-2,3-dihydro-1,4-benzoxazepin-4(5H)-yl]carbonyl}piperidin-4-one. Synthesized according to the method of example 27 using methyl chloroformate in step 2 and 2-(3-fluorophenyl)piperidin-4-one (reagent preparation 20) in step 5. MS (EI) for $C_{29}H_{27}FN_4O_3$: 499 (MH$^+$).

4-Methyl-1-{[7-(2-methyl-1H-benzimidazol-6-yl)-2,3-dihydro-1,4-benzoxazepin-4(5H)-yl]carbonyl}piperidine-4-carboxamide. Prepared according to the method of example 27 by using 4-methylpiperidine-4-carboxamide (synthesized according to the procedure disclosed in WO2008011499) in step 5. $^1$H NMR (400 MHz, methanol-d$_4$): 7.59 (br, 1H), 7.43 to 7.32 (m, 4H), 6.93 (d, 1H), 4.38 (s, 2H), 4.01 (m, 2H), 3.57 (m, 2H), 3.37 to 3.30 (m, 2H), 3.00 (t, 2H), 2.45 (s, 3H), 2.01 to 1.93 (m, 2H), 1.44 to 1.36 (m, 2H), 1.12 (s, 3H); MS (EI) for $C_{25}H_{29}N_5O_3$: 448 (MH$^+$).

(±)-4-{[(2R,4S)-2-(3,4-difluorophenyl)-4-(fluoromethyl)piperidin-1-yl]carbonyl}-7-(2-methyl-1H-benzimidazol-6-yl)-2,3,4,5-tetrahydro-1,4-benzoxazepine. Prepared according to the method of example 27 by using methyl chloroformate in step 2 and racemic (2R,4S)-2-(3,4-difluorophenyl)-4-(fluoromethyl)piperidine reagent preparation 33) in step 5. $^1$H NMR (400 MHz, methanol-d$_4$): 7.65 (s, 1H), 7.56 to 7.47 (m, 3H), 7.43 (dd, 1H), 7.04 (d, 1H), 7.00 to 6.94 (m, 1H), 6.92 to 6.87 (m, 2H), 4.70 (q, 2H), 4.30 (dd, 2H), 4.17 to 4.02 (m, 2H), 4.01 to 3.87 (m, 2H), 3.78 to 3.72 (m, 1H), 3.59 to 3.53 (m, 1H), 2.83, (t, 1H), 2.57 (s, 3H), 2.00 to 1.92 (m, 1H), 1.85 to 1.78 (m, 2H), 1.68 to 1.55 (m, 1H), 1.33 (dd, 1H); MS (EI) for $C_{30}H_{29}F_3N_4O_2$: 535 (MH$^+$).

(±)-(2R,4R)-2-(3,4-difluorophenyl)-1-{[7-(2-methyl-1H-benzimidazol-6-yl)-2,3-dihydro-1,4-benzoxazepin-4(5H)-yl]carbonyl}piperidine-4-carbonitrile. Prepared according to the method of example 27 by using methyl chloroformate in step 2 and racemic (2R,4R)-2-(3,4-difluorophenyl)piperidine-4-carbonitrile hydrochloride (reagent preparation 34) in step 5. $^1$H NMR (400 MHz, methanol-d$_4$): 7.61 (br, 1H), 7.52 to 7.45 (m, 2H), 7.36 to 7.31 (m, 2H), 7.20 to 7.14 (m, 1H), 7.09 to 7.01 (m, 3H), 4.68 to 4.66 (m, 1H), 4.60 (d, 2H), 4.25 to 4.09 (m, 2H), 3.78 (dd, 2H), 3.48 to 3.41 (m, 1H), 3.26 to 3.18 (m, 1H), 3.02 to 2.96 (m, 1H), 2.57 (s, 3H), 2.33 to 2.26 (m, 1H), 2.12 to 1.93 (m, 4H); MS (EI) for $C_{30}H_{27}F_2N_5O_2$: 528 (MH$^+$).

9-{[7-(2-methyl-1H-benzimidazol-6-yl)-2,3-dihydro-1,4-benzoxazepin-4 (5H)-yl]carbonyl}-1,2,3,4-tetrahydro-1,4-epiminonaphthalene. Synthesized according to the method of example 27 using 1,2,3,4-tetrahydro-1,4-epiminonaphthalene in step 5. $^1$H NMR (400 MHz, DMSO-d$_6$): δ 12.24 (bs, 1H), 7.08-7.74 (m, 9H), 6.97 (d, 1H), 4.98 (s, 2H), 4.50 (s, 2H), 4.13-4.22 (m, 2H), 3.67-3.77 (m, 2H), 2.46 (s, 3H), 2.05-2.17 (m, 2H), 1.11-1.21 (m, 2H); MS (EI) for $C_{28}H_{26}N_4O_2$: 451 (MH$^+$).

Synthetic Example 28

7-(2-methyl-1H-benzimidazol-6-yl)-4-[(4-pyrimidin-2-ylpiperazin-1-yl)carbonyl]-2,3,4,5-tetrahydro-1,4-benzoxazepine STEP 1: To a solution of 1,1-dimethylethyl 6-[4-(chlorocarbonyl)-2,3,4,5-tetrahydro-1,4-benzoxazepin-7-yl]-1H-benzimidazole-1-carboxylate (5.5 mg, 16 μmol) and 2-(piperazin-1-yl)pyrimidine (7.9 mg, 48 μmol) in anhydrous DCM (2 mL) was added PL-DIPAM (85 mg, 3.27 mmol/g loading, 315 μmol, Polymer Labs) and the reaction mixture was shaken overnight at room temperature. The resulting mixture was drained into PL-PETA (55 mg, 2.7 mmol/g loading, 175 μmol, Polymer Labs) and PL-MIA, (35 mg, 2.65 mmol/g loading, 104 μmol, Polymer Labs). The reaction mixture was shaken overnight at room temperature, drained and the resin was washed with 3.0 mL of methanol. The combined methanol solution was transferred to a 2 dram vial and concentrated under reduced pressure. The resulting oil was dissolved in methanol (2 mL) followed by the addition of 4 N anhydrous hydrogen chloride in dioxane (0.5 mL, Aldrich). The mixture was shaken at room temperature for an additional 18 hours. The resulting solution was concentrated under reduced pressure to give 7-(2-methyl-1H-benzimidazol-6-yl)-4-[(4-pyrimidin-2-ylpiperazin-1-yl)carbonyl]-2,3,4,5-tetrahydro-1,4-benzoxazepine. MS (EI) for $C_{26}H_{27}N_7O_2$: 470.5 (MH$^+$).

The compound was analyzed by LC-MS (Mux) and demonstrated purity requirement was measured above 80% AUC based on UV absorbance.

Using the above automated synthesis technique and substituting with alternative starting amines the following compounds of the invention were prepared. Alternative starting materials were obtained commercially unless otherwise indicated. All compounds of the invention demonstrated purity requirement was measured above 80% AUC based on UV absorbance.

4-(azocan-1-ylcarbonyl)-7-(2-methyl-1H-benzimidazol-6-yl)-2,3,4,5-tetrahydro-1,4-benzoxazepine. MS (EI) for $C_{25}H_{30}N_4O_2$: 419.5 (MH$^+$).

7-(2-methyl-1H-benzimidazol-6-yl)-4-[(4-phenylpiperazin-1-yl)carbonyl]-2,3,4,5-tetrahydro-1,4-benzoxazepine. MS (EI) for $C_{28}H_{29}N_5O_2$: 468.6 (MH$^+$).

4-{[4-(4-fluorophenyl)piperazin-1-yl]carbonyl}-7-(2-methyl-1H-benzimidazol-6-yl)-2,3,4,5-tetrahydro-1,4-benzoxazepine. MS (EI) for $C_{28}H_{28}FN_5O_2$: 486.6 (MH$^+$).

7-(2-methyl-1H-benzimidazol-6-yl)-4-{[4-(4-nitrophenyl)piperazin-1-yl]carbonyl}-2,3,4,5-tetrahydro-1,4-benzoxazepine. MS (EI) for $C_{28}H_{28}N_6O_4$: 513.6 (MH$^+$).

1-[4-(4-{[7-(2-methyl-1H-benzimidazol-6-yl)-2,3-dihydro-1,4-benzoxazepin-4(5H)-yl]carbonyl}piperazin-1-yl)phenyl]ethanone. MS (EI) for $C_{30}H_{31}N_5O_3$: 510.6 (MH$^+$).

7-(2-methyl-1H-benzimidazol-6-yl)-4-[(4-phenylpiperidin-1-yl)carbonyl]-2,3,4,5-tetrahydro-1,4-benzoxazepine. MS (EI) for $C_{29}H_{30}N_4O_2$: 467.6 (MH$^+$).

7-(2-methyl-1H-benzimidazol-6-yl)-4-{[4-(phenylmethyl)piperidin-1-yl]carbonyl}-2,3,4,5-tetrahydro-1,4-benzoxazepine. MS (EI) for $C_{30}H_{32}N_4O_2$: 481.6 (MH$^+$).

7-(2-methyl-1H-benzimidazol-6-yl)-4-[(4-pyridin-2-ylpiperazin-1-yl)carbonyl]-2,3,4,5-tetrahydro-1,4-benzoxazepine. MS (EI) for $C_{27}H_{28}N_6O_2$: 469.6 (MH$^+$).

7-(2-methyl-1H-benzimidazol-6-yl)-4-(octahydroquinolin-1(2H)-ylcarbonyl)-2,3,4,5-tetrahydro-1,4-benzoxazepine. MS (EI) for $C_{27}H_{32}N_4O_2$: 445.6 (MH$^+$).

N-ethyl-7-(2-methyl-1H-benzimidazol-6-yl)-N-(phenylmethyl)-2,3-dihydro-1,4-benzoxazepine-4(5H)-carboxamide. MS (EI) for $C_{27}H_{28}N_4O_2$: 441.5 (MH$^+$).

N-butyl-7-(2-methyl-1H-benzimidazol-6-yl)-N-(phenylmethyl)-2,3-dihydro-1,4-benzoxazepine-4(5H)-carboxamide. MS (EI) for $C_{29}H_{32}N_4O_2$: 469.6 (MH$^+$).

7-(2-methyl-1H-benzimidazol-6-yl)-4-[(4-phenyl-3,6-dihydropyridin-1(2H)-yl)carbonyl]-2,3,4,5-tetrahydro-1,4-benzoxazepine. MS (EI) for $C_{29}H_{28}N_4O_2$: 465.6 (MH$^+$).

4-{[4-(furan-2-ylcarbonyl)piperazin-1-yl]carbonyl}-7-(2-methyl-1H-benzimidazol-6-yl)-2,3,4,5-tetrahydro-1,4-benzoxazepine. MS (EI) for $C_{27}H_{27}N_5O_4$: 486.5 (MH$^+$)

4-{[4-(3-chlorophenyl)piperazin-1-yl]carbonyl}-7-(2-methyl-1H-b enzimidazol-6-yl)-2,3,4,5-tetrahydro-1,4-benzoxazepine. MS (EI) for $C_{28}H_{28}ClN_5O_2$: 503.0 (MH$^+$).

4-{[4-(2-fluorophenyl)piperazin-1-yl]carbonyl}-7-(2-methyl-1H-benzimidazol-6-yl)-2,3,4,5-tetrahydro-1,4-benzoxazepine. MS (EI) for $C_{28}H_{28}FN_5O_2$: 486.6 (MH$^+$).

4-{[4-(2-chlorophenyl)piperazin-1-yl]carbonyl}-7-(2-methyl-1H-b enzimidazol-6-yl)-2,3,4,5-tetrahydro-1,4-benzoxazepine. MS (EI) for $C_{28}H_{28}ClN_5O_2$: 503.0 (MH$^+$).

7-(2-methyl-1H-benzimidazol-6-yl)-4-({4-[3-(methyloxy)phenyl]piperazin-1-yl}carbonyl)-2,3,4,5-tetrahydro-1,4-benzoxazepine. MS (EI) for $C_{29}H_{31}N_5O_3$: 498.6 (MH$^+$).

7-(2-methyl-1H-benzimidazol-6-yl)-4-[(4-pyrazin-2-ylpiperazin-1-yl)carbonyl]-2,3,4,5-tetrahydro-1,4-benzoxazepine. MS (EI) for $C_{26}H_{27}N_7O_2$: 470.5 (MH$^+$).

7-(2-methyl-1H-benzimidazol-6-yl)-N-[(1r,3r,5R,7R)-tricyclo[3.3.1.1$^{3,7}$]dec-2-yl]-2,3-dihydro-1,4-benzoxazepine-4(5H)-carboxamide. MS (EI) for $C_{28}H_{32}N_4O_2$: 457.6 (MH$^+$).

7-(2-methyl-1H-benzimidazol-6-yl)-4-({4-[5-(trifluoromethyl)pyridin-2-yl]piperazin-1-yl}carbonyl)-2,3,4,5-tetrahydro-1,4-benzoxazepine. MS (EI) for $C_{28}H_{27}F_3N_6O_2$: 537.6 (MH$^+$).

ethyl N-{[7-(2-methyl-1H-benzimidazol-6-yl)-2,3-dihydro-1,4-benzoxazepin-4(5H)-yl]carbonyl}-N-(phenylmethyl)glycinate. MS (EI) for $C_{29}H_{30}N_4O_4$: 499.6 (MH$^+$).

4-({4-[(2-chloro-6-fluorophenyl)methyl]piperazin-1-yl}carbonyl)-7-(2-methyl-1H-benzimidazol-6-yl)-2,3,4,5-tetrahydro-1,4-benzoxazepine. MS (EI) for $C_{29}H_{29}ClFN_5O_2$: 535.0 (MH$^+$).

N-methyl-7-(2-methyl-1H-benzimidazol-6-yl)-N-[(3-methylphenyl)methyl]-2,3-dihydro-1,4-benzoxazepine-4(5H)-carboxamide. MS (EI) for $C_{27}H_{28}N_4O_2$: 441.5 (MH$^+$).

7-(2-methyl-1H-benzimidazol-6-yl)-4-{[4-(5-methyl-1,2,4-oxadiazol-3-yl)piperidin-1-yl]carbonyl}-2,3,4,5-tetrahydro-1,4-benzoxazepine. MS (EI) for $C_{26}H_{28}N_6O_3$: 473.5 (MH$^+$).

4-{[4-(5-cyclopropyl-1,2,4-oxadiazol-3-yl)piperidin-1-yl]carbonyl}-7-(2-methyl-1H-benzimidazol-6-yl)-2,3,4,5-tetrahydro-1,4-benzoxazepine. MS (EI) for $C_{28}H_{30}N_6O_3$: 499.6 (MH$^+$).

7-(2-methyl-1H-benzimidazol-6-yl)-4-[(2-{[(4-methylphenyl)oxy]methyl}morpholin-4-yl)carbonyl]-2,3,4,5-tetrahydro-1,4-benzoxazepine. MS (EI) for $C_{30}H_{32}N_4O_4$: 513.6 (MH$^+$).

4-ethyl-9-{[7-(2-methyl-1H-benzimidazol-6-yl)-2,3-dihydro-1,4-benzoxazepin-4(5H)-yl]carbonyl}-3,9-diazaspiro[5.5]undecan-2-one. MS (EI) for $C_{29}H_{35}N_5O_3$: 502.6 (MH$^+$).

7-(2-methyl-1H-benzimidazol-6-yl)-N-(4-pentylphenyl)-2,3-dihydro-1,4-benzoxazepine-4(5H)-carboxamide. MS (EI) for $C_{29}H_{32}N_4O_2$: 469.6 (MH$^+$).

N-methyl-7-(2-methyl-1H-benzimidazol-6-yl)-N-(phenylmethyl)-2,3-dihydro-1,4-benzoxazepine-4(5H)-carboxamide. MS (EI) for $C_{26}H_{26}N_4O_2$: 428 (MH$^+$).

N-methyl-7-(2-methyl-1H-benzimidazol-6-yl)-N-(2-phenylethyl)-2,3-dihydro-1,4-benzoxazepine-4(5H)-carboxamide. MS (EI) for $C_{27}H_{28}N_4O_2$: 442 (MH$^+$).

4-(3,4-dihydroisoquinolin-2(1H)-ylcarbonyl)-7-(2-methyl-1H-benzimidazol-6-yl)-2,3,4,5-tetrahydro-1,4-benzoxazepine. MS (EI) for $C_{27}H_{26}N_4O_2$: 440 (MH$^+$).

7-(2-methyl-1H-benzimidazol-6-yl)-4-(octahydroisoquinolin-2(1H)-ylcarbonyl)-2,3,4,5-tetrahydro-1,4-benzoxazepine. MS (EI) for $C_{27}H_{32}N_4O_2$: 446 (MH$^+$).

BIOLOGICAL EXAMPLES

Biological Example 1 mTOR/GbL/Raptor (mTORC1) ELISA Assay

The measurement of mTORC1 enzyme activity was performed in an ELISA assay format following the phosphorylation of 4E-BP1 protein. All experiments were performed in the 384-well format. Generally, 0.5 µL DMSO containing varying concentrations of the test compound was mixed with 15 µL enzyme solution. Kinase reactions were initiated with the addition of 15 µL of substrates-containing solution. The assay conditions were as follows; 0.2 nM mTORC1, 10 µM ATP and 50 nM NHis-tagged 4E-BP1 in 20 mM Hepes, pH 7.2, 1 mM DTT, 50 mM NaCl, 10 mM MnCl$_2$, 0.02 mg/mL BSA, 0.01% CHAPS, 50 mM β-glycerophosphate. Following an incubation of 120 minutes at ambient temperature, 20 µL of the reaction volume was transferred to a Ni-Chelatecoated 384-well plate. The binding step of the 4E-BP1 protein proceeded for 60 minutes, followed by washing 4 times each with 50 μL of Tris-buffered saline solution (TBS). Anti-phospho-4E-BP1 rabbit-IgG (20 μL, 1:5000) in 5% BSA-TBST (0.2% Tween-20 in TBS) was added and further incubated for 60 minutes. Incubation with a secondary HRP-tagged anti-IgG was similarly performed after washing off the primary antibody (4 washes of 50 μL). Following the final wash step with TBST, 20 μL of SuperSignal ELISA Femto (Pierce Biotechnology) was added and the luminescence measured using an EnVision plate reader.

In the above assay, Compounds 7, 20, 22, 23, 26-35, 36, 41-49, 53, 54, 55-62, 65, 66, 81, 73, 96, 109, 111, 114, 116, 118, 120, 123, 124, 125, 128-130, 142, and 179-181 have an IC50 of less than or equal to 50 nM. Compounds 2, 11-16, 18, 19, 21, 25, 37-40, 51, 52, 63, 64, 69, 70, 72, 76, 83-85, 79, 90-92, 94, 95, 98, 102, 103, 105, 113, 121, 135, 136, 138-140, 143, 148, 156, 157, 170, and 176-178 have an IC50 of greater than 50 nM but less than or equal to 250 nM. Compounds 5, 6, 8, 24, 50, 67, 68, 74, 80, 86, 88, 89, 97, 100, 104, 106-108, 110, 122, 127, 137, 141, 145-147, 152, 153, 155, 161, 162, 163, 171, 173, and 174 have an IC50 of greater than 250 nM but less than or equal to 700 nM. Compounds 1, 3, 4, 10, 17, 75, 77, 93, 99, 117, 126, 131, 133, 134, 149, 154, 159, 160, 165-167, 172, and 175 have an IC50 of greater than 700 nM but less than or equal to 2600 nM. Compounds 9, 71, 78, 82, 87, 101, 112, 115, 119, 132, 144, 150, 151, 158, 164, 168, and 169 were not active under the conditions the assay were run.

Biological Example 2

Immune-Complex mTORC2 Kinase (mTORC2 IP-Kinase) Assay

HeLa (ATCC) cells are grown in suspension culture and lysed in ice-cold lysis buffer containing 40 mM HEPES pH 7.5, 120 mM NaCl, 1 mM EDTA, 10 mM sodium pyrophosphate, 10 mM (β-glycerophosphate, 10 mM NaF, 10 mM NaN$_3$, one tablet of protease inhibitors (Complete-Mini, EDTA-free, Roche), 0.3% cholamidopropyldimethylammoniopropanesulfonate (CHAPS), 1 mM AEBSF, 0.5 mM benzamidine HCl, 20 μg/mL heparin, and 1.5 mM Na$_3$VO$_4$. The mTORC2 complex is immunoprecipitated with anti-RICTOR antibody for 2 h. The immune complexes are immobilized on Protein A sepharose (GE Healthcare, 17-5280-01), washed sequentially 3 times with wash buffer (40 mM HEPES pH 7.5, 120 mM NaCl, 10 mM β-glycerophosphate, 0.3% CHAPS, 1 mM AEBSF, 20 μg/mL heparin, 1.5 mM Na$_3$VO$_4$, and Complete-Mini, EDTA-free) and resuspended in kinase buffer (40 mM HEPES, pH 7.5, 120 mM NaCl, 0.3% CHAPS, 20 μg/mL heparin, 4 mM MgCl$_2$, 4 mM MnCl$_2$, 10% Glycerol, and 10 mM DTT). The immune complexes (equivalent to 1×10$^7$ cells) are pre-incubated at 37° C. with a test compound or 0.6% DMSO for 5 min, and then subjected to a kinase reaction for 8 min in a final volume of 33 μL, (including 5 μL, bed volume) containing kinase buffer, 50 μM ATP, and 0.75 μg full length dephosphorylated AKT1. Kinase reactions are terminated by addition of 11 μL, 4×SDS sample buffer containing 20% β-mercaptoethanol and resolved in a 10% Tris Glycine gels. The gels are transferred onto PVDF membrane at 50 V for 20 h at 4° C. The membranes are blocked in 5% non-fat milk in TBST for 1 h and incubated overnight at 4° C. with 1/1000 dilution of rabbit anti-pAKT (S473) (Cell Signaling Technology, 4060) in 3% BSA/TBST. The membranes are washed 3 times in TBST and incubated for 1 h with a 1/10000 dilution of secondary goat anti-rabbit HRP antibody (Cell Signaling Technology, 2125) in 5% non-fat milk/TBST. The signal is detected using Amersham ECL-plus. The scanned data are analyzed using ImageQuant software. IC$_{50}$ for the test compound is determined relative to DMSO treated sample using XLfit4 software.

Biological Example 3

PI3K Biochemical Assays

PI3Kα activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, substrate (PIP2), and kinase in a 20 μL volume in a buffer solution. The standard PI3Kalpha assay buffer is composed 50 mM Tris, pH 7.5, 1 mM EGTA, 10 mM MgCl$_2$, 1 mM DTT and 0.03% CHAPS. The standard assay concentrations for enzyme, ATP, and substrate are 1.5 nM, 1 μM, and 10 μM, respectively. The reaction mixture was incubated at ambient temperature for approximately 2 h. Following the kinase reaction, a 10 μL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references. Substituting PI3Kα with PI3KIβ, PI3Kγ, or PI3Kγ, the inhibitory activity of the compounds for the other isoforms of I3K were measured.

All Compounds in Table 1 were tested in the assays described in Biological Examples 1 and 3. The Compounds demonstrated activity against PI3K, mTOR, or both. In the above assay, Compounds 7, 11, 12, 14, 16, 18, 20, 30, 32, 34-37, 39, 41, 42, 44-49, 53-56, 57, 59, 60, 66, 73, 81, 114, 130, 179, 179, and 181 have an IC50 of less than or equal to 75 nM. Compounds 13, 17, 21, 23, 27-29, 38, 43, 58, 61, 62, 96, 109, 111, 116, 118, 121, 123-125, 128, 129, and 180 have an IC50 of greater than 75 nM but less than or equal to 200 nM. Compounds 2, 15, 19, 22, 24, 25, 26, 31, 33, 40, 51, 52, 71, 72, 76, 84, 86, 88, 90, 91, 110, 112, 120, 127, 137, 140, 142, 143, 148, 156, 157, 161, 166, 168, 172, 177, and 178 have an IC50 of greater than 200 nM but less than or equal to 500 nM. Compounds 50, 63, 64, 71, 78, 79, 87, 89, 92, 95, 97-100, 102, 105, 107, 108, 113, 122, 132, 136, 138, 150, 169, and 174 have an IC50 of greater than 500 nM but less than or equal to 1000 nM. Compounds 3, 5, 8, 9, 67-70, 74, 75, 80, 82, 83, 85, 93, 94, 101, 103, 106, 115, 119, 131, 134, 135, 139, 144, 145, 147, 151, 153, 154, 158, 162, 163, 164, 167, 170, 175, and 176 have an IC50 of greater than 1000 nM but less than or equal to 3000 nM. Compounds 1, 4, 6, 10, 65, 77, 104, 117, 126, 133, 141, 146, 149, 152, 155, 159-160, 165, 171, and 173 were not active under the conditions the assay were run.

Embodiments 1

In one embodiment the invention comprises a compound of the invention having a PI3K-alpha-inhibitory activity of about 0.5 μM or less and is inactive for mTOR (when tested at a concentration of 2.0 μM or greater) or is selective for PI3K-alpha over mTOR by about 5-fold or greater, about 7-fold or greater, or about 10-fold or greater. In another embodiment, the invention comprises a compound of the invention having a PI3K-alpha-inhibitory activity of about 0.35 μM or less and is inactive for mTOR (when tested at a concentration of 2.0 μM or greater) or is selective for PI3K-alpha over mTOR by about 5-fold or greater, about 7-fold or greater, or about 10-fold or greater. In another embodiment, the invention comprises a compound of the invention having a PI3K-alpha-inhibitory activity of about 0.25 µM or less and is inactive for mTOR (when tested at a concentration of 2.0 µM or greater) or is selective for PI3K-alpha over mTOR by about 5-fold or greater, about 7-fold or greater, or about 10-fold or greater. In another embodiment the compounds of the invention have an PI3K-alpha-inhibitory activity of about 0.1 µM or less and is inactive for mTOR (when tested at a concentration of 2.0 µM or greater) or is selective for PI3K-alpha over mTOR by about 5-fold or greater, about 7-fold or greater, or about 10-fold or greater. In another embodiment the invention comprises a compound of the invention having an PI3K-alpha-inhibitory activity of about 0.05 µM or less and is selective for PI3K-alpha over mTOR by about 5-fold or greater, about 7-fold or greater, or about 10-fold or greater.

Embodiments 2

In one embodiment the invention comprises a compound of the invention having a PI3K-alpha-inhibitory activity of about 2.0 µM or less and an mTOR-inhibitory activity of about 2.0 µM or less and the selectivity for one of the targets over the other does not exceed 3-fold. In another embodiment the invention comprises a compound of the invention having a PI3K-alpha-inhibitory activity of about 1.0 µM or less and an mTOR-inhibitory activity of about 1.0 µM or less and the selectivity for one of the targets over the other does not exceed 3-fold. In another embodiment the invention comprises a compound of the invention having a PI3K-alpha-inhibitory activity of about 0.5 µM or less and an mTOR-inhibitory activity of about 0.5 µM or less and the selectivity for one of the targets over the other does not exceed 3-fold. In another embodiment the invention comprises a compound of the invention having a PI3K-alpha-inhibitory activity of about 0.3 µM or less and an mTOR-inhibitory activity of about 0.3 µM or less and the selectivity for one of the targets over the other does not exceed 3-fold. In another embodiment the invention comprises a compound of the invention having a PI3K-alpha-inhibitory activity of about 0.2 µM or less and an mTOR-inhibitory activity of about 0.2 µM or less and the selectivity for one of the targets over the other does not exceed 2-fold. In another embodiment the invention comprises a compound of the invention having a PI3K-alpha-inhibitory activity of about 0.15 µM or less and an mTOR-inhibitory activity of about 0.15 µM or less and the selectivity for one of the targets over the other does not exceed 2-fold. In another embodiment the invention comprises a compound of the invention having a PI3K-alpha-inhibitory activity of about 0.1 µM or less and an mTOR-inhibitory activity of about 0.1 µM or less. In another embodiment the invention comprises a compound of the invention having a PI3K-alpha-inhibitory activity of about 0.05 µM or less and an mTOR-inhibitory activity of about 0.05 µM or less. In another embodiment the invention comprises a compound of the invention have a PI3K-alpha-inhibitory activity of about 0.02 µM or less and an mTOR-inhibitory activity of about 0.02 µM or less. In another embodiment the invention comprises a compound of the invention have a PI3K-alpha-inhibitory activity of about 0.01 µM or less and an mTOR-inhibitory activity of about 0.01 µM or less.

Biological Example 5 pS6 (S240/244) ELISA Assay

MCF-7 cells (ATCC) cells were seeded at 24000 cells per well in 96-well plates (Corning, 3904) in DMEM (Cellgro) containing 10% FBS (Cellgro), 1% NEAA (Cellgro) and 1% penicillin-streptomycin (Cellgro). Cells were incubated at 37° C., 5% CO2 for 48 h, and the growth medium was replaced with serum-free DMEM or in medium containing 0.4% BSA. Serial dilutions of the test compound in 0.3% DMSO (vehicle) were added to the cells and incubated for 3 h. To fix the cells, medium was removed and 100 µL/well of 4% formaldehyde (Sigma Aldrich, F8775) in TBS (20 mM Tris, 500 mM NaCl) was added to each well at RT for 30 min. Cells were washed 4 times with 200 µL TBS containing 0.1% Triton X-100 (Sigma, catalog #T9284). Plates were blocked with 100 µL Odyssey blocking buffer (Li-Cor Biosciences, 927-40000) for 1 h at RT. Anti-pS6 (S240/244) antibody (Cell Signaling Technology, 2215) and anti-total-S6 antibody (R&D systems, MAB5436) were diluted 1:400 in Odyssey blocking buffer, and 50 µL of the antibody solution containing both antibodies was added to one plate to detect pS6 and total S6. After incubation overnight at 4° C., plates were washed 4 times with 200 µL TBS containing 0.1% Tween20 (Bio-Rad, catalog #170-6351) (TBST). Goat anti-rabbit and Goat anti-mouse secondary antibody (Li-Cor Biosciences, catalog #926-32221 and 926-32210) conjugated to IRDye were diluted 1:400 in Odyssey blocking buffer containing 0.1% Tween20. 50 µL of antibody solution containing both antibodies was added to each well and incubated for 1 h at RT. Plates were washed 3 times with 200 µL TBST and 2 times with 200 µL TBS. Fluorescence was read on an Odyssey plate reader. IC50 values were determined based on the ratio of pS6 to total S6 signal for compound treated wells, normalized to the DMSO-treated control wells.

In one embodiment, the Compounds of the Invention tested in this assay in MCF-7 cells had an inhibitory activity of about 1.0 µM or less. In another embodiment, the Compounds of the Invention tested in this assay in MCF-7 cells had an inhibitory activity of about 0.5 µM or less. In another embodiment, the Compounds of the Invention tested in this assay in MCF-7 cells had an inhibitory activity of about 0.25 µM or less. In another embodiment, the Compounds of the Invention tested in this assay in MCF-7 cells had an inhibitory activity of about 0.2 µM or less. In another embodiment, the Compounds of the Invention tested in this assay in MCF-7 cells had an inhibitory activity of about 0.15 µM or less.

Biological Example 6 pAKT (T308) ELISA Assay

MCF-7 cells (ATCC) cells were seeded at 24000 cells per well in 96-well plates (Corning, 3904) in DMEM (Cellgro) containing 10% FBS (Cellgro), 1% NEAA (Cellgro) and 1% penicillin-streptomycin (Cellgro). Cells were incubated at 37° C., 5% CO2 for 48 h, and the growth medium was replaced with serum-free DMEM or in medium containing 0.4% BSA. Serial dilutions of the test compound in 0.3% DMSO (vehicle) were added to the cells and incubated for 3 h. At the end of the incubation period, cells were stimulated for 10 minutes by the addition of L-IGF (Sigma, I-1271) at a final concentration of 100 ng/ml. Afterwards, media was discarded from cell plates and 110 ul/well of cold lysis buffer (see table below) were added. Cell plates were incubated on ice and then put on shaker in 4° C. cold room for 1 h. Two capture plates (Thermo Scientific, Reacti-bind plate, 15042) were prepared for each cell plate by pre-coating with capture Akt antibody from the two sandwich ELISA antibody pairs used (Cell Signaling Technology 7142 and 7144). The Akt capture antibodies were diluted 1:100 in PBS and 100 ul of diluted capture antibody was added per well. Capture plates were incubated at 4 C overnight. Prior to use, capture plates were washed 3 times in TBS containing 0.1% Tween20 (Bio-Rad, 170-6351) (TBST) and blocked in blocking buffer (Thermo Scientific, Starting Block T20, 37543) for 1-2 h at room temperature. After 1 h of cell lysis, 85 ul of cell lysate/well was transferred to the capture plate for detection of pAkt(T308). 15 µl of cell lysate was transferred from same well to the second capture plate for detection of total Akt1. After incubation overnight at 4° C., plates were washed 3 times with 2004, TBST. Primary antibodies, diluted 1:100 in blocking buffer, were added to the corresponding capture plates for pAkt(T308) (Cell Signaling Technology, 7144) and total Akt1 (Cell Signaling Technology, 7142) detection and incubated at room temperature for 1 h. Plates were washed 3 times with 2004, of TBST. Goat anti-mouse secondary antibody (Cell Signaling Technology, 7076) conjugated to HRP was diluted 1:1000 in blocking buffer and 100 ul were added to each well and incubated for 30 minutes at room temperature. Plates were then washed 3 times with 2004, of TBST. 1004, of SuperSignal ELISA Femto stable peroxidase solution (Thermo Scientific, 37075) was added to each well. After 1 minute incubation, chemiluminescence was read on a Wallac Victor2 1420 multilabel counter. IC50 values were determined based on the ratio of pAkt(T308) to total Akt1 signal for compound treated wells, normalized to the DMSO-treated control wells.

|  | Stock | Final | /10 mL |
|---|---|---|---|
| Water |  |  | 6 mL |
| Complete Protease Inhibitors (Roche 1 836 170) |  |  | 1 mini-tablet |
| 5x RIPA | 5x | 1x | 2 mL |
| NaF | 200 mM | 1 mM | 50 µL |
| B-glycerophosphate | 100 mM | 20 mM | 1.8 mL |
| Phosphatase Inhibitor I (Sigma P2850) | 100x | 1x | 100 µL |
| Na orthovanadate | 200 mM | 1 mM | 50 µL |
| EDTA, pH 8 | 500 mM | 1 mM | 20 µL |

In one embodiment, the Compounds of the Invention tested in this assay in MCF-7 cells had an inhibitory activity of about 1.5 µM or less. In another embodiment, the Compounds of the Invention tested in this assay in MCF-7 cells had an inhibitory activity of about 1.0 µM or less. In another embodiment, the Compounds of the Invention tested in this assay in MCF-7 cells had an inhibitory activity of about 0.75 µM or less. In another embodiment, the Compounds of the Invention tested in this assay in MCF-7 cells had an inhibitory activity of about 0.5 µM or less. In another embodiment, the Compounds of the Invention tested in this assay in MCF-7 cells had an inhibitory activity of about 0.25 µM or less. In another embodiment, the Compounds of the Invention tested in this assay in MCF-7 cells had an inhibitory activity of about 0.2 µM or less. In another embodiment, the Compounds of the Invention tested in this assay in MCF-7 cells had an inhibitory activity of about 0.15 µM or less.

Biological Example 7-13

Pharmacodynamic Xenograft Tumor Models

Female and male athymic nude mice (NCr) 5-8 weeks of age and weighing approximately 20-25 g are used in the following models. Prior to initiation of a study, the animals are allowed to acclimate for a minimum of 48 h. During these studies, animals are provided food and water ad libitum and housed in a room conditioned at 70-75° F. and 60% relative humidity. A 12 h light and 12 h dark cycle is maintained with automatic timers. All animals are examined daily for compound-induced or tumor-related deaths.

MCF-7 Breast Adenocarcinoma Model

MCF7 human mammary adenocarcinoma cells are cultured in vitro in DMEM (Cellgro) supplemented with 10% Fetal Bovine Serum (Cellgro), Penicillin-Streptomycin and non-essential amino acids at 37° C. in a humidified 5% $CO_2$ atmosphere. On day 0, cells are harvested by trypsinization, and $5 \times 10^6$ cells in 100 µL of a solution made of 50% cold Hanks balanced salt solution with 50% growth factor reduced matrigel (Becton Dickinson) implanted subcutaneously into the hindflank of female nude mice. A transponder is implanted into each mouse for identification and data tracking, and animals are monitored daily for clinical symptoms and survival.

Tumors are established in female athymic nude mice and staged when the average tumor weight reached 100-200 mg. A Compound of the Invention is orally administered as a solution/fine suspension in water (with 1:1 molar ratio of 1 NHCL) once-daily (qd) or twice-daily (bid) at 10, 25, 50 and 100 mg/kg for 14 days. During the dosing period of 14-19 days, tumor weights are determined twice-weekly and body weights are recorded daily.

Colo-205 Colon Model

Colo-205 human colorectal carcinoma cells are cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells are harvested by trypsinization, and $3 \times 10^6$ cells (passage 10-15, >95% viability) in 0.1 mL ice-cold Hank's balanced salt solution are implanted intradermally in the hind-flank of 5-8 week old female athymic nude mice. A transponder is implanted in each mouse for identification, and animals are monitored daily for clinical symptoms and survival.

Tumors are established in female athymic nude mice and staged when the average tumor weight reached 100-200 mg. A Compound of the Invention is orally administered as a solution/fine suspension in water (with 1:1 molar ratio of 1 NHCL) once-daily (qd) or twice-daily (bid) at 10, 25, 50 and 100 mg/kg for 14 days. During the dosing period of 14 days, tumor weights are determined twice-weekly and body weights are recorded daily.

PC-3 Prostate Adenocarcinoma Model

PC-3 human prostate adenocarcinoma cells are cultured in vitro in DMEM (Mediatech) supplemented with 20% Fetal Bovine Serum (Hyclone), Penicillin-Streptomycin and non-essential amino acids at 37° C. in a humidified 5% $CO_2$ atmosphere. On day 0, cells are harvested by trypsinization and $3 \times 10^6$ cells (passage 10-14, >95% viability) in 0.1 mL of ice-cold Hank's balanced salt solution are implanted subcutaneously into the hindflank of 5-8 week old male nude mice. A transponder is implanted in each mouse for identification, and animals are monitored daily for clinical symptoms and survival.

Tumors are established in male athymic nude mice and staged when the average tumor weight reached 100-200 mg. A Compound of the Invention is orally administered as a solution/fine suspension in water (with 1:1 molar ratio of 1 N HCl) once-daily (qd) or twice-daily (bid) at 10, 25, 50, or 100-mg/kg for 19 days. During the dosing period of 14-19 days, tumor weights are determined twice-weekly and body weights are recorded daily.

U-87 MG Human Glioblastoma Model

U-87 MG human glioblastoma cells are cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells are harvested by trypsinization and $2 \times 10^6$ cells (passage 5, 96% viability) in 0.1 mL of ice-cold Hank's balanced salt solution are implanted intradermally into the hindflank of 5-8 week old female nude mice. A transponder is implanted in each mouse for identification, and animals are monitored daily for clinical symptoms and survival. Body weights are recorded daily.

A549 Human Lung Carcinoma Model

A549 human lung carcinoma cells are cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells are harvested by trypsinization and $10 \times 10^6$ cells (passage 12, 99% viability) in 0.1 mL of ice-cold Hank's balanced salt solution are implanted intradermally into the hindflank of 5-8 week old female nude mice. A transponder is implanted in each mouse for identification, and animals are monitored daily for clinical symptoms and survival. Body weights are recorded daily.

A2058 Human Melanoma Model

A2058 human melanoma cells are cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells are harvested by trypsinization and $3 \times 10^6$ cells (passage 3, 95% viability) in 0.1 mL ice-cold Hank's balanced salt solution are implanted intradermally in the hindflank of 5-8 week old female athymic nude mice. A transponder is implanted in each mouse for identification, and animals are monitored daily for clinical symptoms and survival. Body weights are recorded daily.

WM-266-4 Human Melanoma Model

WM-266-4 human melanoma cells are cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells are harvested by trypsinization and $3 \times 10^6$ cells (passage 5, 99% viability) in 0.1 mL ice-cold Hank's balanced salt solution are implanted intradermally in the hindflank of 5-8 week old female athymic nude mice. A transponder is implanted in each mouse for identification, and animals are monitored daily for clinical symptoms and survival. Body weights are recorded daily.

Tumor weight (TW) in the above models is determined by measuring perpendicular diameters with a caliper, using the following formula:

tumor weight (mg)=[tumor volume=length (mm)× width$^2$ (mm$^2$)]/2

These data were recorded and plotted on a tumor weight vs. days post-implantation line graph and presented graphically as an indication of tumor growth rates. Percent inhibition of tumor growth (TGI) is determined with the following formula:

$$\left[1 - \left(\frac{(X_f - X_0)}{(Y_f - X_0)}\right)\right] * 100$$

where $X_0$=average TW of all tumors on group day
$X_f$=TW of treated group on Day f
$Y_f$=TW of vehicle control group on Day f
If tumors regress below their starting sizes, then the percent tumor regression is determined with the following formula:

$$\left(\frac{X_0 - X_f}{X_0}\right) * 100$$

Tumor size is calculated individually for each tumor to obtain a mean±SEM value for each experimental group. Statistical significance is determined using the 2-tailed Student's t-test (significance defined as P<0.05).

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:
1. A compound of Formula I:

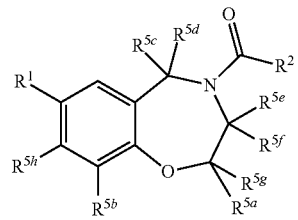

I or a single stereoisomer or mixture of isomers thereof and additionally optionally as a pharmaceutically acceptable salt thereof, where
$R^1$ is phenyl optionally substituted with one, two, or three $R^6$ groups; or
$R^1$ is heteroaryl optionally substituted with one, two, or three $R^7$;
$R^2$ is —$NR^3R^4$;

$R^3$ is hydrogen, alkyl, or alkoxycarbonylalkyl; and $R^4$ is optionally substituted cycloalkyl, optionally substituted phenyl, optionally substituted phenylalkyl, optionally substituted heteroaryl, or optionally substituted heteroarylalkyl; or $R^3$ and $R^4$ together with the nitrogen to which they are attached form HET optionally substituted on any substitutable atom of the ring with $R^{10}$, $R^{10a}$, $R^{10b}$, $R^{10c}$, $R^{10d}$, $R^{10e}$, and $R^{10f}$;

HET is
  i. a saturated or partially unsaturated, but non-aromatic, monocyclic 5- to 8-membered ring optionally containing an additional one or two ring heteroatoms which are independently oxygen, sulfur, or nitrogen where the remaining ring atoms are carbon; or
  ii. a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; or
  iii. a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; or
  iv. a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring;

$R^{5a}$ and $R^{5c}$ are independently hydrogen or alkyl;
$R^{5h}$ is hydrogen or halo;
$R^{5b}$ is hydrogen, amino, or halo;
$R^{5d}$, $R^{5e}$, $R^{5f}$, and $R^{5g}$ are hydrogen;
each $R^6$, when $R^6$ is present, is independently nitro; cyano; halo; alkyl; alkenyl; alkynyl; halo; haloalkyl; —$OR^{8a}$; —$NR^8R^{8a}$; —$C(O)NR^8R^{8a}$; —$NR^8C(O)OR^9$; —$NR^8C(O)R^9$; —$NR^8S(O)_2R^{8a}$; —$NR^8C(O)NR^{8a}R^9$; carboxy, —$C(O)OR^9$; alkylcarbonyl; alkyl substituted with one or two —$C(O)NR^8R^{8a}$; heteroaryl optionally substituted with 1, 2, or 3 $R^{14}$; or optionally substituted heterocycloalkyl;
each $R^7$, when $R^7$ is present, is independently oxo; nitro; cyano; alkyl; alkenyl; alkynyl; halo; haloalkyl; hydroxyalkyl; alkoxyalkyl; —$OR^{8a}$; —$SR^{13}$; —$S(O)R^{13}$; —$S(O)_2R^{13}$; —$NR^8R^{8a}$; —$C(O)NR^8R^{8a}$; —$NR^8C(O)OR^9$; —$NR^8C(O)R^9$; —$NR^8S(O)_2R^{8a}$; —$NR^8C(O)NR^{8a}R^9$; carboxy; —$C(O)OR^9$; alkylcarbonyl; —$S(O)_2NR^8R^9$; alkyl substituted with one or two —$NR^8R^{8a}$; alkyl substituted with one or two —$NR^8C(O)R^{8a}$; optionally substituted cycloalkyl; optionally substituted cycloalkylalkyl; optionally substituted heterocycloalkyl; optionally substituted heterocycloalkylalkyl; optionally substituted heteroaryl; or optionally substituted heteroarylalkyl;
$R^8$ is hydrogen, alkyl, alkenyl, alkynyl, hydroxyalkyl, or haloalkyl;
$R^{8a}$ is hydrogen, alkyl, alkenyl, alkynyl, haloalkyl, hydroxyalkyl, cyanoalkyl, aminoalkyl, alkylaminoalkyl, dialkylaminoalkyl, alkoxyalkyl, optionally substituted cycloalkyl, optionally substituted cycloalkylalkyl, optionally substituted heterocycloalkyl, optionally substituted heterocycloalkylalkyl, optionally substituted phenyl, optionally substituted phenylalkyl, optionally substituted heteroaryl, or optionally substituted heteroarylalkyl;
$R^9$ is alkyl, alkenyl, alkynyl, hydroxyalkyl, alkoxyalkyl, haloalkyl, or optionally substituted heterocycloalkylalkyl;
$R^{10}$, $R^{10a}$, $R^{10b}$, $R^{10c}$, $R^{10d}$, $R^{10e}$, and $R^{10f}$ are independently hydrogen; halo; alkyl; haloalkyl; haloalkenyl; hydroxyalkyl; alkylthio; alkylsulfonyl; hydroxy; alkoxy; haloalkoxy; cyano; alkoxycarbonyl; carboxy; amino; alkylamino; dialkylamino; —$C(O)R^{12}$; —$C(O)NR^{11}R^{11a}$; optionally substituted cycloalkyl; optionally substituted cycloalkylalkyl; optionally substituted phenyl; optionally substituted phenylalkyl; optionally substituted phenyloxy; optionally substituted phenoxyalkyl; optionally substituted heterocycloalkyl; optionally substituted heterocycloalkylalkyl; optionally substituted heteroaryl; or optionally substituted heteroarylalkyl; or two of $R^{10}$, $R^{10a}$, $R^{10b}$, $R^{10c}$, $R^{10d}$, $R^{10e}$, and $R^{10f}$ when attached to the same carbon form oxo, imino, or thiono;
$R^{11}$ hydrogen, alkyl, or alkenyl;
$R^{11a}$ hydrogen, alkyl, or alkenyl;
$R^{12}$ is alkyl, or optionally substituted heteroaryl;
$R^{13}$ is alkyl or haloalkyl; and
each $R^{14}$, when $R^{14}$ present, is independently amino, alkylamino, dialkylamino, acylamino, halo, hydroxy, alkyl, haloalkyl, hydroxyalkyl, aminoalkyl, alkylaminoalkyl, dialkylaminoalkyl, alkoxycarbonyl, aminocarbonyl, alkylaminocarbonyl, dialkylaminocarbonyl, or optionally substituted phenyl.

2. The compound of claim 1, or a single stereoisomer or mixture of isomers thereof and additionally optionally as a pharmaceutically acceptable salt thereof, where
$R^1$ is phenyl substituted with one or two $R^6$ groups; or
$R^1$ is heteroaryl optionally substituted with one, two, or three $R^7$;
$R^2$ is —$NR^3R^4$;
$R^3$ is hydrogen, alkyl, or alkoxycarbonylalkyl; and $R^4$ is optionally substituted cycloalkyl, optionally substituted phenyl, optionally substituted phenylalkyl, or optionally substituted heteroarylalkyl; or
$R^3$ and $R^4$ together with the nitrogen to which they are attached form HET optionally substituted on any substitutable atom of the ring with $R^{10}$, $R^{10a}$, and $R^{10b}$;
HET is
  (a) a saturated or partially unsaturated, but non-aromatic, monocyclic 5- to 8-membered ring optionally containing an additional one or two ring heteroatoms which are independently oxygen, sulfur, or nitrogen where the remaining ring atoms are carbon; or
  (b) a partially unsaturated, but not aromatic, monocyclic 5- to 8-membered ring optionally containing an additional one or two ring heteroatoms which are independently oxygen, sulfur, or nitrogen and the remaining ring atoms are carbon and which ring is fused to a benzo ring; or
  (c) a fused, bridged, or spirocyclic, bicyclic 7- to 11-membered ring optionally containing an additional one or two heteroatoms which are independently oxygen, sulfur, or nitrogen and the remaining ring atoms are carbon and where each ring of the 7- to 11-membered ring is saturated or partially unsaturated but not fully aromatic; or (d) a fused, bridged, or spirocyclic, bicyclic 7- to 11-membered ring optionally containing an additional one or two ring heteroatoms which are independently oxygen, sulfur, or nitrogen and the remaining ring atoms are carbon where each ring of the bicyclic 7- to 11-membered ring is saturated or partially unsaturated but not fully aromatic, and where the bicyclic 7- to 11-membered ring is fused to a benzo ring;

$R^{5a}$, $R^{5c}$, $R^{5h}$, $R^{5b}$, $R^{5d}$, $R^{5e}$, $R^{5f}$, and $R^{5g}$ are hydrogen;

each $R^6$, when $R^6$ is present, is independently nitro, —$NR^8R^{8a}$, —$C(O)NR^8R^{8a}$, —$NR^8C(O)OR^9$, or heteroaryl optionally substituted with 1, 2, or 3 $R^{14}$;

each $R^7$, when present, is independently alkyl, cycloalkyl, —$NR^8R^{8a}$, —$C(O)NR^8R^{8a}$, —$NR^8C(O)OR^9$, or —$NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and $R^{10}$, $R^{10a}$, $R^{10b}$, $R^{10c}$, $R^{10d}$, $R^{10e}$, and $R^{10f}$ are independently hydrogen, alkyl, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, —$C(O)R^{12}$, —$C(O)NR^{11}R^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; or two of $R^{10}$, $R^{10a}$, $R^{10b}$, $R^{10c}$, $R^{10d}$, $R^{10e}$, and $R^{10f}$ when attached to the same carbon form oxo;

$R^{11}$ hydrogen, alkyl, or alkenyl;

$R^{11a}$ hydrogen, alkyl, or alkenyl;

$R^{12}$ is alkyl, or optionally substituted heteroaryl; and each $R^{14}$, when present, is halo, alkyl, or alkoxycarbonyl.

3. The compound according to claim 1, or a single stereoisomer or mixture of isomers thereof and additionally optionally as a pharmaceutically acceptable salt thereof, where $R^1$ is phenyl substituted with one or two $R^6$ groups; or $R^1$ is heteroaryl optionally substituted with one, two, or three $R^7$;

$R^2$ is —$NR^3R^4$ where $R^3$ is hydrogen, alkyl, or alkoxycarbonylalkyl; and $R^4$ is optionally substituted cycloalkyl, optionally substituted phenyl, optionally substituted phenylalkyl, or optionally substituted heteroarylalkyl; or $R^2$ is —$NR^3R^4$ where $R^3$ and $R^4$ together with the nitrogen to which they are attached form indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminonaphth-9-yl, where any substitutable atom on the ring is optionally substituted with $R^{10}$, $R^{10a}$, and $R^{10b}$; or $R^2$ is —$NR^3R^4$ where $R^3$ and $R^4$ together with the nitrogen to which they are attached form HET according to formula (a):

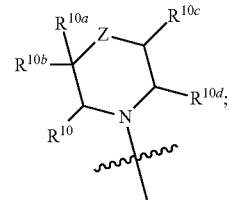

(a)

where Z is a bond, —C(O)—, —O—, —S—, —S(O)—, —$S(O)_2$—, —$N(R^z)$—, —$C(R^{10e})(R^{10f})$—, or $C_{2-3}$-alkylene; or $R^2$ is —$NR^3R^4$ where $R^3$ and $R^4$ together with the nitrogen to which they are attached form HET according to formula (b):

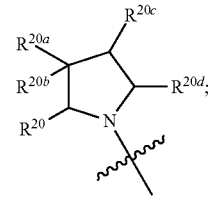

(b)

where (a) $R^{20}$ and $R^{20c}$ or $R^{20}$ and $R^{20d}$ together with the carbons to which they are bonded form a cycloalkyl or hetercyloalkyl such that HET is a bridged moiety; or (b) $R^{20a}$ and $R^{20c}$ together with the carbons to which they are bonded form a cycloalkyl or hetercyloalkyl such that HET is a fused bicyclic moiety; or (c) $R^{20a}$ and $R^{20b}$ together with the carbon to which they are attached form cycloalkyl or heterocycloalkyl such that HET is a spirocyclic moiety;

and the remaining of $R^{20}$, $R^{20a}$, $R^{20b}$, $R^{20c}$, and $R^{20d}$ are hydrogen; and where the cycloalkyl and heterocycloalkyl are optionally substituted with $R^{10}$ and $R^{10a}$; or $R^2$ is —$NR^3R^4$ where $R^3$ and $R^4$ together with the nitrogen to which they are attached form HET according to formula (c):

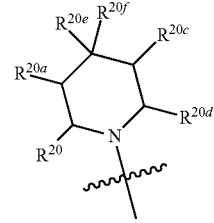

(c)

where (a) $R^{20}$ and $R^{20d}$ or $R^{20}$ and $R^{20c}$ together with the carbons to which they are bonded form a cycloalkyl or hetercyloalkyl such that HET is a bridged moiety (b) $R^{20e}$ and $R^{20f}$ together with the carbons to which they are bonded form cycloalkyl or heterocycloalkyl such that HET is a spirocyclic moiety, (c) $R^{20}$ and $R^{20a}$ or $R^{20a}$ and $R^{20e}$ together with the carbons to which they are bonded form a cycloalkyl or hetercyloalkyl such that HET is a fused bicyclic moiety;

and the remaining of $R^{20}$, $R^{20a}$, $R^{20c}$, $R^{20d}$, $R^{20e}$, and $R^{20f}$ are $R^{10}$, $R^{10a}$, $R^{10c}$, $R^{10d}$, $R^{10e}$, and $R^{10f}$, respectively; and where the cycloalkyl and heterocycloalkyl are optionally substituted with $R^{10}$ and $R^{10a}$;

each $R^6$, when $R^6$ is present, is independently nitro, $-NR^8R^{8a}$, $-C(O)NR^8R^{8a}$, $-NR^8C(O)OR^9$, or heteroaryl optionally substituted with 1, 2, or 3 $R^{14}$;

each $R^7$, when present, is independently alkyl, cycloalkyl, $-NR^8R^{8a}$, $-C(O)NR^8R^{8a}$, $-NR^8C(O)OR^9$, or $-NR^8C(O)R^9$;

$R^8$ is hydrogen, alkyl, or alkenyl;

$R^{8a}$ is hydrogen, alkyl, haloalkyl, optionally substituted heterocycloalkyl, or optionally substituted phenylalkyl;

$R^9$ is alkyl or haloalkyl; and $R^z$ is hydrogen, alkyl, haloalkyl, haloalkenyl, hydroxyalkyl, alkylsulfonyl, hydroxy, alkoxy, alkoxycarbonyl, $-C(O)R^{12}$, $-C(O)NR^{11}R^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl;

$R^{10}$, each $R^{10a}$, $R^{10b}$, $R^{10c}$, $R^{10d}$, $R^{10e}$, and $R^{10f}$ are independently hydrogen, alkyl, halo, haloalkyl, haloalkenyl, hydroxyalkyl, alkylthio, alkylsulfonyl, hydroxy, alkoxy, haloalkoxy, cyano, alkoxycarbonyl, carboxy, amino, alkylamino, dialkylamino, $-C(O)R^{12}$, $-C(O)NR^{11}R^{11a}$, optionally substituted cycloalkyl, optionally substituted cycloalkylalkyl, optionally substituted phenyl, optionally substituted phenylalkyl, optionally substituted phenyloxy, optionally substituted phenyloxyalkyl, optionally substituted heterocycloalkyl, optionally substituted heterocycloalkylalkyl, optionally substituted heteroaryl, or optionally substituted heteroarylalkyl; or two of $R^{10}$, each $R^{10a}$, $R^{10b}$, $R^{10c}$, $R^{10d}$, $R^{10e}$, and $R^{10f}$ when attached to the same carbon form oxo;

$R^{11}$ is hydrogen, alkyl, alkenyl, or alkynyl;

$R^{11a}$ is hydrogen, alkyl, alkenyl, or alkynyl;

$R^{12}$ is alkyl, or optionally substituted heteroaryl; and each $R^{14}$, when present, is halo, alkyl, or alkoxycarbonyl.

4. The compound according to claim 1, or a single stereoisomer or mixture of isomers thereof and additionally optionally as a pharmaceutically acceptable salt thereof, where the Compound is according to Formula I(b)

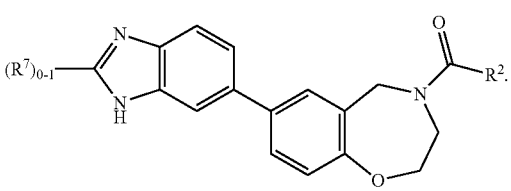

I(b)

5. The compound according to claim 1, or a single stereoisomer or mixture of isomers thereof and additionally optionally as a pharmaceutically acceptable salt thereof, where the Compound is according to Formula I(c1) or I(c2)

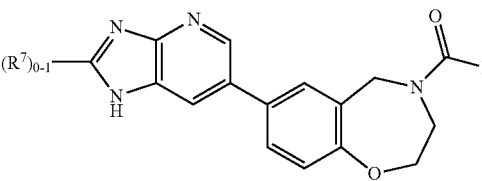

I(c1)

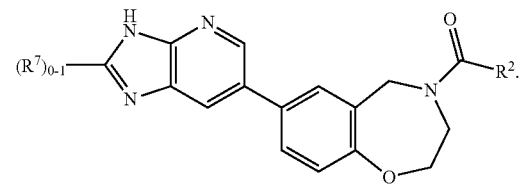

I(c2)

6. The compound according to claim 1, or a single stereoisomer or mixture of isomers thereof and additionally optionally as a pharmaceutically acceptable salt thereof, where the Compound is according to Formula I(d1) or I(d2)

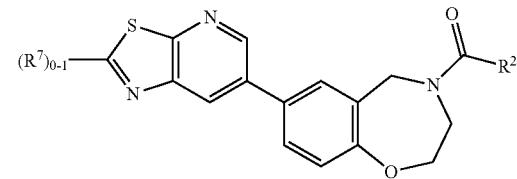

I(d1)

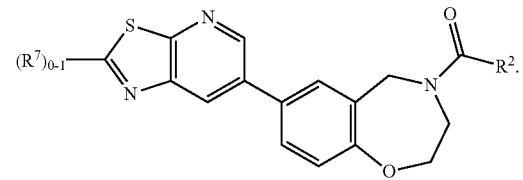

I(d2)

7. The compound according to claim 1, or a single stereoisomer or mixture of isomers thereof and additionally optionally as a pharmaceutically acceptable salt thereof, where $R^1$ is a 6-membered heteroaryl optionally substituted with one or two $R^7$.

8. The compound according to claim 1, or a single stereoisomer or mixture of isomers thereof and additionally optionally as a pharmaceutically acceptable salt thereof, where $R^1$ is pyridin-3-yl optionally substituted with one or two $R^7$.

9. The compound according to claim 1, or a single stereoisomer or mixture of isomers thereof and additionally optionally as a pharmaceutically acceptable salt thereof, where $R^1$ is a 5-membered heteroaryl optionally substituted with one or two $R^7$.

10. The compound according to claim 1, or a single stereoisomer or mixture of isomers thereof and additionally optionally as a pharmaceutically acceptable salt thereof, where $R^7$, when present, is alkyl, haloalkyl, cycloalkyl, $-NR^8R^{8a}$, or $-NR^8C(O)OR^9$.

11. The compound according to claim 1, or a single stereoisomer or mixture of isomers thereof and additionally optionally as a pharmaceutically acceptable salt thereof, where $R^1$ is phenyl substituted with one or two $R^6$ groups.

12. The compound of claim 11, or a single stereoisomer or mixture of isomers thereof and additionally optionally as a pharmaceutically acceptable salt thereof, where $R^1$ is phenyl substituted with one $R^6$ group which is —$OR^{8a}$; —$NR^8R^{8a}$; —$C(O)NR^8R^{8a}$; or heteroaryl optionally substituted with 1, 2, or 3 $R^{14}$.

13. The compound of claim 1, or a single stereoisomer or mixture of isomers thereof and additionally optionally as a pharmaceutically acceptable salt thereof, where $R^2$ is —$NR^3R^4$ and $R^3$ is hydrogen, alkyl, or alkoxycarbonylalkyl; and $R^4$ is optionally substituted cycloalkyl, optionally substituted phenyl, optionally substituted phenylalkyl, or optionally substituted heteroarylalkyl.

14. The compound of claim 1, or a single stereoisomer or mixture of isomers thereof and additionally optionally as a pharmaceutically acceptable salt thereof, where $R^2$ is indolin-1-yl, isoindolin-2-yl, 1,2,3,4-tetrahydroquinolin-1-yl, 1,2,3,4-tetrahydroisoquinolin-2-yl, or 1,2,3,4-tetrahydro-1,4-epiminomaphth-9-yl, where any substitutable atom on HET is optionally substituted with $R^{10}$, $R^{10a}$, and $R^{10b}$.

15. The compound of claim 1, or a single stereoisomer or mixture of isomers thereof and additionally optionally as a pharmaceutically acceptable salt thereof, where $R^2$ is —$NR^3R^4$ and $R^3$ and $R^4$ together with the nitrogen to which they are attached form HET according to formula (a):

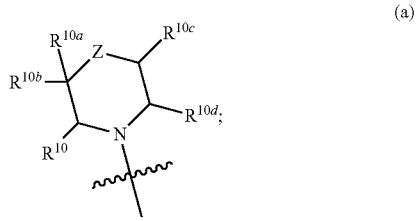

(a)

where Z is a bond, —C(O)—, —O—, —S—, —S(O)—, —S(O)$_2$—, —N($R^z$)—, —C($R^{10c}$)($R^{10f}$)—, or $C_{2-3}$-alkylene; $R^z$ is hydrogen, alkyl, haloalkyl, haloalkenyl, hydroxyalkyl, alkylsulfonyl, hydroxy, alkoxy, alkoxycarbonyl, —C(O)$R^{12}$, —C(O)$NR^{11}R^{11a}$, optionally substituted cycloalkyl, optionally substituted cycloalkylalkyl, optionally substituted phenyl, optionally substituted phenylalkyl, optionally substituted heterocycloalkyl, optionally substituted heterocycloalkylalkyl, optionally substituted heteroaryl, or optionally substituted heteroarylalkyl.

16. The compound of claim 1, or a single stereoisomer or mixture of isomers thereof and additionally optionally as a pharmaceutically acceptable salt thereof, where $R^2$ is —$NR^3R^4$ where $R^3$ and $R^4$ together with the nitrogen to which they are attached form HET according to formula (b):

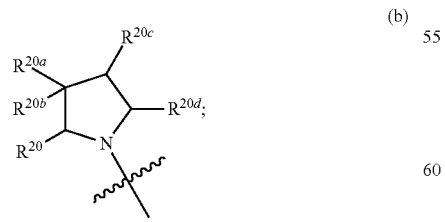

(b)

where
(a) $R^{20}$ and $R^{20c}$ or $R^{20}$ and $R^{20d}$ together with the carbons to which they are bonded form a cycloalkyl or hetercyloalkyl such that HET is a bridged moiety; or (b) $R^{20a}$ and $R^{20c}$ together with the carbons to which they are bonded form a cycloalkyl or hetercyloalkyl such that HET is a fused bicyclic moiety; or (c) $R^{20a}$ and $R^{20b}$ together with the carbon to which they are attached form cycloalkyl or heterocycloalkyl such that HET is a spirocyclic moiety;

where the cycloalkyl and heterocycloalkyl are optionally substituted with $R^{10}$ and $R^{10a}$; and the remaining of $R^{20}$, $R^{20a}$, $R^{20b}$, $R^{20c}$, and $R^{20d}$ are hydrogen.

17. The compound of claim 1, or a single stereoisomer or mixture of isomers thereof and additionally optionally as a pharmaceutically acceptable salt thereof, where $R^2$ is —$NR^3R^4$ where $R^3$ and $R^4$ together with the nitrogen to which they are attached form HET according to formula (c):

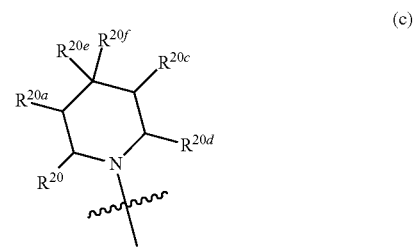

(c)

where
(a) $R^{20}$ and $R^{20d}$ or $R^{20}$ and $R^{20c}$ together with the carbons to which they are bonded form a cycloalkyl or hetercyloalkyl such that HET is a bridged moiety (b) $R^{20e}$ and $R^{20f}$ together with the carbons to which they are bonded form cycloalkyl or heterocycloalkyl such that HET is a spirocyclic moiety, (c) $R^{20}$ and $R^{20a}$ or $R^{20a}$ and $R^{20c}$ together with the carbons to which they are bonded form a cycloalkyl or heterocycloalkyl such that HET is a fused bicyclic moiety;

where the cycloalkyl and heterocycloalkyl are optionally substituted with $R^{10}$ and $R^{10a}$; and the remaining of $R^{20}$, $R^{20a}$, $R^{20c}$, $R^{20d}$, $R^{20e}$, and $R^{20f}$ are $R^{10}$, $R^{10a}$, $R^{10c}$, $R^{10d}$, $R^{10e}$, and $R^{10f}$, respectively.

18. The compound of claim 1, or a single stereoisomer or mixture of isomers thereof and additionally optionally as a pharmaceutically acceptable salt thereof, where $R^2$ is —$NR^3R^4$ where $R^3$ and $R^4$ together with the nitrogen to which they are attached form HET according to formula (g):

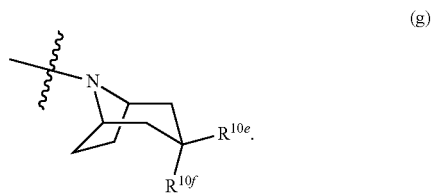

(g)

19. The compound of claim 1, or a single stereoisomer or mixture of isomers thereof and additionally optionally as a pharmaceutically acceptable salt thereof, where $R^2$ is —$NR^3R^4$ where $R^3$ and $R^4$ together with the nitrogen to which they are attached form HET according to formula (h):

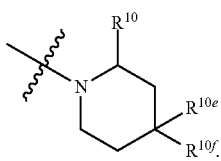

(h)

20. A compound according to claim 1 which is:
6-{4-[(4-methylpiperidin-1-yl)carbonyl]-2,3,4,5-tetrahydro-1,4-benzoxazepin-7-yl}pyridazin-3-amine
methyl (6-{4-[(4-methylpiperidin-1-yl)carbonyl]-2,3,4,5-tetrahydro-1,4-benzoxazepin-7-yl}-1H-benzimidazol-2-yl)carbamate
5-{4-[(4-methylpiperidin-1-yl)carbonyl]-2,3,4,5-tetrahydro-1,4-benzoxazepin-7-yl}pyrimidin-2-amine
5-{4-[(4-methylpiperidin-1-yl)carbonyl]-2,3,4,5-tetrahydro-1,4-benzoxazepin-7-yl}pyrazin-2-amine
N-(5-{4-[(4-methylpiperidin-1-yl)carbonyl]-2,3,4,5-tetrahydro-1,4-benzoxazepin-7-yl}-1,3-thiazol-2-yl)acetamide
5-(4-{[4-(trifluoromethyl)piperidin-1-yl]carbonyl}-2,3,4,5-tetrahydro-1,4-benzoxazepin-7-yl)pyrazin-2-amine
7-[4-(1H-imidazol-2-yl)phenyl]-4-{[4-(trifluoromethyl)piperidin-1-yl]carbonyl}-2,3,4,5-tetrahydro-1,4-benzoxazepine
4-[(4-methylpiperidin-1-yl)carbonyl]-7-(1,3-thiazol-5-yl)-2,3,4,5-tetrahydro-1,4-benzoxazepine
3-{4-[(4-methylpiperidin-1-yl)carbonyl]-2,3,4,5-tetrahydro-1,4-benzoxazepin-7-yl}-N-(phenylmethyl)-1H-pyrazol-5-amine
3-{4-[(4-methylpiperidin-1-yl)carbonyl]-2,3,4,5-tetrahydro-1,4-benzoxazepin-7-yl}-1H-pyrazol-5-amine
methyl [6-(4-{[2-(3-fluorophenyl)-4-oxopiperidin-1-yl]carbonyl}-2,3,4,5-tetrahydro-1,4-benzoxazepin-7-yl)-1H-benzimidazol-2-yl]carbamate
methyl [6-(4-{[2-(4-fluorophenyl)piperidin-1-yl]carbonyl}-2,3,4,5-tetrahydro-1,4-benzoxazepin-7-yl)-1H-benzimidazol-2-yl]carbamate
methyl [6-(4-{[4-(fluoromethyl)piperidin-1-yl]carbonyl}-2,3,4,5-tetrahydro-1,4-benzoxazepin-7-yl)-1H-benzimidazol-2-yl]carbamate
methyl [6-(4-{[2-(4-fluorophenyl)-4-oxopiperidin-1-yl]carbonyl}-2,3,4,5-tetrahydro-1,4-benzoxazepin-7-yl)-1H-benzimidazol-2-yl]carbamate
methyl [6-(4-{[4-(fluoromethyl)-4-hydroxypiperidin-1-yl]carbonyl}-2,3,4,5-tetrahydro-1,4-benzoxazepin-7-yl)-1H-benzimidazol-2-yl]carbamate
methyl [6-(4-{[2-(3,4-difluorophenyl)-4-oxopiperidin-1-yl]carbonyl}-2,3,4,5-tetrahydro-1,4-benzoxazepin-7-yl)-1H-benzimidazol-2-yl]carbamate
(±)-methyl [5-(4-{[2R,4S)-2-(4-fluorophenyl)-4-hydroxypiperidin-1-yl]carbonyl}-2,3,4,5-tetrahydro-1,4-benzoxazepin-7-yl]-1H-benzimidazol-2-yl]carbamate
methyl {6-[4-({4-hydroxy-4-[3-(trifluoromethyl)phenyl]piperidin-1-yl}carbonyl)-2,3,4,5-tetrahydro-1,4-benzoxazepin-7-yl]-1H-benzimidazol-2-yl}carbamate
methyl [6-(4-{[4-(difluoromethyl)piperidin-1-yl]carbonyl}-2,3,4,5-tetrahydro-1,4-benzoxazepin-7-yl)-1H-benzimidazol-2-yl]carbamate
methyl [6-(4-{[3-(endo)-hydroxy-3-(trifluoromethyl)-8-azabicyclo[3.2.1]oct-8-yl]carbonyl}-2,3,4,5-tetrahydro-1,4-benzoxazepin-7-yl)-1H-benzimidazol-2-yl]carbamate
methyl (6-{4-[(4-cyanopiperidin-1-yl)carbonyl]-2,3,4,5-tetrahydro-1,4-benzoxazepin-7-yl}-1H-benzimidazol-2-yl)carbamate
methyl [6-(4-{[4-hydroxy-4-(trifluoromethyl)piperidin-1-yl]carbonyl}-2,3,4,5-tetrahydro-1,4-benzoxazepin-7-yl)-1H-benzimidazol-2-yl]carbamate
1-{[7-(2-amino-1H-benzimidazol-6-yl)-2,3-dihydro-1,4-benzoxazepin-4(5H)-yl]carbonyl}-4-methylpiperidin-4-ol
methyl (6-{4-[(4-hydroxy-4-methylpiperidin-1-yl)carbonyl]-2,3,4,5-tetrahydro-1,4-benzoxazepin-7-yl}-1H-benzimidazol-2-yl)carbamate
methyl (6-{4-[(3-oxo-8-azabicyclo[3.2.1]oct-8-yl)carbonyl]-2,3,4,5-tetrahydro-1,4-benzoxazepin-7-yl}-1H-benzimidazol-2-yl)carbamate
6-(4-{[4-(fluoromethyl)piperidin-1-yl]carbonyl}-2,3,4,5-tetrahydro-1,4-benzoxazepin-7-yl)-1H-benzimidazol-2-amine
1-{[7-(2-amino-1H-benzimidazol-6-yl)-2,3-dihydro-1,4-benzoxazepin-4(5H)-yl]carbonyl}-2-(3,4-difluorophenyl)piperidin-4-one
1-{[7-(2-amino-1H-benzimidazol-6-yl)-2,3-dihydro-1,4-benzoxazepin-4(5H)-yl]carbonyl}-2-(3-fluorophenyl)piperidin-4-one
N-ethyl-6-(4-{[4-(fluoromethyl)piperidin-1-yl]carbonyl}-2,3,4,5-tetrahydro-1,4-benzoxazepin-7-yl)-1H-benzimidazol-2-amine
1-({7-[2-(ethylamino)-1H-benzimidazol-6-yl]-2,3-dihydro-1,4-benzoxazepin-4(5H)-yl}carbonyl)-2-(3-fluorophenyl)piperidin-4-one
2-(3-fluorophenyl)-1-{[7-{2-[(2,2,2-trifluoroethyl)amino]-1H-benzimidazol-5-yl}-2,3-dihydro-1,4-benzoxazepin-4(5H)-yl]carbonyl}piperidin-4-one
1-{[7-{2-[(2-fluoroethyl)amino]-1H-benzimidazol-5-yl}-2,3-dihydro-1,4-benzoxazepin-4(5H)-yl]carbonyl}-2-(3-fluorophenyl)piperidin-4-one
6-(4-{[4-(1,1-difluoroethyl)piperidin-1-yl]carbonyl}-2,3,4,5-tetrahydro-1,4-benzoxazepin-7-yl)-N-ethyl-1H-benzimidazol-2-amine
methyl [6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-yl]carbamate
methyl [6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-yl]carbamate
methyl [6-(4-{[4-(fluoromethyl)piperidin-1-yl]carbonyl}-2,3,4,5-tetrahydro-1,4-benzoxazepin-7-yl)-1H-imidazo[4,5-b]pyridin-2-yl]carbamate
methyl [6-(4-{[2-(4-fluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate
methyl [6-(4-{[4-(fluoromethyl)-4-hydroxypiperidin-1-yl]carbonyl}-2,3,4,5-tetrahydro-1,4-benzoxazepin-7-yl)-1H-imidazo[4,5-b]pyridin-2-yl]carbamate
methyl [6-(4-{[2-(3,4-difluorophenyl)-4-oxopiperidin-1-yl]carbonyl}-2,3,4,5-tetrahydro-1,4-benzoxazepin-7-yl)-1H-imidazo[4,5-b]pyridin-2-yl]carbamate
methyl (6-{4-[(4-cyanopiperidin-1-yl)carbonyl]-2,3,4,5-tetrahydro-1,4-benzoxazepin-7-yl}-1H-imidazo[4,5-b]pyridin-2-yl)carbamate
methyl (6-{4-[(4-methylpiperidin-1-yl)carbonyl]-2,3,4,5-tetrahydro-1,4-benzoxazepin-7-yl}-1H-imidazo[4,5-b]pyridin-2-yl)carbamate
6-(4-{[4-(1,1-difluoroethyl)piperidin-1-yl]carbonyl}-2,3,4,5-tetrahydro-1,4-benzoxazepin-7-yl)-1H-imidazo[4,5-b]pyridin-2-amine 6-(4-{[4-(difluoromethyl)piperidin-1-yl]carbonyl}-2,3,4,5-tetrahydro-1,4-benzoxazepin-7-yl)-1H-imidazo[4,5-b]pyridin-2-amine
6-(4-{[4-(2-fluoroethyl)piperidin-1-yl]carbonyl}-2,3,4,5-tetrahydro-1,4-benzoxazepin-7-yl)-1H-imidazo[4,5-b]pyridin-2-amine
6-(4-{[4-(fluoromethyl)piperidin-1-yl]carbonyl}-2,3,4,5-tetrahydro-1,4-benzoxazepin-7-yl)-1H-imidazo[4,5-b]pyridin-2-amine
1-{[7-(2-amino-1H-imidazo[4,5-b]pyridin-6-yl)-2,3-dihydro-1,4-benzoxazepin-4(5H)-yl]carbonyl}piperidine-4-carbonitrile
1-{[7-(2-amino-1H-imidazo[4,5-b]pyridin-6-yl)-2,3-dihydro-1,4-benzoxazepin-4(5H)-yl]carbonyl}piperidine-4-carboxamide
1-{[7-(2-amino-1H-imidazo[4,5-b]pyridin-6-yl)-2,3-dihydro-1,4-benzoxazepin-4(5H)-yl]carbonyl}-2-(3-fluorophenyl)piperidin-4-one
8-{[7-(2-amino-1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-(endo)-ol
N-[5-(4-{[4-(fluoromethyl)piperidin-1-yl]carbonyl}-2,3,4,5-tetrahydro-1,4-benzoxazepin-7-yl)-1H-benzimidazol-2-yl]acetamide
2-(3-fluorophenyl)-1-{[7-(2-methyl-3H-imidazo[4,5-b]pyridin-6-yl)-2,3-dihydro-1,4-benzoxazepin-4(5H)-yl]carbonyl}piperidin-4-one
2-(3-fluorophenyl)-1-{[7-(3H-imidazo[4,5-b]pyridin-6-yl)-2,3-dihydro-1,4-benzoxazepin-4(5H)-yl]carbonyl}piperidin-4-one
2-(3,4-difluorophenyl)-1-({7-[4-(1H-imidazol-2-yl)phenyl]-2,3-dihydro-1,4-benzoxazepin-4(5H)-yl}carbonyl)piperidin-4-one
2-(4-fluorophenyl)-1-({7-[4-(1H-imidazol-2-yl)phenyl]-2,3-dihydro-1,4-benzoxazepin-4(5H)-yl}carbonyl)piperidin-4-one
2-(3-fluorophenyl)-1-({7-[4-(1H-imidazol-2-yl)phenyl]-2,3-dihydro-1,4-benzoxazepin-4(5H)-yl}carbonyl)piperidin-4-one
(2R)-2-(4-fluorophenyl)-1-({7-[4-(1H-imidazol-2-yl)phenyl]-2,3-dihydro-1,4-benzoxazepin-4(5H)-yl}carbonyl)piperidin-4-one
(2S)-2-(4-fluorophenyl)-1-({7-[4-(1H-imidazol-2-yl)phenyl]-2,3-dihydro-1,4-benzoxazepin-4(5H)-yl}carbonyl)piperidin-4-one
4-{[4-(fluoromethyl)piperidin-1-yl]carbonyl}-7-[4-(1H-imidazol-2-yl)phenyl]-2,3,4,5-tetrahydro-1,4-benzoxazepine
8-({7-[4-(1H-imidazol-2-yl)phenyl]-2,3-dihydro-1,4-benzoxazepin-4(5H)-yl}carbonyl)-3-(trifluoromethyl)-8-azabicyclo[3.2.1]octan-3-(endo)-ol
7-[4-(1H-imidazol-2-yl)phenyl]-4-[(4-methylpiperidin-1-yl)carbonyl]-2,3,4,5-tetrahydro-1,4-benzoxazepine
1-({7-[4-(1H-imidazol-2-yl)phenyl]-2,3-dihydro-1,4-benzoxazepin-4(5H)-yl}carbonyl)piperidine-4-carbonitrile
4-{[4-(difluoromethyl)piperidin-1-yl]carbonyl}-7-[4-(1H-imidazol-2-yl)phenyl]-2,3,4,5-tetrahydro-1,4-benzoxazepine
1-({7-[6-(1H-imidazol-2-yl)pyridin-3-yl]-2,3-dihydro-1,4-benzoxazepin-4(5H)-yl}carbonyl)piperidine-4-carbonitrile
N-(2,2-difluoroethyl)-4-(4-{[2-(3-fluorophenyl)-4-oxopiperidin-1-yl]carbonyl}-2,3,4,5-tetrahydro-1,4-benzoxazepin-7-yl)benzamide
7-(2-methyl-1H-benzimidazol-6-yl)-4-{[(2S)-2-phenylpiperidin-1-yl]carbonyl}-2,3,4,5-tetrahydro-1,4-benzoxazepine
7-(2-methyl-1H-benzimidazol-6-yl)-4-{[(2R)-2-phenylpiperidin-1-yl]carbonyl}-2,3,4,5-tetrahydro-1,4-benzoxazepine
4-[(4,4-difluoropiperidin-1-yl)carbonyl]-7-(2-methyl-1H-benzimidazol-6-yl)-2,3,4,5-tetrahydro-1,4-benzoxazepine
1-{[7-(2-methyl-1H-benzimidazol-6-yl)-2,3-dihydro-1,4-benzoxazepin-4(5H)-yl]carbonyl}piperidin-4-ol
4-({4-[(4-chlorophenyl)methyl]piperidin-1-yl}carbonyl)-7-(2-methyl-1H-benzimidazol-6-yl)-2,3,4,5-tetrahydro-1,4-benzoxazepine
4-({4-[(4-chlorophenyl)oxy]piperidin-1-yl}carbonyl)-7-(2-methyl-1H-benzimidazol-6-yl)-2,3,4,5-tetrahydro-1,4-benzoxazepine
1-{[7-(2-methyl-1H-benzimidazol-6-yl)-2,3-dihydro-1,4-benzoxazepin-4(5H)-yl]carbonyl}-4,4'-bipiperidine
4-[(3-ethylpiperidin-1-yl)carbonyl]-7-(2-methyl-1H-benzimidazol-6-yl)-2,3,4,5-tetrahydro-1,4-benzoxazepine
4-{[2-(4-fluorophenyl)piperidin-1-yl]carbonyl}-7-(2-methyl-1H-benzimidazol-6-yl)-2,3,4,5-tetrahydro-1,4-benzoxazepine
ethyl (3S)-1-{[7-(2-methyl-1H-benzimidazol-6-yl)-2,3-dihydro-1,4-benzoxazepin-4(5H)-yl]carbonyl}piperidine-3-carboxylate
ethyl 1-{[7-(2-methyl-1H-benzimidazol-6-yl)-2,3-dihydro-1,4-benzoxazepin-4(5H)-yl]carbonyl}piperidine-2-carboxylate
4-[(5-ethyl-2-methylpiperidin-1-yl)carbonyl]-7-(2-methyl-1H-benzimidazol-6-yl)-2,3,4,5-tetrahydro-1,4-benzoxazepine
8-{[7-(2-methyl-1H-benzimidazol-6-yl)-2,3-dihydro-1,4-benzoxazepin-4(5H)-yl]carbonyl}-8-azabicyclo[3.2.1]octan-3-(endo)-amine
(3R)-1-{[7-(2-methyl-1H-benzimidazol-6-yl)-2,3-dihydro-1,4-benzoxazepin-4(5H)-yl]carbonyl}pyrrolidin-3-ol
4-methyl-1-{[7-(2-methyl-1H-benzimidazol-6-yl)-2,3-dihydro-1,4-benzoxazepin-4(5H)-yl]carbonyl}piperidin-4-ol
(±)-7-(2-methyl-1H-benzimidazol-6-yl)-4-[(4aS,8aR)-octahydroisoquinolin-2(1H)-ylcarbonyl]-2,3,4,5-tetrahydro-1,4-benzoxazepine
4-{[2-(3-fluorophenyl)piperidin-1-yl]carbonyl}-7-(2-methyl-1H-benzimidazol-6-yl)-2,3,4,5-tetrahydro-1,4-benzoxazepine
(3S)-1-{[7-(2-methyl-1H-benzimidazol-6-yl)-2,3-dihydro-1,4-benzoxazepin-4(5H)-yl]carbonyl}pyrrolidin-3-ol
4-[(4-fluoro-4-methylpiperidin-1-yl)carbonyl]-7-(2-methyl-1H-benzimidazol-6-yl)-2,3,4,5-tetrahydro-1,4-benzoxazepine
4-(hexahydrocyclopenta[c]pyrrol-2(1H)-ylcarbonyl)-7-(2-methyl-1H-benzimidazol-6-yl)-2,3,4,5-tetrahydro-1,4-benzoxazepine
4-(3,4-dihydroquinolin-1(2H)-ylcarbonyl)-7-(2-methyl-1H-benzimidazol-6-yl)-2,3,4,5-tetrahydro-1,4-benzoxazepine
7-(2-methyl-1H-benzimidazol-6-yl)-4-(piperidin-1-ylcarbonyl)-2,3,4,5-tetrahydro-1,4-benzoxazepine
7-(2-methyl-1H-benzimidazol-6-yl)-4-(pyrrolidin-1-ylcarbonyl)-2,3,4,5-tetrahydro-1,4-benzoxazepine
7-(2-methyl-1H-benzimidazol-6-yl)-4-[(3-methylpiperidin-1-yl)carbonyl]-2,3,4,5-tetrahydro-1,4-benzoxazepine 4-(azepan-1-ylcarbonyl)-7-(2-methyl-1H-benzimidazol-6-yl)-2,3,4,5-tetrahydro-1,4-benzoxazepine 7-(2-methyl-1H-benzimidazol-5-yl)-4-{[(3aR,6aS)-5-methylhexahydrocyclopenta[c]pyrrol-2(1H)-yl]carbonyl}-2,3,4,5-tetrahydro-1,4-benzoxazepine (±)-7-(2-methyl-1H-benzimidazol-5-yl)-4-{[(3aS,6aR)-5-methyl-3,3a,4,6a-tetrahydrocyclopenta[c]pyrrol-2(1H)-yl]carbonyl}-2,3,4,5-tetrahydro-1,4-benzoxazepine N-methyl-7-(2-methyl-1H-benzimidazol-6-yl)-N-(phenylmethyl)-2,3-dihydro-1,4-benzoxazepine-4(5H)-carboxamide N-methyl-7-(2-methyl-1H-benzimidazol-6-yl)-N-(2-phenylethyl)-2,3-dihydro-1,4-benzoxazepine-4(5H)-carboxamide 7-(2-methyl-1H-benzimidazol-6-yl)-4-{[2-(phenylmethyl)pyrrolidin-1-yl]carbonyl}-2,3,4,5-tetrahydro-1,4-benzoxazepine 7-(2-methyl-1H-benzimidazol-6-yl)-4-[(2-phenylpyrrolidin-1-yl)carbonyl]-2,3,4,5-tetrahydro-1,4-benzoxazepine 7-(2-methyl-1H-benzimidazol-6-yl)-4-[(2-phenylpiperidin-1-yl)carbonyl]-2,3,4,5-tetrahydro-1,4-benzoxazepine 7-(2-methyl-1H-benzimidazol-6-yl)-4-[(3-phenylpiperidin-1-yl)carbonyl]-2,3,4,5-tetrahydro-1,4-benzoxazepine 7-(2-methyl-1H-benzimidazol-6-yl)-4-[(3-phenylpyrrolidin-1-yl)carbonyl]-2,3,4,5-tetrahydro-1,4-benzoxazepine 7-(2-methyl-1H-benzimidazol-6-yl)-4-[(2-methylpyrrolidin-1-yl)carbonyl]-2,3,4,5-tetrahydro-1,4-benzoxazepine 7-(2-methyl-1H-benzimidazol-6-yl)-4-{[3-(phenylmethyl)pyrrolidin-1-yl]carbonyl}-2,3,4,5-tetrahydro-1,4-benzoxazepine 7-(2-methyl-1H-benzimidazol-6-yl)-4-[(1-oxidothiomorpholin-4-yl)carbonyl]-2,3,4,5-tetrahydro-1,4-benzoxazepine 7(2-methyl-1H-benzimidazol-6-yl)-4-{[4-(methylsulfonyl)piperidin-1-yl]carbonyl}-2,3,4,5-tetrahydro-1,4-benzoxazepine 7-(2-methyl-1H-benzimidazol-6-yl)-N-(1-methylethyl)-N-(phenylmethyl)-2,3-dihydro-1,4-benzoxazepine-4(5H)-carboxamide 7-(2-methyl-1H-benzimidazol-6-yl)-4-{[2-(phenylmethyl)piperidin-1-yl]carbonyl}-2,3,4,5-tetrahydro-1,4-benzoxazepine 7-(2-methyl-1H-benzimidazol-6-yl)-4-{[4-(methyloxy)piperidin-1-yl]carbonyl}-2,3,4,5-tetrahydro-1,4-benzoxazepine 7-(2-methyl-1H-benzimidazol-6-yl)-4-{[3-(phenylmethyl)piperidin-1-yl]carbonyl}-2,3,4,5-tetrahydro-1,4-benzoxazepine 4-(2-azabicyclo[2.2.1]hept-2-ylcarbonyl)-7-(2-methyl-1H-benzimidazol-6-yl)-2,3,4,5-tetrahydro-1,4-benzoxazepine 1-{[7-(2-methyl-1H-benzimidazol-6-yl)-2,3-dihydro-1,4-benzoxazepin-4(5H)-yl]carbonyl}piperidin-3-ol N-methyl-7-(2-methyl-1H-benzimidazol-6-yl)-N-[(1R)-1-phenylethyl]-2,3-dihydro-1,4-benzoxazepine-4(5H)-carboxamide 7-(2-methyl-1H-benzimidazol-6-yl)-4-[(5-phenylhexahydropyrrolo[3,4-c]pyrrol-2(1H)-yl)carbonyl]-2,3,4,5-tetrahydro-1,4-benzoxazepine 1-{[7-(2-methyl-1H-benzimidazol-6-yl)-2,3-dihydro-1,4-benzoxazepin-4(5H)-yl]carbonyl}-2-phenylpiperidin-4-one (8-{[7-(2-methyl-1H-benzimidazol-6-yl)-2,3-dihydro-1,4-benzoxazepin-4(5H)-yl]carbonyl}-8-azabicyclo[3.2.1]oct-3-(endo)-yl)methanol 4-(3,4-dihydroisoquinolin-2(1H)-ylcarbonyl)-7-(2-methyl-1H-benzimidazol-6-yl)-2,3,4,5-tetrahydro-1,4-benzoxazepine 4-{[2-(3,4-difluorophenyl)piperidin-1-yl]carbonyl}-7-(2-methyl-1H-benzimidazol-6-yl)-2,3,4,5-tetrahydro-1,4-benzoxazepine 4-({2-[3,5-bis(trifluoromethyl)phenyl]piperidin-1-yl}carbonyl)-7-(2-methyl-1H-benzimidazol-6-yl)-2,3,4,5-tetrahydro-1,4-benzoxazepine 4-{[2-(3-chloro-5-fluorophenyl)piperidin-1-yl]carbonyl}-7-(2-methyl-1H-benzimidazol-6-yl)-2,3,4,5-tetrahydro-1,4-benzoxazepine 4-{[2-(4-fluoro-2-methylphenyl)piperidin-1-yl]carbonyl}-7-(2-methyl-1H-benzimidazol-6-yl)-2,3,4,5-tetrahydro-1,4-benzoxazepine 4-{[2-(4-fluoro-3-methylphenyl)piperidin-1-yl]carbonyl}-7-(2-methyl-1H-benzimidazol-6-yl)-2,3,4,5-tetrahydro-1,4-benzoxazepine 2-(3,4-difluorophenyl)-1-{[7-(2-methyl-1H-benzimidazol-6-yl)-2,3-dihydro-1,4-benzoxazepin-4(5H)-yl]carbonyl}-4-(trifluoromethyl)piperidin-4-ol 7(2-methyl-1H-benzimidazol-6-yl)-4-({2-[4-(trifluoromethyl)phenyl]piperidin-1-yl}carbonyl)-2,3,4,5-tetrahydro-1,4-benzoxazepine 2-(3,4-difluorophenyl)-1-{[7-(2-methyl-1H-benzimidazol-6-yl)-2,3-dihydro-1,4-benzoxazepin-4(5H)-yl]carbonyl}piperidin-4-one 7-(2-methyl-1H-benzimidazol-5-yl)-4-[(2-phenylazepan-1-yl)carbonyl]-2,3,4,5-tetrahydro-1,4-benzoxazepine 4-{[2-(3-fluoro-4-methylphenyl)piperidin-1-yl]carbonyl}-7-(2-methyl-1H-benzimidazol-6-yl)-2,3,4,5-tetrahydro-1,4-benzoxazepine 4-{[2-(3-chlorophenyl)piperidin-1-yl]carbonyl}-7-(2-methyl-1H-benzimidazol-6-yl)-2,3,4,5-tetrahydro-1,4-benzoxazepine 2(3-fluorophenyl)-1-{[7-(2-methyl-1H-benzimidazol-6-yl)-2,3-dihydro-1,4-benzoxazepin-4(5H)-yl]carbonyl}piperidin-4-one 7-(2-methyl-1H-benzimidazol-6-yl)-4-{[2-(2-methylphenyl)piperidin-1-yl]carbonyl}-2,3,4,5-tetrahydro-1,4-benzoxazepine 7(2-methyl-1H-benzimidazol-6-yl)-4-({2-[3-(trifluoromethyl)phenyl]piperidin-1-yl}carbonyl)-2,3,4,5-tetrahydro-1,4-benzoxazepine 4-{[2-(3-chloro-4-fluorophenyl)piperidin-1-yl]carbonyl}-7-(2-methyl-1H-benzimidazol-6-yl)-2,3,4,5-tetrahydro-1,4-benzoxazepine 7-(2-methyl-1H-benzimidazol-6-yl)-4-{[2-(3,4,5-trifluorophenyl)piperidin-1-yl]carbonyl}-2,3,4,5-tetrahydro-1,4-benzoxazepine 4-{[2-(3,5-difluorophenyl)piperidin-1-yl]carbonyl}-7-(2-methyl-1H-benzimidazol-6-yl)-2,3,4,5-tetrahydro-1,4-benzoxazepine N,N-dimethyl-4-(1-{[7-(2-methyl-1H-benzimidazol-6-yl)-2,3-dihydro-1,4-benzoxazepin-4(5H)-yl]carbonyl}piperidin-2-yl)aniline 7-(2-methyl-1H-benzimidazol-6-yl)-4-(morpholin-4-ylcarbonyl)-2,3,4,5-tetrahydro-1,4-benzoxazepine (±)-(2R,4R)-4-methyl-1-{[7(2-methyl-1H-benzimidazol-5-yl)-2,3-dihydro-1,4-benzoxazepin-4(5H)-yl]carbonyl}-2-phenylpiperidin-4-ol (±)-(2R,4S)-4-methyl-1-{[7-(2-methyl-1H-benzimidazol-5-yl)-2,3-dihydro-1,4-benzoxazepin-4(5H)-yl]carbonyl}-2-phenylpiperidin-4-ol 4-methyl-1-{[7-(2-methyl-1H-benzimidazol-6-yl)-2,3-dihydro-1,4-benzoxazepin-4(5H)-yl]carbonyl}piperidine-4-carboxamide (±)-(2R,4S)-2-(4-fluorophenyl)-1-{[7-(2-methyl-1H-benzimidazol-6-yl)-2,3-dihydro-1,4-benzoxazepin-4(5H)-yl]carbonyl}piperidin-4-ol 4-{[4-(difluoromethylidene)piperidin-1-yl]carbonyl}-7-(2-methyl-1H-benzimidazol-6-yl)-2,3,4,5-tetrahydro-1,4-benzoxazepine 4-[(4,4-difluoro-2-phenylpiperidin-1-yl)carbonyl]-7-(2-methyl-1H-benzimidazol-6-yl)-2,3,4,5-tetrahydro-1,4-benzoxazepine 2-(1-{[7-(2-methyl-1H-benzimidazol-6-yl)-2,3-dihydro-1,4-benzoxazepin-4(5H)-yl]carbonyl}piperidin-4-yl)propan-2-ol (±)-(2R,4S)-2-(3,4-difluorophenyl)-1-{[7-(2-methyl-1H-benzimidazol-6-yl)-2,3-dihydro-1,4-benzoxazepin-4(5H)-yl]carbonyl}piperidin-4-ol 1-{[7-(2-methyl-1H-benzimidazol-6-yl)-2,3-dihydro-1,4-benzoxazepin-4(5H)-yl]carbonyl}-4-[4-(trifluoromethyl)phenyl]piperidin-4-ol 4-(4-fluorophenyl)-1-{[7-(2-methyl-1H-benzimidazol-6-yl)-2,3-dihydro-1,4-benzoxazepin-4(5H)-yl]carbonyl}piperidin-4-ol 9-{[7-(2-methyl-1H-benzimidazol-6-yl)-2,3-dihydro-1,4-benzoxazepin-4(5H)-yl]carbonyl}-1,2,3,4-tetrahydro-1,4-epiminonaphthalene 7-(2-methyl-1H-benzimidazol-6-yl)-4-[(4-methyl-2-phenylpiperazin-1-yl)carbonyl]-2,3,4,5-tetrahydro-1,4-benzoxazepine 4-[(2,4-diphenylpiperazin-1-yl)carbonyl]-7-(2-methyl-1H-benzimidazol-6-yl)-2,3,4,5-tetrahydro-1,4-benzoxazepine 1-methyl-4-{[7-(2-methyl-1H-benzimidazol-6-yl)-2,3-dihydro-1,4-benzoxazepin-4(5H)-yl]carbonyl}piperazin-2-one (±)-4-{[(2R,4S)-2-(3,4-difluorophenyl)-4-(fluoromethyl)piperidin-1-yl]carbonyl}-7-(2-methyl-1H-benzimidazol-6-yl)-2,3,4,5-tetrahydro-1,4-benzoxazepine (±)-(2R,4R)-2-(3,4-difluorophenyl)-1-{[7-(2-methyl-1H-benzimidazol-6-yl)-2,3-dihydro-1,4-benzoxazepin-4(5H)-yl]carbonyl}piperidine-4-carbonitrile 7-(2-methyl-1H-benzimidazol-6-yl)-N-[(1r,3r,5R,7R)-tricyclo[3.3.1.1~3,7~]dec-2-yl]-2,3-dihydro-1,4-benzoxazepine-4(5H)-carboxamide 7-(2-methyl-1H-benzimidazol-6-yl)-4-({4-[5-(trifluoromethyl)pyridin-2-yl]piperazin-1-yl}carbonyl)-2,3,4,5-tetrahydro-1,4-benzoxazepine ethyl N-{[7-(2-methyl-1H-benzimidazol-6-yl)-2,3-dihydro-1,4-benzoxazepin-4(5H)-yl]carbonyl}-N-(phenylmethyl)glycinate 4-({4-[(2-chloro-6-fluorophenyl)methyl]piperazin-1-yl}carbonyl)-7-(2-methyl-1H-benzimidazol-6-yl)-2,3,4,5-tetrahydro-1,4-benzoxazepine N-methyl-7-(2-methyl-1H-benzimidazol-6-yl)-N-[(3-methylphenyl)methyl]-2,3-dihydro-1,4-benzoxazepine-4(5H)-carboxamide 7-(2-methyl-1H-benzimidazol-6-yl)-4-[(2-{[(4-methylphenyl)oxy]methyl}morpholin-4-yl)carbonyl]-2,3,4,5-tetrahydro-1,4-benzoxazepine 4-ethyl-9-{[7-(2-methyl-1H-benzimidazol-6-yl)-2,3-dihydro-1,4-benzoxazepin-4(5H)-yl]carbonyl}-3,9-diazaspiro[5.5]undecan-2-one 7-(2-methyl-1H-benzimidazol-6-yl)-4-(octahydroisoquinolin-2(1H)-ylcarbonyl)-2,3,4,5-tetrahydro-1,4-benzoxazepine 7-(2-methyl-1H-benzimidazol-6-yl)-4-[(4-phenyl-3,6-dihydropyridin-1(2H)-yl)carbonyl]-2,3,4,5-tetrahydro-1,4-benzoxazepine 4-{[4-(furan-2-ylcarbonyl)piperazin-1-yl]carbonyl}-7-(2-methyl-1H-benzimidazol-6-yl)-2,3,4,5-tetrahydro-1,4-benzoxazepine 4-{[4-(2-chlorophenyl)piperazin-1-yl]carbonyl}-7-(2-methyl-1H-benzimidazol-6-yl)-2,3,4,5-tetrahydro-1,4-benzoxazepine 7-(2-methyl-1H-benzimidazol-6-yl)-4-({4-[3-(methyloxy)phenyl]piperazin-1-yl}carbonyl)-2,3,4,5-tetrahydro-1,4-benzoxazepine 7-(2-methyl-1H-benzimidazol-6-yl)-4-[(4-pyrazin-2-ylpiperazin-1-yl)carbonyl]-2,3,4,5-tetrahydro-1,4-benzoxazepine 7-(2-methyl-1H-benzimidazol-6-yl)-4-{[4-(5-methyl-1,2,4-oxadiazol-3-yl)piperidin-1-yl]carbonyl}-2,3,4,5-tetrahydro-1,4-benzoxazepine 4-{[4-(5-cyclopropyl-1,2,4-oxadiazol-3-yl)piperidin-1-yl]carbonyl}-7-(2-methyl-1H-benzimidazol-6-yl)-2,3,4,5-tetrahydro-1,4-benzoxazepine 7-(2-methyl-1H-benzimidazol-6-yl)-N-(4-pentylphenyl)-2,3-dihydro-1,4-benzoxazepine-4(5H)-carboxamide 4-{[4-(2-fluorophenyl)piperazin-1-yl]carbonyl}-7-(2-methyl-1H-benzimidazol-6-yl)-2,3,4,5-tetrahydro-1,4-benzoxazepine 7-(2-methyl-1H-benzimidazol-6-yl)-4-[(4-pyrimidin-2-ylpiperazin-1-yl)carbonyl]-2,3,4,5-tetrahydro-1,4-benzoxazepine 4-(azocan-1-ylcarbonyl)-7-(2-methyl-1H-benzimidazol-6-yl)-2,3,4,5-tetrahydro-1,4-benzoxazepine 7-(2-methyl-1H-benzimidazol-6-yl)-4-{[4-(4-nitrophenyl)piperazin-1-yl]carbonyl}-2,3,4,5-tetrahydro-1,4-benzoxazepine 1-[4-(4-{[7-(2-methyl-1H-benzimidazol-6-yl)-2,3-dihydro-1,4-benzoxazepin-4(5H)-yl]carbonyl}piperazin-1-yl)phenyl]ethanone 7-(2-methyl-1H-benzimidazol-6-yl)-4-[(4-phenylpiperidin-1-yl)carbonyl]-2,3,4,5-tetrahydro-1,4-benzoxazepine 7-(2-methyl-1H-benzimidazol-6-yl)-4-{[4-(phenylmethyl)piperidin-1-yl]carbonyl}-2,3,4,5-tetrahydro-1,4-benzoxazepine 7-(2-methyl-1H-benzimidazol-6-yl)-4-[(4-pyridin-2-ylpiperazin-1-yl)carbonyl]-2,3,4,5-tetrahydro-1,4-benzoxazepine N-butyl-7-(2-methyl-1H-benzimidazol-6-yl)-N-(phenylmethyl)-2,3-dihydro-1,4-benzoxazepine-4(5H)-carboxamide 7-(2-methyl-1H-benzimidazol-6-yl)-4-[(4-phenylpiperazin-1-yl)carbonyl]-2,3,4,5-tetrahydro-1,4-benzoxazepine 4-{[4(4-fluorophenyl)piperazin-1-yl]carbonyl}-7-(2-methyl-1H-benzimidazol-6-yl)-2,3,4,5-tetrahydro-1,4-benzoxazepine 4-{[4-(3-chlorophenyl)piperazin-1-yl]carbonyl}-7-(2-methyl-1H-benzimidazol-6-yl)-2,3,4,5-tetrahydro-1,4-benzoxazepine N-ethyl-7-(2-methyl-1H-benzimidazol-6-yl)-N-(phenylmethyl)-2,3-dihydro-1,4-benzoxazepine-4(5H)-carboxamide 8-{[7-(1H-imidazo[4,5-b]pyridin-6-yl)-2,3-dihydro-1,4-benzoxazepin-4(5H)-yl]carbonyl}-3-(trifluoromethyl)-8-azabicyclo[3.2.1]octan-3-(endo)-ol 8-({7-[2-(ethylamino)-1H-imidazo[4,5-b]pyridin-6-yl]-2,3-dihydro-1,4-benzoxazepin-4(5H)-yl}carbonyl)-3-(trifluoromethyl)-8-azabicyclo[3.2.1]octan-3-(endo)-ol 8-{[7-{6-amino-5-[(3-aminoazetidin-1-yl)sulfonyl]pyridin-3-yl}-2,3-dihydro-1,4-benzoxazepin-4(5H)-yl]carbonyl}-3-(trifluoromethyl)-8-azabicyclo[3.2.1]octan-3-ol N-[2-chloro-5-(4-{[3-hydroxy-3-(trifluoromethyl)-8-azabicyclo[3.2.1]oct-8-yl]carbonyl}-2,3,4,5-tetrahydro-1,4-benzoxazepin-7-yl)pyridin-3-yl]methanesulfonamide optionally as a pharmaceutically acceptable salt thereof.

21. A pharmaceutical composition which comprises a compound optionally as pharmaceutically acceptable salt thereof of claim 1, and a pharmaceutically acceptable carrier, excipient, or diluent.

22. A method of making a compound of Formula I, according to claim 1, which method comprises
(a) reacting the following, or a salt thereof;

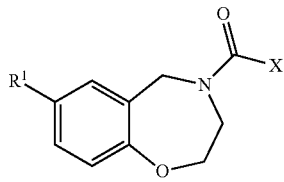

where X is halo and $R^1$ is as defined in claim 1, with an intermediate of formula $R^2H$ where $R^2$ is as defined in claim 1 to yield a compound of Formula I; and optionally separating individual isomers; and optionally modifying any of the $R^1$ and $R^2$ groups; and optionally forming a pharmaceutically acceptable salt thereof; or (b) reacting the following, or a salt thereof

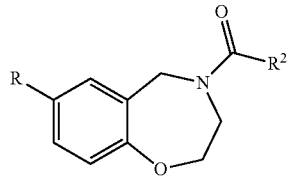

where R is halo or —B(OR')$_2$ (where both R' are hydrogen or the two R' together form a boronic ester), and $R^2$ is as defined in claim 1; with an intermediate of formula $R^1Y$ where Y is halo when R is —B(OR')$_2$ and Y is —B(OR')$_2$ when R is halo, and $R^2$ is as defined in claim 1 to yield a compound of Formula I; and optionally separating individual isomers; and optionally modifying any of the $R^1$ and $R^2$ groups; and optionally forming a pharmaceutically acceptable salt, hydrate, solvate or combination thereof.

23. A method for treating cancer, where the cancer is mammary adenocarcinoma, colorectal carcinoma, prostate adenocarcinoma, glioblastoma, lung carcinoma, or melanoma, the method comprising administering to a patient a therapeutically effective amount of a compound of claim 1, optionally as a pharmaceutically acceptable salt thereof, or a pharmaceutical composition comprising a compound of claim 1, and a pharmaceutically acceptable carrier, excipient, or diluent.

* * * * *